United States Patent
Zhang et al.

(10) Patent No.: US 12,384,797 B2
(45) Date of Patent: Aug. 12, 2025

(54) THIOENO[3,2-B] PYRIDIN-7-AMINE COMPOUNDS FOR TREATING FAMILIAL DYSAUTONOMIA

(71) Applicant: PTC THERAPEUTICS, INC., Warren, NJ (US)

(72) Inventors: Nanjing Zhang, Princeton, NJ (US); Michael A. Arnold, Flemington, NJ (US); Amal Dakka, Whitehouse Station, NJ (US); Gary Mitchell Karp, Princeton Junction, NJ (US); Tom Tuan Luong, Cupertino, CA (US); Jana Narasimhan, Scotch Plains, NJ (US); Nikolai A. Naryshkin, East Brunswick, NJ (US); Jiashi Wang, West New York, NJ (US); Xiaoyan Zhang, Belle Mead, NJ (US)

(73) Assignee: PTC THERAPEUTICS, INC., Warren, NJ (US)

( * ) Notice: Subject to any disclaimer, the term of this patent is extended or adjusted under 35 U.S.C. 154(b) by 841 days.

(21) Appl. No.: 17/430,511

(22) PCT Filed: Feb. 10, 2020

(86) PCT No.: PCT/US2020/017430
§ 371 (c)(1),
(2) Date: Aug. 12, 2021

(87) PCT Pub. No.: WO2020/167628
PCT Pub. Date: Aug. 20, 2020

(65) Prior Publication Data
US 2022/0135586 A1    May 5, 2022

Related U.S. Application Data

(60) Provisional application No. 62/805,283, filed on Feb. 13, 2019.

(51) Int. Cl.
C07D 495/04 (2006.01)
A61P 25/00 (2006.01)

(52) U.S. Cl.
CPC ............ C07D 495/04 (2013.01); A61P 25/00 (2018.01)

(58) Field of Classification Search
CPC ............................... C07D 495/04; A61P 25/00
See application file for complete search history.

(56) References Cited

U.S. PATENT DOCUMENTS

| | | | |
|---|---|---|---|
| 3,475,429 A | 10/1969 | Woitun et al. | |
| 5,532,257 A | 7/1996 | Hase et al. | |
| 5,654,307 A | 8/1997 | Bridges et al. | |
| 6,211,195 B1 | 4/2001 | Webb et al. | |
| 6,492,383 B1 | 12/2002 | Munchhof et al. | |
| 7,737,110 B2 | 6/2010 | Slaugenhaupt et al. | |
| 2004/0138251 A1 | 7/2004 | Boschelli et al. | |
| 2012/0053173 A1 | 3/2012 | Banno et al. | |
| 2013/0209549 A1 | 8/2013 | Dickey | |
| 2013/0317045 A1 | 11/2013 | Hadd et al. | |
| 2014/0005183 A1 | 1/2014 | Galatsis et al. | |
| 2014/0323544 A1 | 10/2014 | Bestwick et al. | |
| 2015/0344497 A1 | 12/2015 | Zhou et al. | |
| 2016/0002273 A1 | 1/2016 | Blum et al. | |
| 2018/0118748 A1 | 5/2018 | Slaugenhaupt et al. | |
| 2018/0258425 A1 | 9/2018 | Rigo et al. | |
| 2019/0000844 A1 | 1/2019 | Babu et al. | |
| 2020/0239940 A1 | 7/2020 | Guo et al. | |
| 2022/0056043 A1 | 2/2022 | Li et al. | |
| 2024/0024490 A1 | 1/2024 | Choudhary et al. | |

FOREIGN PATENT DOCUMENTS

| | | |
|---|---|---|
| CA | 3082907 A1 | 5/2019 |
| CL | 202102104 | 4/2022 |
| CN | 103242341 A | 8/2013 |
| CN | 110312528 A | 10/2019 |
| CO | NC20170011017 A2 | 3/2018 |
| CO | NC20180001425 A2 | 5/2018 |

(Continued)

OTHER PUBLICATIONS

Cheishvili, Human Molecular Genetics, 2011, vol. 20(8), 1585-1594. (Year: 2011).*
Gold-Von Simson, Pediatric Research, 2009, vol. 65(3), 341-46. (Year: 2009).*
Cheishvili, Human Molecular Genetics, 2007, vol. 16(17), 2097-2104. (Year: 2007).*
Anderson, 2001, Am J Hum Genet, vol. 68, 753-758. (Year: 2001).*
Munchhof, Bioorg & Med Chem Lett, vol. 14, 2004, 21-24. (Year: 2004).*
Campos, Tetrahedron, vol. 55, 1999, 14079-14488. (Year: 1999).*
International Search Report for PCT/US2022/075966 date mailed Jan. 19, 2023.
Written Opinion for PCT/US2022/075966 date mailed Jan. 19, 2023.
Pubchem, SID 274791846, Modify Date: Nov. 21, 2016, Available: Dec. 18, 2015.

(Continued)

*Primary Examiner* — D Margaret M Seaman
(74) *Attorney, Agent, or Firm* — Hoffmann & Baron, LLP

(57) ABSTRACT

The present description relates' to compounds of formula (I) useful for improving pre-mRNA splicing in a cell. In particular, another aspect of the present description relates to substituted thieno[3,2-b]pyridine compounds, forms, and pharmaceutical compositions thereof and methods of use for treating or ameliorating familial dysautonomia.

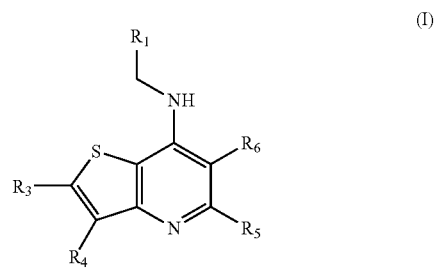

17 Claims, No Drawings

(56) References Cited

FOREIGN PATENT DOCUMENTS

| | | | |
|---|---|---|---|
| CO | NC20180013803 A2 | 1/2019 | |
| CO | NC20210008895 A2 | 7/2021 | |
| EP | 2014663 A1 | 1/2009 | |
| EP | 3020829 A1 | 5/2016 | |
| EP | 3828829 A1 | 6/2021 | |
| JP | 2009007341 A | 1/2009 | |
| KR | 102390370 B1 | 4/2022 | |
| WO | 2004/065392 A1 | 8/2004 | |
| WO | 2005007083 A2 | 1/2005 | |
| WO | 2009085226 A2 | 7/2009 | |
| WO | 2010/118367 A2 | 10/2010 | |
| WO | 2013026516 A1 | 2/2013 | |
| WO | 2014/124458 A1 | 8/2014 | |
| WO | 2015053624 A2 | 4/2015 | |
| WO | 2016115434 A1 | 7/2016 | |
| WO | 2017053781 A1 | 3/2017 | |
| WO | 2018075937 A1 | 4/2018 | |
| WO | 2018134685 A2 | 7/2018 | |
| WO | 2020167624 A1 | 8/2020 | |
| WO | 2020167628 A1 | 8/2020 | |
| WO | 2020245233 A1 | 12/2020 | |
| WO | 2021118929 A1 | 6/2021 | |
| WO | 2021142351 A1 | 7/2021 | |
| WO | 2022169864 A1 | 8/2022 | |
| WO | 2022169866 A1 | 8/2022 | |
| WO | 2022169868 A1 | 8/2022 | |
| WO | 2023039368 A1 | 3/2023 | |
| WO | 2023039369 A1 | 3/2023 | |
| WO | 2023039370 A1 | 3/2023 | |
| WO | 2023081858 A1 | 5/2023 | |
| WO | 2023250316 A1 | 12/2023 | |

OTHER PUBLICATIONS

International Search Report for PCT/US2022/2075967 date mailed Jan. 19, 2023.
Written Opinion for PCT/US2022/075967 date mailed Jan. 19, 2023.
Pubchem, SID 365025105, Available Date: May 25, 2018.
Pubchem, SID 439055238, Available Date: Dec. 19, 2020.
International Search Report for PCT/US2022/075969 date mailed Jan. 19, 2023.
Written Opinion for PCT/US2022/075969 date mailed Jan. 19, 2023.
Pubchem, SID 377008396, Available Date: Dec. 4, 2018.
International Search Report for PCT/US2020/017423 date mailed May 12, 2020.
Written Opinion for PCT/US2020/017423 date mailed May 12, 2020.
International Search Report for PCT/US2020/017430 date mailed May 19, 2020.
Written Opinion for PCT/US2020/017430 date mailed May 19, 2020.
International Search Report for PCT/US2020/063612 date mailed Mar. 1, 2021.
Written Opinion for PCT/US2020/063612 date mailed Mar. 1, 2021.
Panchal et al., "Evaluation of basic, heterocyclic ring systems as templates for use as potassium competitive acid blockers (pCABs)", Bioorganic & Medicinal Chemistry Letters, vol. 19, No. 23, Dec. 1, 2009 (Dec. 1, 2009), available online Jul. 4, 2009, pp. 6813-6817, XP026736113.
Database Registry [Online] Chemical Abstracts Service, Columbus, Ohio, US; May 2, 2017 (May 2, 2017), XP002802124, Database accession No. 2094356-55-3, 7-methyl-N-[[1-methyl-3-(trifluoromethyl)-thieno[3,2-d]pyrimidin-4-amine.
International Search Report for PCT/US2022/014929 date mailed Jun. 21, 2022.
Written Opinion for PCT/US2022/014929 date mailed Jun. 21, 2022.
International Search Report for PCT/US2022/014932 date mailed Jun. 15, 2022.
Written Opinion for PCT/US2022/014932 date mailed Jun. 15, 2022.
International Search Report for PCT/US2022/014934 date mailed Jun. 15, 2022.
Written Opinion for PCT/US2022/014934 date mailed Jun. 15, 2022.
Pubchem, SID 389066036, Available Date: Dec. 6, 2019.
Vippagunta et al., "Crystalline solids," Advanced Drug Delivery Reviews, vol. 48, Issue 1, May 16, 2001, pp. 3-26.
V. Craig Jordan, "Tamoxifen: A Most Unlikely Pioneering Medicine," Nature Reviews: Drug Discovery, vol. 2 (Mar. 2003) pp. 205-213.
Xiong Shu-Hua et al., "Diagnosis and Treatment Update on Autoimmune Autonomic Gangliopathy," pp. 690-693 A Chinese journal of clinical neuroscience No. 20 vol. 6 2012-12-31.
CAS Database Registry STN No. 1349454-03-0, entered on Dec. 6, 2011.
"Chemical Encyclopedia", scientific publishing house "Great Russian Encyclopedia," Moskva, vol. 4, pp. 499-501, 1995.
CAS Database Registry STN No. 2167522-70-3, entered on Jan. 1, 2018.
CAS Database Registry STN No. 2021176-84-9, entered on Oct. 28, 2016.
CAS Database Registry STN No. 1881342-47-7, entered on Mar. 8, 2016.
CAS Database Registry STN No. 1878819-09-0, entered on Mar. 3, 2016.
CAS Database Registry STN No. 1876870-61-9, entered on Mar. 1, 2016.
CAS Database Registry STN No. 1876583-64-0, entered on Mar. 1, 2016.
CAS Database Registry STN No. 1876399-06-2, entered on Feb. 29, 2016.
CAS Database Registry STN No. 1874906-94-1, entered on Feb. 26, 2016.
CAS Database Registry STN No. 1870492-22-0, entered on Feb. 19, 2016.
CAS Database Registry STN No. 1858986-81-8, entered on Feb. 3, 2016.
CAS Database Registry STN No. 1858871-72-3, entered on Feb. 3, 2016.
CAS Database Registry STN No. 2302366-29-4, entered on Apr. 7, 2016.
CAS Database Registry STN No. 2300574-14-3, entered on Apr. 4, 2016.
CAS Database Registry STN No. 2299694-59-8, entered on Apr. 3, 2019.
CAS Database Registry STN No. 2299370-15-1, entered on Apr. 3, 2019.
CAS Database Registry STN No. 2295625-99-7, entered on Mar. 28, 2019.
CAS Database Registry STN No. 2295625-98-6, entered on Mar. 28, 2019.
CAS Database Registry STN No. 2294501-42-9, entered on Mar. 27, 2019.
CAS Database Registry STN No. 2294382-59-3, entered on Mar. 27, 2019.
CAS Database Registry STN No. 2294379-83-0, entered on Mar. 27, 2019.
CAS Database Registry STN No. 2294353-32-3, entered on Mar. 27, 2019.
CAS Database Registry STN No. 2293758-23-1, entered on Mar. 26, 2019.
CAS Database Registry STN No. 2293235-24-0, entered on Mar. 26, 2019.
CAS Database Registry STN No. 2293231-63-5, entered on Mar. 26, 2019.
CAS Database Registry STN No. 2293211-33-1, entered on Mar. 26, 2019.
CAS Database Registry STN No. 2293211-30-8, entered on Mar. 26, 2019.

(56) References Cited

OTHER PUBLICATIONS

Gold-Von Simson, et al., "Kinetin in Familial Dysautonomia Carriers: Implication for a New Therapeutic Strategy Targeting mRNA Splicing," Pediatric Research, vol. 65(3), pp. 341-346, Mar. 2009.
Pedro J. Campos et al., "A Versatile Synthesis of Pyrrolo-, Furo- and Thienopyridines via Photocyclization of 3-Amino-2-alkene Imines in an Acid Medium," Tetrahedron, vol. 55, pp. 14079-14088, Dec. 3, 1999.
Sylvia L. Anderson et al., "Familial Dysautonomia Is Caused by Mutations of the IKAP Gene," Am. J. Hum, Genet., vol. 68, pp. 753-758, electronically published Jan. 22, 2001.
David Cheishvili et al., "IKAP/Elp1 involvement in cytoskeleton regulation and implication for familial dysautonomia," Human Molecular Genetics, vol. 20(8), pp. 1584-1594, Advance Access published Jan. 27, 2011.
Michael J. Munchhof et al., "Design and SAR of thienopyrimidine and thienopyridine inhibitors of VEGFR-2 kinase activity," Bioorg. & Med. Chem. Lett., vol. 14, 2004, pp. 21-24, Jan. 5, 2004.
David Cheishvili et al., "IKAP/hELPI deficiency in the cerebrum of familial dysautonomia patients results in down regulation of genes involved in oligodendrocyte differentiation and in myelination," Human Molecular Genetics, 2007, vol. 16(17), pp. 2097-2104, Advanced Access published Jun. 25, 2007.
Evers Melvin M. et al., "Ataxin-3 protein modification as a treatment strategy for spinocerebellar ataxia type 3: Removal of the CAG containing exon", Neurobiology of Disease, [Online] vol. 58, May 6, 2013 (May 6, 2013), pp. 49-56, XP093217684.
Craig S. McIntosh et al., "Removal of the Polyglutamine Repeat of Ataxin-3 by Redirecting pre-mRNA Processing", International Journal of Molecular Sciences, vol. 20, No. 21, Oct. 31, 2019 (Oct. 31, 2019), p. 5434, XP055712430.
Lodewijk J. A. Toonen et al., "Antisense oligonucleotide-mediated exon skipping as a strategy to reduce proteolytic cleavage of ataxin-3," Scientific Reports, vol. 6, No. 1, Oct. 12, 2016 (Oct. 12, 2016), XP055563933.
CAS Database Registry STN No. 2371515-24-9, entered on Sep. 1, 2019.
CAS Database Registry STN No. 1981326-49-1, entered on Aug. 28, 2016.
CAS Database Registry STN No. 1967610-91-8, entered Aug. 5, 2016.
CAS Database Registry STN No. 2327421-67-8, entered on Jun. 10, 2019.
CAS Database Registry STN No. 878601-07-1, entered on Mar. 30, 2006.
CAS Database Registry STN No. 879332-90-8, entered on Apr. 5, 2006.
CAS Database Registry STN No. 1349123-32-5, entered on Dec. 5, 2011.
CAS Database Registry STN No. 1967539-15-6, entered on Aug. 5, 2016.
CAS Database Registry STN No. 1914470-24-8, entered on May 20, 2016.
Klockgether Thomas et al: "Spinocerebellar ataxia", Nature Reviews Disease Primers, Nature Publishing Group UK, London, vol. 5, No. 1, Apr. 11, 2019 (Apr. 11, 2019), pp. 1-21, XP036756583.
Written Opinion for PCT/US2023/068717 date mailed Nov. 8, 2023.
International Search Report for PCT/US2023/068717 date mailed Nov. 8, 2023.
Berish Y Rubin et al., "IKBKAP/ELP1 gene mutations: mechanisms of familial dysautonomia and gene-targeting therapies," The Application of Clinical Genetics, 10, pp. 95-103 Dec. 15, 2017.
Ranjit S. Shetty et al., "Specific correction of a splice defect in brain by nutritional supplementation," Human Molecular Genetics, vol. 20, No. 21, pp. 4093-4101, Aug. 5, 2011.
Felicia B. Axelrod et al., "Kinetin improves IKBKAP mRNA splicing in patients with familial dysautonomia," Pediatric Research, 70(5), pp. 480-483, Nov. 2011.
Mayumi Yoshida et al., "Rectifier of aberrant mRNA splicing recovers tRNA modification in familial dysautonomia," PNAS vol. 112, No. 9, pp. 2764-2769, Mar. 3, 2015.
Elisabetta Morini et al., "Development of an oral treatment that rescues gait ataxia and retinal degeneration in a phenotypic mouse model of familial dysautonomia," The American Journal of Human Genetics, 110(3), pp. 531-547, Mar. 2, 2023, E-publication on Feb. 20, 2023.
Reeteka Sud et al., "Antisense-mediated Exon Skipping Decreases Tau Protein expression: A Potential Therapy For Tauopathies," Molecular Therapy-Nucleic Acids, 3, 2014, 7, published online Jul. 29, 2014, p. e180.
Fei Liu et al., "Tau exon 10 alternative splicing and tauopathies," Molecular Neurodegeneration, 3, 2008, 1, published Jul. 10, 2008, p. 8.
CAS Database Registry STN No. 939979-48-3, entered on Jun. 28, 2007.
CAS Database Registry STN No. 1098386-78-7, entered on Feb. 1, 2009.

\* cited by examiner

THIOENO[3,2-B] PYRIDIN-7-AMINE COMPOUNDS FOR TREATING FAMILIAL DYSAUTONOMIA

CROSS-REFERENCE TO RELATED APPLICATIONS

This application is the National Stage of International Application No. PCT/US2020/017430, filed Feb. 10, 2020, which claims priority to U.S. Provisional Application No. 62/805,283 filed on Feb. 13, 2019.

STATEMENT OF JOINT RESEARCH AGREEMENT

The subject matter disclosed was developed and the claimed invention was made by, or on behalf of, one or more parties to a joint research agreement that was in effect on or before the effective filing date of the claimed invention. The claimed invention was made as a result of activities undertaken within the scope of the joint research agreement. The parties of the joint research agreement are PTC Therapeutics, Inc. and The General Hospital Corporation, d/b/a Massachusetts General Hospital.

TECHNICAL FIELD

An aspect of the present description relates to compounds useful for improving pre-mRNA splicing in a cell. In particular, another aspect of the present description relates to substituted thieno[3,2-b]pyridine compounds, forms, and pharmaceutical compositions thereof and methods of use for treating or ameliorating familial dysautonomia.

BACKGROUND

Familial dysautonomia (FD) is a congenital sensory and autonomic neuropathy (HSAN) of the central and peripheral nervous system characterized by widespread sensory and variable autonomic dysfunction. FD affects neuronal development and is associated with progressive neuronal degeneration. Multiple systems are affected resulting in a markedly reduced quality of life and premature death. FD is caused by mutations in the IKBKAP (also referred to as ELP1) gene and in all cases described to date there is at least one allele carrying a T to C mutation at position 6 in intron 20 that results in a unique pattern of tissue-specific exon skipping.

Kinetin derivatives useful for therapeutically targeting pre-mRNA splicing mechanisms and the treatment of FD have been described in International Patent Application No. WO2016/115434, the disclosure of which is incorporated by reference in its entirety.

All other documents referred to herein are incorporated by reference into the present application as though fully set forth herein.

SUMMARY

An aspect of the present description includes compounds comprising, a compound of Formula (I):

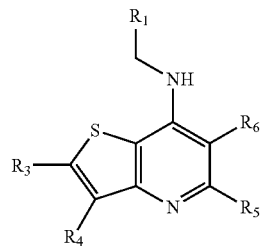

or a form thereof, wherein $R_1$, $R_3$, $R_4$, $R_5$, and $R_6$ are defined herein.

An aspect of the present description includes a method for use of a compound of Formula (I) or a form or composition thereof for treating or ameliorating FD in a subject in need thereof comprising, administering to the subject an effective amount of the compound of Formula (I) or a form or composition thereof.

An aspect of the present description includes a use for a compound of Formula (I) or a form thereof for treating or ameliorating FD in a subject in need thereof comprising, administering to the subject an effective amount of the compound of Formula (I) or a form thereof.

An aspect of the present description includes a use for a compound of Formula (I) or a form thereof in the manufacture of a medicament for treating or ameliorating FD in a subject in need thereof comprising, administering to the subject an effective amount of the medicament.

DETAILED DESCRIPTION

An aspect of the present description relates to compounds comprising, a compound of Formula (I):

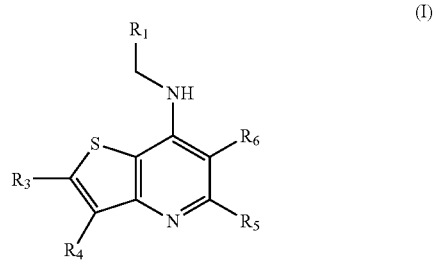

or a form thereof, wherein:
  $R^1$ is phenyl or heteroaryl, optionally substituted with one, two, three, or four, independently selected $R_{1a}$ substituents,
    wherein heteroaryl is a 5-8 membered monocyclic or bicyclic aromatic carbon atom ring structure radical containing 1-3 heteroatoms selected from N, O, and S;
  $R_{1a}$ is cyano, halo, hydroxy, $C_{1-6}$alkyl, halo-$C_{1-6}$alkyl, or $C_{1-6}$alkoxy;
  $R_3$ is hydrogen, $C_{1-6}$alkyl, $C_{2-6}$alkenyl, $C_{2-6}$alkynyl, and $C_{1-6}$alkyl-amino,
    wherein $C_{1-6}$alkyl, $C_{2-6}$alkenyl, and $C_{2-6}$alkynyl is optionally substituted with one, two, three, or four independently selected $R_{3a}$ substituents, and
    wherein each instance of $C_{1-6}$alkyl, $C_{2-6}$alkenyl, and $C_{2-6}$alkynyl may optionally contain a chiral carbon having an (R) or (S) configuration;

$R_{3a}$ is cyano, halo, hydroxy, oxo, $C_{1-6}$alkyl, halo-$C_{1-6}$alkyl, $C_{1-6}$alkoxy, halo-$C_{1-6}$alkoxy, carboxyl, amino, $C_{1-6}$alkoxy-carbonyl, $C_{1-6}$alkyl-amino, halo-$C_{1-6}$alkyl-amino, ($C_{1-6}$alkyl)$_2$-amino, phenyl-amino, heterocyclyl-amino, heteroaryl-amino, phenyl-($C_{1-6}$alkyl)-amino, heterocyclyl-($C_{1-6}$alkyl)-amino, heteroaryl-($C_{1-6}$alkyl)-amino, $C_{1-6}$alkyl-thio, $C_{1-6}$alkyl-sulfoxyl, and $C_{1-6}$alkyl-sulfonyl, wherein heterocyclyl is a 3-7 membered monocyclic carbon atom ring structure radical containing 1-3 heteroatoms selected from N, O, and S, wherein heteroaryl is a 5-8 membered monocyclic or bicyclic aromatic carbon atom ring structure radical containing 1-3 heteroatoms selected from N, O, and S;
wherein each instance of phenyl, heterocyclyl, and heteroaryl is optionally substituted with one, two, three or four independently selected $R_{3a'}$ substituents;

$R_{3a'}$ is cyano, halo, hydroxy, $C_{1-6}$alkyl, halo-$C_{1-6}$alkyl, $C_{1-6}$alkoxy, or amino;

$R_4$ is hydrogen, cyano, halo, hydroxy, $C_{1-6}$alkyl, halo-$C_{1-6}$alkyl, $C_{1-6}$alkoxy, halo-$C_{1-6}$alkoxy, amino, $C_{1-6}$alkyl-amino, ($C_{1-6}$alkyl)$_2$-amino, $C_{3-10}$cycloalkyl, phenyl, heterocyclyl, or heteroaryl, wherein heterocyclyl is a 3-7 membered monocyclic carbon atom ring structure radical containing 1-3 heteroatoms selected from N, O, and S, wherein heteroaryl is a 5-8 membered monocyclic or bicyclic aromatic carbon atom ring structure radical containing 1-3 heteroatoms selected from N, O, and S, and wherein each instance of $C_{1-6}$alkyl, $C_{3-10}$cycloalkyl, phenyl, heterocyclyl, or heteroaryl are optionally substituted with one, two, three, or four independently selected $R_{4a}$ substituents;

$R_{4a}$ is cyano, halo, hydroxy, $C_{1-6}$alkyl, halo-$C_{1-6}$alkyl, or $C_{1-6}$alkoxy;

$R_5$ is hydrogen, cyano, halo, hydroxy, $C_{1-6}$alkyl, halo-$C_{1-6}$alkyl, $C_{1-6}$alkoxy, carbamoyl, $C_{3-10}$cycloalkyl, or heterocyclyl, wherein heterocyclyl is a 3-7 membered monocyclic carbon atom ring structure radical containing 1-3 heteroatoms selected from N, O, and S; and $R_6$ is hydrogen, halo, or $C_{1-6}$alkyl;

wherein the form of the compound is selected from the group consisting of a salt, hydrate, solvate, and tautomer form thereof.

One aspect includes a compound of Formula (I), wherein $R_1$ is phenyl or heteroaryl, optionally substituted with one, two, three, or four, independently selected $R_{1a}$ substituents, wherein heteroaryl is a 5-8 membered monocyclic or bicyclic aromatic carbon atom ring structure radical containing 1-3 heteroatoms selected from N, O, and S.

Another aspect includes a compound of Formula (I), wherein $R_1$ is phenyl, optionally substituted with one, two, three, or four, independently selected $R_{1a}$ substituents.

Another aspect includes a compound of Formula (I), wherein $R_1$ is phenyl, optionally substituted with one $R_{1a}$ substituent.

Another aspect includes a compound of Formula (I), wherein $R_1$ is heteroaryl, optionally substituted with one, two, three, or four, independently selected $R_{1a}$ substituents, wherein heteroaryl is a 5-8 membered monocyclic or bicyclic aromatic carbon atom ring structure radical containing 1-3 heteroatoms selected from N, O, and S.

Another aspect includes a compound of Formula (I), wherein $R_1$ is heteroaryl, optionally substituted with one $R_{1a}$ substituent, wherein heteroaryl is a 5-8 membered monocyclic or bicyclic aromatic carbon atom ring structure radical containing 1-3 heteroatoms selected from N, O, and S.

Another aspect of includes a compound of Formula (I), wherein $R_1$ is heteroaryl selected from furanyl, thiophenyl, 1H-pyrazolyl, 1H-imidazolyl, isoxazolyl, 1,3-thiazolyl, 1,3-oxazolyl, tetrazolyl, 1,2,3-triazolyl, 1,2,4-oxadiazolyl, 1,3,4-oxadiazolyl, 1,2,3-thiadiazolyl, pyridinyl, pyrimidinyl, pyrazinyl, pyridazinyl, benzofuranyl, and quinolinyl, wherein heteroaryl is optionally substituted with one, two, three, or four, independently $R_{1a}$ substituents.

Another aspect of includes a compound of Formula (I), wherein $R_1$ is heteroaryl selected from furanyl, thiophenyl, 1,3-thiazolyl, and pyridinyl, wherein heteroaryl is optionally substituted with one, two, three, or four, independently $R_{1a}$ substituents.

Another aspect includes a compound of Formula (I), wherein $R_1$ is heteroaryl selected from furan-2-yl, furan-3-yl, thiophen-2-yl, thiophen-3-yl, 1H-pyrazol-1-yl, 1H-pyrazol-3-yl, 1H-pyrazol-4-yl, 1H-pyrazol-5-yl, 1H-imidazol-1-yl, 1H-imidazol-4-yl, isoxazol-3-yl, isoxazol-4-yl, isoxazol-5-yl, 1,3-thiazol-2-yl, 1,3-thiazol-4-yl, 1,3-thiazol-5-yl, 1,3-oxazol-2-yl, 1,3-oxazol-4-yl, 1,3-oxazol-5-yl, 1,2,4-oxadiazol-3-yl, 1,3,4-oxadiazol-2-yl, tetrazol-5-yl, 1,2,3-triazol-4-yl, 1,2,3-triazol-5-yl, 1,2,3-thiadiazol-4-yl, 1,2,3-thiadiazol-5-yl, pyridin-2-yl, pyridin-3-yl, pyridin-4-yl, pyrimidin-4-yl, pyrazin-2-yl, pyridazin-3-yl, pyridazin-4-yl, benzofuran-2-yl, benzofuran-5-yl, and quinoline-4-yl, wherein, heteroaryl is optionally substituted with one, two, three, or four, independently $R_{1a}$ substituents.

Another aspect includes a compound of Formula (I), wherein $R_1$ is heteroaryl selected from furan-2-yl, thiophen-2-yl, 1,3-thiazol-2-yl, and pyridin-4-yl, wherein heteroaryl is optionally substituted with one, two, three, or four, independently $R_{1a}$ substituents.

One aspect includes a compound of Formula (I), wherein $R_{1a}$ is cyano, halo, hydroxy, $C_{1-6}$alkyl, halo-$C_{1-6}$alkyl, or $C_{1-6}$alkoxy.

Another aspect includes a compound of Formula (I), wherein $R_{1a}$ is halo.

Another aspect includes a compound of Formula (I), wherein $R_{1a}$ is halo selected from fluoro, chloro, bromo, and iodo.

Another aspect includes a compound of Formula (I), wherein $R_{1a}$ is fluoro.

One aspect includes a compound of Formula (I), wherein $R_3$ is hydrogen, $C_{1-6}$alkyl, $C_{2-6}$alkenyl, $C_{2-6}$alkynyl, or $C_{1-6}$alkyl-amino, wherein each instance of $C_{1-6}$alkyl, $C_{2-6}$alkenyl, and $C_{2-6}$alkynyl is optionally substituted with one, two, three, or four independently selected $R_{3a}$ substituents, and wherein each instance of $C_{1-6}$alkyl, $C_{2-6}$alkenyl, and $C_{2-6}$alkynyl may optionally contain a chiral carbon having an (R) or (S) configuration.

Another aspect includes a compound of Formula (I), wherein $R_3$ is hydrogen, $C_{1-6}$alkyl, $C_{2-6}$alkenyl, or $C_{2-6}$alkynyl, optionally substituted with one, two, three, or four, independently selected $R_{3a}$ substituents, wherein $C_{1-6}$alkyl, $C_{2-6}$alkenyl, or $C_{2-6}$alkynyl may optionally contain a chiral carbon having an (R) or (S) configuration.

Another aspect includes a compound of Formula (I), wherein $R_3$ is hydrogen.

Another aspect includes a compound of Formula (I), wherein $R_3$ is $C_{1-6}$alkyl, optionally substituted with one, two, three, or four, independently selected $R_{3a}$ substituents, and wherein, $C_{1-6}$alkyl optionally contains a chiral carbon having an (R) or (S) configuration.

Another aspect includes a compound of Formula (I), wherein $R_3$ is $C_{1-6}$alkyl, optionally substituted with one, two, three, or four independently selected $R_{3a}$ substituents.

Another aspect includes a compound of Formula (I), wherein $R_3$ is $C_{1-6}$alkyl selected from methyl, ethyl, propyl, butyl, pentyl, and hexyl, optionally substituted with one, two, three, or four independently selected $R_{3a}$ substituents.

Another aspect includes a compound of Formula (I), wherein $R_3$ is $C_{1-6}$alkyl selected from methyl, ethyl, propyl, butyl, and pentyl, optionally substituted with one, two, three, or four independently selected $R_{3a}$ substituents.

Another aspect includes a compound of Formula (I), wherein $R_3$ is $C_{1-6}$alkyl, optionally substituted with one, two, three, or four independently selected $R_{3a}$ substituents, and wherein $C_{1-6}$alkyl optionally contains a chiral carbon having an (R) configuration.

Another aspect includes a compound of Formula (I), wherein $R_3$ is $C_{1-6}$alkyl selected from methyl, ethyl, propyl, butyl, pentyl, and hexyl, optionally substituted with one, two, three, or four independently selected $R_{3a}$ substituents, and wherein $C_{1-6}$alkyl optionally contains a chiral carbon having an (R) configuration.

Another aspect includes a compound of Formula (I), wherein $R_3$ is $C_{1-6}$alkyl selected from methyl, ethyl, propyl, butyl, and pentyl, optionally substituted with one, two, three, or four independently selected $R_{3a}$ substituents, and wherein $C_{1-6}$alkyl optionally contains a chiral carbon having an (R) configuration.

Another aspect includes a compound of Formula (I), wherein $R_3$ is $C_{1-6}$alkyl, optionally substituted with one, two, three, or four independently selected $R_{3a}$ substituents, and wherein $C_{1-6}$alkyl optionally contains a chiral carbon having an (S) configuration.

Another aspect includes a compound of Formula (I), wherein $R_3$ is $C_{1-6}$alkyl selected from methyl, ethyl, propyl, butyl, pentyl, and hexyl, optionally substituted with one, two, three, or four independently selected $R_{3a}$ substituents, and wherein $C_{1-6}$alkyl optionally contains a chiral carbon having an (S) configuration.

Another aspect includes a compound of Formula (I), wherein $R_3$ is $C_{1-6}$alkyl selected from methyl, ethyl, propyl, butyl, and pentyl, optionally substituted with one, two, three, or four independently selected $R_{3a}$ substituents, and wherein $C_{1-6}$alkyl optionally contains a chiral carbon having an (S) configuration.

Another aspect includes a compound of Formula (I), wherein $R_3$ is $C_{2-6}$alkenyl, optionally substituted with one, two, three, or four, independently selected $R_{3a}$ substituents, and wherein, $C_{2-6}$alkenyl optionally contains a chiral carbon having an (R) or (S) configuration.

Another aspect includes a compound of Formula (I), wherein $R_3$ is $C_{2-6}$alkenyl selected from ethenyl, propenyl, butenyl, pentenyl, hexenyl, and heptenyl, optionally substituted with one, two, three, or four independently selected $R_{3a}$ substituents.

Another aspect includes a compound of Formula (I), wherein $R_3$ is butenyl, optionally substituted with one, two, three, or four independently selected $R_{3a}$ substituents.

Another aspect includes a compound of Formula (I), wherein $R_3$ is $C_{2-6}$alkenyl selected from ethenyl, propenyl, butenyl, pentenyl, hexenyl, and heptenyl, optionally substituted with one, two, three, or four independently selected $R_{3a}$ substituents, and wherein $C_{2-6}$alkenyl optionally contains a chiral carbon having an (R) configuration.

Another aspect includes a compound of Formula (I), wherein $R_3$ is butenyl, optionally substituted with one, two, three, or four independently selected $R_{3a}$ substituents, and wherein $C_{2-6}$alkenyl optionally contains a chiral carbon having an (R) configuration.

Another aspect includes a compound of Formula (I), wherein $R_3$ is $C_{2-6}$alkynyl, optionally substituted with one, two, three, or four, independently selected $R_{3a}$ substituents, and wherein, $C_{2-6}$alkynyl optionally contains a chiral carbon having an (R) or (S) configuration.

Another aspect includes a compound of Formula (I), wherein $R_3$ is $C_{2-6}$alkenyl selected from ethenyl, propenyl, butenyl, pentenyl, hexenyl, and heptenyl, optionally substituted with one, two, three, or four independently selected $R_{3a}$ substituents, and wherein $C_{2-6}$alkenyl optionally contains a chiral carbon having an (S) configuration.

Another aspect includes a compound of Formula (I), wherein $R_3$ is butenyl, optionally substituted with one, two, three, or four independently selected $R_{3a}$ substituents, and wherein $C_{2-6}$alkenyl optionally contains a chiral carbon having an (S) configuration.

Another aspect includes a compound of Formula (I), wherein $R_3$ is $C_{2-6}$alkynyl selected from ethynyl, propynyl, butynyl, pentynyl, hexynyl, and heptynyl, optionally substituted with one, two, three, or four independently selected $R_{3a}$ substituents.

Another aspect includes a compound of Formula (I), wherein $R_3$ is butynyl, optionally substituted with one, two, three, or four independently selected $R_{3a}$ substituents.

Another aspect includes a compound of Formula (I), wherein $R_3$ is $C_{2-6}$alkynyl selected from ethynyl, propynyl, butynyl, pentynyl, hexynyl, and heptynyl, optionally substituted with one, two, three, or four independently selected $R_{3a}$ substituents, and wherein $C_{2-6}$alkynyl optionally contains a chiral carbon having an (R) configuration.

Another aspect includes a compound of Formula (I), wherein $R_3$ is butynyl, optionally substituted with one, two, three, or four independently selected $R_{3a}$ substituents, and wherein $C_{2-6}$alkynyl optionally contains a chiral carbon having an (R) configuration.

Another aspect includes a compound of Formula (I), wherein $R_3$ is $C_{2-6}$alkynyl selected from ethynyl, propynyl, butynyl, pentynyl, hexynyl, and heptynyl, optionally substituted with one, two, three, or four independently selected $R_{3a}$ substituents, and wherein $C_{2-6}$alkynyl optionally contains a chiral carbon having an (S) configuration.

Another aspect includes a compound of Formula (I), wherein $R_3$ is butynyl, optionally substituted with one, two, three, or four independently selected $R_{3a}$ substituents, and wherein $C_{2-6}$alkynyl optionally contains a chiral carbon having an (S) configuration.

Another aspect includes a compound of Formula (I), wherein $R_3$ is $C_{1-6}$alkyl-amino, optionally substituted with one, two, three, or four, independently selected $R_{3a}$ substituents, and wherein, $C_{1-6}$alkyl optionally contains a chiral carbon having an (R) or (S) configuration.

Another aspect includes a compound of Formula (I), wherein $R_3$ is $C_{1-6}$alkyl-amino, optionally substituted with one, two, three, or four independently selected $R_{3a}$ substituents.

Another aspect includes a compound of Formula (I), wherein $R_3$ is $C_{1-6}$alkyl-amino, wherein $C_{1-6}$alkyl is selected from methyl, ethyl, propyl, isopropyl, butyl, sec-butyl, isobutyl, and tert-butyl, optionally substituted with one, two, three, or four independently selected $R_{3a}$ substituents.

Another aspect includes a compound of Formula (I), wherein $R_3$ is $C_{1-6}$alkyl-amino, wherein $C_{1-6}$alkyl is propyl, optionally substituted with one, two, three, or four independently selected $R_{3a}$ substituents.

Another aspect includes a compound of Formula (I), wherein $R_3$ is $C_{1-6}$alkyl-amino, optionally substituted with one, two, three, or four independently selected $R_{3a}$ substituents, and wherein $C_{1-6}$alkyl optionally contains a chiral carbon having an (R) configuration.

Another aspect includes a compound of Formula (I), wherein $R_3$ is $C_{1-6}$alkyl-amino, wherein $C_{1-6}$alkyl is selected from methyl, ethyl, propyl, isopropyl, butyl, sec-butyl, isobutyl, and tert-butyl, optionally substituted with one, two, three, or four independently selected $R_{3a}$ substituents, and wherein $C_{1-6}$alkyl optionally contains a chiral carbon having an (R) configuration.

Another aspect includes a compound of Formula (I), wherein $R_3$ is $C_{1-6}$alkyl-amino, wherein $C_{1-6}$alkyl is propyl, optionally substituted with one, two, three, or four independently selected $R_{3a}$ substituents, and wherein $C_{1-6}$alkyl optionally contains a chiral carbon having an (R) configuration.

Another aspect includes a compound of Formula (I), wherein $R_3$ is $C_{1-6}$alkyl-amino, optionally substituted with one, two, three, or four independently selected $R_{3a}$ substituents, and wherein $C_{1-6}$alkyl optionally contains a chiral carbon having an (S) configuration.

Another aspect includes a compound of Formula (I), wherein $R_3$ is $C_{1-6}$alkyl-amino, wherein $C_{1-6}$alkyl is selected from methyl, ethyl, propyl, isopropyl, butyl, sec-butyl, isobutyl, and tert-butyl, optionally substituted with one, two, three, or four independently selected $R_{3a}$ substituents, and wherein $C_{1-6}$alkyl optionally contains a chiral carbon having an (S) configuration.

Another aspect includes a compound of Formula (I), wherein $R_3$ is $C_{1-6}$alkyl-amino, wherein $C_{1-6}$alkyl is propyl, optionally substituted with one, two, three, or four independently selected $R_{3a}$ substituents, and wherein $C_{1-6}$alkyl optionally contains a chiral carbon having an (S) configuration.

Another aspect includes a compound of Formula (I), wherein $R_3$ is $C_{3-10}$cycloalkyl selected from cyclopropyl, cyclobutyl, cyclopentyl, cylcohexyl, cycloheptyl, and cyclooctyl, optionally substituted with one, two, three or four independently selected $R_{3a}$ substituents.

Another aspect includes a compound of Formula (I), wherein $R_3$ is cyclopropyl or cyclopentyl, optionally substituted with one, two, three or four independently selected $R_{3a}$ substituents.

Another aspect includes a compound of Formula (I), wherein $R_3$ is heterocyclyl, optionally substituted with one, two, three, or four, independently selected $R_{3a}$ substituents, wherein heterocyclyl is a 3-7 membered monocyclic carbon atom ring structure radical containing 1-3 heteroatoms selected from N, O, and S, and wherein heterocyclyl optionally contains a chiral carbon having an (R) or (S) configuration.

Another aspect includes a compound of Formula (I), wherein $R_3$ is heterocyclyl selected from azetidinyl, oxetanyl, pyrazolidinyl, tetrahydrofuranyl, oxazolidinyl, thiazolidinyl, isothiazolidinyl, pyrrolidinyl, piperidinyl, piperazinyl, 2H-pyranyl, tetrahydropyranyl, morpholinyl, 1,3-oxazinanyl, and azepanyl, optionally substituted with one, two, three, or four independently selected $R_{3a}$ substituents.

Another aspect includes a compound of Formula (I), wherein $R_3$ is azetidinyl, optionally substituted with one, two, three, or four independently selected $R_{3a}$ substituents.

Another aspect includes a compound of Formula (I), wherein $R_3$ is heterocyclyl selected from azetidin-2-yl, azetidin-3-yl, oxetan-2-yl, oxetan-3-yl, pyrazolidine-1-yl, pyrazolidine-2-yl, pyrazolidine-3-yl, pyrazolidine-4-yl, pyrazolidine-5-yl, tetrahydrofuran-1-yl, tetrahydrofuran-2-yl, oxazolidin-2-yl, oxazolidin-4-yl, oxazolidine-5-yl, thiazolidin-2-yl, thiazolidin-4-yl, thiazolidin-5-yl, isothiazolidin-3-yl, isothiazolidin-4-yl, isothiazolidin-5-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, piperazin-3-yl, 2H-pyran-2-yl, 2H-pyran-3-yl, 2H-pyran-4-yl, 2H-pyran-5-yl, 2H-pyran-6-yl, tetrahydropyran-2-yl, tetrahydropyran-3-yl, tetrahydropyran-4-yl, morpholin-2-yl, morpholin-3-yl, morpholin-4-yl, 1,3-oxazinan-2-yl, 1,3-oxazinan-3-yl, 1,3-oxazinan-4-yl, azepan-1-yl, azepan-2-yl, azepan-3-yl, and azepan-4-yl, optionally substituted with one, two, three, or four independently selected $R_{3a}$ substituents.

Another aspect includes a compound of Formula (I), wherein $R_3$ is azetidin-3-yl, optionally substituted with one, two, three, or four independently selected $R_{3a}$ substituents.

One aspect includes a compound of Formula (I), wherein $R_{3a}$ is cyano, halo, hydroxy, oxo, $C_{1-6}$alkyl, halo-$C_{1-6}$alkyl, $C_{1-6}$alkoxy, halo-$C_{1-6}$alkoxy, carboxyl, amino, $C_{1-6}$alkoxycarbonyl, $C_{1-6}$alkyl-amino, halo-$C_{1-6}$alkyl-amino, $(C_{1-6}$alkyl$)_2$-amino, phenyl-amino, heterocyclyl-amino, heteroaryl-amino, phenyl-$(C_{1-6}$alkyl$)$-amino, heterocyclyl-$(C_{1-6}$alkyl$)$-amino, heteroaryl-$(C_{1-6}$alkyl$)$-amino, $C_{1-6}$alkyl-thio, $C_{1-6}$alkyl-sulfoxyl, or $C_{1-6}$alkyl-sulfonyl wherein each instance of $C_{3-10}$cycloalkyl, phenyl, heterocyclyl and heteroaryl is optionally substituted with one, two, three or four independently selected $R_{3a'}$ substituents.

Another aspect includes a compound of Formula (I), wherein $R_{3a}$ is cyano, halo, hydroxy, oxo, $C_{1-6}$alkyl, $C_{1-6}$alkoxy, halo-$C_{1-6}$alkoxy, carboxyl, amino, $C_{1-6}$alkoxycarbonyl, $C_{1-6}$alkyl-amino, halo-$C_{1-6}$alkyl-amino, $(C_{1-6}$alkyl$)_2$-amino, phenyl-amino, heterocyclyl-amino, phenyl-$(C_{1-6}$alkyl$)$-amino, heterocyclyl-$(C_{1-6}$alkyl$)$-amino, heteroaryl-$(C_{1-6}$alkyl$)$-amino, $C_{1-6}$alkyl-thio, $C_{1-6}$alkyl-sulfoxyl, or $C_{1-6}$alkyl-sulfonyl, wherein heterocyclyl is a 3-7 membered monocyclic carbon atom ring structure radical containing 1-3 heteroatoms selected from N, O, and S, wherein heteroaryl is a 5-8 membered monocyclic or bicyclic aromatic carbon atom ring structure radical containing 1-3 heteroatoms selected from N, O, and S, and wherein each instance of $C_{3-10}$cycloalkyl, phenyl, heterocyclyl and heteroaryl is optionally substituted with one, two, three or four independently selected $R_{3a'}$ substituents.

Another aspect includes a compound of Formula (I), wherein $R_{3a}$ is cyano.

Another aspect includes a compound of Formula (I), wherein $R_{3a}$ is halo selected from fluoro, chloro, bromo, and iodo.

Another aspect includes a compound of Formula (I), wherein $R_{3a}$ is fluoro.

Another aspect includes a compound of Formula (I), wherein $R_{3a}$ is hydroxy.

Another aspect includes a compound of Formula (I), wherein $R_{3a}$ is oxo.

Another aspect includes a compound of Formula (I), wherein $R_{3a}$ is $C_{1-6}$alkyl selected from $C_{1-6}$alkyl selected from methyl, ethyl, propyl, butyl, pentyl, and hexyl.

Another aspect includes a compound of Formula (I), wherein $R_{3a}$ is $C_{1-6}$alkyl selected from methyl and isopropyl.

Another aspect includes a compound of Formula (I), wherein $R_{3a}$ is $C_{1-6}$alkoxy selected from methoxy, ethoxy, propoxy, isopropoxy, butoxy, sec-butoxy, iso-butoxy, tert-butoxy, pentoxy, and hexyloxy.

Another aspect includes a compound of Formula (I), wherein $R_{3a}$ methoxy.

Another aspect includes a compound of Formula (I), wherein $R_{3a}$ is halo-$C_{1-6}$alkoxy wherein $C_{1-6}$alkoxy is selected from methoxy, methoxy, ethoxy, propoxy, iso-propoxy, butoxy, sec-butoxy, iso-butoxy, tert-butoxy, pentoxy, and hexyloxy partially or completely substituted with one or more halogen atoms where allowed by available valences.

Another aspect includes a compound of Formula (I), wherein $R_{3a}$ is halo-$C_{1-6}$alkoxy, wherein $C_{1-6}$alkoxy is methoxy substituted with three fluorine atoms.

Another aspect includes a compound of Formula (I), wherein $R_{3a}$ is carboxyl.

Another aspect includes a compound of Formula (I), wherein $R_{3a}$ is amino.

Another aspect includes a compound of Formula (I), wherein $R_{3a}$ is $C_{1-6}$alkoxy-carbonyl wherein $C_{1-6}$alkoxy is selected from methoxy, methoxy, ethoxy, propoxy, iso-propoxy, butoxy, sec-butoxy, iso-butoxy, tert-butoxy, pentoxy, and hexyloxy.

Another aspect includes a compound of Formula (I), wherein $R_{3a}$ is $C_{1-6}$alkoxy-carbonyl wherein $C_{1-6}$alkoxy is methoxy.

Another aspect includes a compound of Formula (I), wherein $R_{3a}$ is $C_{1-6}$alkyl-amino, wherein $C_{1-6}$alkyl is selected from methyl, ethyl, propyl, isopropyl, butyl, sec-butyl, iso-butyl, tert-butyl, pentyl, and hexyl.

Another aspect includes a compound of Formula (I), wherein $R_{3a}$ is $C_{1-6}$alkyl-amino, wherein $C_{1-6}$alkyl is methyl.

Another aspect includes a compound of Formula (I), wherein $R_{3a}$ is halo-$C_{1-6}$alkyl-amino, wherein $C_{1-6}$alkyl is selected from methyl, ethyl, propyl, isopropyl, butyl, sec-butyl, iso-butyl, tert-butyl, pentyl, and hexyl partially or completely substituted with one or more halogen atoms where allowed by available valences.

Another aspect includes a compound of Formula (I), wherein $R_{3a}$ is halo-$C_{1-6}$alkyl-amino, wherein $C_{1-6}$alkyl is methyl substituted with three fluorine atoms.

Another aspect includes a compound of Formula (I), wherein $R_{3a}$ is $(C_{1-6}alkyl)_2$-amino, wherein $C_{1-6}$alkyl is selected from methyl, ethyl, propyl, isopropyl, butyl, sec-butyl, iso-butyl, tert-butyl, pentyl, and hexyl.

Another aspect includes a compound of Formula (I), wherein $R_{3a}$ is $(C_{1-6}alkyl)_2$-amino, wherein $C_{1-6}$alkyl is methyl.

Another aspect includes a compound of Formula (I), wherein $R_{3a}$ is phenyl-amino, wherein phenyl is optionally substituted with one, two, three or four independently selected $R_{3a'}$ substituents.

Another aspect includes a compound of Formula (I), wherein $R_{3a}$ is phenyl-amino wherein phenyl is optionally substituted with one independently selected $R_{3a'}$ substituents.

Another aspect includes a compound of Formula (I), wherein $R_{3a}$ is heteroaryl-amino, wherein heteroaryl is a 5-8 membered monocyclic or bicyclic aromatic carbon atom ring structure radical containing 1-3 heteroatoms selected from N, O, and S, wherein heteroaryl is optionally substituted with one, two, three or four independently selected $R_{3a'}$ substituents.

Another aspect includes a compound of Formula (I), wherein $R_{3a}$ is heteroaryl-amino, wherein heteroaryl is selected from furanyl, thiophenyl, 1H-pyrazolyl, 1H-imidazolyl, isoxazolyl, 1,3-thiazolyl, 1,3-oxazolyl, tetrazolyl, 1,2,3-triazolyl, 1,2,4-oxadiazolyl, 1,3,4-oxadiazolyl, 1,2,3-thiadiazolyl, pyridinyl, pyrimidinyl, pyrazinyl, pyridazinyl, benzofuranyl, and quinolinyl, wherein heteroaryl is optionally substituted with one, two, three or four independently selected $R_{3a'}$ substituents.

Another aspect includes a compound of Formula (I), wherein $R_{3a}$ is heteroaryl-amino, wherein heteroaryl is selected 1H-pyrazolyl, pyridinyl, and pyrazinyl, wherein each instance is optionally substituted with one, two, three or four independently selected $R_{3a'}$ substituents.

Another aspect includes a compound of Formula (I), wherein $R_{3a}$ is phenyl-($C_{1-6}$alkyl)-amino, wherein $C_{1-6}$alkyl is selected from methyl, ethyl, propyl, butyl, pentyl, and hexyl, wherein phenyl is phenyl is optionally substituted with one, two, three, or four independently selected $R_{3a'}$ substituents.

Another aspect includes a compound of Formula (I), wherein $R_{3a}$ is phenyl-($C_{1-6}$alkyl)-amino, wherein $C_{1-6}$alkyl is selected from methyl, ethyl, propyl, butyl, pentyl, and hexyl, wherein phenyl is phenyl is optionally substituted with one independently selected $R_{3a'}$ substituents.

Another aspect includes a compound of Formula (I), wherein $R_{3a}$ is phenyl-($C_{1-6}$alkyl)-amino, wherein $C_{1-6}$alkyl is methyl.

Another aspect includes a compound of Formula (I), wherein $R_{3a}$ is $C_{1-6}$alkyl-thio, wherein $C_{1-6}$alkyl is selected from methyl, ethyl, propyl, isopropyl, butyl, sec-butyl, tert-butyl, pentyl, and hexyl.

Another aspect includes a compound of Formula (I), wherein $R_{3a}$ is $C_{1-6}$alkyl-thio, wherein $C_{1-6}$alkyl is methyl.

Another aspect includes a compound of Formula (I), wherein $R_{3a}$ is $C_{1-6}$alkyl-sulfoxyl, wherein $C_{1-6}$alkyl is selected from methyl, ethyl, propyl, isopropyl, butyl, sec-butyl, iso-butyl, tert-butyl, pentyl, and hexyl.

Another aspect includes a compound of Formula (I), wherein $R_{3a}$ is $C_{1-6}$alkyl-sulfoxyl, wherein $C_{1-6}$alkyl is methyl.

Another aspect includes a compound of Formula (I), wherein $R_{3a}$ is $C_{1-6}$alkyl-sulfonyl, wherein $C_{1-6}$alkyl is selected from methyl, ethyl, propyl, isopropyl, butyl, sec-butyl, iso-butyl, tert-butyl, pentyl, and hexyl.

Another aspect includes a compound of Formula (I), wherein $R_{3a}$ is $C_{1-6}$alkyl-sulfonyl, wherein $C_{1-6}$alkyl is methyl.

One aspect includes a compound of Formula (I), wherein $R_{3a'}$ is cyano, halo, hydroxy, $C_{1-6}$alkyl, halo-$C_{1-6}$alkyl, $C_{1-6}$alkoxy, or amino.

Another aspect includes a compound of Formula (I), wherein $R_{3a'}$ is halo or $C_{1-6}$alkyl.

Another aspect includes a compound of Formula (I), wherein $R_{3a'}$ is cyano.

Another aspect includes a compound of Formula (I), wherein $R_{3a'}$ is halo selected from fluoro, chloro, bromo, and iodo.

Another aspect includes a compound of Formula (I), wherein $R_{3a'}$ is fluoro or chloro.

Another aspect includes a compound of Formula (I), wherein $R_{3a'}$ is $C_{1-6}$alkyl selected from methyl, ethyl, propyl, butyl, pentyl, and hexyl.

Another aspect includes a compound of Formula (I), wherein $R_{3a'}$ is from methyl.

Another aspect includes a compound of Formula (I), wherein $R_{3a'}$ is $C_{1-6}$alkoxy selected from methoxy, ethoxy, propoxy, isopropoxy, butoxy, sec-butoxy, iso-butoxy, tert-butoxy, pentoxy, and hexyloxy.

Another aspect includes a compound of Formula (I), wherein $R_{3a'}$ is methoxy.

Another aspect includes a compound of Formula (I), wherein $R_{3a'}$ is amino.

One aspect includes a compound of Formula (I), wherein $R_4$ is hydrogen, cyano, halo, hydroxy, $C_{1-6}$alkyl, halo-$C_{1-6}$alkyl, $C_{1-6}$alkoxy, halo-$C_{1-6}$alkoxy, amino, $C_{1-6}$alkyl-amino, $(C_{1-6}alkyl)_2$-amino, $C_{3-10}$cycloalkyl, phenyl, heterocyclyl, or heteroaryl, wherein heterocyclyl is a 3-7 membered monocyclic carbon atom ring structure radical containing 1-3 heteroatoms selected from N, O, and S, wherein heteroaryl is a 5-8 membered monocyclic or bicyclic aromatic carbon atom ring structure radical containing 1-3 heteroatoms selected from N, O, and S, and wherein each instance of $C_{1-6}$alkyl, $C_{3-10}$cycloalkyl, phenyl, heterocyclyl, or heteroaryl are optionally substituted with one, two, three, or four independently selected $R_{4a}$ substituents.

Another aspect includes a compound of Formula (I), wherein $R_4$ is hydrogen, cyano, halo, hydroxy, $C_{1-6}$alkyl, halo-$C_{1-6}$alkoxy, or $C_{3-10}$cycloalkyl, wherein $C_{1-6}$alkyl or $C_{3-10}$cycloalkyl are optionally substituted with one, two, three, or four independently selected $R_{4a}$ substituents.

Another aspect includes a compound of Formula (I), wherein $R_4$ is hydrogen.

Another aspect includes a compound of Formula (I), wherein $R_4$ is cyano.

Another aspect includes a compound of Formula (I), wherein $R_4$ is halo selected from fluoro, chloro, bromo, and iodo.

Another aspect includes a compound of Formula (I), wherein $R_4$ is halo selected from chloro and bromo.

Another aspect includes a compound of Formula (I), wherein $R_4$ is hydroxy.

Another aspect includes a compound of Formula (I), wherein $R_4$ is $C_{1-6}$alkyl selected from methyl, ethyl, propyl, butyl, pentyl, and hexyl, wherein $C_{1-6}$alkyl is optionally substituted with one, two, three, or four independently selected $R_{4a}$ substituents.

Another aspect includes a compound of Formula (I), wherein $R_4$ is methyl optionally substituted with one, two, three, or four independently selected $R_{4a}$ substituents.

Another aspect includes a compound of Formula (I), wherein $R_4$ is halo-$C_{1-6}$alkoxy wherein $C_{1-6}$alkoxy is selected from methoxy, methoxy, ethoxy, propoxy, iso-propoxy, butoxy, sec-butoxy, iso-butoxy, tert-butoxy, pentoxy, and hexyloxy partially or completely substituted with one or more halogen atoms where allowed by available valences.

Another aspect includes a compound of Formula (I), wherein $R_{3a}$ is halo-$C_{1-6}$alkoxy, wherein $C_{1-6}$alkoxy is methoxy substituted with two fluorine atoms.

Another aspect includes a compound of Formula (I), wherein $R_4$ is $C_{3-10}$cycloalkyl, wherein $C_{3-10}$cycloalkyl is optionally substituted with one, two, three, or four independently selected $R_{4a}$ substituents.

Another aspect includes a compound of Formula (I), wherein $R_4$ is $C_{3-10}$cycloalkyl selected from cyclopropyl, cyclobutyl, cyclopentyl, cylcohexyl, cycloheptyl, and cyclooctyl, optionally substituted with one, two, three, or four independently selected $R_{4a}$ substituents.

Another aspect includes a compound of Formula (I), wherein $R_4$ is cyclopropyl, optionally substituted with one, two, three, or four independently selected $R_{4a}$ substituents.

One aspect includes a compound of Formula (I), wherein $R_{4a}$ is cyano, halo, hydroxy, $C_{1-6}$alkyl, halo-$C_{1-6}$alkyl, or $C_{1-6}$alkoxy.

One aspect includes a compound of Formula (I), wherein $R_5$ is hydrogen, cyano, halo, hydroxy, $C_{1-6}$alkyl, halo-$C_{1-6}$alkyl, $C_{1-6}$alkoxy, carbamoyl, $C_{3-10}$cycloalkyl, or heterocyclyl, wherein heterocyclyl is a 3-7 membered monocyclic carbon atom ring structure radical containing 1-3 heteroatoms selected from N, O, and S.

Another aspect includes a compound of Formula (I), wherein $R_5$ is hydrogen, cyano, halo, or $C_{1-6}$alkyl.

Another aspect includes a compound of Formula (I), wherein $R_5$ is hydrogen.

Another aspect includes a compound of Formula (I), wherein $R_5$ is cyano.

Another aspect includes a compound of Formula (I), wherein $R_5$ is halo selected from fluoro, chloro, bromo, and iodo.

Another aspect includes a compound of Formula (I), wherein $R_5$ is chloro.

Another aspect includes a compound of Formula (I), wherein $R_5$ is $C_{1-6}$alkyl selected from methyl, ethyl, propyl, butyl, pentyl, and hexyl.

Another aspect includes a compound of Formula (I), wherein $R_5$ is methyl.

One aspect includes a compound of Formula (I), wherein $R_6$ is hydrogen, halo, or $C_{1-6}$alkyl.

Another aspect includes a compound of Formula (I), wherein $R_6$ is hydrogen.

One aspect of the compound of Formula (I) or a form thereof includes a compound selected from the group consisting of:

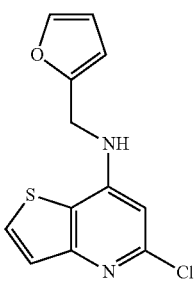

1

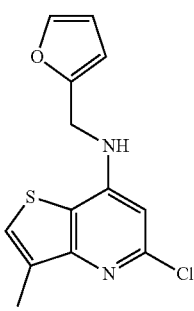

2

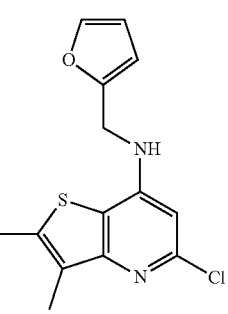

3

-continued
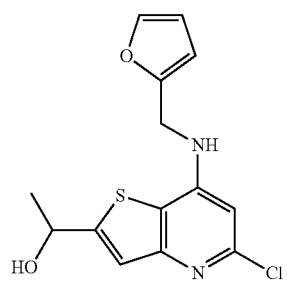
4
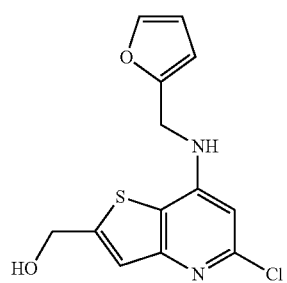
5
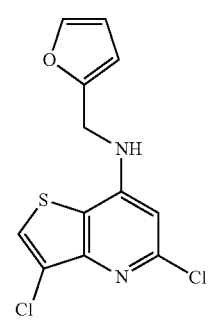
6
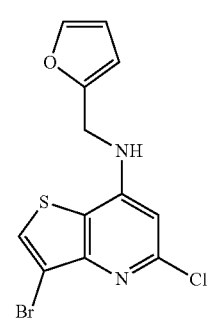
7
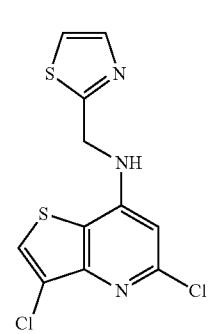
8
-continued
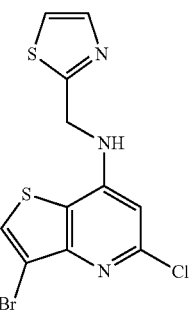
9
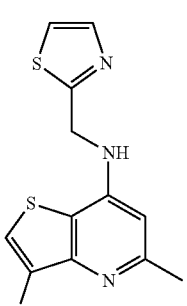
10
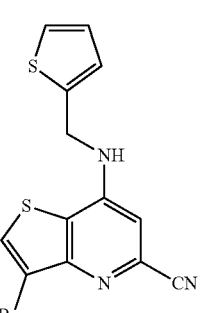
11
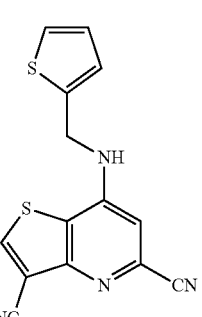
12
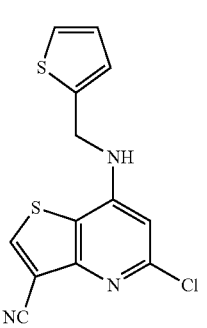
13

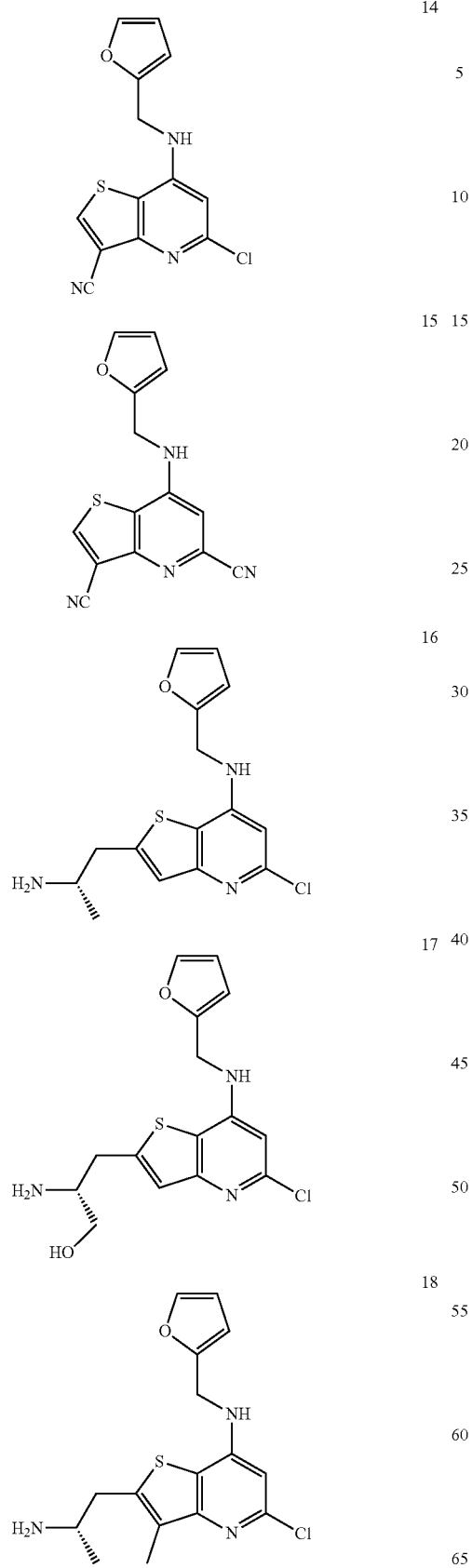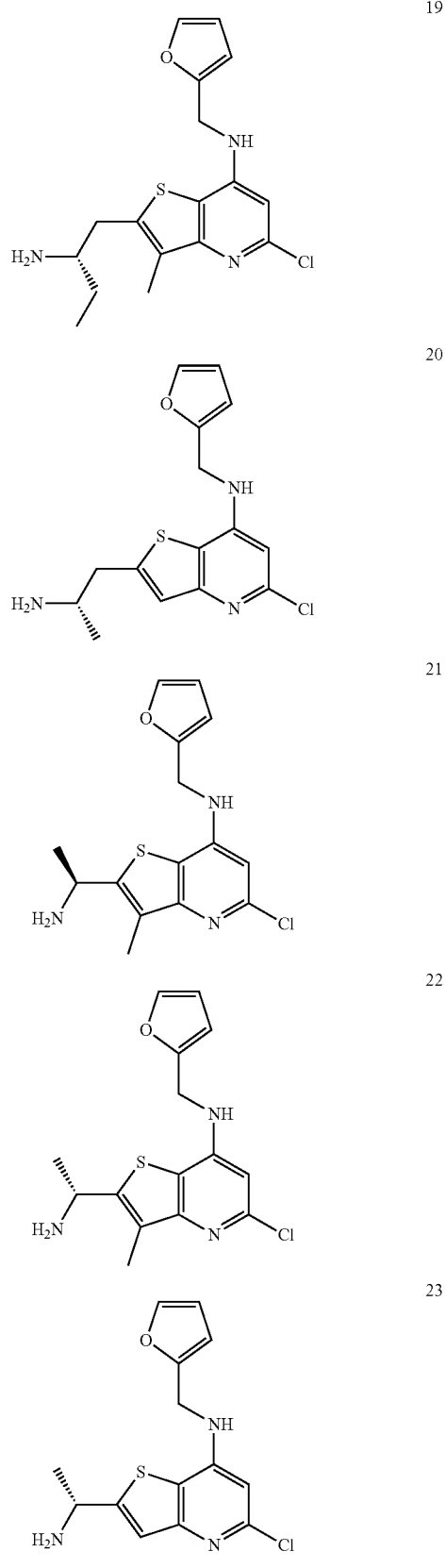

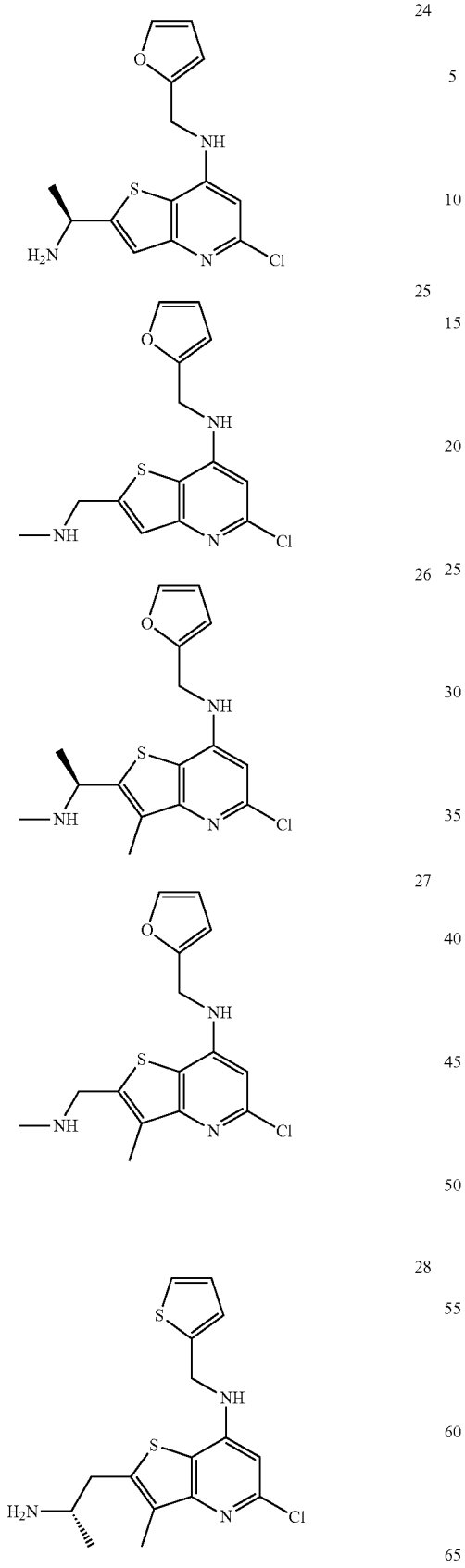
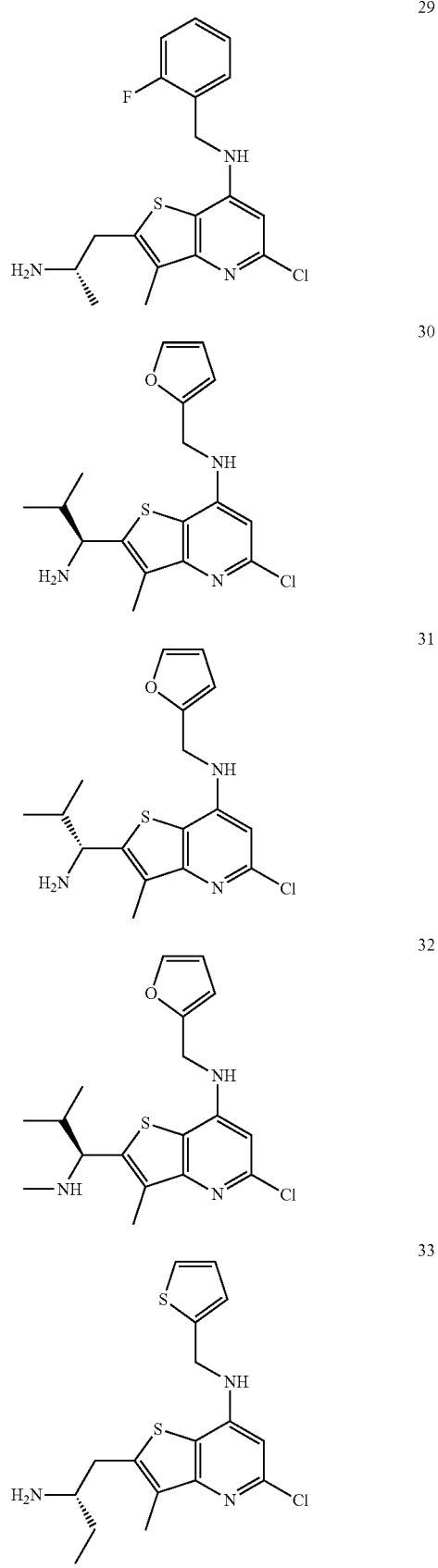

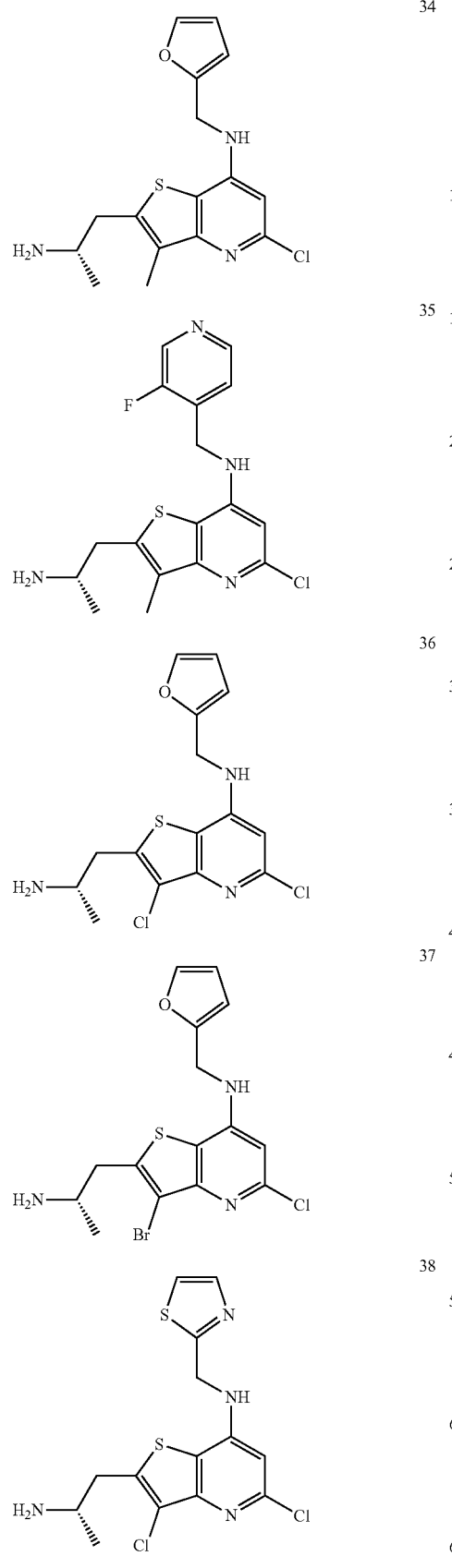
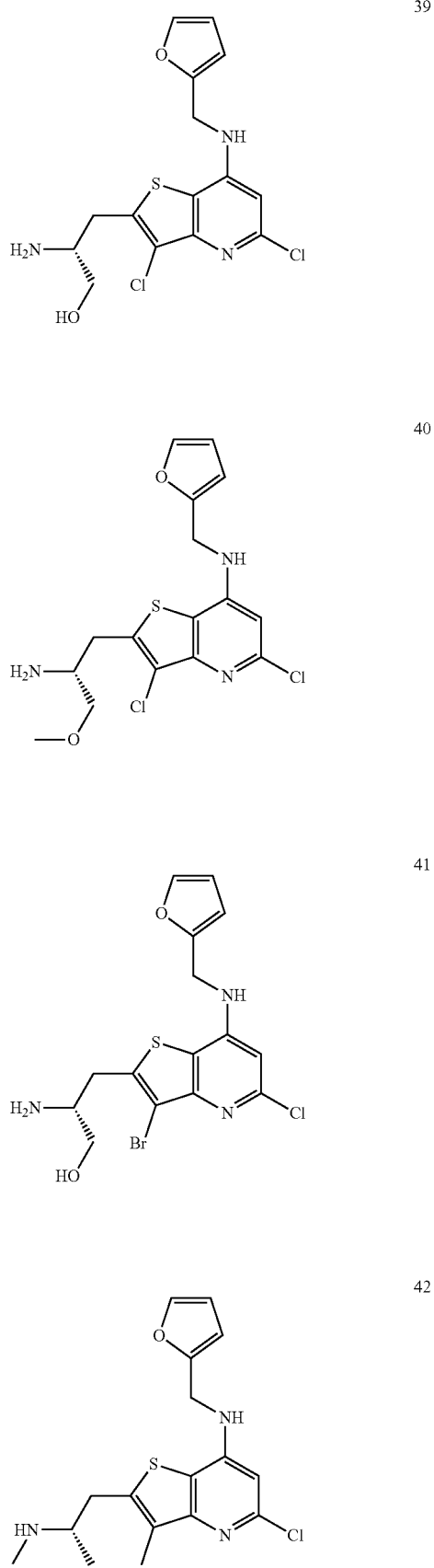

-continued
43
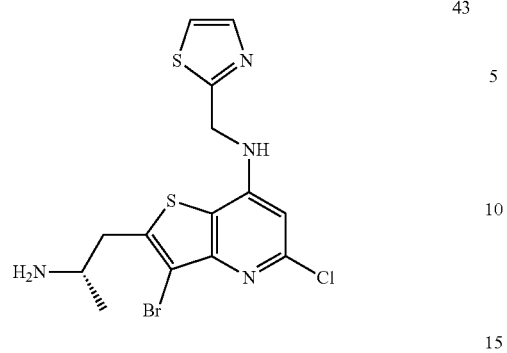
44
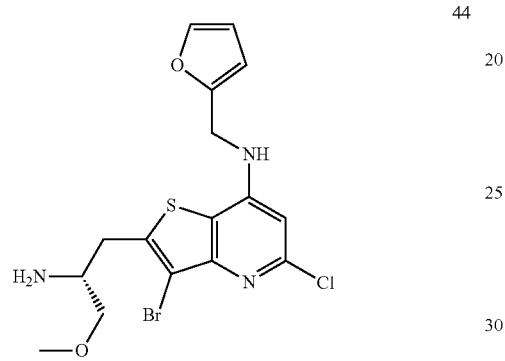
45
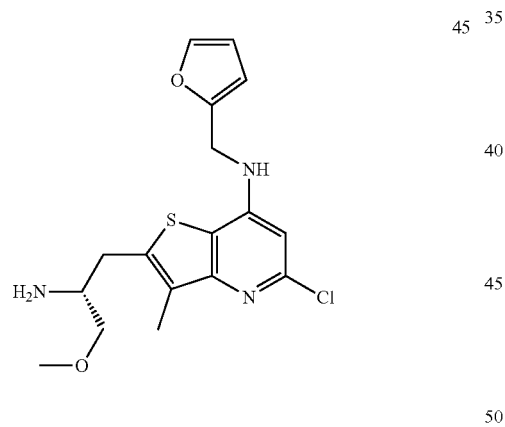
46
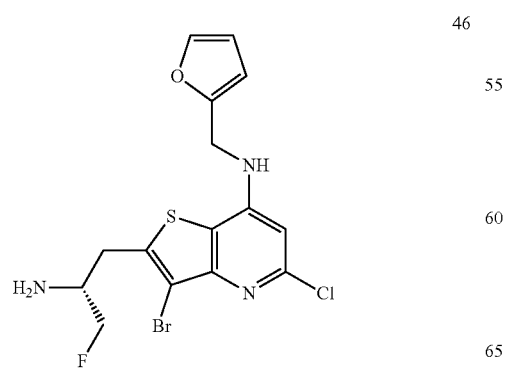
-continued
47
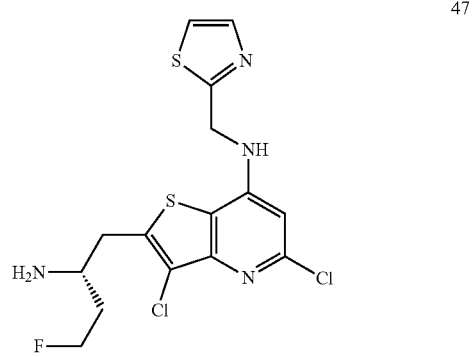
48
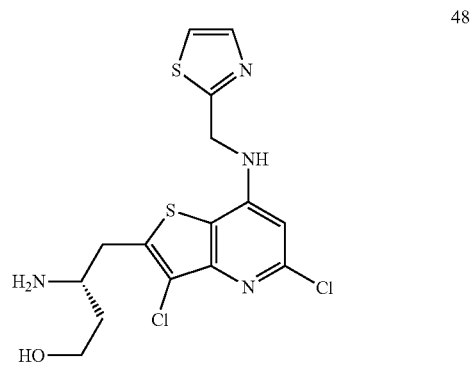
49
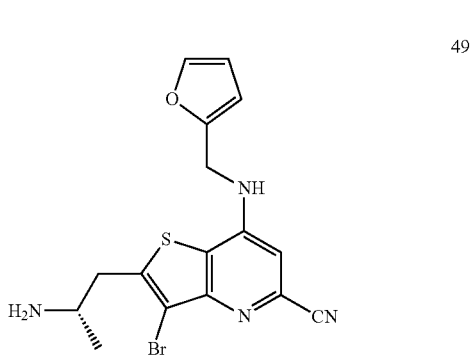
50
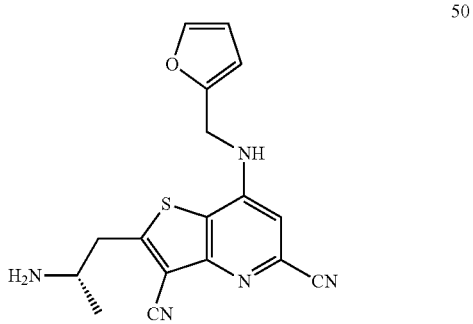

51
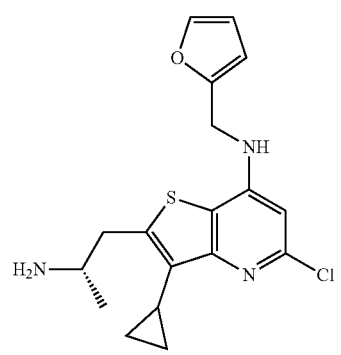
52
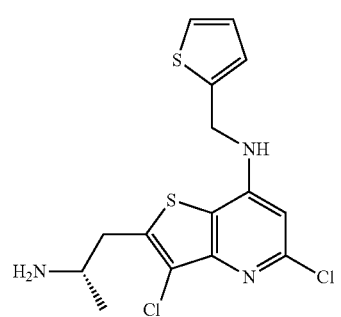
53
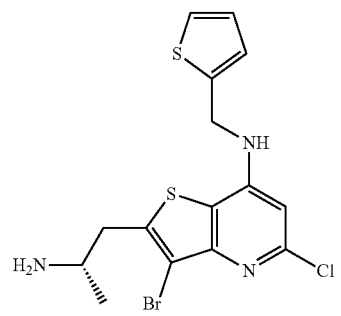
54
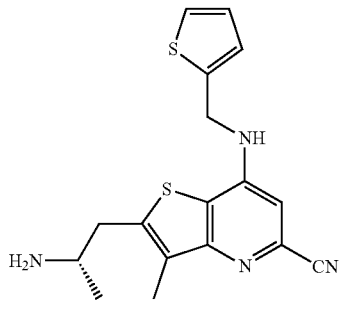
55
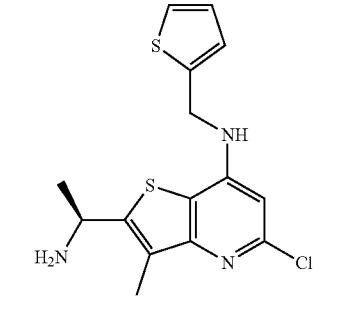
56
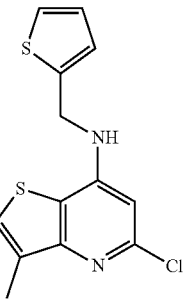
57
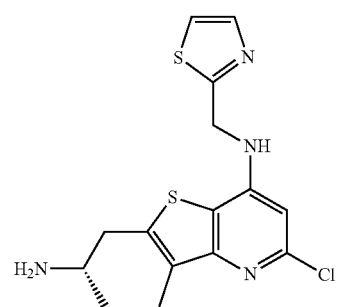
58
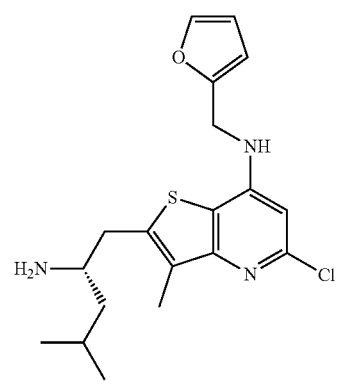
59
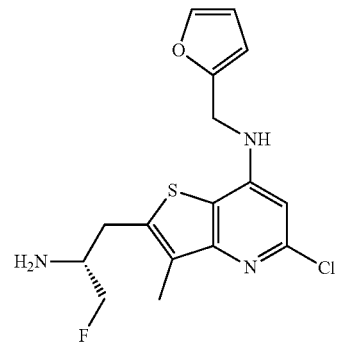
60
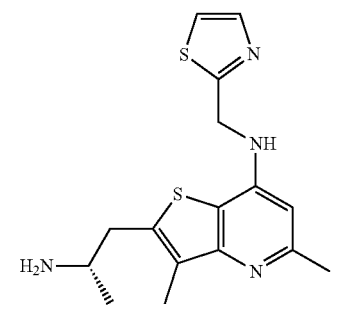

61
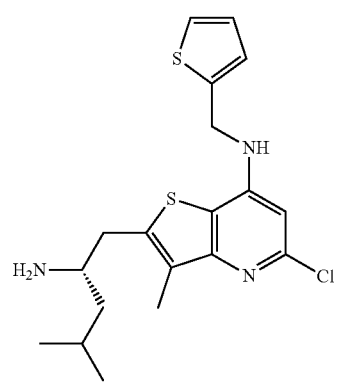
62
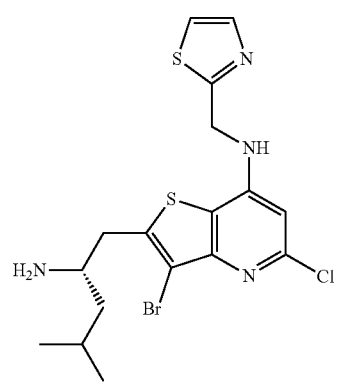
63
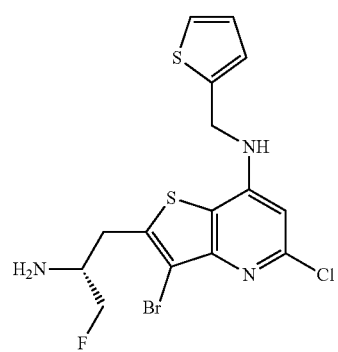
64
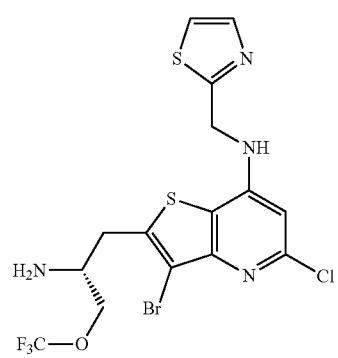
65
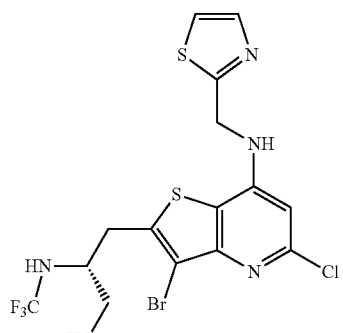
66
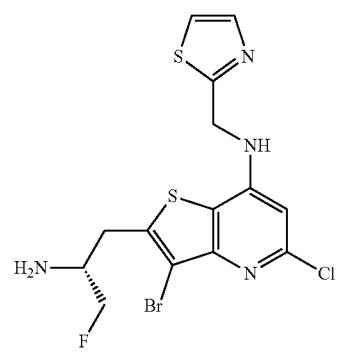
67
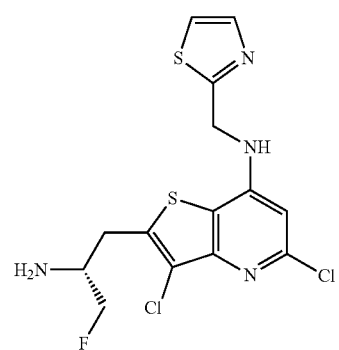
68
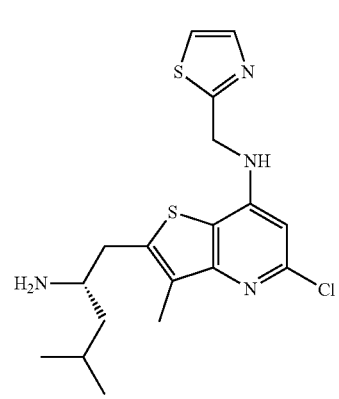

69
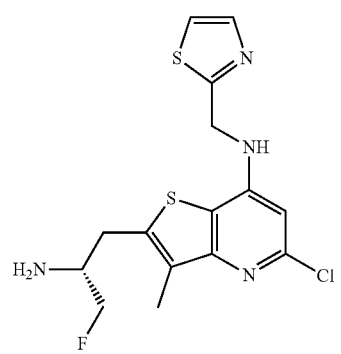
70
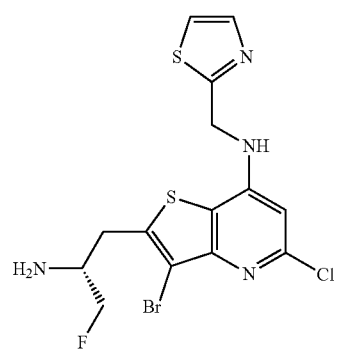
71
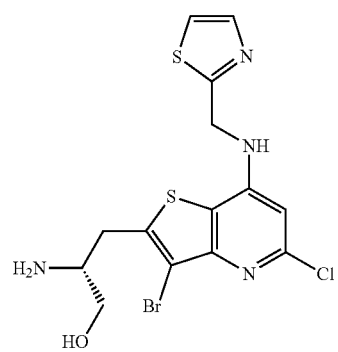
72
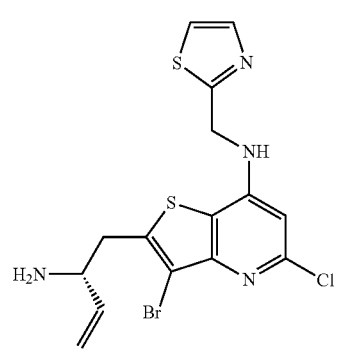
73
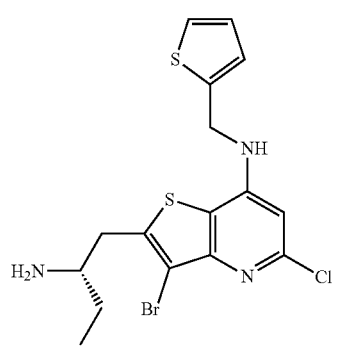
74
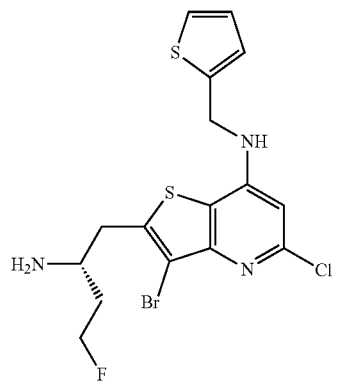
75
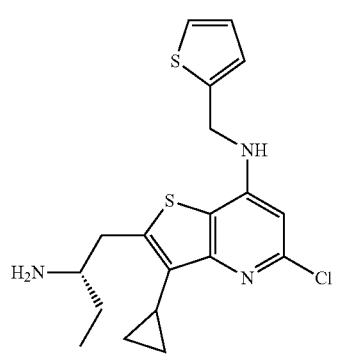
76
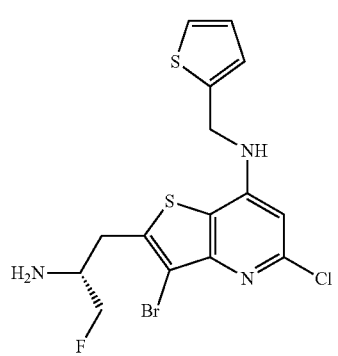

77
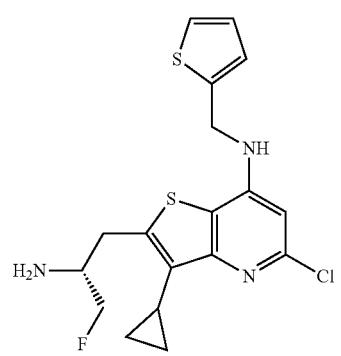
78
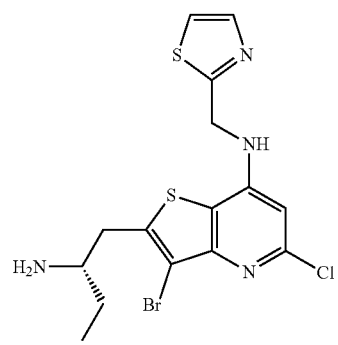
79
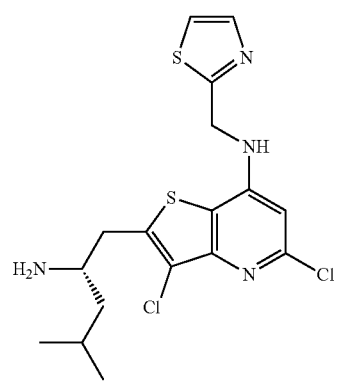
80
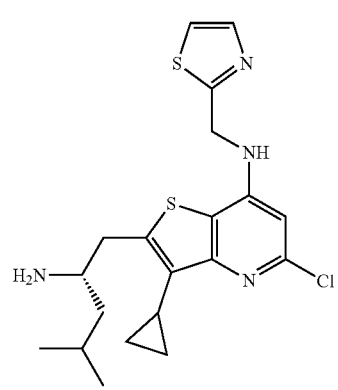
81
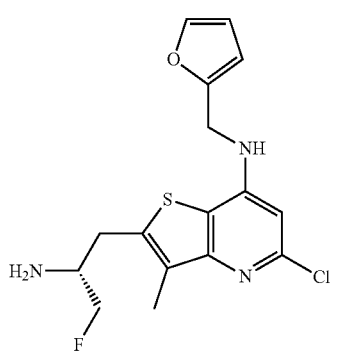
82
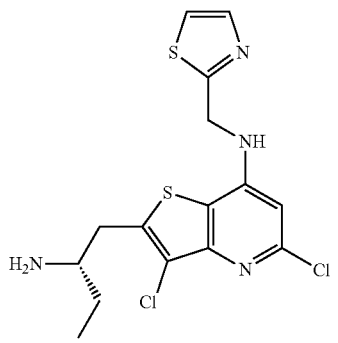
83
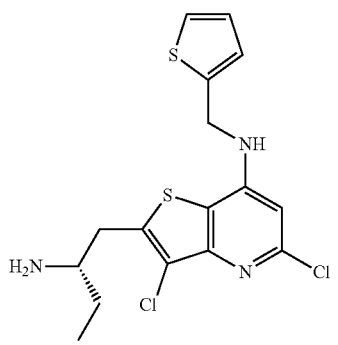
84
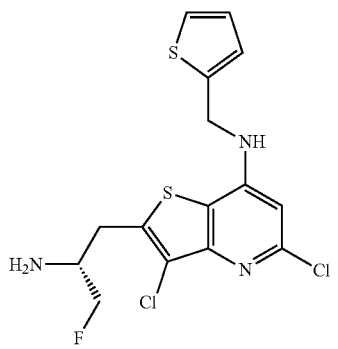

-continued
85
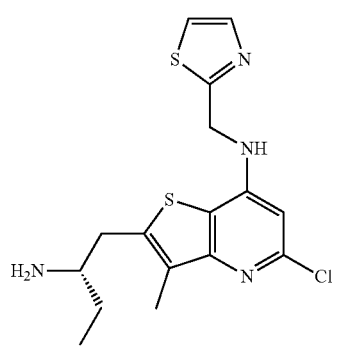
86
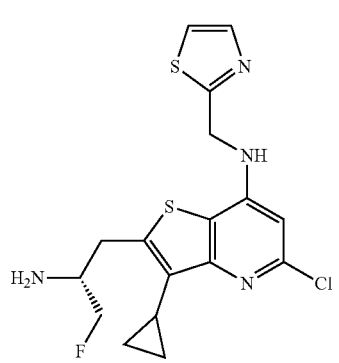
87
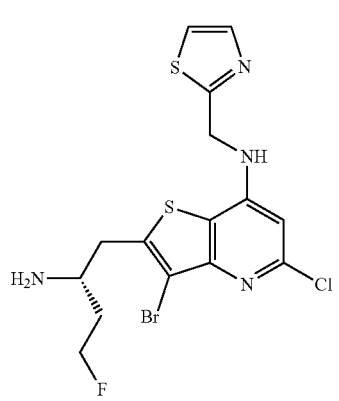
-continued
89
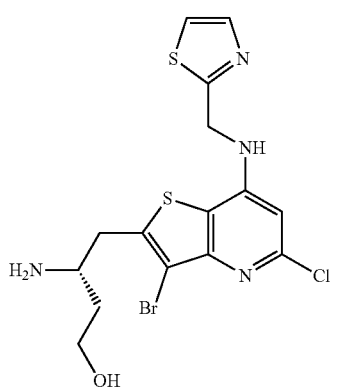
90
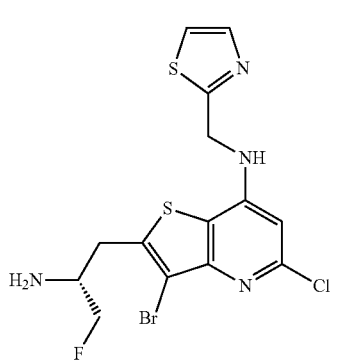
91
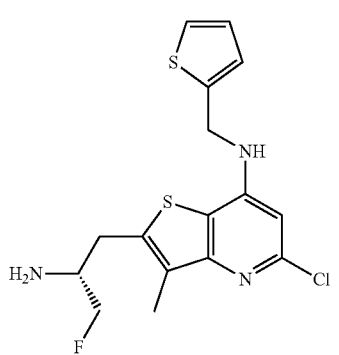
88
92
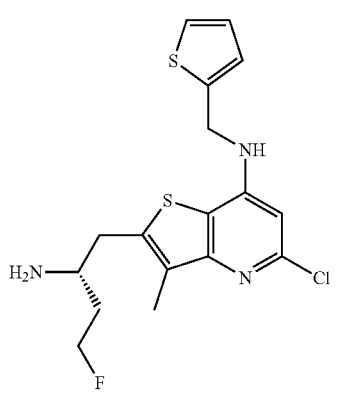

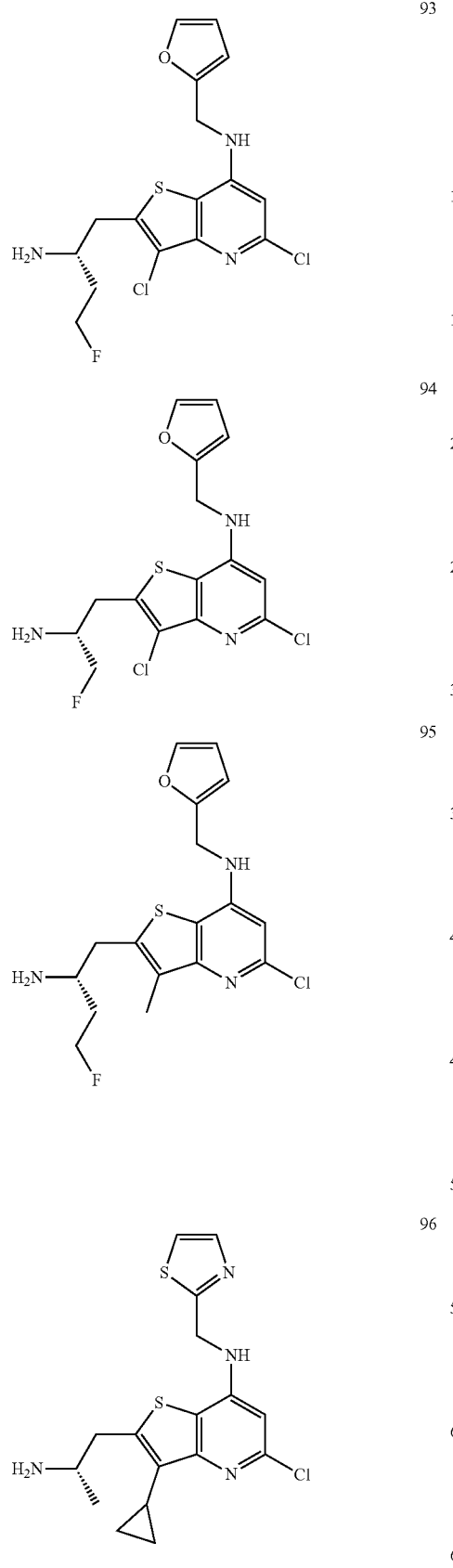
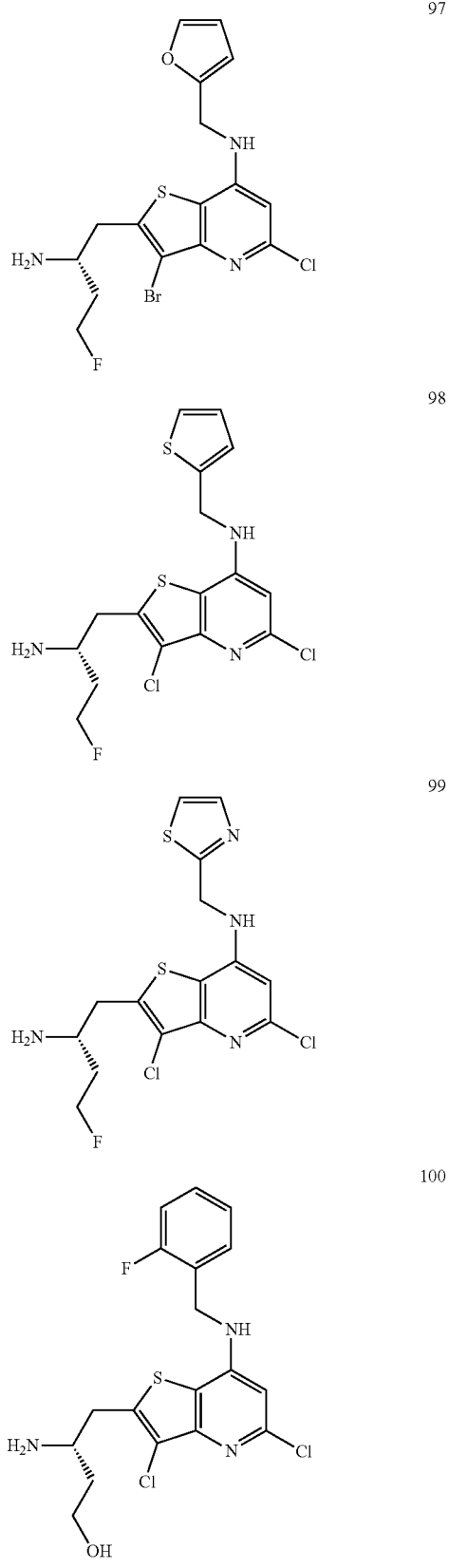

-continued
101
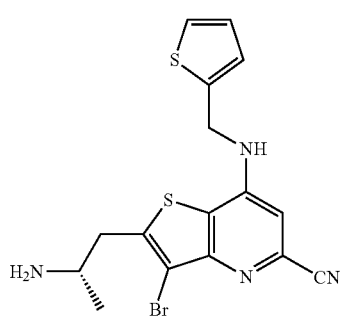
102
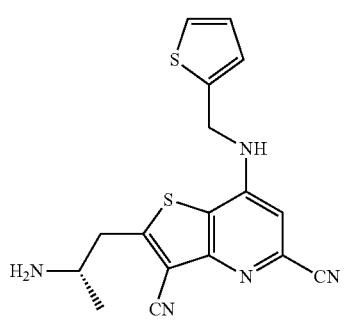
103
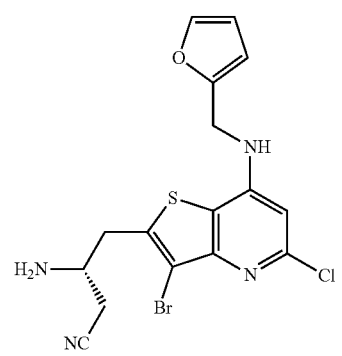
104
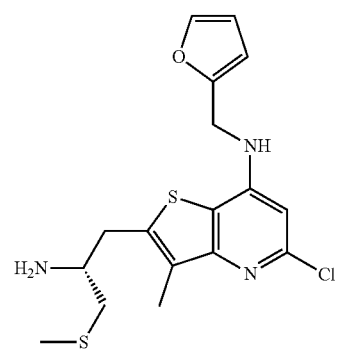
-continued
105
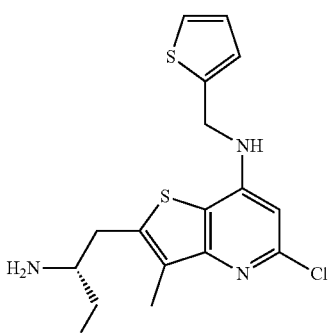
106
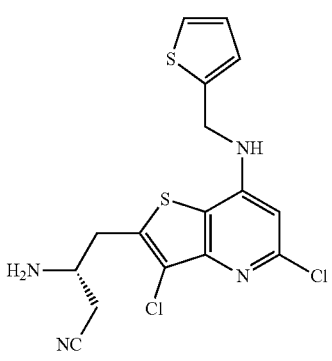
107
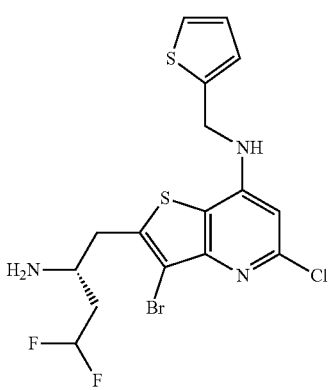
108
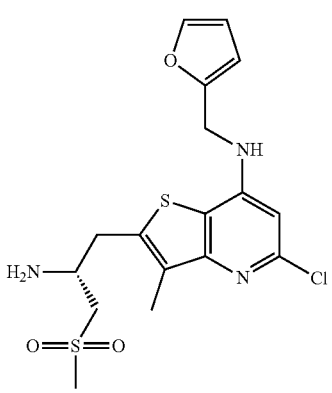

109 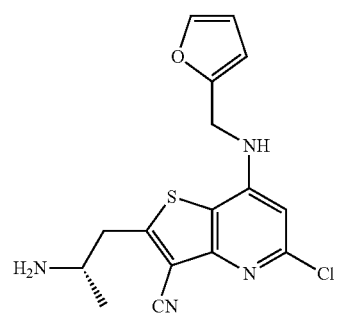
110 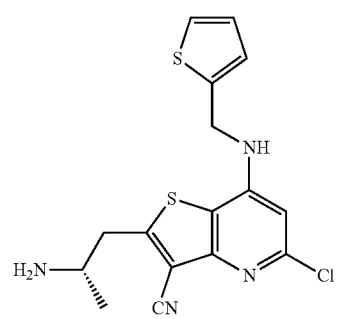
111 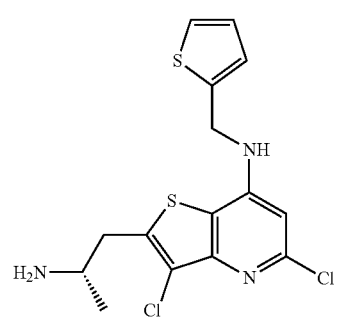
112 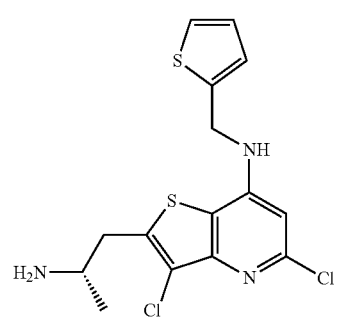
113 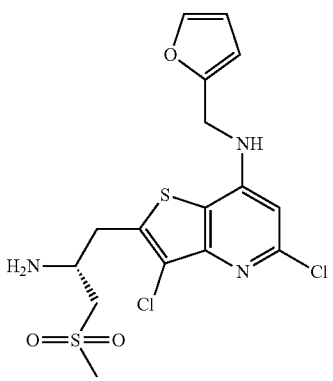
114 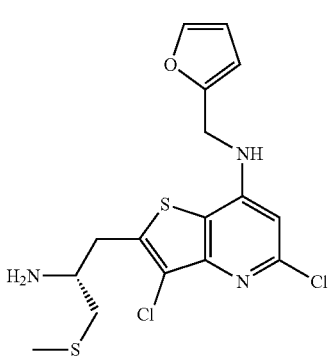
115 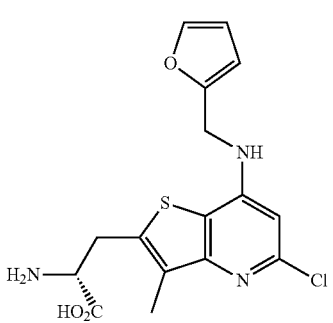
116 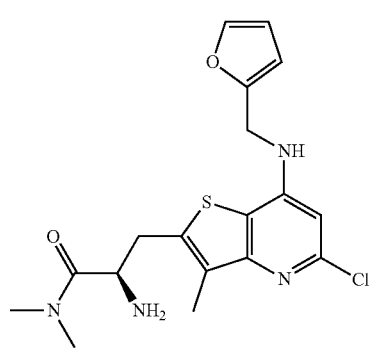

117 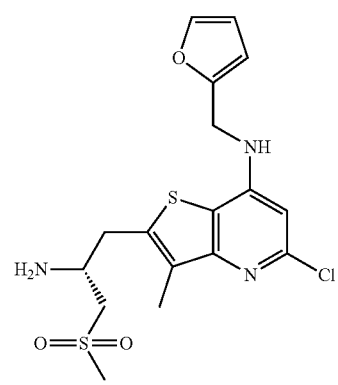
118 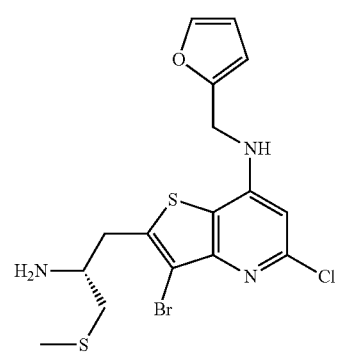
119 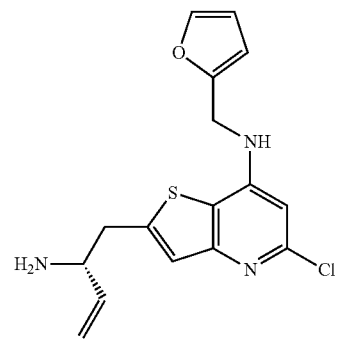
120 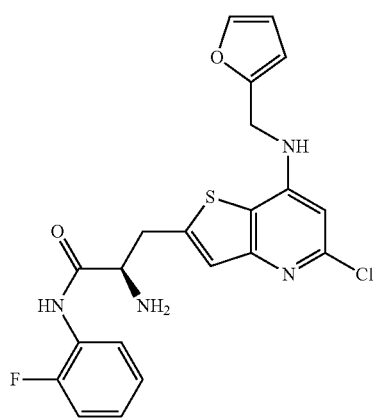
121 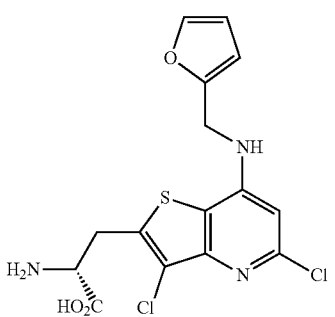
122 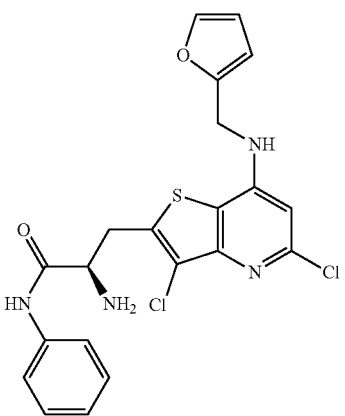
123 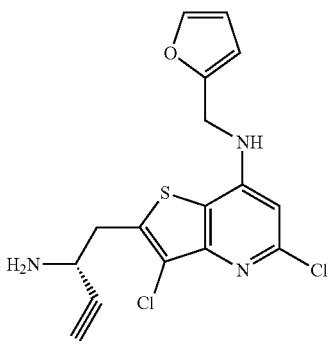
124 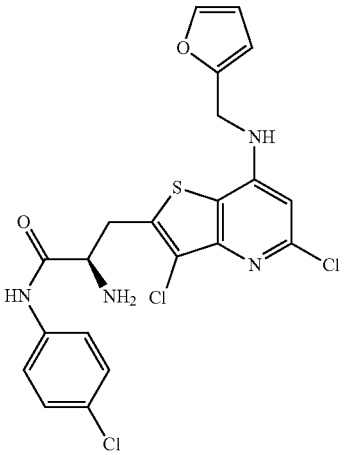

125 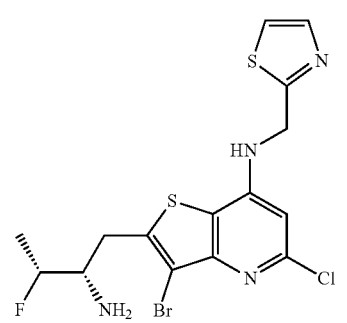
126 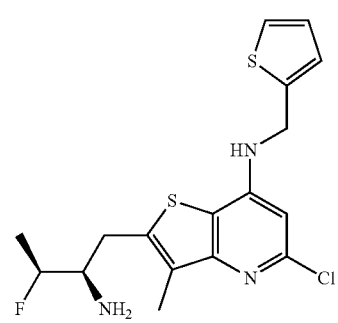
127 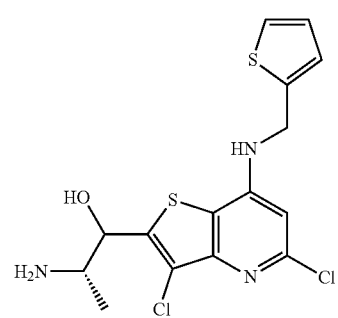
128 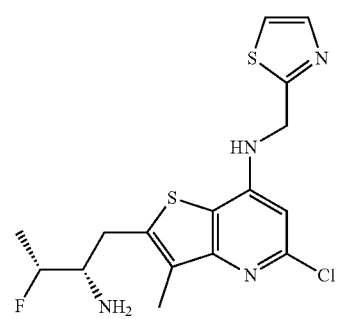
129 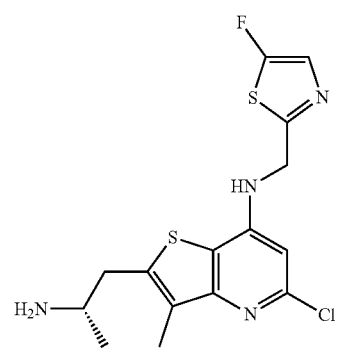
130 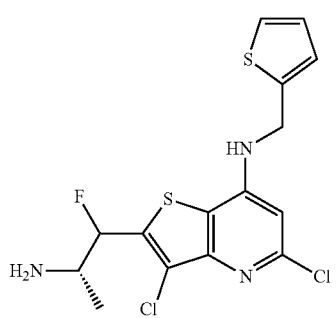
131 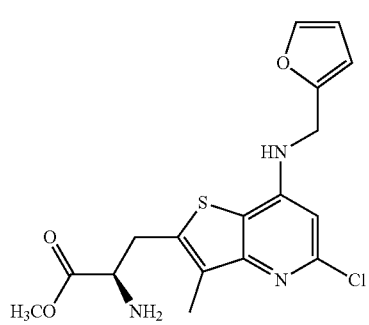
132 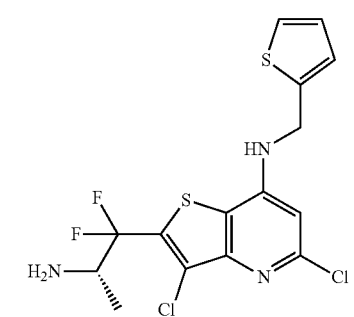
133 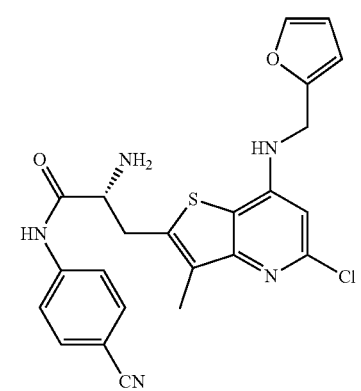

134
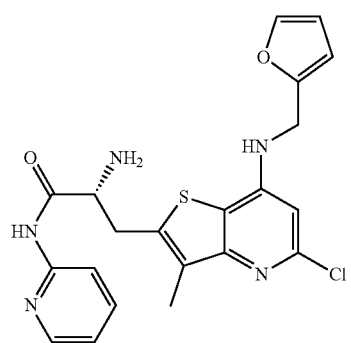
135
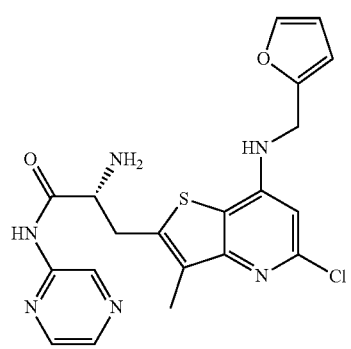
136
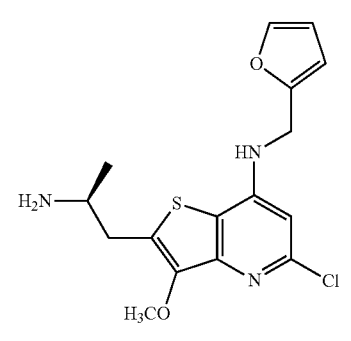
137
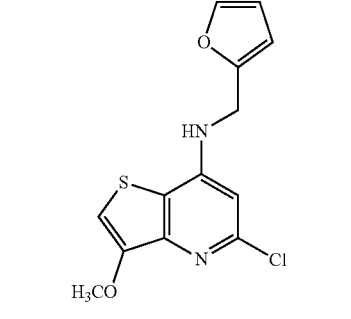
138
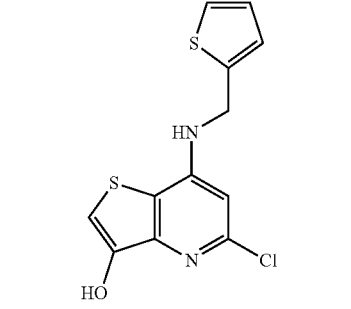
139
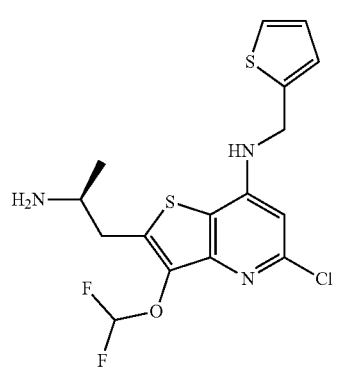
140
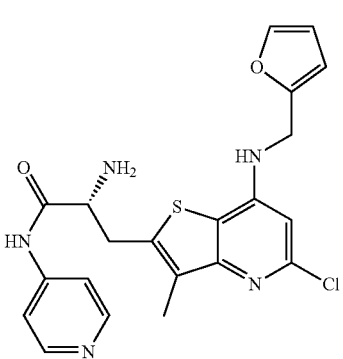
141
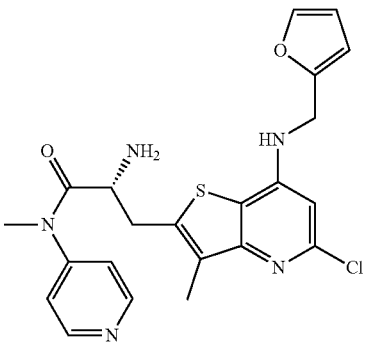
142
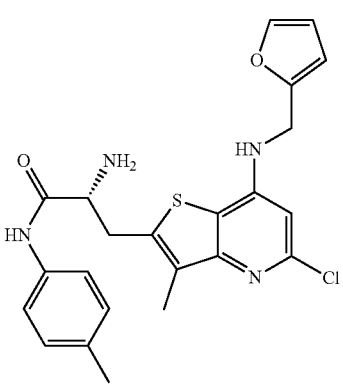

| 143 | 147 |
|---|---|
| 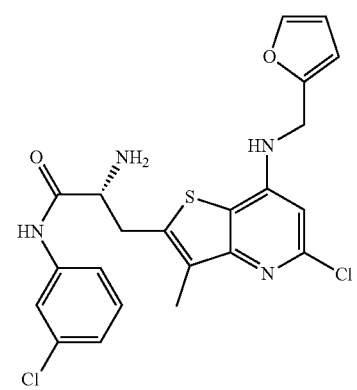 | 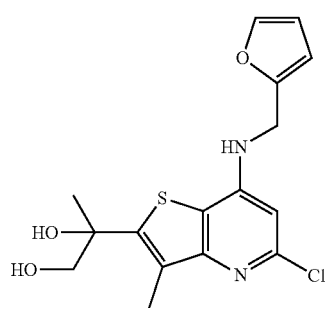 |
| 144 | 148 |
| 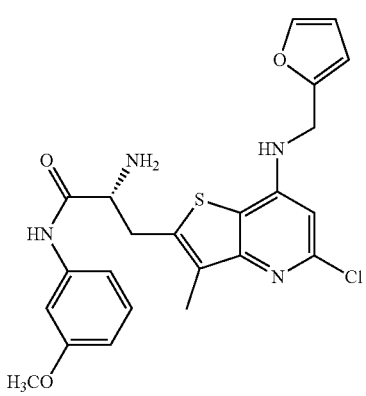 | 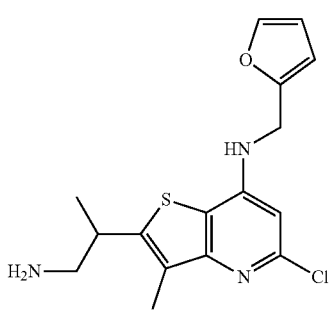 |
| 145 | 149 |
| 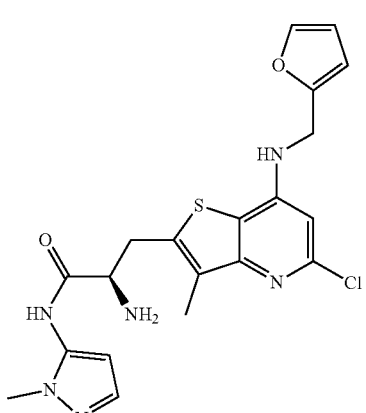 | 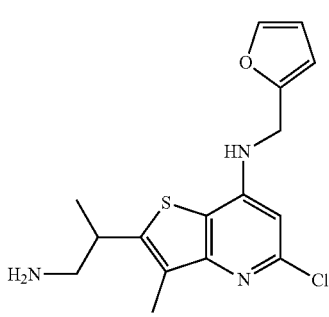 |
| 146 | 150 |
| 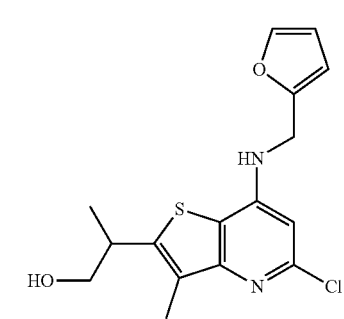 | 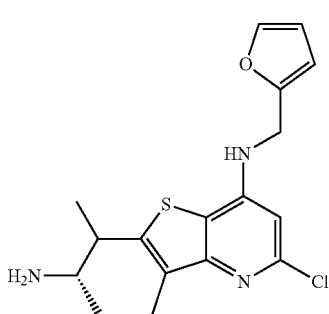 |
| | 151 |
| | 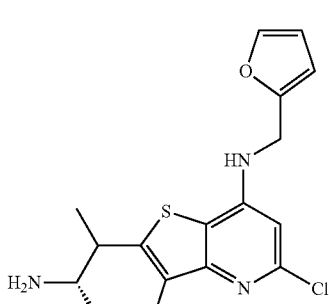 |

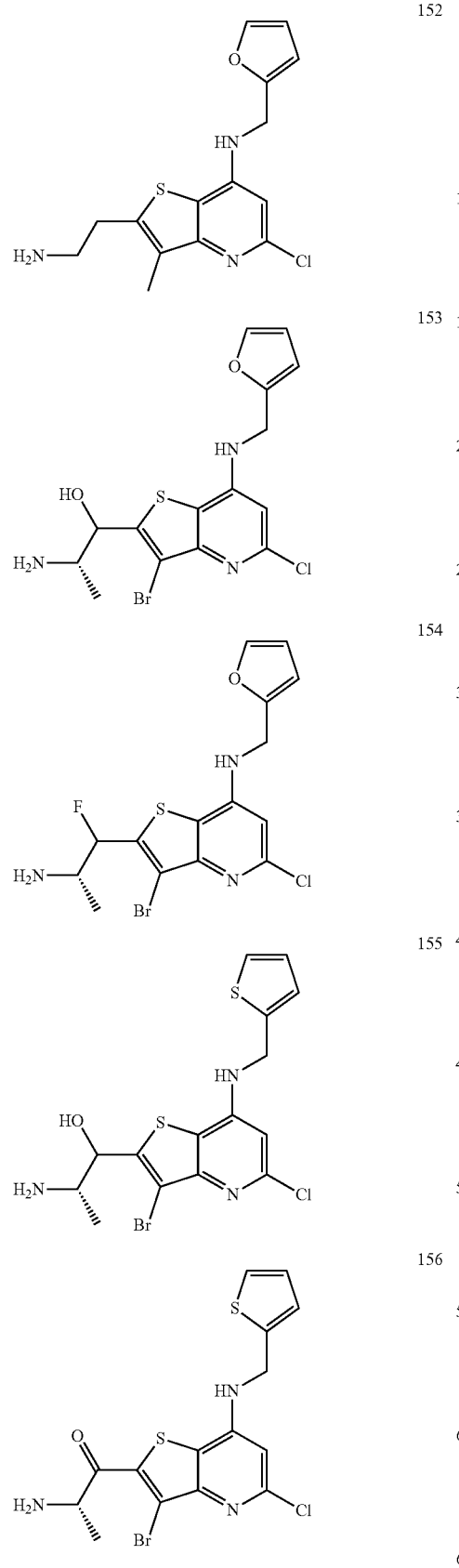
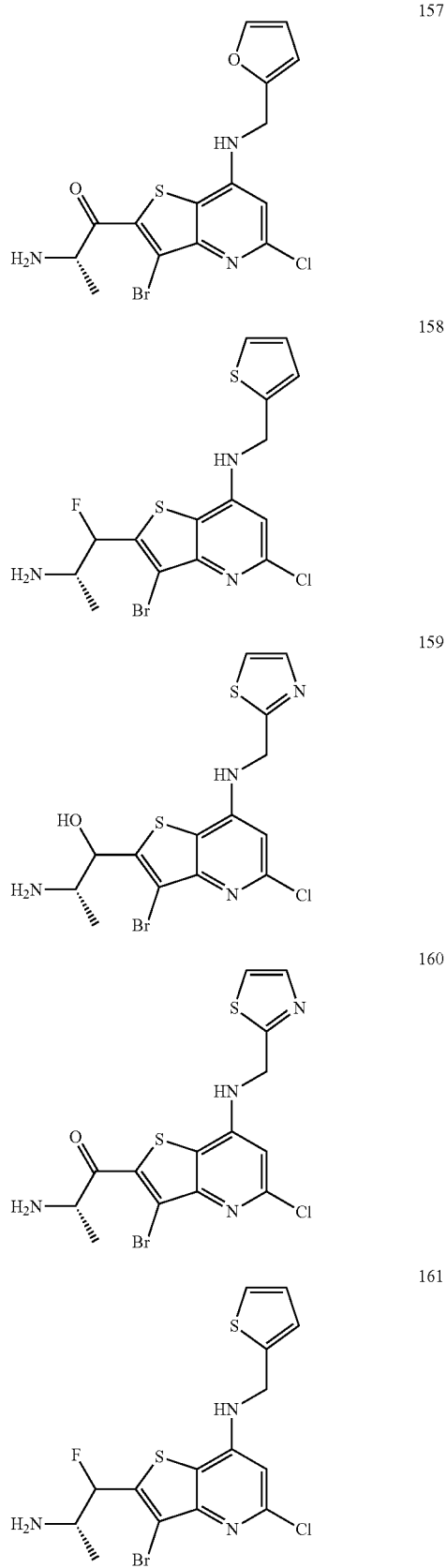

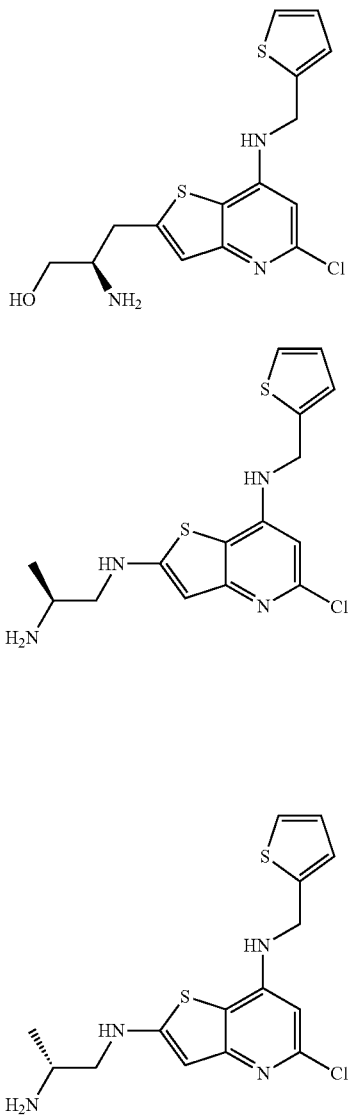

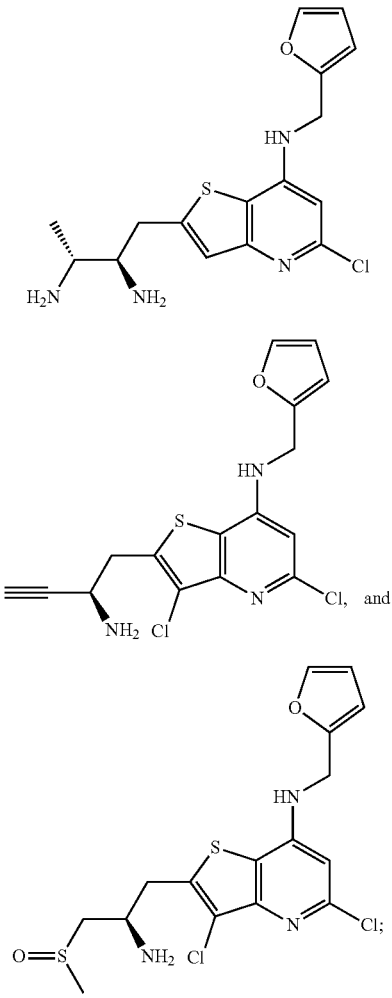

wherein the form of the compound is selected from the group consisting of a salt, hydrate, solvate, and tautomer form thereof.

An aspect the compound of Formula (I) or a form thereof (wherein compound number (#[1]) indicates that the salt form was isolated) includes a compound selected from the group consisting of:

| Cpd | Name |
|---|---|
| 1 | 5-chloro-N-[(furan-2-yl)methyl]thieno[3,2-b]pyridin-7-amine |
| 2 | 5-chloro-N-[(furan-2-yl)methyl]-3-methylthieno[3,2-b]pyridin-7-amine |
| 3 | 1-(5-chloro-7-{[(furan-2-yl)methyl]amino}-3-methylthieno[3,2-b]pyridin-2-yl)ethan-1-ol |
| 4 | 1-(5-chloro-7-{[(furan-2-yl)methyl]amino}thieno[3,2-b]pyridin-2-yl)ethan-1-ol |
| 5 | (5-chloro-7-{[(furan-2-yl)methyl]amino}thieno[3,2-b]pyridin-2-yl)methanol |
| 6[1] | 3,5-dichloro-N-[(furan-2-yl)methyl]thieno[3,2-b]pyridin-7-amine |
| 7[1] | 3-bromo-5-chloro-N-[(furan-2-yl)methyl]thieno[3,2-b]pyridin-7-amine |
| 8 | 3,5-dichloro-N-[(1,3-thiazol-2-yl)methyl]thieno[3,2-b]pyridin-7-amine |
| 9 | 3-bromo-5-chloro-N-[(1,3-thiazol-2-yl)methyl]thieno[3,2-b]pyridin-7-amine |
| 10[1] | 3-chloro-5-methyl-N-[(1,3-thiazol-2-yl)methyl]thieno[3,2-b]pyridin-7-amine |
| 11 | 3-bromo-7-{[(thiophen-2-yl)methyl]amino}thieno[3,2-b]pyridine-5-carbonitrile |
| 12 | 7-{[(thiophen-2-yl)methyl]amino}thieno[3,2-b]pyridine-3,5-dicarbonitrile |
| 13 | 5-chloro-7-{[(thiophen-2-yl)methyl]amino}thieno[3,2-b]pyridine-3-carbonitrile |
| 14 | 5-chloro-7-{[(furan-2-yl)methyl]amino}thieno[3,2-b]pyridine-3-carbonitrile |
| 15 | 7-{[(furan-2-yl)methyl]amino}thieno[3,2-b]pyridine-3,5-dicarbonitrile |
| 16[1] | 2-[(2S)-2-aminopropyl]-5-chloro-N-[(furan-2-yl)methyl]thieno[3,2-b]pyridin-7-amine |

| Cpd | Name |
|---|---|
| 17[1] | (2R)-2-amino-3-(5-chloro-7-{[(furan-2-yl)methyl]amino}thieno[3,2-b]pyridin-2-yl)propan-1-ol |
| 18[1] | 2-[(2S)-2-aminopropyl]-5-chloro-N-[(furan-2-yl)methyl]-3-methylthieno[3,2-b]pyridin-7-amine |
| 19[1] | 2-[(2S)-2-aminobutyl]-5-chloro-N-[(furan-2-yl)methyl]-3-methylthieno[3,2-b]pyridin-7-amine |
| 20[1] | 2-[(2S)-2-aminopropyl]-7-{[(furan-2-yl)methyl]amino}-3-methylthieno[3,2-b]pyridine-5-carbonitrile |
| 21[1] | 2-[(1S)-1-aminoethyl]-5-chloro-N-[(furan-2-yl)methyl]-3-methylthieno[3,2-b]pyridin-7-amine |
| 22[1] | 2-[(1R)-1-aminoethyl]-5-chloro-N-[(furan-2-yl)methyl]-3-methylthieno[3,2-b]pyridin-7-amine |
| 23[1] | 2-[(1R)-1-aminoethyl]-5-chloro-N-[(furan-2-yl)methyl]thieno[3,2-b]pyridin-7-amine |
| 24[1] | 2-[(1S)-1-aminoethyl]-5-chloro-N-[(furan-2-yl)methyl]thieno[3,2-b]pyridin-7-amine |
| 25[1] | 5-chloro-N-[(furan-2-yl)methyl]-2-[(methylamino)methyl]thieno[3,2-b]pyridin-7-amine |
| 26[1] | 5-chloro-N-[(furan-2-yl)methyl]-3-methyl-2-[(1S)-1-(methylamino)ethyl]thieno[3,2-b]pyridin-7-amine |
| 27[1] | 5-chloro-N-[(furan-2-yl)methyl]-3-methyl-2-[(methylamino)methyl]thieno[3,2-b]pyridin-7-amine |
| 28[1] | 2-[(2S)-2-aminopropyl]-5-chloro-3-methyl-N-[(thiophen-2-yl)methyl]thieno[3,2-b]pyridin-7-amine |
| 29[1] | 2-[(2S)-2-aminopropyl]-5-chloro-N-[(2-fluorophenyl)methyl]-3-methylthieno[3,2-b]pyridin-7-amine |
| 30[1] | 2-[(1S)-1-amino-2-methylpropyl]-5-chloro-N-[(furan-2-yl)methyl]-3-methylthieno[3,2-b]pyridin-7-amine |
| 31[1] | 2-[(1R)-1-amino-2-methylpropyl]-5-chloro-N-[(furan-2-yl)methyl]-3-methylthieno[3,2-b]pyridin-7-amine |
| 32[1] | 5-chloro-N-[(furan-2-yl)methyl]-3-methyl-2-[(1S)-2-methyl-1-(methylamino)propyl]thieno[3,2-b]pyridin-7-amine |
| 33[1] | 2-[(2S)-2-aminobutyl]-5-chloro-3-methyl-N-[(thiophen-2-yl)methyl]thieno[3,2-b]pyridin-7-amine |
| 34[1] | 2-[(2S)-2-aminopropyl]-N-[(furan-2-yl)methyl]-3-methylthieno[3,2-b]pyridin-7-amine |
| 35[1] | 2-[(2S)-2-aminopropyl]-5-chloro-N-[(3-fluoropyridin-4-yl)methyl]-3-methylthieno[3,2-b]pyridin-7-amine |
| 36[1] | 2-[(2S)-2-aminopropyl]-3,5-dichloro-N-[(furan-2-yl)methyl]thieno[3,2-b]pyridin-7-amine |
| 37[1] | 2-[(2S)-2-aminopropyl]-3-bromo-5-chloro-N-[(furan-2-yl)methyl]thieno[3,2-b]pyridin-7-amine |
| 38[1] | 2-[(2S)-2-aminopropyl]-3,5-dichloro-N-[(1,3-thiazol-2-yl)methyl]thieno[3,2-b]pyridin-7-amine |
| 39[1] | (2R)-2-amino-3-(3,5-dichloro-7-{[(furan-2-yl)methyl]amino}thieno[3,2-b]pyridin-2-yl)propan-1-ol |
| 40[1] | 2-[(2R)-2-amino-3-methoxypropyl]-3,5-dichloro-N-[(furan-2-yl)methyl]thieno[3,2-b]pyridin-7-amine |
| 41[1] | (2R)-2-amino-3-(3-bromo-5-chloro-7-{[(furan-2-yl)methyl]amino}thieno[3,2-b]pyridin-2-yl)propan-1-ol |
| 42[1] | 5-chloro-N-[(furan-2-yl)methyl]-3-methyl-2-[(2S)-2-(methylamino)propyl]thieno[3,2-b]pyridin-7-amine |
| 43[1] | 2-[(2S)-2-aminopropyl]-3-bromo-5-chloro-N-[(1,3-thiazol-2-yl)methyl]thieno[3,2-b]pyridin-7-amine |
| 44[1] | 2-[(2R)-2-amino-3-methoxypropyl]-3-bromo-5-chloro-N-[(furan-2-yl)methyl]thieno[3,2-b]pyridin-7-amine |
| 45[1] | 2-[(2R)-2-amino-3-methoxypropyl]-5-chloro-N-[(furan-2-yl)methyl]-3-methylthieno[3,2-b]pyridin-7-amine |
| 46[1] | 2-[(2R)-2-amino-3-fluoropropyl]-3-bromo-5-chloro-N-[(furan-2-yl)methyl]thieno[3,2-b]pyridin-7-amine |
| 47[1] | 2-[(2S)-2-amino-4-fluorobutyl]-3,5-dichloro-N-[(1,3-thiazol-2-yl)methyl]thieno[3,2-b]pyridin-7-amine |
| 48[1] | (3S)-3-amino-4-(3,5-dichloro-7-{[(1,3-thiazol-2-yl)methyl]amino}thieno[3,2-b]pyridin-2-yl)butan-1-ol |
| 49[1] | 2-[(2S)-2-aminopropyl]-3-bromo-7-{[(furan-2-yl)methyl]amino}thieno[3,2-b]pyridine-5-carbonitrile |
| 50[1] | 2-[(2S)-2-aminopropyl]-7-{[(furan-2-yl)methyl]amino}thieno[3,2-b]pyridine-3,5-dicarbonitrile |
| 51[1] | 2-[(2S)-2-aminopropyl]-5-chloro-3-cyclopropyl-N-[(furan-2-yl)methyl]thieno[3,2-b]pyridin-7-amine |
| 52[1] | 2-[(2S)-2-aminopropyl]-3,5-dichloro-N-[(thiophen-2-yl)methyl]thieno[3,2-b]pyridin-7-amine |
| 53[1] | 2-[(2S)-2-aminopropyl]-3-bromo-5-chloro-N-[(thiophen-2-yl)methyl]thieno[3,2-b]pyridin-7-amine |

-continued

| Cpd | Name |
|---|---|
| 54[1] | 2-[(2S)-2-aminopropyl]-3-methyl-7-{[(thiophen-2-yl)methyl]amino}thieno[3,2-b]pyridine-5-carbonitrile |
| 55[1] | 2-[(1S)-1-aminoethyl]-5-chloro-3-methyl-N-[(thiophen-2-yl)methyl]thieno[3,2-b]pyridin-7-amine |
| 56[1] | 2-[(1R)-1-aminoethyl]-5-chloro-3-methyl-N-[(thiophen-2-yl)methyl]thieno[3,2-b]pyridin-7-amine |
| 57[1] | 2-[(2S)-2-aminopropyl]-5-chloro-3-methyl-N-[(1,3-thiazol-2-yl)methyl]thieno[3,2-b]pyridin-7-amine |
| 58[1] | (2R)-2-amino-3-(5-chloro-7-{[(furan-2-yl)methyl]amino}-3-methylthieno[3,2-b]pyridin-2-yl)propan-1-ol |
| 59[1] | 2-[(2S)-2-amino-3-fluoropropyl]-5-chloro-N-[(furan-2-yl)methyl]-3-methylthieno[3,2-b]pyridin-7-amine |
| 60[1] | 2-[(2S)-2-aminopropyl]-3-chloro-5-methyl-N-[(1,3-thiazol-2-yl)methyl]thieno[3,2-b]pyridin-7-amine |
| 61[1] | 2-[(2S)-2-amino-4-methylpentyl]-5-chloro-3-methyl-N-[(thiophen-2-yl)methyl]thieno[3,2-b]pyridin-7-amine |
| 62[1] | 2-[(2S)-2-amino-4-methylpentyl]-3-bromo-5-chloro-N-[(1,3-thiazol-2-yl)methyl]thieno[3,2-b]pyridin-7-amine |
| 63[1] | 2-[(2S)-2-amino-3-fluoropropyl]-3-bromo-5-chloro-N-[(thiophen-2-yl)methyl]thieno[3,2-b]pyridin-7-amine |
| 64[1] | 2-[(2R)-2-amino-3-(trifluoromethoxy)propyl]-3-bromo-5-chloro-N-[(1,3-thiazol-2-yl)methyl]thieno[3,2-b]pyridin-7-amine |
| 65[1] | (2R)-3-(3-bromo-5-chloro-7-{[(1,3-thiazol-2-yl)methyl]amino}thieno[3,2-b]pyridin-2-yl)-2-[(trifluoromethyl)amino]propan-1-ol |
| 65[1] | 2-[(2S)-2-amino-3-fluoropropyl]-3-bromo-5-chloro-N-[(1,3-thiazol-2-yl)methyl]thieno[3,2-b]pyridin-7-amine |
| 67[1] | 2-[(2S)-2-amino-3-fluoropropyl]-3,5-dichloro-N-[(1,3-thiazol-2-yl)methyl]thieno[3,2-b]pyridin-7-amine |
| 68[1] | 2-[(2S)-2-amino-4-methylpentyl]-5-chloro-3-methyl-N-[(1,3-thiazol-2-yl)methyl]thieno[3,2-b]pyridin-7-amine |
| 69[1] | 2-[(2R)-2-amino-3-fluoropropyl]-5-chloro-3-methyl-N-[(1,3-thiazol-2-yl)methyl]thieno[3,2-b]pyridin-7-amine |
| 70[1] | 2-[(2R)-2-amino-3-fluoropropyl]-3-bromo-5-chloro-N-[(1,3-thiazol-2-yl)methyl]thieno[3,2-b]pyridin-7-amine |
| 71[1] | (2R)-2-amino-3-(3-bromo-5-chloro-7-{[(1,3-thiazol-2-yl)methyl]amino}thieno[3,2-b]pyridin-2-yl)propan-1-ol |
| 72[1] | 2-[(2R)-2-aminobut-3-en-1-yl]-3-bromo-5-chloro-N-[(1,3-thiazol-2-yl)methyl]thieno[3,2-b]pyridin-7-amine |
| 73[1] | 2-[(2S)-2-aminobutyl]-3-bromo-5-chloro-N-[(thiophen-2-yl)methyl]thieno[3,2-b]pyridin-7-amine |
| 74[1] | 2-[(2S)-2-amino-4-fluorobutyl]-3-bromo-5-chloro-N-[(thiophen-2-yl)methyl]thieno[3,2-b]pyridin-7-amine |
| 75[1] | 2-[(2S)-2-aminobutyl]-5-chloro-3-cyclopropyl-N-[(thiophen-2-yl)methyl]thieno[3,2-b]pyridin-7-amine |
| 76[1] | 2-[(2R)-2-amino-3-fluoropropyl]-3-bromo-5-chloro-N-[(thiophen-2-yl)methyl]thieno[3,2-b]pyridin-7-amine |
| 77[1] | 2-[(2R)-2-amino-3-fluoropropyl]-5-chloro-3-cyclopropyl-N-[(thiophen-2-yl)methyl]thieno[3,2-b]pyridin-7-amine |
| 78[1] | 2-[(2S)-2-aminobutyl]-3-bromo-5-chloro-N-[(1,3-thiazol-2-yl)methyl]thieno[3,2-b]pyridin-7-amine |
| 79[1] | 2-[(2S)-2-amino-4-methylpentyl]-3,5-dichloro-N-[(1,3-thiazol-2-yl)methyl]thieno[3,2-b]pyridin-7-amine |
| 80[1] | 2-[(2S)-2-amino-4-methylpentyl]-5-chloro-3-cyclopropyl-N-[(1,3-thiazol-2-yl)methyl]thieno[3,2-b]pyridin-7-amine |
| 81[1] | 2-[(2R)-2-amino-3-fluoropropyl]-5-chloro-N-[(furan-2-yl)methyl]-3-methylthieno[3,2-b]pyridin-7-amine |
| 82[1] | 2-[(2S)-2-aminobutyl]-3,5-dichloro-N-[(1,3-thiazol-2-yl)methyl]thieno[3,2-b]pyridin-7-amine |
| 83[1] | 2-[(2S)-2-aminobutyl]-3,5-dichloro-N-[(thiophen-2-yl)methyl]thieno[3,2-b]pyridin-7-amine |
| 84 | 2-[(2R)-2-amino-3-fluoropropyl]-3,5-dichloro-N-[(thiophen-2-yl)methyl]thieno[3,2-b]pyridin-7-amine |
| 85[1] | 2-[(2S)-2-aminobutyl]-5-chloro-3-methyl-N-[(1,3-thiazol-2-yl)methyl]thieno[3,2-b]pyridin-7-amine |
| 86[1] | 2-[(2S)-2-aminobutyl]-5-chloro-3-cyclopropyl-N-[(1,3-thiazol-2-yl)methyl]thieno[3,2-b]pyridin-7-amine |
| 87[1] | 2-[(2R)-2-amino-3-fluoropropyl]-5-chloro-3-cyclopropyl-N-[(1,3-thiazol-2-yl)methyl]thieno[3,2-b]pyridin-7-amine |
| 88[1] | 2-[(2S)-2-amino-4-fluorobutyl]-3-bromo-5-chloro-N-[(1,3-thiazol-2-yl)methyl]thieno[3,2-b]pyridin-7-amine |
| 89[1] | (3S)-3-amino-4-(3-bromo-5-chloro-7-{[(1,3-thiazol-2-yl)methyl]amino}thieno[3,2-b]pyridin-2-yl)butan-1-ol |
| 90[1] | 2-[(2R)-2-amino-3-fluoropropyl]-3,5-dichloro-N-[(1,3-thiazol-2-yl)methyl]thieno[3,2-b]pyridin-7-amine |

-continued

| Cpd | Name |
|---|---|
| 91[1] | 2-[(2R)-2-amino-3-fluoropropyl]-5-chloro-3-methyl-N-[(thiophen-2-yl)methyl]thieno[3,2-b]pyridin-7-amine |
| 92[1] | 2-[(2S)-2-amino-4-fluorobutyl]-5-chloro-3-methyl-N-[(thiophen-2-yl)methyl]thieno[3,2-b]pyridin-7-amine |
| 93[1] | 2-[(2S)-2-amino-4-fluorobutyl]-3,5-dichloro-N-[(furan-2-yl)methyl]thieno[3,2-b]pyridin-7-amine |
| 94[1] | 2-[(2R)-2-amino-3-fluoropropyl]-3,5-dichloro-N-[(furan-2-yl)methyl]thieno[3,2-b]pyridin-7-amine |
| 95[1] | 2-[(2S)-2-amino-4-fluorobutyl]-5-chloro-N-[(furan-2-yl)methyl]-3-methylthieno[3,2-b]pyridin-7-amine |
| 96[1] | 2-[(2S)-2-aminopropyl]-5-chloro-3-cyclopropyl-N-[(1,3-thiazol-2-yl)methyl]thieno[3,2-b]pyridin-7-amine |
| 97[1] | 2-[(2S)-2-amino-4-fluorobutyl]-3-bromo-5-chloro-N-[(furan-2-yl)methyl]thieno[3,2-b]pyridin-7-amine |
| 98[1] | 2-[(2S)-2-amino-4-fluorobutyl]-3,5-dichloro-N-[(thiophen-2-yl)methyl]thieno[3,2-b]pyridin-7-amine |
| 99[1] | 2-[(2S)-2-amino-4-fluorobutyl]-5-chloro-3-methyl-N-[(1,3-thiazol-2-yl)methyl]thieno[3,2-b]pyridin-7-amine |
| 100[1] | (3S)-3-amino-4-(3-bromo-5-chloro-7-{[(2-fluorophenyl)methyl]amino}thieno[3,2-b]pyridin-2-yl)butan-1-ol |
| 101[1] | 2-[(2S)-2-aminopropyl]-3-bromo-7-{[(thiophen-2-yl)methyl]amino}thieno[3,2-b]pyridine-5-carbonitrile |
| 102[1] | 2-[(2S)-2-aminopropyl]-7-{[(thiophen-2-yl)methyl]amino}thieno[3,2-b]pyridine-3,5-dicarbonitrile |
| 103[1] | (3S)-3-amino-4-(3-bromo-5-chloro-7-{[(furan-2-yl)methyl]amino}thieno[3,2-b]pyridin-2-yl)butanenitrile |
| 104[1] | 2-[(2R)-2-amino-3-(methylsulfanyl)propyl]-5-chloro-N-[(furan-2-yl)methyl]-3-methylthieno[3,2-b]pyridin-7-amine |
| 105[1] | (3S)-3-amino-4-(5-chloro-3-methyl-7-{[(thiophen-2-yl)methyl]amino}thieno[3,2-b]pyridin-2-yl)butanenitrile |
| 106[1] | (3S)-3-amino-4-(3,5-dichloro-7-{[(thiophen-2-yl)methyl]amino}thieno[3,2-b]pyridin-2-yl)butanenitrile |
| 107[1] | 2-[(2S)-2-amino-4,4-difluorobutyl]-3-bromo-5-chloro-N-[(thiophen-2-yl)methyl]thieno[3,2-b]pyridin-7-amine |
| 108[1] | 2-[(2R)-2-amino-3-(methanesulfonyl)propyl]-5-chloro-N-[(furan-2-yl)methyl]-3-methylthieno[3,2-b]pyridin-7-amine |
| 109[1] | 2-[(2S)-2-aminopropyl]-5-chloro-7-{[(furan-2-yl)methyl]amino}thieno[3,2-b]pyridine-3-carbonitrile |
| 110[1] | 2-[(2S)-2-aminopropyl]-5-chloro-7-{[(thiophen-2-yl)methyl]amino}thieno[3,2-b]pyridine-3-carbonitrile |
| 111[1] | (3S)-3-amino-4-(5-chloro-7-{[(furan-2-yl)methyl]amino}-3-methylthieno[3,2-b]pyridin-2-yl)butanenitrile |
| 112[1] | 2-[(2S)-2-aminopropyl]-3-chloro-7-{[(thiophen-2-yl)methyl]amino}thieno[3,2-b]pyridine-5-carbonitrile |
| 113[1] | 2-[(2R)-2-amino-3-(methanesulfonyl)propyl]-3,5-dichloro-N-[(furan-2-yl)methyl]thieno[3,2-b]pyridin-7-amine |
| 114[1] | 2-[(2R)-2-amino-3-(methylsulfanyl)propyl]-3,5-dichloro-N-[(furan-2-yl)methyl]thieno[3,2-b]pyridin-7-amine |
| 115[1] | 3-(5-chloro-7-{[(furan-2-yl)methyl]amino}-3-methylthieno[3,2-b]pyridin-2-yl)-D-alanine |
| 116[1] | 3-(5-chloro-7-{[(furan-2-yl)methyl]amino}-3-methylthieno[3,2-b]pyridin-2-yl)-N,N-dimethyl-D-alaninamide |
| 117[1] | 2-[(2R)-2-amino-3-(methanesulfonyl)propyl]-3-bromo-5-chloro-N-[(furan-2-yl)methyl]thieno[3,2-b]pyridin-7-amine |
| 118[1] | 2-[(2R)-2-amino-3-(methylsulfanyl)propyl]-3-bromo-5-chloro-N-[(furan-2-yl)methyl]thieno[3,2-b]pyridin-7-amine |
| 119[1] | 2-[(2R)-2-aminobut-3-en-1-yl]-5-chloro-N-[(furan-2-yl)methyl]thieno[3,2-b]pyridin-7-amine |
| 120[1] | 3-(3,5-dichloro-7-{[(furan-2-yl)methyl]amino}thieno[3,2-b]pyridin-2-yl)-N-(2-fluorophenyl)-D-alaninamide |
| 121[1] | 3-(3,5-dichloro-7-{[(furan-2-yl)methyl]amino}thieno[3,2-b]pyridin-2-yl)-D-alanine |
| 122[1] | 3-(3,5-dichloro-7-{[(furan-2-yl)methyl]amino}thieno[3,2-b]pyridin-2-yl)-N-phenyl-D-alaninamide |
| 123[1] | 2-[(2R)-2-aminobut-3-yn-1-yl]-3-methyl-5-chloro-N-[(furan-2-yl)methyl]thieno[3,2-b]pyridin-7-amine |
| 124[1] | 3-(3,5-dichloro-7-{[(furan-2-yl)methyl]amino}thieno[3,2-b]pyridin-2-yl)-N-(2-fluorophenyl)-D-alaninamide |
| 125[1] | 2-[(2R,3S)-2-amino-3-fluorobutyl]-3-bromo-5-chloro-N-[(1,3-thiazol-2-yl)methyl]thieno[3,2-b]pyridin-7-amine |
| 126[1] | 2-[(2R,3S)-2-amino-3-fluorobutyl]-5-chloro-3-methyl-N-[(thiophen-2-yl)methyl]thieno[3,2-b]pyridin-7-amine |
| 127[1] | (2S)-2-amino-1-(3,5-dichloro-7-{[(thiophen-2-yl)methyl]amino}thieno[3,2-b]pyridin-2-yl)propan-1-ol |
| 128[1] | 2-[(2R,3S)-2-amino-3-fluorobutyl]-5-chloro-3-methyl-N-[(1,3-thiazol-2-yl)methyl]thieno[3,2-b]pyridin-7-amine |
| 129[1] | 2-[(2S)-2-aminopropyl]-5-chloro-N-[(5-fluoro-1,3-thiazol-2-yl)methyl]-3-methylthieno[3,2-b]pyridin-7-amine |

-continued

| Cpd | Name |
|---|---|
| 130[1] | 2-[(2S)-2-amino-1-fluoropropyl]-3,5-dichloro-N-[(thiophen-2-yl)methyl]thieno[3,2-b]pyridin-7-amine |
| 131[1] | methyl 3-(5-chloro-7-{[(furan-2-yl)methyl]amino}-3-methylthieno[3,2-b]pyridin-2-yl)-D-alaninate |
| 132 | 2-[(2S)-2-amino-1,1-difluoropropyl]-3,5-dichloro-N-[(thiophen-2-yl)methyl]thieno[3,2-b]pyridin-7-amine |
| 133[1] | 3-(5-chloro-7-{[(furan-2-yl)methyl]amino}-3-methylthieno[3,2-b]pyridin-2-yl)-N-(4-cyanophenyl)-D-alaninamide |
| 134[1] | 3-(5-chloro-7-{[(furan-2-yl)methyl]amino}-3-methylthieno[3,2-b]pyridin-2-yl)-N-pyridin-2-yl-D-alaninamide |
| 135[1] | 3-(5-chloro-7-{[(furan-2-yl)methyl]amino}-3-methylthieno[3,2-b]pyridin-2-yl)-N-pyrazin-2-yl-D-alaninamide |
| 136[1] | 2-[(2S)-2-aminopropyl]-5-chloro-N-[(furan-2-yl)methyl]-3-methoxythieno[3,2-b]pyridin-7-amine |
| 137[1] | 5-chloro-N-[(furan-2-yl)methyl]-3-methoxythieno[3,2-b]pyridin-7-amine |
| 138[1] | 5-chloro-7-{[(thiophen-2-yl)methyl]amino}thieno[3,2-b]pyridin-3-ol |
| 139[1] | 2-[(2S)-2-aminopropyl]-5-chloro-3-(difluoromethoxy)-N-[(thiophen-2-yl)methyl]thieno[3,2-b]pyridin-7-amine |
| 140[1] | 3-(5-chloro-7-{[(furan-2-yl)methyl]amino}-3-methylthieno[3,2-b]pyridin-2-yl)-N-pyridin-4-yl-D-alaninamide |
| 141[1] | 3-(5-chloro-7-{[(furan-2-yl)methyl]amino}-3-methylthieno[3,2-b]pyridin-2-yl)-N-methyl-N-phenyl-D-alaninamide |
| 142[1] | 3-(5-chloro-7-{[(furan-2-yl)methyl]amino}-3-methylthieno[3,2-b]pyridin-2-yl)-N-(4-methylphenyl)-D-alaninamide |
| 143[1] | 3-(5-chloro-7-{[(furan-2-yl)methyl]amino}-3-methylthieno[3,2-b]pyridin-2-yl)-N-(3-chlorophenyl)-D-alaninamide |
| 144[1] | 3-(5-chloro-7-{[(furan-2-yl)methyl]amino}-3-methylthieno[3,2-b]pyridin-2-yl)-N-(3-methoxyphenyl)-D-alaninamide |
| 145[1] | 3-(5-chloro-7-{[(furan-2-yl)methyl]amino}-3-methylthieno[3,2-b]pyridin-2-yl)-N-(1-methyl-1H-pyrazol-5-yl)-D-alaninamide |
| 146 | 2-(5-chloro-7-{[(furan-2-yl)methyl]amino}-3-methylthieno[3,2-b]pyridin-2-yl)propan-1-ol |
| 147 | 2-(5-chloro-7-{[(furan-2-yl)methyl]amino}-3-methylthieno[3,2-b]pyridin-2-yl)propane-1,2-diol |
| 148[1] | 2-(1-aminopropan-2-yl)-5-chloro-N-[(furan-2-yl)methyl]-3-methylthieno[3,2-b]pyridin-7-amine |
| 149 | 5-chloro-3-(difluoromethoxy)-N-[(thiophen-2-yl)methyl]thieno[3,2-b]pyridin-7-amine |
| 150[1] | 2-[(2R,3S)-3-aminobutan-2-yl]-5-chloro-N-[(furan-2-yl)methyl]-3-methylthieno[3,2-b]pyridin-7-amine |
| 151[1] | 2-[(2S,3S)-3-aminobutan-2-yl]-5-chloro-N-[(furan-2-yl)methyl]-3-methylthieno[3,2-b]pyridin-7-amine |
| 153[1] | (2S)-2-amino-1-(3-bromo-5-chloro-7-{[(furan-2-yl)methyl]amino}thieno[3,2-b]pyridin-2-yl)propan-1-ol |
| 154[1] | 2-[(2S)-2-amino-1-fluoropropyl]-3-bromo-5-chloro-N-[(furan-2-yl)methyl]thieno[3,2-b]pyridin-7-amine |
| 155[1] | (2S)-2-amino-1-(3-bromo-5-chloro-7-{[(thiophen-2-yl)methyl]amino}thieno[3,2-b]pyridin-2-yl)propan-1-ol |
| 156[1] | (2S)-2-amino-1-(3-bromo-5-chloro-7-{[(thiophen-2-yl)methyl]amino}thieno[3,2-b]pyridin-2-yl)propan-1-one |
| 157[1] | (2S)-2-amino-1-(3-bromo-5-chloro-7-{[(furan-2-yl)methyl]amino}thieno[3,2-b]pyridin-2-yl)propan-1-one |
| 158[1] | 2-[(2S)-2-amino-1-fluoropropyl]-3-bromo-5-chloro-N-[(thiophen-2-yl)methyl]thieno[3,2-b]pyridin-7-amine |
| 159[1] | (2S)-2-amino-1-(3-bromo-5-chloro-7-{[(1,3-thiazol-2-yl)methyl]amino}thieno[3,2-b]pyridin-2-yl)propan-1-ol |
| 160[1] | (2S)-2-amino-1-(3-bromo-5-chloro-7-{[(1,3-thiazol-2-yl)methyl]amino}thieno[3,2-b]pyridin-2-yl)propan-1-one |
| 161[1] | 2-[(2S)-2-amino-1-fluoropropyl]-3-bromo-5-chloro-N-[(1,3-thiazol-2-yl)methyl]thieno[3,2-b]pyridin-7-amine |
| 162[1] | (2R)-2-amino-3-(5-chloro-7-{[(thiophen-2-yl)methyl]amino}thieno[3,2-b]pyridin-2-yl)propan-1-ol |
| 163[1] | $N^2$-[(2S)-2-aminopropyl]-5-chloro-3-methyl-$N^7$-[(thiophen-2-yl)methyl]thieno[3,2-b]pyridine-2,7-diamine |
| 164[1] | $N^2$-[(2R)-2-aminopropyl]-5-chloro-3-methyl-$N^7$-[(thiophen-2-yl)methyl]thieno[3,2-b]pyridine-2,7-diamine |
| 165[1] | (2R,3R)-3-amino-4-(3-bromo-5-chloro-7-{[(furan-2-yl)methyl]amino}thieno[3,2-b]pyridin-2-yl)butan-2-ol |
| 166[1] | 2-[(2R)-2-aminobut-3-yn-1-yl]-3,5-dichloro-N-[(furan-2-yl)methyl]thieno[3,2-b]pyridin-7-amine, and |
| 167 | [(2R)-2-amino-3-(3,5-dichloro-7-{[(furan-2-yl)methyl]amino}thieno[3,2-b]pyridin-2-yl)propyl](methyl)sulfaniumolate; | wherein the form of the compound is selected from the group consisting of a salt, hydrate, solvate, and tautomer form thereof.

Another aspect of the compound of Formula (I) or a form thereof is a compound salt selected from the group consisting of:

| Cpd | Name |
|---|---|
| 6 | 3,5-dichloro-N-[(furan-2-yl)methyl]thieno[3,2-b]pyridin-7-amine hydrochloride |
| 7 | 3-bromo-5-chloro-N-[(furan-2-yl)methyl]thieno[3,2-b]pyridin-7-amine hydrochloride |
| 10 | 3-chloro-5-methyl-N-[(1,3-thiazol-2-yl)methyl]thieno[3,2-b]pyridin-7-amine hydrochloride |
| 16 | 2-[(2S)-2-aminopropyl]-5-chloro-N-[(furan-2-yl)methyl]thieno[3,2-b]pyridin-7-amine dihydrochloride |
| 17 | (2R)-2-amino-3-(5-chloro-7-{[(furan-2-yl)methyl]amino}thieno[3,2-b]pyridin-2-yl)propan-1-ol dihydrochloride |
| 18 | 2-[(2S)-2-aminopropyl]-5-chloro-N-[(furan-2-yl)methyl]-3-methylthieno[3,2-b]pyridin-7-amine dihydrochloride |
| 19 | 2-[(2S)-2-aminobutyl]-5-chloro-N-[(furan-2-yl)methyl]-3-methylthieno[3,2-b]pyridin-7-amine dihydrochloride |
| 20 | 2-[(2S)-2-aminopropyl]-7-{[(furan-2-yl)methyl]amino}-3-methylthieno[3,2-b]pyridine-5-carbonitrile trifluoroacetate |
| 21 | 2-[(1S)-1-aminoethyl]-5-chloro-N-[(furan-2-yl)methyl]-3-methylthieno[3,2-b]pyridin-7-amine hydrochloride |
| 22 | 2-[(1R)-1-aminoethyl]-5-chloro-N-[(furan-2-yl)methyl]-3-methylthieno[3,2-b]pyridin-7-amine hydrochloride |
| 23 | 2-[(1R)-1-aminoethyl]-5-chloro-N-[(furan-2-yl)methyl]thieno[3,2-b]pyridin-7-amine hydrochloride |
| 24 | 2-[(1S)-1-aminoethyl]-5-chloro-N-[(furan-2-yl)methyl]thieno[3,2-b]pyridin-7-amine hydrochloride |
| 25 | 5-chloro-N-[(furan-2-yl)methyl]-2-[(methylamino)methyl]thieno[3,2-b]pyridin-7-amine hydrochloride |
| 26 | 5-chloro-N-[(furan-2-yl)methyl]-3-methyl-2-[(1S)-1-(methylamino)ethyl]thieno[3,2-b]pyridin-7-amine hydrochloride |
| 27 | 5-chloro-N-[(furan-2-yl)methyl]-3-methyl-2-[(methylamino)methyl]thieno[3,2-b]pyridin-7-amine hydrochloride |
| 28 | 2-[(2S)-2-aminopropyl]-5-chloro-3-methyl-N-[(thiophen-2-yl)methyl]thieno[3,2-b]pyridin-7-amine dihydrochloride |
| 29 | 2-[(2S)-2-aminopropyl]-5-chloro-N-[(2-fluorophenyl)methyl]-3-methylthieno[3,2-b]pyridin-7-amine dihydrochloride |
| 30 | 2-[(1S)-1-amino-2-methylpropyl]-5-chloro-N-[(furan-2-yl)methyl]-3-methylthieno[3,2-b]pyridin-7-amine hydrochloride |
| 31 | 2-[(1R)-1-amino-2-methylpropyl]-5-chloro-N-[(furan-2-yl)methyl]-3-methylthieno[3,2-b]pyridin-7-amine hydrochloride |
| 32 | 5-chloro-N-[(furan-2-yl)methyl]-3-methyl-2-[(1S)-2-methyl-1-(methylamino)propyl]thieno[3,2-b]pyridin-7-amine hydrochloride |
| 33 | 2-[(2S)-2-aminobutyl]-5-chloro-3-methyl-N-[(thiophen-2-yl)methyl]thieno[3,2-b]pyridin-7-amine dihydrochloride |
| 34 | 2-[(2S)-2-aminopropyl]-N-[(furan-2-yl)methyl]-3-methylthieno[3,2-b]pyridin-7-amine dihydrochloride |
| 35 | 2-[(2S)-2-aminopropyl]-5-chloro-N-[(3-fluoropyridin-4-yl)methyl]-3-methylthieno[3,2-b]pyridin-7-amine dihydrochloride |
| 36 | 2-[(2S)-2-aminopropyl]-3,5-dichloro-N-[(furan-2-yl)methyl]thieno[3,2-b]pyridin-7-amine dihydrochloride |
| 37 | 2-[(2S)-2-aminopropyl]-3-bromo-5-chloro-N-[(furan-2-yl)methyl]thieno[3,2-b]pyridin-7-amine dihydrochloride |
| 38 | 2-[(2S)-2-aminopropyl]-3,5-dichloro-N-[(1,3-thiazol-2-yl)methyl]thieno[3,2-b]pyridin-7-amine dihydrochloride |
| 39 | (2R)-2-amino-3-(3,5-dichloro-7-{[(furan-2-yl)methyl]amino}thieno[3,2-b]pyridin-2-yl)propan-1-ol dihydrochloride |
| 40 | 2-[(2R)-2-amino-3-methoxypropyl]-3,5-dichloro-N-[(furan-2-yl)methyl]thieno[3,2-b]pyridin-7-amine dihydrochloride |
| 41 | (2R)-2-amino-3-(3-bromo-5-chloro-7-{[(furan-2-yl)methyl]amino}thieno[3,2-b]pyridin-2-yl)propan-1-ol dihydrochloride |
| 42 | 5-chloro-N-[(furan-2-yl)methyl]-3-methyl-2-[(2S)-2-(methylamino)propyl]thieno[3,2-b]pyridin-7-amine hydrochloride |
| 43 | 2-[(2S)-2-aminopropyl]-3-bromo-5-chloro-N-[(1,3-thiazol-2-yl)methyl]thieno[3,2-b]pyridin-7-amine dihydrochloride |
| 44 | 2-[(2R)-2-amino-3-methoxypropyl]-3-bromo-5-chloro-N-[(furan-2-yl)methyl]thieno[3,2-b]pyridin-7-amine dihydrochloride |
| 45 | 2-[(2R)-2-amino-3-methoxypropyl]-5-chloro-N-[(furan-2-yl)methyl]-3-methylthieno[3,2-b]pyridin-7-amine dihydrochloride |
| 46 | 2-[(2R)-2-amino-3-fluoropropyl]-3-bromo-5-chloro-B-[(furan-2-yl)methyl]thieno[3,2-b]pyridin-7-amine formate |
| 47 | 2-[(2S)-2-amino-4-fluorobutyl]-3,5-dichloro-N-[(1,3-thiazol-2-yl)methyl]thieno[3,2-b]pyridin-7-amine dihydrochloride |
| 48 | (3S)-3-amino-4-(3,5-dichloro-7-{[(1,3-thiazol-2-yl)methyl]amino}thieno[3,2-b]pyridin-2-yl)butan-1-ol dihydrochloride |

| Cpd | Name |
|---|---|
| 49 | 2-[(2S)-2-aminopropyl]-3-bromo-7-{[(furan-2-yl)methyl]amino}thieno[3,2-b]pyridine-5-carbonitrile hydrochloride |
| 50 | 2-[(2S)-2-aminopropyl]-7-{[(furan-2-yl)methyl]amino}thieno[3,2-b]pyridine-3,5-dicarbonitrile hydrochloride |
| 51 | 2-[(2S)-2-aminopropyl]-5-chloro-3-cyclopropyl-N-[(furan-2-yl)methyl]thieno[3,2-b]pyridin-7-amine hydrochloride |
| 52 | 2-[(2S)-2-aminopropyl]-3,5-dichloro-N-[(thiophen-2-yl)methyl]thieno[3,2-b]pyridin-7-amine dihydrochloride |
| 53 | 2-[(2S)-2-aminopropyl]-3-bromo-5-chloro-N-[(thiophen-2-yl)methyl]thieno[3,2-b]pyridin-7-amine dihydrochloride |
| 54 | 2-[(2S)-2-aminopropyl]-3-methyl-7-{[(thiophen-2-yl)methyl]amino}thieno[3,2-b]pyridine-5-carbonitrile formate |
| 55 | 2-[(1S)-1-aminoethyl]-5-chloro-3-methyl-N-[(thiophen-2-yl)methyl]thieno[3,2-b]pyridin-7-amine hydrochloride |
| 56 | 2-[(1R)-1-aminoethyl]-5-chloro-3-methyl-N-[(thiophen-2-yl)methyl]thieno[3,2-b]pyridin-7-amine hydrochloride |
| 57 | 2-[(2S)-2-aminopropyl]-5-chloro-3-methyl-N-[(1,3-thiazol-2-yl)methyl]thieno[3,2-b]pyridin-7-amine dihydrochloride |
| 58 | (2R)-2-amino-3-(5-chloro-7-{[(furan-2-yl)methyl]amino}-3-methylthieno[3,2-b]pyridin-2-yl)propan-1-ol dihydrochloride |
| 59 | 2-[(2S)-2-amino-3-fluoropropyl]-5-chloro-N-[(furan-2-yl)methyl]-3-methylthieno[3,2-b]pyridin-7-amine dihydrochloride |
| 60 | 2-[(2S)-2-aminopropyl]-3-chloro-5-methyl-N-[(1,3-thiazol-2-yl)methyl]thieno[3,2-b]pyridin-7-amine dihydrochloride |
| 61 | 2-[(2S)-2-amino-4-methylpentyl]-5-chloro-3-methyl-N-[(thiophen-2-yl)methyl]thieno[3,2-b]pyridin-7-amine hydrochloride |
| 62 | 2-[(2S)-2-amino-4-methylpentyl]-3-bromo-5-chloro-N-[(1,3-thiazol-2-yl)methyl]thieno[3,2-b]pyridin-7-amine hydrochloride |
| 63 | 2-[(2S)-2-amino-3-fluoropropyl]-3-bromo-5-chloro-N-[(thiophen-2-yl)methyl]thieno[3,2-b]pyridin-7-amine hydrochloride |
| 64 | 2-[(2R)-2-amino-3-(trifluoromethoxy)propyl]-3-bromo-5-chloro-N-[(1,3-thiazol-2-yl)methyl]thieno[3,2-b]pyridin-7-amine formate |
| 65 | (2R)-3-(3-bromo-5-chloro-7-{[(1,3-thiazol-2-yl)methyl]amino}thieno[3,2-b]pyridin-2-yl)-2-[(trifluoromethyl)amino]propan-1-ol formate |
| 66 | 2-[(2S)-2-amino-3-fluoropropyl]-3-bromo-5-chloro-N-[(1,3-thiazol-2-yl)methyl]thieno[3,2-b]pyridin-7-amine dihydrochloride |
| 67 | 2-[(2S)-2-amino-3-fluoropropyl]-3,5-dichloro-N-[(1,3-thiazol-2-yl)methyl]thieno[3,2-b]pyridin-7-amine dihydrochloride |
| 68 | 2-[(2S)-2-amino-4-methylpentyl]-5-chloro-3-methyl-N-[(1,3-thiazol-2-yl)methyl]thieno[3,2-b]pyridin-7-amine hydrochloride |
| 69 | 2-[(2R)-2-amino-3-fluoropropyl]-5-chloro-3-methyl-N-[(1,3-thiazol-2-yl)methyl]thieno[3,2-b]pyridin-7-amine dihydrochloride |
| 70 | 2-[(2R)-2-amino-3-fluoropropyl]-3-bromo-5-chloro-N-[(1,3-thiazol-2-yl)methyl]thieno[3,2-b]pyridin-7-amine dihydrochloride |
| 71 | (2R)-2-amino-3-(3-bromo-5-chloro-7-{[(1,3-thiazol-2-yl)methyl]amino}thieno[3,2-b]pyridin-2-yl)propan-1-ol dihydrochloride |
| 72 | 2-[(2R)-2-aminobut-3-en-1-yl]-3-bromo-5-chloro-N-[(1,3-thiazol-2-yl)methyl]thieno[3,2-b]pyridin-7-amine dihydrochloride |
| 73 | 2-[(2S)-2-aminobutyl]-3-bromo-5-chloro-N-[(thiophen-2-yl)methyl]thieno[3,2-b]pyridin-7-amine dihydrochloride |
| 74 | 2-[(2S)-2-amino-4-fluorobutyl]-3-bromo-5-chloro-N-[(thiophen-2-yl)methyl]thieno[3,2-b]pyridin-7-amine hydrochloride |
| 75 | 2-[(2S)-2-aminobutyl]-5-chloro-3-cyclopropyl-N-[(thiophen-2-yl)methyl]thieno[3,2-b]pyridin-7-amine dihydrochloride |
| 76 | 2-[(2R)-2-amino-3-fluoropropyl]-3-bromo-5-chloro-N-[(thiophen-2-yl)methyl]thieno[3,2-b]pyridin-7-amine hydrochloride |
| 77 | 2-[(2R)-2-amino-3-fluoropropyl]-5-chloro-3-cyclopropyl-N-[(thiophen-2-yl)methyl]thieno[3,2-b]pyridin-7-amine hydrochloride |
| 78 | 2-[(2S)-2-aminobutyl]-3-bromo-5-chloro-N-[(1,3-thiazol-2-yl)methyl]thieno[3,2-b]pyridin-7-amine hydrochloride |
| 79 | 2-[(2S)-2-amino-4-methylpentyl]-3,5-dichloro-N-[(1,3-thiazol-2-yl)methyl]thieno[3,2-b]pyridin-7-amine hydrochloride |
| 80 | 2-[(2S)-2-amino-4-methylpentyl]-5-chloro-3-cyclopropyl-N-[(1,3-thiazol-2-yl)methyl]thieno[3,2-b]pyridin-7-amine hydrochloride |
| 81 | 2-[(2R)-2-amino-3-fluoropropyl]-5-chloro-N-[(furan-2-yl)methyl]-3-methylthieno[3,2-b]pyridin-7-amine dihydrochloride |
| 82 | 2-[(2S)-2-aminobutyl]-3,5-dichloro-N-[(1,3-thiazol-2-yl)methyl]thieno[3,2-b]pyridin-7-amine hydrochloride |
| 83 | 2-[(2S)-2-aminobutyl]-3,5-dichloro-N-[(thiophen-2-yl)methyl]thieno[3,2-b]pyridin-7-amine dihydrochloride |
| 85 | 2-[(2S)-2-aminobutyl]-5-chloro-3-methyl-N-[(1,3-thiazol-2-yl)methyl]thieno[3,2-b]pyridin-7-amine formate |
| 86 | 2-[(2S)-2-aminobutyl]-5-chloro-3-cyclopropyl-N-[(1,3-thiazol-2-yl)methyl]thieno[3,2-b]pyridin-7-amine hydrochloride |

| Cpd | Name |
|---|---|
| 87 | 2-[(2R)-2-amino-3-fluoropropyl]-5-chloro-3-cyclopropyl-N-[(1,3-thiazol-2-yl)methyl]thieno[3,2-b]pyridin-7-amine dihydrochloride |
| 88 | 2-[(2S)-2-amino-4-fluorobutyl]-3-bromo-5-chloro-N-[(1,3-thiazol-2-yl)methyl]thieno[3,2-b]pyridin-7-amine dihydrochloride |
| 89 | (3S)-3-amino-4-(3-bromo-5-chloro-7-{[(1,3-thiazol-2-yl)methyl]amino}thieno[3,2-b]pyridin-2-yl)butan-1-ol dihydrochloride |
| 90 | 2-[(2R)-2-amino-3-fluoropropyl]-3,5-dichloro-N-[(1,3-thiazol-2-yl)methyl]thieno[3,2-b]pyridin-7-amine dihydrochloride |
| 91 | 2-[(2R)-2-amino-3-fluoropropyl]-5-chloro-3-methyl-N-[(thiophen-2-yl)methyl]thieno[3,2-b]pyridin-7-amine dihydrochloride |
| 92 | 2-[(2S)-2-amino-4-fluorobutyl]-5-chloro-3-methyl-N-[(thiophen-2-yl)methyl]thieno[3,2-b]pyridin-7-amine dihydrochloride |
| 93 | 2-[(2S)-2-amino-4-fluorobutyl]-3,5-dichloro-N-[(furan-2-yl)methyl]thieno[3,2-b]pyridin-7-amine dihydrochloride |
| 94 | 2-[(2R)-2-amino-3-fluoropropyl]-3,5-dichloro-N-[(furan-2-yl)methyl]thieno[3,2-b]pyridin-7-amine dihydrochloride |
| 95 | 2-[(2S)-2-amino-4-fluorobutyl]-5-chloro-N-[(furan-2-yl)methyl]-3-methylthieno[3,2-b]pyridin-7-amine hydrochloride |
| 96 | 2-[(2S)-2-aminopropyl]-5-chloro-3-cyclopropyl-N-[(1,3-thiazol-2-yl)methyl]thieno[3,2-b]pyridin-7-amine hydrochloride |
| 97 | 2-[(2S)-2-amino-4-fluorobutyl]-3-bromo-5-chloro-N-[(furan-2-yl)methyl]thieno[3,2-b]pyridin-7-amine dihydrochloride |
| 98 | 2-[(2S)-2-amino-4-fluorobutyl]-3,5-dichloro-N-[(thiophen-2-yl)methyl]thieno[3,2-b]pyridin-7-amine dihydrochloride |
| 99 | 2-[(2S)-2-amino-4-fluorobutyl]-5-chloro-3-methyl-N-[(1,3-thiazol-2-yl)methyl]thieno[3,2-b]pyridin-7-amine formate |
| 100 | (3S)-3-amino-4-(3-bromo-5-chloro-7-{[(2-fluorophenyl)methyl]amino}thieno[3,2-b]pyridin-2-yl)butan-1-ol dihydrochloride |
| 101 | 2-[(2S)-2-aminopropyl]-3-bromo-7-{[(thiophen-2-yl)methyl]amino}thieno[3,2-b]pyridine-5-carbonitrile formate |
| 102 | 2-[(2S)-2-aminopropyl]-7-{[(thiophen-2-yl)methyl]amino}thieno[3,2-b]pyridine-3,5-dicarbonitrile formate |
| 103 | (3S)-3-amino-4-(3-bromo-5-chloro-7-{[(furan-2-yl)methyl]amino}thieno[3,2-b]pyridin-2-yl)butanenitrile formate |
| 104 | 2-[(2R)-2-amino-3-(methylsulfanyl)propyl]-5-chloro-N-[(furan-2-yl)methyl]-3-methylthieno[3,2-b]pyridin-7-amine dihydrochloride |
| 105 | (3S)-3-amino-4-(5-chloro-3-methyl-7-{[(thiophen-2-yl)methyl]amino}thieno[3,2-b]pyridin-2-yl)butanenitrile dihydrochloride |
| 106 | (3S)-3-amino-4-(3,5-dichloro-7-{[(thiophen-2-yl)methyl]amino}thieno[3,2-b]pyridin-2-yl)butanenitrile dihydrochloride |
| 107 | 2-[(2S)-2-amino-4,4-difluorobutyl]-3-bromo-5-chloro-N-[(thiophen-2-yl)methyl]thieno[3,2-b]pyridin-7-amine dihydrochloride |
| 109 | 2-[(2R)-2-amino-3-(methanesulfonyl)propyl]-5-chloro-N-[(furan-2-yl)methyl]-3-methylthieno[3,2-b]pyridin-7-amine dihydrochloride |
| 109 | 2-[(2S)-2-aminopropyl]-5-chloro-7-{[(furan-2-yl)methyl]amino}thieno[3,2-b]pyridine-3-carbonitrile formate |
| 110 | 2-[(2S)-2-aminopropyl]-5-chloro-7-{[(thiophen-2-yl)methyl]amino}thieno[3,2-b]pyridine-3-carbonitrile formate |
| 111 | (3S)-3-amino-4-(5-chloro-7-{[(furan-2-yl)methyl]amino}-3-methylthieno[3,2-b]pyridin-2-yl)butanenitrile dihydrochloride |
| 112 | 2-[(2S)-2-aminopropyl]-3-chloro-7-{[(thiophen-2-yl)methyl]amino}thieno[3,2-b]pyridine-5-carbonitrile formate |
| 113 | 2-[(2R)-2-amino-3-(methanesulfonyl)propyl]-3,5-dichloro-N-[(furan-2-yl)methyl]thieno[3,2-b]pyridin-7-amine dihydrochloride |
| 114 | 2-[(2R)-2-amino-3-(methylsulfanyl)propyl]-3,5-dichloro-N-[(furan-2-yl)methyl]thieno[3,2-b]pyridin-7-amine hydrochloride |
| 115 | 3-(5-chloro-7-{[(furan-2-yl)methyl]amino}-3-methylthieno[3,2-b]pyridin-2-yl)-D-alanine dihydrochloride |
| 116 | 3-(5-chloro-7-{[(furan-2-yl)methyl]amino}-3-methylthieno[3,2-b]pyridin-2-yl)-N,n-dimethyl-D-alaninamide dihydrochloride |
| 117 | 2-[(2R)-2-amino-3-(methanesulfonyl)propyl]-3-bromo-5-chloro-N-[(furan-2-yl)methyl]thieno[3,2-b]pyridin-7-amine dihydrochloride |
| 118 | 2-[(2R)-2-amino-3-(methylsulfanyl)propyl]-3-bromo-5-chloro-N-[(furan-2-yl)methyl]thieno[3,2-b]pyridin-7-amine dihydrochloride |
| 119 | 2-[(2R)-2-aminobut-3-en-1-yl]-5-chloro-N-[(furan-2-yl)methyl]thieno[3,2-b]pyridin-7-amine formate |
| 120 | 3-(3,5-dichloro-7-{[(furan-2-yl)methyl]amino}thieno[3,2-b]pyridin-2-yl)-N-(2-fluorophenyl)-D-alaninamide dihydrochloride |
| 121 | 3-(3,5-dichloro-7-{[(furan-2-yl)methyl]amino}thieno[3,2-b]pyridin-2-yl)-D-alanine dihydrochloride |
| 122 | 3-(3,5-dichloro-7-{[(furan-2-yl)methyl]amino}thieno[3,2-b]pyridin-2-yl)-N-phenyl-D-alaninamide hydrochloride |
| 123 | 2-[(2R)-2-aminobut-3-yn-1-yl]-3-methyl-5-chloro-N-[(furan-2-yl)methyl]thieno[3,2-b]pyridin-7-amine dihydrochloride |
| 124 | 3-(3,5-dichloro-7-{[(furan-2-yl)methyl]amino}thieno[3,2-b]pyridin-2-yl)-N-(2-fluorophenyl)-D-alaninamide dihydrochloride |

| Cpd | Name |
|---|---|
| 125 | 2-[(2R,3S)-2-amino-3-fluorobutyl]-3-bromo-5-chloro-N-[(1,3-thiazol-2-yl)methyl]thieno[3,2-b]pyridin-7-amine dihydrochloride |
| 126 | 2-[(2R,3S)-2-amino-3-fluorobutyl]-5-chloro-3-methyl-N-[(thiophen-2-yl)methyl]thieno[3,2-b]pyridin-7-amine dihydrochloride |
| 127 | (2S)-2-amino-1-(3,5-dichloro-7-{[(thiophen-2-yl)methyl]amino}thieno[3,2-b]pyridin-2-yl)propan-1-ol dihydrochloride |
| 128 | 2-[(2R,3S)-2-amino-3-fluorobutyl]-5-chloro-3-methyl-N-[(1,3-thiazol-2-yl)methyl]thieno[3,2-b]pyridin-7-amine dihydrochloride |
| 129 | 2-[(2S)-2-aminopropyl]-5-chloro-N-[(5-fluoro-1,3-thiazol-2-yl)methyl]-3-methylthieno[3,2-b]pyridin-7-amine dihydrochloride |
| 130 | 2-[(2S)-2-amino-1-fluoropropyl]-3,5-dichloro-N-[(thiophen-2-yl)methyl]thieno[3,2-b]pyridin-7-amine formate |
| 131 | methyl 3-(5-chloro-7-{[(furan-2-yl)methyl]amino}-3-methylthieno[3,2-b]pyridin-2-yl)-D-alaninate dihydrochloride |
| 133 | 3-(5-chloro-7-{[(furan-2-yl)methyl]amino}-3-methylthieno[3,2-b]pyridin-2-yl)-N-(4-cyanophenyl)-D-alaninamide hydrochloride |
| 134 | 3-(5-chloro-7-{[(furan-2-yl)methyl]amino}-3-methylthieno[3,2-b]pyridin-2-yl)-N-pyridin-2-yl-D-alaninamide hydrochloride |
| 135 | 3-(5-chloro-7-{[(furan-2-yl)methyl]amino}-3-methylthieno[3,2-b]pyridin-2-yl)-N-pyrazin-2-yl-D-alaninamide hydrochloride |
| 136 | 2-[(2S)-2-aminopropyl]-5-chloro-N-[(furan-2-yl)methyl]-3-methoxythieno[3,2-b]pyridin-7-amine dihydrochloride |
| 137 | 5-chloro-N-[(furan-2-yl)methyl]-3-methoxythieno[3,2-b]pyridin-7-amine hydrochloride |
| 138 | 5-chloro-7-{[(thiophen-2-yl)methyl]amino}thieno[3,2-b]pyridin-3-ol hydrochloride |
| 139 | 2-[(2S)-2-aminopropyl]-5-chloro-3-(difluoromethoxy)-N-[(thiophen-2-yl)methyl]thieno[3,2-b]pyridin-7-amine formate |
| 140 | 3-(5-chloro-7-{[(furan-2-yl)methyl]amino}-3-methylthieno[3,2-b]pyridin-2-yl)-N-pyridin-4-yl-D-alaninamide hydrochloride |
| 141 | 3-(5-chloro-7-{[(furan-2-yl)methyl]amino}-3-methylthieno[3,2-b]pyridin-2-yl)-N-methyl-N-phenyl-D-alaninamide hydrochloride |
| 142 | 3-(5-chloro-7-{[(furan-2-yl)methyl]amino}-3-methylthieno[3,2-b]pyridin-2-yl)-N-(4-methylphenyl)-D-alaninamide hydrochloride |
| 143 | 3-(5-chloro-7-{[(furan-2-yl)methyl]amino}-3-methylthieno[3,2-b]pyridin-2-yl)-N-(3-chlorophenyl)-D-alaninamide hydrochloride |
| 144 | 3-(5-chloro-7-{[(furan-2-yl)methyl]amino}-3-methylthieno[3,2-b]pyridin-2-yl)-N-(3-methoxyphenyl)-D-alaninamide hydrochloride |
| 145 | 3-(5-chloro-7-{[(furan-2-yl)methyl]amino}-3-methylthieno[3,2-b]pyridin-2-yl)-N-(1-methyl-1H-pyrazol-5-yl)-D-alaninamide hydrochloride |
| 148 | 2-(1-aminopropan-2-yl)-5-chloro-N-[(furan-2-yl)methyl]-3-methylthieno[3,2-b]pyridin-7-amine formate |
| 150 | 2-[(2R,3S)-3-aminobutan-2-yl]-5-chloro-N-[(furan-2-yl)methyl]-3-methylthieno[3,2-b]pyridin-7-amine dihydrochloride |
| 151 | 2-[(2S,3S)-3-aminobutan-2-yl]-5-chloro-N-[(furan-2-yl)methyl]-3-methylthieno[3,2-b]pyridin-7-amine dihydrochloride |
| 152 | 2-(2-aminoethyl)-5-chloro-N-[(furan-2-yl)methyl]-3-methylthieno[3,2-b]pyridin-7-amine formate |
| 153 | (2S)-2-amino-1-(3-bromo-5-chloro-7-{[(furan-2-yl)methyl]amino}thieno[3,2-b]pyridin-2-yl)propan-1-ol dihydrochloride |
| 154 | 2-[(2S)-2-amino-1-fluoropropyl]-3-bromo-5-chloro-N-[(furan-2-yl)methyl]thieno[3,2-b]pyridin-7-amine dihydrochloride |
| 155 | (2S)-2-amino-1-(3-bromo-5-chloro-7-{[(thiophen-2-yl)methyl]amino}thieno[3,2-b]pyridin-2-yl)propan-1-ol dihydrochloride |
| 156 | (2S)-2-amino-1-(3-bromo-5-chloro-7-{[(thiophen-2-yl)methyl]amino}thieno[3,2-b]pyridin-2-yl)propan-1-one dihydrochloride |
| 157 | (2S)-2-amino-1-(3-bromo-5-chloro-7-{[(furan-2-yl)methyl]amino}thieno[3,2-b]pyridin-2-yl)propan-1-one dihydrochloride |
| 158 | 2-[(2S)-2-amino-1-fluoropropyl]-3-bromo-5-chloro-N-[(thiophen-2-yl)methyl]thieno[3,2-b]pyridin-7-amine dihydrochloride |
| 159 | (2S)-2-amino-1-(3-bromo-5-chloro-7-{[(1,3-thiazol-2-yl)methyl]amino}thieno[3,2-b]pyridin-2-yl)propan-1-ol dihydrochloride |
| 160 | (2S)-2-amino-1-(3-bromo-5-chloro-7-{[(1,3-thiazol-2-yl)methyl]amino}thieno[3,2-b]pyridin-2-yl)propan-1-one dihydrochloride |
| 161 | 2-[(2S)-2-amino-1-fluoropropyl]-3-bromo-5-chloro-N-[(1,3-thiazol-2-yl)methyl]thieno[3,2-b]pyridin-7-amine dihydrochloride |
| 162 | (2R)-2-amino-3-(5-chloro-7-{[(thiophen-2-yl)methyl]amino}thieno[3,2-b]pyridin-2-yl)propan-1-ol formate |
| 163 | $N^2$-[(2S)-2-aminopropyl]-5-chloro-3-methyl-$N^7$-[(thiophen-2-yl)methyl]thieno[3,2-b]pyridine-2,7-diamine hydrochloride |
| 164 | $N^2$-[(2R)-2-aminopropyl]-5-chloro-3-methyl-$N^7$-[(thiophen-2-yl)methyl]thieno[3,2-b]pyridine-2,7-diamine hydrochloride |
| 165 | (2R,3R)-3-amino-4-(3-bromo-5-chloro-7-{[(furan-2-yl)methyl]amino}thieno[3,2-b]pyridin-2-yl)butan-2-ol hydrochloride, and |
| 166 | 2-[(2R)-2-aminobut-3-yn-1-yl]-3,5-dichloro-N-[(furan-2-yl)methyl]thieno[3,2-b]pyridin-7-amine dihydrochloride; | wherein the form of the compound is selected from the group consisting of a salt, hydrate, solvate, and tautomer.

The present application further provides a pharmaceutical composition comprising a compound provided herein, or a pharmaceutically acceptable salt thereof, and at least one pharmaceutically acceptable carrier.

The present application further provides a method of treating familial dysautonomia, a disease of the central and peripheral nervous system associated with one or more pre-mRNA splicing defects in a subject in need thereof, the method comprising administering to the subject a therapeutically effective amount of a compound provided herein, or a pharmaceutically acceptable salt thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used.

The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Chemical Definitions

The chemical terms used above and throughout the description herein, unless specifically defined otherwise, shall be understood by one of ordinary skill in the art to have the following indicated meanings.

As used herein, the term "$C_{1-6}$alkyl" generally refers to saturated hydrocarbon radicals having from one to eight carbon atoms in a straight or branched chain configuration, including, but not limited to, methyl, ethyl, n-propyl (also referred to as propyl or propanyl), isopropyl, n-butyl (also referred to as butyl or butanyl), isobutyl, sec-butyl, tert-butyl, n-pentyl (also referred to as pentyl or pentanyl), n-hexyl (also referred to as hexyl or hexanyl), and the like. In certain aspects, $C_{1-6}$alkyl includes, but is not limited to, $C_{1-6}$alkyl, $C_{1-4}$alkyl and the like. A $C_{1-6}$alkyl radical is optionally substituted with substituent species as described herein where allowed by available valences.

As used herein, the term "hetero-$C_{1-6}$alkyl" generally refers to saturated hydrocarbon radicals having from one to six carbon atoms in a straight or branched chain configuration, in which one or more heteroatoms, such as an O, S or N atom, are members in the chain, including, but not limited to, but not limited to, hetero-methyl, hetero-ethyl, hetero-propyl, hetero-butyl, hetero-pentyl, hetero-hexyl and the like. In certain aspects, hetero-$C_{1-6}$alkyl includes, but is not limited to, hetero-$C_{2-6}$alkyl, hetero-$C_{1-4}$alkyl, hetero-$C_{2-4}$alkyl and the like. A hetero-$C_{1-6}$alkyl radical is optionally substituted with substituent species as described herein where allowed by available valences.

As used herein, the term "$C_{2-6}$alkenyl" generally refers to partially unsaturated hydrocarbon radicals having from two to eight carbon atoms in a straight or branched chain configuration and one or more carbon-carbon double bonds therein, including, but not limited to, ethenyl (also referred to as vinyl), allyl, propenyl and the like. In certain aspects, $C_{2-6}$alkenyl includes, but is not limited to, $C_{2-6}$alkenyl, $C_{2-4}$alkenyl and the like. A $C_{2-6}$alkenyl radical is optionally substituted with substituent species as described herein where allowed by available valences.

As used herein, the term "$C_{2-6}$alkynyl" generally refers to partially unsaturated hydrocarbon radicals having from two to eight carbon atoms in a straight or branched chain configuration and one or more carbon-carbon triple bonds therein, including, but not limited to, ethynyl (also referred to as acetylenyl), propynyl, butynyl and the like. In certain aspects, $C_{2-6}$alkynyl includes, but is not limited to, $C_{2-6}$alkynyl, $C_{2-4}$alkynyl and the like. A $C_{2-6}$alkynyl radical is optionally substituted with substituent species as described herein where allowed by available valences.

As used herein, the term "$C_{1-6}$alkoxy" generally refers to saturated hydrocarbon radicals having from one to eight carbon atoms in a straight or branched chain configuration of the formula: —O—$C_{1-6}$alkyl, including, but not limited to, methoxy, ethoxy, n-propoxy, isopropoxy, n-butoxy, isobutoxy, sec-butoxy, tert-butoxy, n-pentoxy, n-hexoxy and the like. In certain aspects, $C_{1-6}$alkoxy includes, but is not limited to, $C_{1-6}$alkoxy, $C_{1-4}$alkoxy and the like. A $C_{1-6}$alkoxy radical is optionally substituted with substituent species as described herein where allowed by available valences.

As used herein, the term "oxo" refers to a radical of the formula: =O.

As used herein, the term "carboxyl" refers to a radical of the formula: —COOH, —C(O)OH or —CO$_2$H.

As used herein, the term "$C_{1-6}$alkoxy-carbonyl" refers to a radical of the formula: —COO—$C_{1-6}$alkyl, —C(O)O—$C_{1-6}$alkyl or —CO$_2$—$C_{1-6}$alkyl.

As used herein, the term "carbamoyl" refers to a radical of the formula: —C(O)NH$_2$.

As used herein, the term "$C_{3-10}$cycloalkyl" generally refers to a saturated or partially unsaturated monocyclic, bicyclic or polycyclic hydrocarbon radical, including, but not limited to, cyclopropyl, cyclobutyl, cyclopentyl, cyclohexyl, cyclohexenyl, cycloheptyl, cyclooctyl, 1H-indanyl, indenyl, tetrahydro-naphthalenyl and the like. In certain aspects, $C_{3-10}$cycloalkyl includes, but is not limited to, $C_{3-8}$cycloalkyl, $C_{5-8}$cycloalkyl, $C_{3-10}$cycloalkyl and the like. A $C_{3-10}$cycloalkyl radical is optionally substituted with substituent species as described herein where allowed by available valences.

As used herein, the term "aryl" generally refers to a monocyclic, bicyclic or polycyclic aromatic carbon atom ring structure radical, including, but not limited to, phenyl, naphthyl, anthracenyl, fluorenyl, azulenyl, phenanthrenyl and the like. An aryl radical is optionally substituted with substituent species as described herein where allowed by available valences.

As used herein, the term "heteroaryl" generally refers to a monocyclic, bicyclic or polycyclic aromatic carbon atom ring structure radical in which one or more carbon atom ring members have been replaced, where allowed by structural stability, with one or more heteroatoms, such as an O, S or N atom, including, but not limited to, furanyl, thiophenyl, pyrrolyl, pyrazolyl, imidazolyl, isoxazolyl, isothiazolyl, oxazolyl, 1,3-thiazolyl, triazolyl, oxadiazolyl, thiadiazolyl, tetrazolyl, pyridinyl, pyrimidinyl, pyrazinyl, pyridazinyl, triazinyl, indolyl, indazolyl, indolizinyl, isoindolyl, benzofuranyl, benzothiophenyl, benzoimidazolyl, 1,3-benzothiazolyl, 1,3-benzoxazolyl, purinyl, quinolinyl, isoquinolinyl, quinazolinyl, quinoxalinyl and the like. A heteroaryl radical is optionally substituted on a carbon or nitrogen atom ring member with substituent species as described herein where allowed by available valences.

In certain aspects, the nomenclature for a heteroaryl radical may differ, such as in non-limiting examples where furanyl may also be referred to as furyl, thiophenyl may also be referred to as thienyl, pyridinyl may also be referred to as pyridyl, benzothiophenyl may also be referred to as benzothienyl and 1,3-benzoxazolyl may also be referred to as 1,3-benzooxazolyl.

In certain other aspects, the term for a heteroaryl radical may also include other regioisomers, such as in non-limiting examples where the term pyrrolyl may also include 2H-pyrrolyl, 3H-pyrrolyl and the like, the term pyrazolyl may also include 1H-pyrazolyl and the like, the term imidazolyl may also include 1H-imidazolyl and the like, the term triazolyl may also include 1H-1,2,3-triazolyl and the like, the term oxadiazolyl may also include 1,2,4-oxadiazolyl, 1,3,4-oxadiazolyl and the like, the term tetrazolyl may also include 1H-tetrazolyl, 2H-tetrazolyl and the like, the term indolyl may also include 1H-indolyl and the like, the term indazolyl may also include 1H-indazolyl, 2H-indazolyl and the like, the term benzoimidazolyl may also include 1H-benzoimidazolyl and the term purinyl may also include 9H-purinyl and the like.

As used herein, the term "heterocyclyl" generally refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including, but not limited to, oxiranyl, oxetanyl, azetidinyl, tetrahydrofuranyl, pyrrolinyl, pyrrolidinyl, pyrazolinyl, pyrazolidinyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, pyranyl, dihydro-2H-pyranyl, tetrahydropyranyl, thiopyranyl, 1,3-dioxanyl, 1,3-oxazinanyl, 1,2,5,6-tetrahydropyridinyl, 1,2,3,6-tetrahydropyridinyl, piperidinyl, piperazinyl, morpholinyl, thiomorpholinyl, 1,4-diazepanyl, 1,3-benzodioxolyl, 1,4-benzodioxanyl and the like. A heterocyclyl radical is optionally substituted on a carbon or nitrogen atom ring member with substituent species as described herein where allowed by available valences.

As used herein, the term "$C_{1-6}$alkyl-amino" refers to a radical of the formula: —NH—$C_{1-6}$alkyl.

As used herein, the term "halo-$C_{1-6}$alkyl-amino" refers to a radical of the formula: —NH—$C_{1-6}$alkyl, wherein $C_{1-6}$alkyl is partially or completely substituted with one or more halogen atoms where allowed by available valences.

As used herein, the term "($C_{1-6}$alkyl)$_2$-amino" refers to a radical of the formula: —N($C_{1-6}$alkyl)$_2$.

As used herein, the term "$C_{1-6}$alkyl-carboxyl-amino" refers to a radical of the formula: —NH—C(O)—.

As used herein, the term "aryl-amino" refers to a radical of the formula: —NH-aryl.

As used herein, the term "heterocyclyl-amino" refers to a radical of the formula: —NH-heterocyclyl.

As used herein, the term "heteroaryl-amino" refers to a radical of the formula: —NH-heteroaryl.

As used herein, the term "aryl-($C_{1-6}$alkyl)-amino" refers to a radical of the formula: —N($C_{1-6}$alkyl)-aryl.

As used herein, the term "heterocyclyl-($C_{1-6}$alkyl)-amino" refers to a radical of the formula: —N($C_{1-6}$alkyl)-heterocyclyl.

As used herein, the term "heteroaryl-($C_{1-6}$alkyl)-amino" refers to a radical of the formula: —N($C_{1-6}$alkyl)-heteroaryl.

As used herein, the term "$C_{1-6}$alkyl-thio" refers to a radical of the formula: —S—$C_{1-6}$alkyl.

As used herein, the term "$C_{1-6}$alkyl-sulfoxyl" refers to a radical of the formula: —S(O)—$C_{1-6}$alkyl.

As used herein, the term "$C_{1-6}$alkyl-sulfonyl" refers to a radical of the formula: —SO$_2$—$C_{1-6}$alkyl.

As used herein, the term "halo" or "halogen" generally refers to a halogen atom radical, including fluoro, chloro, bromo and iodo.

As used herein, the term "halo-$C_{1-6}$alkoxy" refers to a radical of the formula: —O—$C_{1-6}$alkyl-halo, wherein $C_{1-6}$alkyl is partially or completely substituted with one or more halogen atoms where allowed by available valences.

As used herein, the term "halo-$C_{1-6}$alkyl" refers to a radical of the formula: —$C_{1-6}$alkyl-halo, wherein $C_{1-6}$alkyl is partially or completely substituted with one or more halogen atoms where allowed by available valences.

As used herein, the term "hydroxy" refers to a radical of the formula: —OH.

As used herein, the term "hydroxy-$C_{1-6}$alkyl" refers to a radical of the formula: —$C_{1-6}$alkyl-OH, wherein $C_{1-6}$alkyl is partially or completely substituted with one or more hydroxy radicals where allowed by available valences.

As used herein, the term "substituent" means positional variables on the atoms of a core molecule that are substituted at a designated atom position, replacing one or more hydrogens on the designated atom, provided that the designated atom's normal valency is not exceeded, and that the substitution results in a stable compound. Combinations of substituents and/or variables are permissible only if such combinations result in stable compounds. A person of ordinary skill in the art should note that any carbon as well as heteroatom with valences that appear to be unsatisfied as described or shown herein is assumed to have a sufficient number of hydrogen atom(s) to satisfy the valences described or shown. In certain instances, one or more substituents having a double bond (e.g., "oxo" or "=O") as the point of attachment may be described, shown or listed herein within a substituent group, wherein the structure may only show a single bond as the point of attachment to the core structure of Formula (I). A person of ordinary skill in the art would understand that, while only a single bond is shown, a double bond is intended for those substituents.

As used herein, the term "and the like," with reference to the definitions of chemical terms provided herein, means that variations in chemical structures that could be expected by one skilled in the art include, without limitation, isomers (including chain, branching or positional structural isomers), hydration of ring systems (including saturation or partial unsaturation of monocyclic, bicyclic or polycyclic ring structures) and all other variations where allowed by available valences which result in a stable compound.

For the purposes of this description, where one or more substituent variables for a compound of Formula (I) or a form thereof encompass functionalities incorporated into a compound of Formula (I), each functionality appearing at any location within the disclosed compound may be independently selected, and as appropriate, independently and/or optionally substituted.

As used herein, the terms "independently selected," or "each selected" refer to functional variables in a substituent list that may occur more than once on the structure of Formula (I), the pattern of substitution at each occurrence is independent of the pattern at any other occurrence. Further, the use of a generic substituent variable on any formula or structure for a compound described herein is understood to include the replacement of the generic substituent with species substituents that are included within the particular genus, e.g., aryl may be replaced with phenyl or naphthalenyl and the like, and that the resulting compound is to be included within the scope of the compounds described herein.

As used herein, the terms "each instance of" or "in each instance, when present," when used preceding a phrase such as " . . . $C_{3-10}$cycloalkyl, $C_{3-10}$cycloalkyl-$C_{1-4}$alkyl, aryl, aryl-$C_{1-4}$alkyl, heteroaryl, heteroaryl-$C_{1-4}$alkyl, heterocyclyl and heterocyclyl-$C_{1-4}$alkyl," are intended to refer to the $C_{3-10}$cycloalkyl, aryl, heteroaryl and heterocyclyl ring systems when each are present either alone or as a substituent.

As used herein, the term "optionally substituted" means optional substitution with the specified substituent variables, groups, radicals or moieties.

Compound Forms

As used herein, the term "form" means a compound of Formula (I) having a form selected from the group consisting of a free acid, free base, salt, hydrate, solvate, racemate, enantiomer, diastereomer, stereoisomer, and tautomer form thereof.

In certain aspects described herein, the form of the compound of Formula (I) is a free acid, free base or salt thereof.

In certain aspects described herein, the form of the compound of Formula (I) is a salt thereof.

In certain aspects described herein, the form of the compound of Formula (I) is a stereoisomer, racemate, enantiomer or diastereomer thereof.

In certain aspects described herein, the form of the compound of Formula (I) is a tautomer thereof.

In certain aspects described herein, the form of the compound of Formula (I) is a pharmaceutically acceptable form.

In certain aspects described herein, the compound of Formula (I) or a form thereof is isolated for use.

As used herein, the term "isolated" means the physical state of a compound of Formula (I) or a form thereof after being isolated and/or purified from a synthetic process (e.g., from a reaction mixture) or natural source or combination thereof according to an isolation or purification process or processes described herein or which are well known to the skilled artisan (e.g., chromatography, recrystallization and the like) in sufficient purity to be characterized by standard analytical techniques described herein or well known to the skilled artisan.

As used herein, the term "protected" means that a functional group in a compound of Formula (I) or a form thereof is in a form modified to preclude undesired side reactions at the protected site when the compound is subjected to a reaction. Suitable protecting groups will be recognized by those with ordinary skill in the art as well as by reference to standard textbooks such as, for example, T. W. Greene et al, Protective Groups in organic Synthesis (1991), Wiley, New York. Such functional groups include hydroxy, phenol, amino and carboxylic acid. Suitable protecting groups for hydroxy or phenol include trialkylsilyl or diarylalkylsilyl (e.g., t-butyldimethylsilyl, t-butyldiphenylsilyl or trimethylsilyl), tetrahydropyranyl, benzyl, substituted benzyl, methyl, methoxymethanol, and the like. Suitable protecting groups for amino, amidino and guanidino include t-butoxycarbonyl, benzyloxycarbonyl, and the like. Suitable protecting groups for carboxylic acid include alkyl, aryl or arylalkyl esters. In certain instances, the protecting group may also be a polymer resin, such as a Wang resin or a 2-chlorotrityl-chloride resin. Protecting groups may be added or removed in accordance with standard techniques, which are well-known to those skilled in the art and as described herein. It will also be appreciated by those skilled in the art, although such protected derivatives of compounds described herein may not possess pharmacological activity as such, they may be administered to a subject and thereafter metabolized in the body to form compounds described herein which are pharmacologically active. Such derivatives may therefore be described as "prodrugs". All prodrugs of compounds described herein are included within the scope of the use described herein.

As used herein, the term "prodrug" means a form of an instant compound (e.g., a drug precursor) that is transformed in vivo to yield an active compound of Formula (I) or a form thereof. The transformation may occur by various mechanisms (e.g., by metabolic and/or non-metabolic chemical processes), such as, for example, by hydrolysis and/or metabolism in blood, liver and/or other organs and tissues. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

In one example, when a compound of Formula (I) or a form thereof contains a carboxylic acid functional group, a prodrug can comprise an ester formed by the replacement of the hydrogen atom of the acid group with a functional group such as alkyl and the like. In another example, when a compound of Formula (I) or a form thereof contains a hydroxyl functional group, a prodrug form can be prepared by replacing the hydrogen atom of the hydroxyl with another functional group such as alkyl, alkylcarbonyl or a phosphonate ester and the like. In another example, when a compound of Formula (I) or a form thereof contains an amine functional group, a prodrug form can be prepared by replacing one or more amine hydrogen atoms with a functional group such as alkyl or substituted carbonyl. Pharmaceutically acceptable prodrugs of compounds of Formula (I) or a form thereof include those compounds substituted with one or more of the following groups: carboxylic acid esters, sulfonate esters, amino acid esters, phosphonate esters and mono-, di- or triphosphate esters or alkyl substituents, where appropriate. As described herein, it is understood by a person of ordinary skill in the art that one or more of such substituents may be used to provide a compound of Formula (I) or a form thereof as a prodrug.

One or more compounds described herein may exist in unsolvated as well as solvated forms with pharmaceutically acceptable solvents such as water, ethanol, and the like, and the description herein is intended to embrace both solvated and unsolvated forms.

As used herein, the term "solvate" means a physical association of a compound described herein with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. As used herein, "solvate" encompasses both solution-phase and isolatable solvates. Non-limiting examples of suitable solvates include ethanolates, methanolates, and the like.

As used herein, the term "hydrate" means a solvate wherein the solvent molecule is water.

The compounds of Formula (I) can form salts, which are intended to be included within the scope of this description. Reference to a compound of Formula (I) or a form thereof herein is understood to include reference to salt forms thereof, unless otherwise indicated. The term "salt(s)", as employed herein, denotes acidic salts formed with inorganic and/or organic acids, as well as basic salts formed with inorganic and/or organic bases. In addition, when a compound of Formula (I) or a form thereof contains both a basic moiety, such as, without limitation an amine moiety, and an acidic moiety, such as, but not limited to a carboxylic acid, zwitterions ("inner salts") may be formed and are included within the term "salt(s)" as used herein.

The term "pharmaceutically acceptable salt(s)", as used herein, means those salts of compounds described herein that are safe and effective (i.e., non-toxic, physiologically acceptable) for use in mammals and that possess biological activity, although other salts are also useful. Salts of the compounds of the Formula (I) may be formed, for example, by reacting a compound of Formula (I) or a form thereof with an amount of acid or base, such as an equivalent amount, in a medium such as one in which the salt precipitates or in an aqueous medium followed by lyophilization.

Pharmaceutically acceptable salts include one or more salts of acidic or basic groups present in compounds described herein. Particular aspects of acid addition salts include, and are not limited to, acetate, ascorbate, benzoate, benzenesulfonate, bisulfate, bitartrate, borate, bromide, butyrate, chloride, citrate, camphorate, camphorsulfonate, ethanesulfonate, formate, fumarate, gentisinate, gluconate, glucaronate, glutamate, iodide, isonicotinate, lactate, maleate, methanesulfonate, naphthalenesulfonate, nitrate, oxalate, pamoate, pantothenate, phosphate, propionate, saccharate, salicylate, succinate, sulfate, tartrate, thiocyanate, toluenesulfonate (also known as tosylate), trifluoroacetate salts and the like. Certain particular aspects of acid addition salts include chloride or dichloride.

Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33, 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Suitable basic salts include, but are not limited to, aluminum, ammonium, calcium, lithium, magnesium, potassium, sodium and zinc salts.

All such acid salts and base salts are intended to be included within the scope of pharmaceutically acceptable salts as described herein. In addition, all such acid and base salts are considered equivalent to the free forms of the corresponding compounds for purposes of this description.

Compounds of Formula (I) and forms thereof, may further exist in a tautomeric form. All such tautomeric forms are contemplated and intended to be included within the scope of the compounds of Formula (I) or a form thereof as described herein.

The compounds of Formula (I) or a form thereof may contain asymmetric or chiral centers, and, therefore, exist in different stereoisomeric forms. The present description is intended to include all stereoisomeric forms of the compounds of Formula (I) as well as mixtures thereof, including racemic mixtures.

The compounds described herein may include one or more chiral centers, and as such may exist as racemic mixtures (R/S) or as substantially pure enantiomers and diastereomers. The compounds may also exist as substantially pure (R) or (S) enantiomers (when one chiral center is present). In one particular aspect, the compounds described herein are (S) isomers and may exist as enantiomerically pure compositions substantially comprising only the (S) isomer. In another particular aspect, the compounds described herein are (R) isomers and may exist as enantiomerically pure compositions substantially comprising only the (R) isomer. As one of skill in the art will recognize, when more than one chiral center is present, the compounds described herein may also exist as a (R,R), (R,S), (S,R) or (S,S) isomer, as defined by IUPAC Nomenclature Recommendations.

As used herein, the term "chiral" refers to a carbon atom bonded to four nonidentical substituents. Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog. (Cahn et al. Angew. Chem. Inter. Edit. 1966, 5, 385; errata 511).

As used herein, the term "substantially pure" refers to compounds consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

In one aspect of the description, a compound of Formula (I) or a form thereof is a substantially pure (S) enantiomer form present in an amount greater than or equal to 90%, in an amount greater than or equal to 92%, in an amount greater than or equal to 95%, in an amount greater than or equal to 98%, in an amount greater than or equal to 99%, or in an amount equal to 100%.

In one aspect of the description, a compound of Formula (I) or a form thereof is a substantially pure (R) enantiomer form present in an amount greater than or equal to 90%, in an amount greater than or equal to 92%, in an amount greater than or equal to 95%, in an amount greater than or equal to 98%, in an amount greater than or equal to 99%, or in an amount equal to 100%.

As used herein, a "racemate" is any mixture of isometric forms that are not "enantiomerically pure", including mixtures such as, without limitation, in a ratio of about 50/50, about 60/40, about 70/30, or about 80/20.

In addition, the present description embraces all geometric and positional isomers. For example, if a compound of Formula (I) or a form thereof incorporates a double bond or a fused ring, both the cis- and trans-forms, as well as mixtures, are embraced within the scope of the description. Diastereomeric mixtures can be separated into their individual diastereomers on the basis of their physical chemical differences by methods well known to those skilled in the art, such as, for example, by chromatography and/or fractional crystallization. Enantiomers can be separated by use of chiral HPLC column or other chromatographic methods known to those skilled in the art. Enantiomers can also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this description.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this description, as are positional isomers (such as, for example, 4-pyridyl and 3-pyridyl). Individual stereoisomers of the compounds described herein may, for example, be substantially free of other isomers, or may be present in a racemic mixture, as described supra.

The use of the terms "salt", "solvate", "ester", "prodrug" and the like, is intended to equally apply to the salt, solvate, ester and prodrug of enantiomers, stereoisomers, rotamers, tautomers, positional isomers, racemates or isotopologues of the instant compounds.

The term "isotopologue" refers to isotopically-enriched compounds described herein which are identical to those recited herein, but for the fact that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, $^{35}$Cl and $^{36}$Cl, respectively, each of which are also within the scope of this description.

Certain isotopically-enriched compounds described herein (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances.

Compound Uses

Provided herein are methods of treating a disease in a subject in need thereof. As used herein, the term "subject," refers to any animal, including mammals. For example, mice, rats, other rodents, rabbits, dogs, cats, swine, cattle, sheep, horses, primates, and humans. In some aspects, the subject is a human. In some aspects, the method comprises administering to the subject a therapeutically effective amount of a compound provided herein (e.g., a compound of Formula (I)), or a pharmaceutically acceptable salt thereof. In a particular aspect, the disease is familial dysautonomia, a disease of the central and peripheral nervous system associated with one or more pre-mRNA splicing defects.

The present application further provides a method of treating familial dysautonomia in a subject in need thereof, comprising administering to the subject a therapeutically effective amount of a compound provided herein (i.e., a compound of Formula (I)).

In some aspects of the methods provided herein, the compound is selected from the group of compounds of Formula (I), or a pharmaceutically acceptable salt thereof.

In some aspects, the method of improving pre-mRNA splicing of the IKBKAP gene comprises contacting the gene (e.g., in a cell or subject expressing the gene) with a compound provided herein (e.g., a compound of Formula (I)).

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some aspects, the dosage of the compound, or a pharmaceutically acceptable salt thereof, administered to a subject or individual is about 1 mg to about 2 g, about 1 mg to about 1000 mg, about 1 mg to about 500 mg, about 1 mg to about 100 mg, about 1 mg to 50 mg, or about 50 mg to about 500 mg.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

Also provided herein are methods for increasing IKBKAP (also referred to as ELP1) protein expression in a patient in need thereof, the method comprising administering an effective amount of a compound provide herein, (i.e., a compound of Formula (I), or a pharmaceutically acceptable salt thereof), to the patient. For example, such methods include increasing IKBKAP protein expression in serum samples from the patient. Further provided herein are methods for increasing the mean percentage of IKBKAP protein expression in a patient in need thereof, the method comprising administering an effective amount of a compound provided herein (i.e., a compound of Formula (I), or a pharmaceutically acceptable salt thereof, to the patient.

Also provided herein are methods for increasing IKBKAP protein expression in a cell (e.g., ex vivo or in vivo), the method comprising contacting the cell with a therapeutically effective amount of a compound provided herein, (i.e., a compound of Formula (I), or a pharmaceutically acceptable salt thereof). In some aspects the method is an in vitro method. In some aspects, the method is an in vivo method. In some aspects, the amount IKBKAP protein expression is increased in a cell selected from the group consisting of a lung cell, a muscle cell, a liver cell, a heart cell, a brain cell, a kidney cell, and a nerve cell (e.g., a sciatic nerve cell or a trigeminal nerve cell), or any combination thereof. In some aspects thereof, the amount of IKBKAP protein expression is increased in plasma.

Also provided herein are methods for increasing IKBKAP protein level in a patient in need thereof, the method comprising administering an effective amount of a compound provide herein, (i.e., a compound of Formula (I), or a pharmaceutically acceptable salt thereof), to the patient. For example, such methods include increasing IKBKAP protein level in serum samples from the patient. Further provided herein are methods for increasing the mean percentage of IKBKAP protein level in a patient in need thereof, the method comprising administering an effective amount of a compound provided herein (i.e., a compound of Formula (I), or a pharmaceutically acceptable salt thereof, to the patient.

Also provided herein are methods for increasing IKBKAP protein level in a cell (e.g., ex vivo or in vivo), the method comprising contacting the cell with a therapeutically effective amount of a compound provided herein, (i.e., a compound of Formula (I), or a pharmaceutically acceptable salt thereof).

In some aspects, the method is an in vitro method. In some aspects, the method is an in vivo method. In some aspects, the amount IKBKAP protein level is increased in a cell selected from the group consisting of a lung cell, a muscle cell, a liver cell, a heart cell, a brain cell, a kidney cell, and a nerve cell (e.g., a sciatic nerve cell or a trigeminal nerve cell), or any combination thereof. In some aspects thereof, the amount of IKBKAP protein level is increased in plasma.

Also provided herein are methods for increasing full-length IKBKAP mRNA in a patient in need thereof, the method comprising administering an effective amount of a compound provided herein, (i.e., a compound of Formula (I), or a pharmaceutically acceptable salt thereof), to the patient. For example, such methods include increasing full-length IKBKAP mRNA concentration in serum samples from the patient. Further provided herein are methods for increasing the mean percentage exon inclusion (i.e. the percentage of correctly spliced or full-length IKBKAP mRNA) in a patient in need thereof, the method comprising administering an effective amount of a compound provided herein (i.e., a compound of Formula (I), or a pharmaceutically acceptable salt thereof, to the patient.

In some aspects, full-length IKBKAP mRNA can be measured in the serum, for example, in blood samples obtained from the patient prior to administration of a compound as provided herein and in blood samples obtained from the patient following administration of a compound as provided herein. In some aspects, the blood samples obtained from the patient following administration are obtained after one day, two days, three days, four days, five days, six days, seven days, eight days, nine days, ten days, fourteen days, twenty-one days, twenty-eight days, and/or thirty days of administration of the compound as provided herein. See, for example, F. B. Axelrod et al., Pediatr Res (2011) 70(5): 480-483; and R. S. Shetty et al., Human Molecular Genetics (2011) 20(21): 4093-4101, both of which are incorporated by reference in their entirety.

Further provided herein is a method of increasing full-length IKBKAP mRNA in a cell, the method comprising contacting the cell with a therapeutically effective amount of a compound provided herein (i.e., a compound of Formula (I)). The amount of full-length IKBKAP mRNA in the treated cell is increased relative to a cell in a subject in the absence of a compound provided herein. The method of increasing the amount of full-length IKBKAP mRNA in a cell may be performed by contacting the cell with a compound provided herein (i.e., a compound of Formula (I), or a pharmaceutically acceptable salt form thereof), in vitro, thereby increasing the amount full-length IKBKAP mRNA of a cell in vitro. Uses of such an in vitro method of increasing the amount of full-length IKBKAP mRNA include, but are not limited to, use in a screening assay (for example, wherein a compound provided herein is used as a positive control or standard compared to a compound or compounds of unknown activity or potency in increasing the amount full-length IKBKAP mRNA).

In some aspects, the amount of full-length IKBKAP mRNA is increased in a cell selected from the group consisting of a lung cell, a muscle cell, a liver cell, a heart cell, a brain cell, a kidney cell, and a nerve cell (e.g., a sciatic nerve cell or a trigeminal nerve cell), or any combination thereof. In some aspects thereof, the amount of full-length IKBKAP mRNA is increased in plasma.

The method of increasing full-length IKBKAP mRNA in a cell may be performed, for example, by contacting a cell, (e.g., a lung cell, a muscle cell, a liver cell, a heart cell, a brain cell, a kidney cell, or a nerve cell), with a compound provided herein (i.e. a compound of Formula (I), or a pharmaceutically acceptable salt thereof), in vivo, thereby increasing the amount of full-length IKBKAP mRNA in a subject in vivo. The contacting is achieved by causing a compound provided herein, or a pharmaceutically acceptable salt form thereof, to be present in a subject in an amount effective to achieve an increase in the amount of full-length IKBKAP mRNA. This may be achieved, for example, by administering an effective amount of a compound provided herein, or a pharmaceutically acceptable salt form thereof, to a subject. Uses of such an in vivo method of increasing the amount of full-length IKBKAP mRNA include, but are not limited to, use in methods of treating a disease or condition, wherein an increase in the amount of full-length IKBKAP mRNA is beneficial.

In some aspects thereof, the amount of full-length IKBKAP mRNA is increased in a cell selected from the group consisting of a lung cell, a muscle cell, a liver cell, a heart cell, a brain cell, a kidney cell, and a nerve cell (e.g., a sciatic nerve cell or a trigeminal nerve cell), or any combination thereof, for example in a patient suffering from a disease or disorder provided herein (e.g., familial dysautonomia). The method is preferably performed by administering an effective amount of a compound provided herein, or a pharmaceutically acceptable salt form thereof, to a subject who is suffering from familial dysautonomia.

In some aspects, one or more of the compounds provided herein may be administered to a subject in need thereof in combination with at least one additional pharmaceutical agent. In some embodiments, the additional pharmaceutical agent is a compound provided herein (e.g., a compound of Formula (I)).

Additional examples of suitable additional pharmaceutical agents for use in combination with the compounds of the present application for treatment of the diseases provided herein include, but are not limited to, antioxidants, anti-inflammatory agents, steroids, immunosuppressants, or other agents such as therapeutic antibodies. In some aspects, the compounds provided herein may be administered to a subject in need thereof in combination with at least one additional pharmaceutical agent for the treatment of familial dysautonomia. In some embodiments, the additional pharmaceutical agent is phosphatidylserine.

When employed as a therapeutic agent, the compounds provided herein can be administered in the form of a pharmaceutical composition; thus, the methods described herein can include administering a pharmaceutical composition. These compositions can be prepared as described herein or elsewhere, and can be administered by a variety of routes, depending upon whether local or systemic treatment is desired and upon the area to be treated. Administration may be pulmonary (e.g., by inhalation or insufflation of powders or aerosols, including by nebulizer; intratracheal or intranasal), oral, or parenteral. Parenteral administration may include, but is not limited to intravenous, intraarterial, subcutaneous, intraperitoneal, intramuscular injection or infusion; or intracranial, (e.g., intrathecal, intraocular, or intraventricular) administration. Parenteral administration can be in the form of a single bolus dose, or may be, for example, by a continuous perfusion pump. Conventional pharmaceutical carriers, aqueous, powder or oily bases, thickeners and the like may be necessary or desirable. In some aspects, the compounds provided herein are suitable for oral and parenteral administration. In some aspects, the compounds provided herein are suitable for oral administration. In some aspects, the compounds provided herein are suitable for parenteral administration. In some aspects, the compounds provided herein are suitable for intravenous administration. In some aspects, the compounds provided herein are suitable for transdermal administration (e.g., administration using a patch or microneedle). Pharmaceutical compositions for topical administration may include transdermal patches (e.g., normal or electrostimulated), ointments, lotions, creams, gels, drops, suppositories, sprays, liquids and powders. Conventional pharmaceutical carriers, aqueous, powder or oily bases, thickeners and the like may be necessary or desirable.

Also provided are pharmaceutical compositions which contain, as the active ingredient, a compound provided herein (e.g., a compound of Formula (I)), or a pharmaceutically acceptable salt thereof, in combination with one or more pharmaceutically acceptable carriers (excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active compound can be effective over a wide dosage range and is generally administered in a pharmaceutically effective amount. It will be understood, that the amount of compound to be administered and the schedule of administration will usually be determined by a physician, according to the relevant circumstances, including the condition to be treated, the chosen route of administration, the actual compound administered, the age, weight, and response of the individual subject, the severity of the subject's symptoms, and the like.

Also provided herein are kits including a compound provided herein, more particularly to a compound of Formula (I), or a pharmaceutically acceptable salt thereof. In some embodiments, a kit can include one or more delivery systems, e.g., for a compound provided herein, or a pharmaceutically acceptable salt thereof, and directions for use of the kit (e.g., instructions for treating a subject). In some embodiments, a kit can include a compound provided herein, or a pharmaceutically acceptable salt thereof, and one or more additional agents as provided herein.

In some aspects, the kit can include one or more compounds or additional pharmaceutical agents as provided herein, or a pharmaceutically acceptable salt thereof, and a label that indicates that the contents are to be administered to a subject resistant to a standard of care agent or adjuvant used for the treatment of familial dysautonomia. In some aspects, the additional pharmaceutical agent is phosphatidylserine. In another aspect, the kit can include a compound provided herein, or a pharmaceutically acceptable salt thereof, and a label that indicates that the contents are to be administered to a subject with cells expressing abnormal IKBKAP pre-mRNA splicing. In another aspect, the kit can include one or more compounds or additional pharmaceutical agents as provided herein, or a pharmaceutically acceptable salt thereof, and a label that indicates that the contents are to be administered to a subject having a disease of the central nervous system or peripheral nervous system resulting from abnormal pre-mRNA splicing.

In another aspect, the kit can include one or more compounds or additional pharmaceutical agents as provided herein, or a pharmaceutically acceptable salt thereof, and a label that indicates that the contents are to be administered to a subject having familial dysautonomia. In some aspects, a kit can include one or more compounds as provided herein, or a pharmaceutically acceptable salt thereof and a label that indicates that the contents are to be administered with one or more additional pharmaceutical agents as provided herein.

In another aspect, the concentration-biological effect relationship observed with regard to a compound of Formula (I) or a form thereof indicate a target plasma concentration ranging from approximately 0.001 µg·hr/mL to approximately 50 µg·hr/mL, from approximately 0.01 µg·hr/mL to approximately 20 µg·hr/mL, from approximately 0.05 µg·hr/mL to approximately 10 µg·hr/mL, or from approximately 0.1 µg·hr/mL to approximately 5 µg·hr/mL. To achieve such plasma concentrations, the compounds described herein may be administered at doses that vary, such as, for example, without limitation, from 1.0 ng to 10,000 mg.

In one aspect, the dose administered to achieve an effective target plasma concentration may be administered based upon subject or patient specific factors, wherein the doses administered on a weight basis may be in the range of from about 0.001 mg/kg/day to about 3500 mg/kg/day, or about 0.001 mg/kg/day to about 3000 mg/kg/day, or about 0.001 mg/kg/day to about 2500 mg/kg/day, or about 0.001 mg/kg/day to about 2000 mg/kg/day, or about 0.001 mg/kg/day to about 1500 mg/kg/day, or about 0.001 mg/kg/day to about 1000 mg/kg/day, or about 0.001 mg/kg/day to about 500 mg/kg/day, or about 0.001 mg/kg/day to about 250 mg/kg/day, or about 0.001 mg/kg/day to about 200 mg/kg/day, or about 0.001 mg/kg/day to about 150 mg/kg/day, or about 0.001 mg/kg/day to about 100 mg/kg/day, or about 0.001 mg/kg/day to about 75 mg/kg/day, or about 0.001 mg/kg/day to about 50 mg/kg/day, or about 0.001 mg/kg/day to about 25 mg/kg/day, or about 0.001 mg/kg/day to about 10 mg/kg/day, or about 0.001 mg/kg/day to about 5 mg/kg/day, or about 0.001 mg/kg/day to about 1 mg/kg/day, or about 0.001 mg/kg/day to about 0.5 mg/kg/day, or about 0.001 mg/kg/day to about 0.1 mg/kg/day, or from about 0.01 mg/kg/day to about 3500 mg/kg/day, or about 0.01 mg/kg/day to about 3000 mg/kg/day, or about 0.01 mg/kg/day to about 2500 mg/kg/day, or about 0.01 mg/kg/day to about 2000 mg/kg/day, or about 0.01 mg/kg/day to about 1500 mg/kg/day, or about 0.01 mg/kg/day to about 1000 mg/kg/day, or about 0.01 mg/kg/day to about 500 mg/kg/day, or about 0.01 mg/kg/day to about 250 mg/kg/day, or about 0.01 mg/kg/day to about 200 mg/kg/day, or about 0.01 mg/kg/day to about 150 mg/kg/day, or about 0.01 mg/kg/day to about 100 mg/kg/day, or about 0.01 mg/kg/day to about 75 mg/kg/day, or about 0.01 mg/kg/day to about 50 mg/kg/day, or about 0.01 mg/kg/day to about 25 mg/kg/day, or about 0.01 mg/kg/day to about 10 mg/kg/day, or about 0.01 mg/kg/day to about 5 mg/kg/day, or about 0.01 mg/kg/day to about 1 mg/kg/day, or about 0.01 mg/kg/day to about 0.5 mg/kg/day, or about 0.01 mg/kg/day to about 0.1 mg/kg/day, or from about 0.1 mg/kg/day to about 3500 mg/kg/day, or about 0.1 mg/kg/day to about 3000 mg/kg/day, or about 0.1 mg/kg/day to about 2500 mg/kg/day, or about 0.1 mg/kg/day to about 2000 mg/kg/day, or about 0.1 mg/kg/day to about 1500 mg/kg/day, or about 0.1 mg/kg/day to about 1000 mg/kg/day, or about 0.1 mg/kg/day to about 500 mg/kg/day, or about 0.1 mg/kg/day to about 250 mg/kg/day, or about 0.1 mg/kg/day to about 200 mg/kg/day, or about 0.1 mg/kg/day to about 150 mg/kg/day, or about 0.1 mg/kg/day to about 100 mg/kg/day, or about 0.1 mg/kg/day to about 75 mg/kg/day, or about 0.1 mg/kg/day to about 50 mg/kg/day, or about 0.1 mg/kg/day to about 25 mg/kg/day, or about 0.1 mg/kg/day to about 10 mg/kg/day, or about 0.1 mg/kg/day to about 5 mg/kg/day, or about 0.1 mg/kg/day to about 1 mg/kg/day, or about 0.1 mg/kg/day to about 0.5 mg/kg/day.

Effective amounts for a given subject may be determined by routine experimentation that is within the skill and judgment of a clinician or a practitioner skilled in the art in light of factors related to the subject. Dosage and administration may be adjusted to provide sufficient levels of the active agent(s) or to maintain the desired effect. Factors which may be taken into account include genetic screening, severity of the disease state, status of disease progression, general health of the subject, ethnicity, age, weight, gender, diet, time of day and frequency of administration, drug combination(s), reaction sensitivities, experience with other therapies, and tolerance/response to therapy.

The dose administered to achieve an effective target plasma concentration may be orally administered once (once in approximately a 24 hour period; i.e., "q.d."), twice (once in approximately a 12 hour period; i.e., "b.i.d." or "q.12 h"), thrice (once in approximately an 8 hour period; i.e., "t.i.d." or "q.8 h"), or four times (once in approximately a 6 hour period; i.e., "q.d.s.", "q.i.d." or "q.6 h") daily.

In certain aspects, the dose administered to achieve an effective target plasma concentration may also be administered in a single, divided, or continuous dose for a patient or subject having a weight in a range of between about 40 to about 200 kg (which dose may be adjusted for patients or subjects above or below this range, particularly children under 40 kg). The typical adult subject is expected to have a median weight in a range of about 70 kg. Long-acting pharmaceutical compositions may be administered every 2, 3 or 4 days, once every week, or once every two weeks depending on half-life and clearance rate of the particular formulation.

The compounds and compositions described herein may be administered to the subject via any drug delivery route known in the art. Nonlimiting examples include oral, ocular, rectal, buccal, topical, nasal, sublingual, transdermal, subcutaneous, intramuscular, intraveneous (bolus and infusion), intracerebral, and pulmonary routes of administration.

In another aspect, the dose administered may be adjusted based upon a dosage form described herein formulated for delivery at about 0.02, 0.025, 0.03, 0.05, 0.06, 0.075, 0.08, 0.09, 0.10, 0.20, 0.25, 0.30, 0.50, 0.60, 0.75, 0.80, 0.90, 1.0, 1.10, 1.20, 1.25, 1.50, 1.75, 2.0, 3.0, 5.0, 10, 20, 30, 40, 50, 100, 150, 200, 250, 300, 400, 500, 1000, 1500, 2000, 2500, 3000 or 4000 mg/day.

For any compound, the effective amount can be estimated initially either in cell culture assays or in relevant animal models, such as a mouse, guinea pig, chimpanzee, marmoset or tamarin animal model. Relevant animal models may also be used to determine the appropriate concentration range and route of administration. Such information can then be used to determine useful doses and routes for administration in humans. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is therapeutic index, and can be expressed as the ratio, $LD_{50}/ED_{50}$. In certain aspects, the effective amount is such that a large therapeutic index is achieved. In further particular aspects, the dosage is within a range of circulating concentrations that include an $ED_{50}$ with little or no toxicity. The dosage may vary within this range depending upon the dosage form employed, sensitivity of the patient, and the route of administration.

Another aspect included within the scope of the present description are the use of in vivo metabolic products of the compounds described herein. Such products may result, for example, from the oxidation, reduction, hydrolysis, amidation, esterification and the like of the administered compound, primarily due to enzymatic processes. Accordingly, the description includes the use of compounds produced by a process comprising contacting a compound described herein with a mammalian tissue or a mammal for a period of time sufficient to yield a metabolic product thereof.

Such products typically are identified by preparing a radio-labeled isotopologue (e.g., $^{14}C$ or $^{3}H$) of a compound described herein, administering the radio-labeled compound in a detectable dose (e.g., greater than about 0.5 mg/kg) to a mammal such as a rat, mouse, guinea pig, dog, monkey or human, allowing sufficient time for metabolism to occur (typically about 30 seconds to about 30 hours), and identifying the metabolic conversion products from urine, bile, blood or other biological samples. The conversion products are easily isolated since they are "radiolabeled" by virtue of being isotopically-enriched (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds described herein even if they possess no biological activity of their own.

Preparation of Compounds

General Synthetic Methods

As disclosed herein, general methods for preparing the compounds of Formula (I) or a form thereof as described herein are available via standard, well-known synthetic methodology. Many of the starting materials are commercially available or, when not available, can be prepared using the routes described below using techniques known to those skilled in the art. The synthetic schemes provided herein comprise multiple reaction steps, each of which is intended to stand on its own and can be carried out with or without any preceding or succeeding step(s). In other words, each of the individual reaction steps of the synthetic schemes provided herein in isolation is contemplated.

Scheme A:

Compounds of Formula (I) may be prepared as described in Scheme A below.

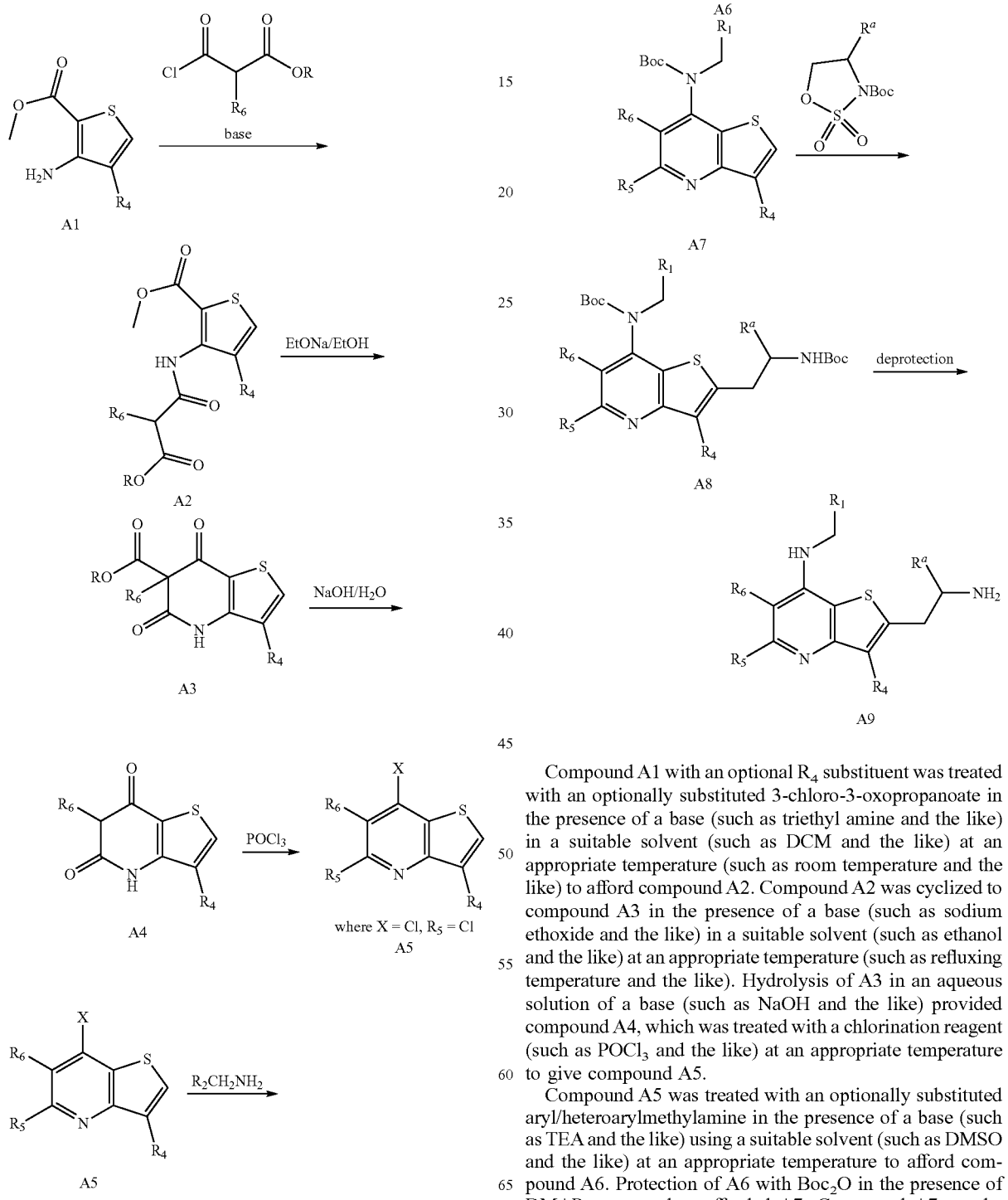

Compound A1 with an optional $R_4$ substituent was treated with an optionally substituted 3-chloro-3-oxopropanoate in the presence of a base (such as triethyl amine and the like) in a suitable solvent (such as DCM and the like) at an appropriate temperature (such as room temperature and the like) to afford compound A2. Compound A2 was cyclized to compound A3 in the presence of a base (such as sodium ethoxide and the like) in a suitable solvent (such as ethanol and the like) at an appropriate temperature (such as refluxing temperature and the like). Hydrolysis of A3 in an aqueous solution of a base (such as NaOH and the like) provided compound A4, which was treated with a chlorination reagent (such as $POCl_3$ and the like) at an appropriate temperature to give compound A5.

Compound A5 was treated with an optionally substituted aryl/heteroarylmethylamine in the presence of a base (such as TEA and the like) using a suitable solvent (such as DMSO and the like) at an appropriate temperature to afford compound A6. Protection of A6 with $Boc_2O$ in the presence of DMAP as a catalyst afforded A7. Compound A7 can be reacted with an optionally substituted cyclic sulfamidate, prepared from the corresponding amino alcohol, in the presence of a strong base (such as LDA and the like) in a suitable solvent (such as THF and the like) at an appropriate temperature such as −78° C. to give A8. Deprotection may be accomplished by treatment with an acid (such as HCl in dioxane or TFA and the like) to afford compound A8.

Scheme B:

Compounds of Formula (I) may be prepared as described in Scheme B below.

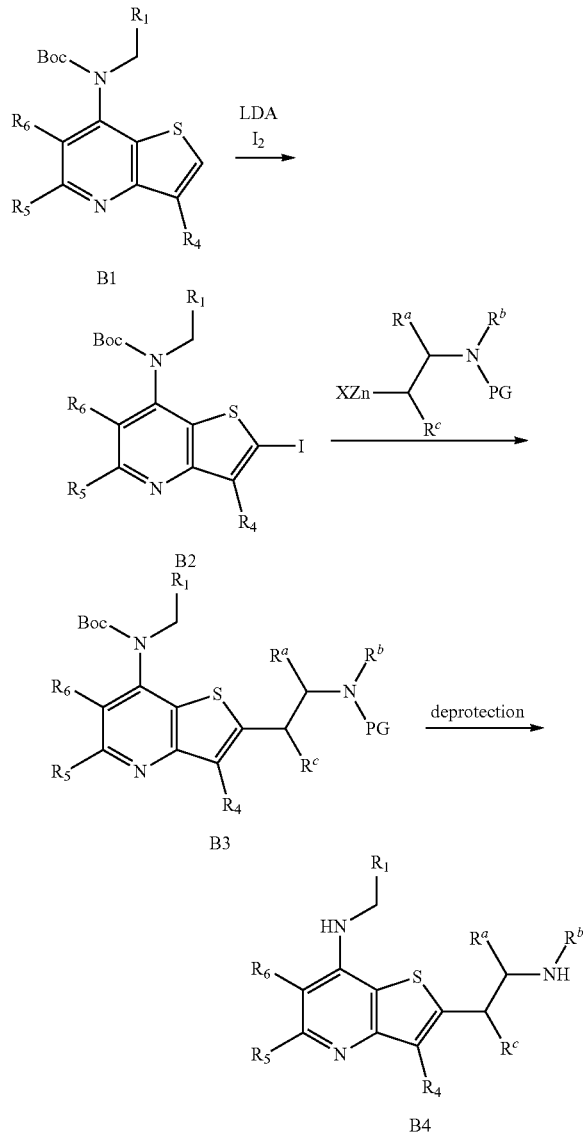

Scheme C:

Compounds of Formula (I) may be prepared as described in Scheme C below.

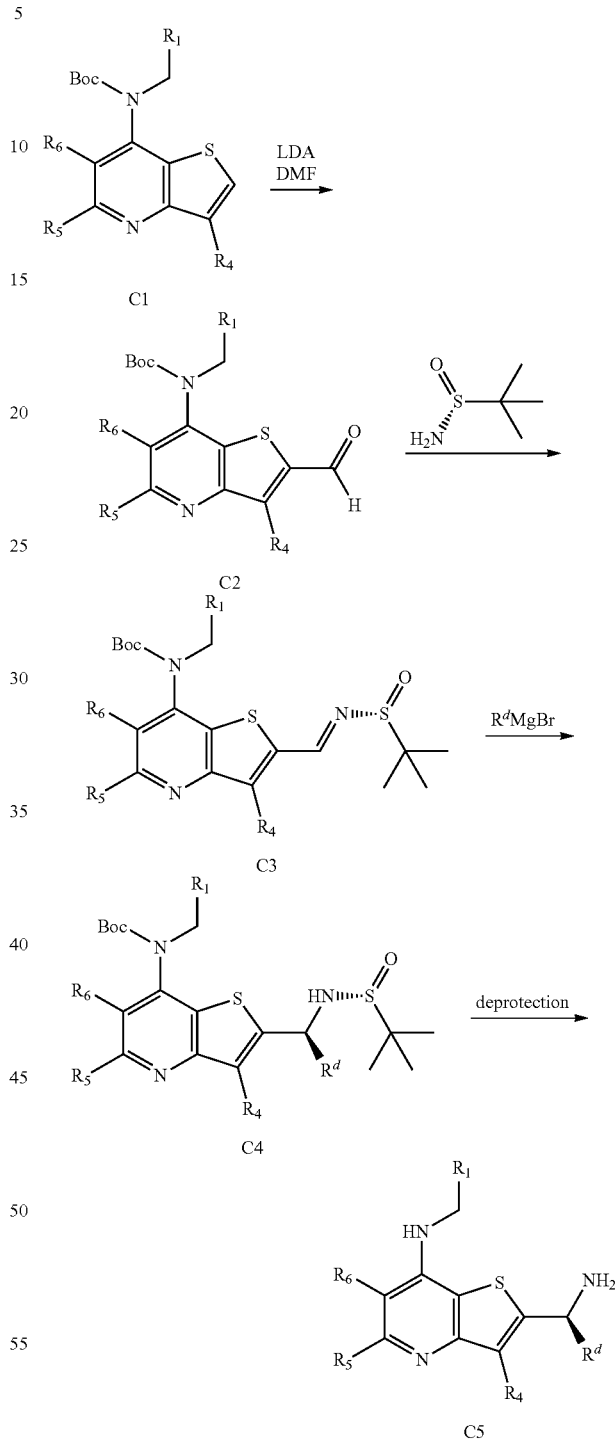

Compound B1 is reacted with iodine in the presence of a strong base (such as LDA and the like) in a suitable solvent (such as THF and the like) at an appropriate temperature such as −78° C. to give B2. Compound B2 may be converted to compound B3 by a Negeshi reaction with an optionally substituted and appropriately protected amino-containing alkyl/cycloalkyl zinc reagent in the presence of a catalyst (such as Pd(dppf)Cl$_2$ and the like) in a suitable solvent (such as THF and the like) at an appropriate temperature. Treatment of B3 with an acid (such as HCl in dioxane or TFA and the like) to afford the compound B4.

Compound C1 can be converted to the corresponding aldehyde C2 by treatment with a strong base (such as LDA and the like) at an appropriate temperature such as −78° C. followed by DMF in a suitable solvent (such as THF and the like). Compound C2 may be condensed with Ellman's sulfinamide in the presence of a Lewis acid (such as CuSO$_4$ and the like) in a suitable solvent (such as DCE and the like) at an appropriate temperature to give compound C3. Reaction of C3 with a Grignard reagent in a suitable solvent (such as THF and the like) afforded compound C4, which may be further deprotected with an acid (such as HCl in dioxane or TFA and the like) to give the compound C5.

SPECIFIC SYNTHETIC EXAMPLES

To describe in more detail and assist in understanding, the following non-limiting examples are offered to more fully illustrate the scope of compounds described herein and are not to be construed as specifically limiting the scope thereof. Such variations of the compounds described herein that may be now known or later developed, which would be within the purview of one skilled in the art to ascertain, are considered to fall within the scope of the compounds as described herein and hereinafter claimed. These examples illustrate the preparation of certain compounds. Those of skill in the art will understand that the techniques described in these examples represent techniques, as described by those of ordinary skill in the art, that function well in synthetic practice, and as such constitute preferred modes for the practice thereof. However, it should be appreciated that those of skill in the art should, in light of the present disclosure, appreciate that many changes can be made in the specific methods that are disclosed and still obtain a like or similar result without departing from the spirit and scope of the present description.

Other than in the following examples of the embodied compounds, unless indicated to the contrary, all numbers expressing quantities of ingredients, reaction conditions, experimental data, and so forth used in the specification and claims are to be understood as being modified by the term "about". Accordingly, all such numbers represent approximations that may vary depending upon the desired properties sought to be obtained by a reaction or as a result of variable experimental conditions. Therefore, within an expected range of experimental reproducibility, the term "about" in the context of the resulting data, refers to a range for data provided that may vary according to a standard deviation from the mean. As well, for experimental results provided, the resulting data may be rounded up or down to present data consistently, without loss of significant figures. At the very least, and not as an attempt to limit the application of the doctrine of equivalents to the scope of the claims, each numerical parameter should be construed in light of the number of significant digits and rounding techniques used by those of skill in the art.

While the numerical ranges and parameters setting forth the broad scope of the present description are approximations, the numerical values set forth in the examples set forth below are reported as precisely as possible. Any numerical value, however, inherently contains certain errors necessarily resulting from the standard deviation found in their respective testing measurements.

COMPOUND EXAMPLES

As used above, and throughout the present description, the following abbreviations, unless otherwise indicated, shall be understood to have the following meanings:

| Abbreviation | Meaning |
| --- | --- |
| Δ | heating (chemistry), deletion (biology), lack of (biology) |
| AcOH or HO c | acetic acid |
| $AC_2O$ | acetic anhydride |
| Ar | argon |
| ACN or $CH_3CN$ | acetonitrile |
| atm | atmosphere(s) |
| 9-BBN | 9-borabicyclo[3.3.1]nonane |
| Boc | tert-butoxy-carbonyl |
| n-BuLi | n-butyl lithium |
| ° C. | degrees Celsius |
| $CaCl_2$ | calcium chloride |
| Celite ® or Celite | diatomaceous earth |
| $CS_2CO_3$ | cesium carbonate |
| CuI | copper (I) iodide |
| $CuSO_4$ | copper (II) sulfate |
| d/h/hr/hrs/min/s | day(d)/hour(h, hr or hrs)/minute(min)/second(s) |
| DAST | diethylaminosulfur trifluoride |
| DCE | 1,2-dichlorethane |
| DCM or $CH_2Cl_2$ | dichloromethane |
| DEAD | diethyl azodicarboxylate |
| Deoxo-Fluor ® | bis(2-methoxyethyl)aminosulfur trifluoride |
| Dess-Martin Reagent or Martin's Reagent | 1,1,1-tris(acetyloxy)-1,1-dihydro-1,2-benziodoxol-3-(1H)-one |
| DIPEA | N,N-diisopropylethylamine |
| DMA | N,N-dimethylaniline |
| DMAP | 4-(dimethylamino)pyridine or N,N-dimethylpyridin-4-amine |
| DMF | dimethylformamide |
| DMSO | dimethylsulfoxide |
| DPPA | diphenylphosphoryl azide |
| EtOAc | ethyl acetate |
| EtOH | ethanol |
| $Et_2O$ | diethyl ether |
| eq. | equivalent(s) |
| HCl | hydrochloric acid |
| $H_2SO_4$ | sulfuric acid |
| $K_2CO_3$ | potassium carbonate |
| LC/MS, LCMS or LC-MS | liquid chromatographic mass spectroscopy |
| LDA | lithium diisopropylamide |
| LHMDS | lithium bis(trimethylsilyl)amide |

| Abbreviation | Meaning |
|---|---|
| MeOH | methanol |
| MgSO$_4$ | magnesium sulfate |
| MS | mass spectroscopy |
| MsCl | methanesulfonyl chloride |
| NEt$_3$ | triethylamine |
| NH$_4$Cl | ammonium chloride |
| NaBH$_4$ | sodium borohydride |
| NaH | sodium hydride |
| NaHCO$_3$ | sodium bicarbonate |
| NaIO$_4$ | sodium periodate |
| NaOEt | sodium ethoxide |
| NaOH | sodium hydroxide |
| Na$_2$SO$_4$ | sodium sulfate |
| N$_2$ | nitrogen |
| NH$_4$Cl | ammonium chloride |
| NMR | nuclear magnetic resonance |
| Pd$_2$(dba)$_3$ | tris(dibenzylideneacetone)dipalladium(0) |
| Pd(dppf)Cl$_2$ or Pd(dppf)Cl$_2$—CH$_2$Cl$_2$ | [1,1'-bis(diphenylphosphino)ferrocene]dichloropalladium(II), complex with dichloromethane |
| PhMe or PhCH$_3$ | toluene |
| POCl$_3$ | phosphoryl chloride or phosphorous(V) oxychloride |
| psi | pounds per square inch pressure |
| PTFE | polytetrafluoroethylene |
| Rt or rt | room temperature |
| RT | retention time |
| RuCl$_3$ | ruthenium (III) chloride |
| Selectfluor® | 1-chloromethyl-4-fluoro-1,4-diazoniabicyclo[2.2.2]octane bis(tetrafluoroborate) |
| SO$_2$Cl$_2$ | sulfuryl chloride |
| TBAF | tetrabutylammonium fluoride |
| TBSCl | tert-butyldimethylsilyl chloride |
| TEA, Et$_3$N or NEt$_3$ | triethylamine |
| TFA | trifluoroacetic acid |
| THF | tetrahydrofuran |
| TLC | thin layer chromatography |
| TMS | trimethylsilyl |
| TMSCl | trimethylsilyl chloride |
| t-Bu | tert-butyl |
| XantPhos | 4,5-bis(diphenylphosphino)-9,9-dimethylxanthene |

Intermediate 1 tert-Butyl (S)-4-(((tert-butyldimethylsilyl)oxy)methyl)-1,2,3-oxathiazolidine-3-carboxylate 2,2-dioxide

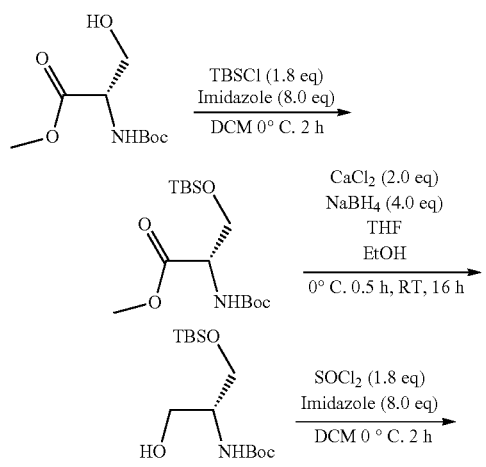

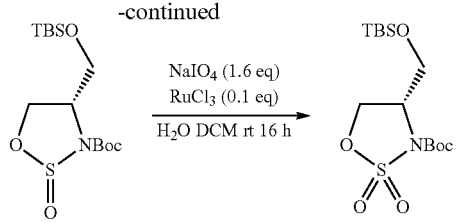

Step 1: N-(tert-Butoxycarbonyl)-O-(tert-butyldimethylsilyl)-L-serinate

To a solution of methyl (tert-butoxycarbonyl)-L-serinate (25 g, 114.0 mmol) in DCM (250 mL) was added imidazole (62.1 g, 912 mmol) and TBSCl (32 g, 205.9 mmol) at 0° C. The mixture was stirred for 2 h and then poured into a mixture of DCM (300 mL) and water (200 mL). The organic phase was separated, washed with water (2×100 mL) and brine (1×100 mL), dried over Na$_2$SO$_4$ and filtered. The filtrate was concentrated in vacuo to give methyl N-(tert-butoxycarbonyl)-O-(tert-butyldimethylsilyl)-L-serinate (35.5 g, 93.3% yield) as an oil. LC-MS: m/z: 356.2 [M+Na]$^+$.

Step 2: tert-Butyl (R)-(1-((tert-butyldimethylsilyl)oxy)-3-hydroxypropan-2-yl)carbamate To a solution of methyl N-(tert-butoxycarbonyl)-O-(tert-butyldimethylsilyl)-L-serinate (35.5 g, 106 mmol) in THF (200 mL) and EtOH (100 mL) was added CaCl₂ (23.6 g, 213 mmol) followed by NaBH₄ (16.1 g, 426 mmol) at 0° C. The mixture was stirred for 0.5 h at 0° C. and room temperature for 16 h, then poured into a mixture of EtOAc (200 mL) and water (150 mL). The organic phase was separated and washed with water (2×200 mL) and brine (1×150 mL), dried over anhydrous Na₂SO₄ and filtered. The filtrate was concentrated in vacuo to give tert-butyl (R)-(1-((tert-butyldimethylsilyl)oxy)-3-hydroxypropan-2-yl)carbamate (30 g, 92.3% yield) as a white solid. LC-MS: m/z: 328.2 [M+Na]⁺; RT=1.93 min.

Step 3: tert-Butyl (4S)-4-(((tert-butyldimethylsilyl)oxy)methyl)-1,2,3-oxathiazolidine-3-carboxylate 2-oxide To a solution of imidazole (54 g, 785.3 mmol) in DCM (300 mL) at 0° C. was added SOCl₂ (12.9 mL, 176.0 mmol). The mixture was stirred at 0° C. for 1 h and tert-butyl (R)-(1-((tert-butyldimethylsilyl)oxy)-3-hydroxypropan-2-yl)carbamate (30 g, 98.2 mmol) was added. The mixture was stirred for another 1 h at 0° C., then poured into a mixture of EtOAc (500 mL) and water (400 mL). The organic layer was separated and washed with water (2×800 mL) and brine (800 mL), then dried over Na₂SO₄ and filtered. The filtrate was concentrated in vacuo to give tert-butyl (4S)-4-(((tert-butyldimethylsilyl)oxy)methyl)-1,2,3-oxathiazolidine-3-carboxylate 2-oxide (32.6 g, 94.4% yield) as a white solid. LC-MS: m/z: 374.1 [M+Na]⁺; RT=2.08 min.

Step 4: tert-Butyl (4S)-4-[[tert-butyl(dimethyl)silyl]oxymethyl]-2,2-dioxo-oxathiazolidine-3-carboxylate To a solution of tert-butyl (4S)-4-(((tert-butyldimethylsilyl)oxy)methyl)-1,2,3-oxathiazolidine-3-carboxylate 2-oxide (32.6 g, 92.7 mmol) in water (300 mL) and DCM (300 mL) was added NaIO₄ (31.8 g, 148.0 mmol) and RuCl₃ (1.94 g, 9.3 mmol) at room temperature. The mixture was stirred overnight and then extracted with DCM (3×500 mL). The combined organic phases were washed with saturated NaHSO₃ (aq., 500 mL), dried over anhydrous Na₂SO₄ and filtered. The filtrate was concentrated in vacuo. The residue was purified by flash chromatography (silica), eluted with DCM/hexane (50-100%) to give tert-butyl (4S)-4-[[tert-butyl(dimethyl)silyl]oxymethyl]-2,2-dioxo-oxathiazolidine-3-carboxylate (18 g, 52.8% yield) as a white solid. LC-MS: m/z: 390.2 [M+Na]⁺; RT=2.05 min; ¹H NMR (400 MHz, CDCl₃) δ ppm 4.53-4.51 (m, 2H), 4.2 (s, 1H), 3.76-3.69 (m, 2H), 1.46 (s, 9H), 0.81 (s, 9H), 0.00 (s, 6H).

Intermediate 2 tert-Butyl (S)-4-(2-((tert-butyldimethylsilyl)oxy)ethyl)-1,2,3-oxathiazolidine-3-carboxylate 2,2-dioxide

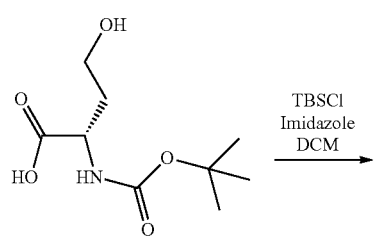
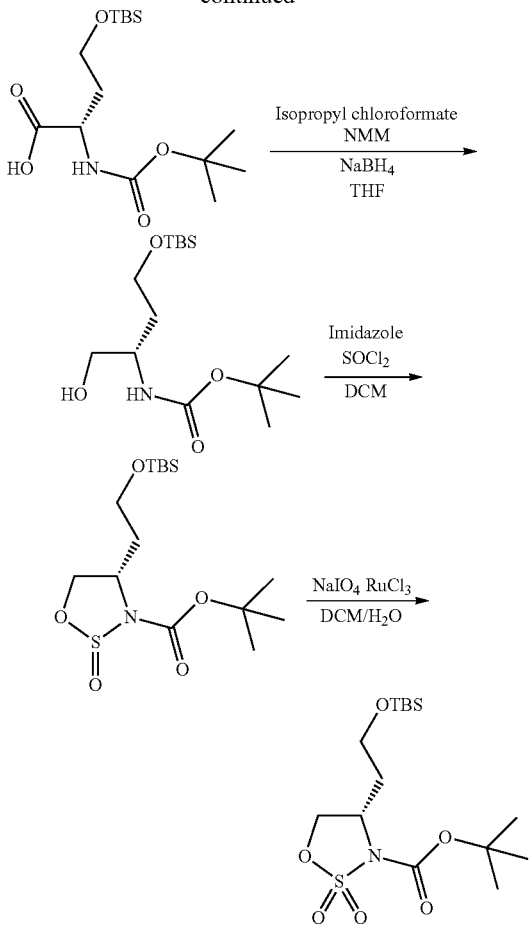

Step 1: N-(tert-Butoxycarbonyl)-O-(tert-butyldimethylsilyl)-L-homoserine

To a solution of (tert-butoxycarbonyl)-L-homoserine (21 g, 96.0 mmol) and imidazole (52 g, 770 mmol) in DCM (210 mL) was added TBSCl (23 g, 153 mmol). The mixture was stirred at room temperature for 5 h. Water (100 mL) was then added, and the organic phase was separated and washed with brine (80 mL), dried over anhydrous Na₂SO₄ and concentrated in vacuo to give N-(tert-butoxycarbonyl)-O-(tert-butyldimethylsilyl)-L-homoserine (31.9 g, 99% yield) as a colorless oil. ¹H NMR (400 MHz, CDCl₃) δ ppm 5.85 (d, 1H), 4.22 (m, 1H), 3.69-3.75 (m, 2H), 1.93-2.01 (m, 2H), 1.36 (s, 9H), 0.83 (s, 9H), 0.00 (s, 6H).

Step 2: tert-Butyl (S)-(4-((tert-butyldimethylsilyl)oxy)-1-hydroxybutan-2-yl)carbamate To a solution of N-(tert-butoxycarbonyl)-O-(tert-butyldimethylsilyl)-L-homoserine (31.9 g, 96 mmol) and N-methyl morpholine (10.7 g, 105 mmol) in THF (300 mL) at 0° C. was added isopropyl chloroformate (12.8 g, 105 mmol). The mixture was stirred at 0° C. for 1 h and then filtered. The filtrate was cooled to 0° C., into which was slowly added a solution of NaBH₄ (4 g, 105.0 mmol) in water. The mixture was stirred for 2 h at 0° C., then diluted with water (100 mL). The organic phase was separated and washed with brine (2×100 mL), dried over Na₂SO₄ and filtered. The filtrate was concentrated in vacuo to give tert-butyl (S)-(4-((tert-butyldimethylsilyl)oxy)-1-hydroxybutan-2-yl)carbamate (20 g, 57% yield) as a colorless oil. ¹H NMR (400 MHz, CDCl₃) δ ppm 5.41 (s, 1H), 3.75-3.79 (m, 1H), 3.66 (t, 1H), 3.55-3.58 (m, 2H), 1.69-1.99 (m, 2H), 1.85-1.66 (m, 2H), 1.36 (s, 9H), 0.83 (s, 9H), 0.00 (s, 6H).

Step 3: tert-Butyl (4S)-4-(2-((tert-butyldimethylsilyl)oxy)ethyl)-1,2,3-oxathiazolidine-3-carboxylate 2-oxide To a solution of imidazole (22 g, 313 mmol) in DCM (200 mL) at 0° C. was added SOCl₂ (13.5 g, 113 mmol). The mixture was stirred at room temperature for 1 h, cooled to 0° C., and a solution of tert-butyl (S)-(4-((tert-butyldimethylsilyl)oxy)-1-hydroxybutan-2-yl)carbamate (20 g, 62.7 mmol) in DCM (100 mL) was added. The mixture was stirred at room temperature for 2 h and diluted with water (100 mL). The organic phase was separated and washed with brine (100 mL), dried over Na₂SO₄ and filtered. The filtrate was concentrated in vacuo to give tert-butyl (4S)-4-(2-((tert-butyldimethylsilyl)oxy)ethyl)-1,2,3-oxathiazolidine-3-carboxylate 2-oxide as a colorless oil (23 g, 99% yield). ¹H NMR (400 MHz, CDCl₃) δ ppm 3.83-4.05 (m, 1H), 3.62-3.69 (m, 2H), 3.53-3.59 (m, 2H), 1.60-1.78 (m, 2H), 1.36 (d, 9H), 0.81 (d, 9H), 0.02 (d, 6H).

Step 4: tert-Butyl (S)-4-(2-((tert-butyldimethylsilyl)oxy)ethyl)-1,2,3-oxathiazolidine-3-carboxylate 2,2-dioxide To a mixture of tert-butyl (4S)-4-(2-((tert-butyldimethylsilyl)oxy)ethyl)-1,2,3-oxathiazolidine-3-carboxylate 2-oxide (23 g, 62.7 mmol) and NaIO₄ (31 g, 144 mmol) in DCM (300 mL) and water (310 mL) was added RuCl₃ (0.83 g, 4 mmol). The reaction was stirred at room temperature for 5 h. The organic phase was separated and washed with 10% NaHSO₃ (4×150 mL) and brine (150 mL), dried over Na₂SO₄ and filtered. The filtrate was concentrated in vacuo. The residue was purified by silica gel column chromatography, eluting with petroleum ether and ethyl acetate (20:1) to afford tert-butyl (S)-4-(2-((tert-butyldimethylsilyl)oxy)ethyl)-1,2,3-oxathiazolidine-3-carboxylate 2,2-dioxide as a white solid (5 g, 21% yield). ¹H NMR (400 MHz, CDCl₃) δ ppm 4.95 (q, 2H), 4.30-3.35 (m, 1H), 3.64-3.77 (m, 2H), 1.96-2.11 (m, 2H), 1.52 (s, 9H), 0.83 (s, 9H), 0.00 (s, 6H). Intermediate 3 tert-Butyl (R)-4-(fluoromethyl)-1,2,3-oxathiazolidine-3-carboxylate 2,2-dioxide

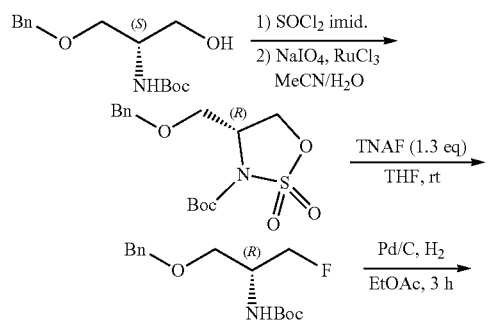

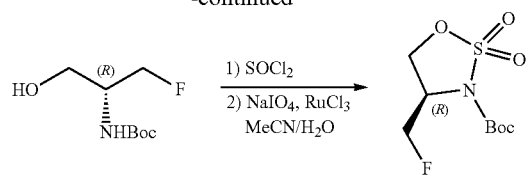

Step 1: tert-Butyl (4R)-4-(benzyloxymethyl)-2-oxo-oxathiazolidine-3-carboxylate

To a solution of imidazole (4.5 g, 4.37 mL, 66.1 mmol, 3.80 eq.) in DCM (160 mL) at −78° C. was added thionyl chloride (2.290 g, 1.40 mL, 19.2 mmol, 1.10 eq.) followed by N,N-diisopropylethylamine (4.450 g, 6.00 mL, 34.1 mmol, 1.96 eq.). After 30 min, a solution of tert-butyl N-[(1S)-1-(benzyloxymethyl)-2-hydroxy-ethyl]carbamate (4.894 g, 17.39 mmol, 1.00 eq.) in DCM (20 mL) was added over 30 min at −78° C. The mixture was warmed to room temperature and stirred overnight. The reaction was quenched by water (50 mL). The organic layer was separated, and the aqueous layer was extracted with DCM (2×50 mL). The combined organic layers were washed with water (50 mL) and brine (100 mL), dried over sodium sulfate then concentrated to give tert-butyl (4R)-4-(benzyloxymethyl)-2-oxo-oxathiazolidine-3-carboxylate (5.9 g, 18.0 mmol, 1.04 eq.) as an oil which was used without purification.

Step 2: tert-Butyl (4R)-4-(benzyloxymethyl)-2,2-dioxo-oxathiazolidine-3-carboxylate To a solution of tert-butyl (4R)-4-(benzyloxymethyl)-2-oxo-oxathiazolidine-3-carboxylate (5.9 g, 18.0 mmol, 1.00 eq.) in CH₃CN (160 mL) and water (100 mL) at 0° C. was added NaIO₄ (6.0 g, 28.0 mmol, 1.55 eq.) followed by RuCl₃ (16 mg, 0.077 mmol, 0.0043 eq.). The mixture was stirred at 0° C. for 45 min, and then diluted with water (50 mL). The mixture was extracted with diethyl ether (2×80 mL). The combined organic extracts were washed with water (50 mL) followed by brine (100 mL) and dried over sodium sulfate. The volatiles were removed under reduced pressure, and the residue was purified by flash column chromatography (120 g, 0-100% DCM/hexanes) to afford tert-butyl (4R)-4-(benzyloxymethyl)-2,2-dioxo-oxathiazolidine-3-carboxylate (5.228 g, 85% yield) as a colorless oil which solidified upon standing at room temperature after trituration with hexanes.

Step 3: tert-Butyl N-[(1R)-1-(benzyloxymethyl)-2-fluoro-ethyl]carbamate

To a solution of tert-butyl (4R)-4-(benzyloxymethyl)-2,2-dioxo-oxathiazolidine-3-carboxylate (5.228 g, 15.22 mmol, 1.00 eq.) in THF (70 mL) was added TBAF (1 M) in THF (18.0 mL, 18.0 mmol, 1.18 eq.) at 0° C. The mixture was stirred at 0° C. for 1 h, and then room temperature overnight. The reaction was quenched with aqueous citric acid (1N, ~20 mL). The mixture was extracted with EtOAc (2×80 mL). The combined organic phases were washed with water followed by brine (~50 mL). The volatiles were removed under reduced pressure, and the residue was purified by flash column chromatography (0-30% EtOAc in hexanes with 10% DCM) to afford tert-butyl N-[(1R)-1-(benzyloxymethyl)-2-fluoro-ethyl]carbamate (3.250 g, 75% yield) as a colorless oil.

Step 4: tert-Butyl N-[(1R)-1-(fluoromethyl)-2-hydroxy-ethyl]carbamate

To a solution of tert-butyl N-[(1R)-1-(benzyloxymethyl)-2-fluoro-ethyl]carbamate (2.505 g, 8.84 mmol, 1.00 eq.) in EtOAc (30 mL) was added 10% palladium on carbon (Degussa type) 128 mg (~5% mass) at room temperature. The flask was evacuated and back-filled by a hydrogen balloon (1 atm) in three cycles. The mixture was stirred at room temperature for 3 h, then filtered and evaporated. The filtrate was concentrated to afford tert-butyl N-[(1R)-1-(fluoromethyl)-2-hydroxy-ethyl]carbamate (1.725 g, quantitative).

Step 5: tert-Butyl (4R)-4-(fluoromethyl)-2-oxo-oxathiazolidine-3-carboxylate To a solution of imidazole (3.0 g, 2.91 mL, 44.07 mmol, 3.73 eq.) in DCM (110 mL) at −78° C. was added thionyl chloride (1.00 mL, 13.73 mmol, 1.16 eq.) followed by N,N-diisopropylethylamine (3.90 mL, 22.2 mmol, 1.87 eq.). The reaction was stirred at −78° C. for 30 min, and a solution of tert-butyl N-[(1R)-1-(fluoromethyl)-2-hydroxy-ethyl]carbamate (2.285 g, 11.83 mmol, 1.00 eq.) in DCM (15 mL) was added over 30 min at −78° C. The mixture was warmed to room temperature and was stirred at room temperature overnight. The reaction was quenched with water (50 mL). The organic layer was separated and washed with water (50 mL) and brine (100 mL), dried over sodium sulfate and concentrated to give tert-butyl (4R)-4-(fluoromethyl)-2-oxo-oxathiazolidine-3-carboxylate (2.830 g) as an oil which was carried over to the next step without further purification.

Step 6: tert-Butyl (4R)-4-(fluoromethyl)-2,2-dioxo-oxathiazolidine-3-carboxylate To a solution of tert-butyl (4R)-4-(fluoromethyl)-2-oxo-oxathiazolidine-3-carboxylate (2.830 g, 11.8 mmol, 1.00 eq.) in a mixed solvent of $CH_3CN$ (100 mL) and water (60 mL) was added $NaIO_4$ (3.940 g, 18.4 mmol, 1.55 eq.) followed by $RuCl_3$ (20 mg, 0.096 mmol, 0.0081 eq.) at 0° C. The mixture was stirred at 0° C. for 45 min, then diluted with water (50 mL) and extracted by diethyl ether (2×80 mL). The combined organic phases were washed with water (50 mL) and brine (100 mL), dried over sodium sulfate and evaporated. The residue was purified by flash column chromatography (120 g, 0-100% DCM/hexanes) to afford tert-butyl (4R)-4-(fluoromethyl)-2,2-dioxo-oxathiazolidine-3-carboxylate (2384 mg, 78.9% yield). $^1$H NMR (400 MHz, $CDCl_3$) δ ppm 4.47-4.74 (m, 5H), 1.56 (s, 9H).

Intermediate 4

3-Bromo-5,7-dichlorothieno[3,2-b]pyridine

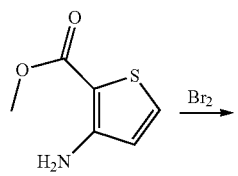

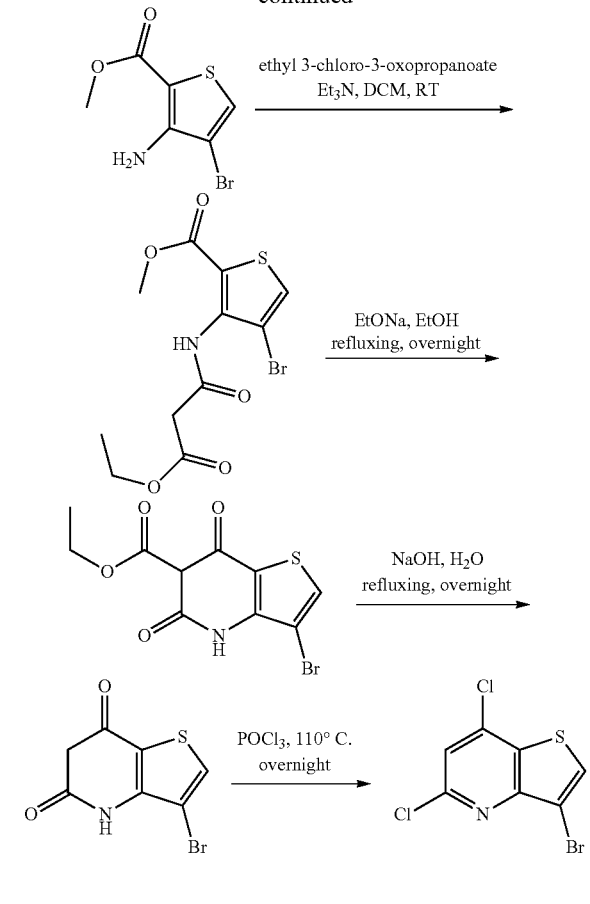

Step 1: Methyl 3-amino-4-bromothiophene-2-carboxylate

To a solution of methyl 3-aminothiophene-2-carboxylate (40.0 g, 255.0 mmol) in AcOH (1000 mL) was added $Br_2$ (80.2 g, 510.0 mmol) at 25° C. The mixture was stirred at 65° C. for 12 h, then cooled to room temperature. Then the mixture was poured into water (2000 mL), and the suspension was filtered. The filter cake was collected and dried in vacuo, then purified by silica gel column chromatography eluting with 10% EtOAc in petroleum ether to give methyl 3-amino-4-bromothiophene-2-carboxylate as a yellow solid (30.0 g, 50.0% yield). $^1$H NMR (400 MHz, $CDCl_3$) δ 7.29 (s, 1H), 5.64 (m, 2H), 3.84 (s, 3H).

Step 2: Methyl 4-bromo-3-(3-ethoxy-3-oxopropanamido)thiophene-2-carboxylate

To a solution of methyl 3-amino-4-bromothiophene-2-carboxylate (30.0 g, 128 mmol) in DCM (500 mL) were added triethylamine (16.8 g, 166 mmol) and ethyl 3-chloro-3-oxopropanoate (25.0 g, 166 mmol) at 0° C. The mixture was stirred at 25° C. for 3 h. The mixture was quenched with ice water (1.5 L) and extracted with DCM (3×500 mL). The combined organic layers were dried over $Na_2SO_4$ and filtered. The filtrate was concentrated to give methyl 4-bromo-3-(3-ethoxy-3-oxopropanamido)thiophene-2-carboxylate as a brown solid (40.0 g, 90.0% yield), which was used in the next step without further purification. LC-MS: m/z: 350.0 [M+H]$^+$; RT=1.59 min.

Step 3: Ethyl 3-bromo-5,7-dioxo-4,5,6,7-tetrahydrothieno[3,2-b]pyridine-6-carboxylate To a solution of methyl 4-bromo-3-(3-ethoxy-3-oxopropanamido)thiophene-2-carboxylate (35.0 g, 100 mmol) in ethanol (500 mL) was added sodium ethanolate (10.0 g, 166 mmol) at 0° C. The mixture was stirred at 100° C. for 12 h, then cooled to room temperature. The mixture was filtered. The filter cake was washed with ethyl acetate (100 mL) and dried in vacuo to give ethyl 3-bromo-5,7-dioxo-4,5,6,7-tetrahydrothieno[3,2-b]pyridine-6-carboxylate as a brown solid (33.0 g, 95.0% yield), which was used in the next step without further purification. LC-MS: m/z: 317.6 [M+H]$^+$; RT=1.53 min.

Step 4: 3-Bromothieno[3,2-b]pyridine-5,7(4H,6H)-dione

To a solution of ethyl 3-bromo-5,7-dioxo-4,5,6,7-tetrahydrothieno[3,2-b]pyridine-6-carboxylate (30.0 g, 94.6 mmol) in water (1000 mL) was added sodium hydroxide (7.60 g, 189 mmol) at 0° C. The mixture was stirred at 110° C. for 12 h, then cooled to room temperature. The pH was adjusted to pH=6 by HCl (10 N), and the mixture was filtered. The filter cake was collected and dried in vacuo to give 3-bromothieno[3,2-b]pyridine-5,7(4H,6H)-dione as a brown solid (20.0 g, 86.0% yield), which was used in the next step without further purification. LC-MS: m/z: 245.9 [M+H]$^+$; RT=1.35 min.

Step 5: 3-Bromo-5,7-dichlorothieno[3,2-b]pyridine

To POCl$_3$ (60 mL) was added 3-bromothieno[3,2-b]pyridine-5,7(4H,6H)-dione (20.0 g, 81.6 mmol). The mixture was stirred and refluxed for 12 h, then cooled to room temperature, quenched with ice water (1.5 L) and extracted with ethyl acetate (3×500 mL). The combined organic layers were dried over Na$_2$SO$_4$ and filtered. The filtrate was concentrated to give a residue. The residue was purified by silica column chromatography using petroleum ether and ethyl acetate (5:1) to give 3-bromo-5,7-dichlorothieno[3,2-b]pyridine as a white solid (20.0 g, 87.0% yield). $^1$H NMR 400 MHz (DMSO-d$_6$) δ ppm 8.58 (s, 1H), 7.99 (s, 1H).

Intermediate 5

3,5,7-Trichloro-thieno[3,2-b]pyridine

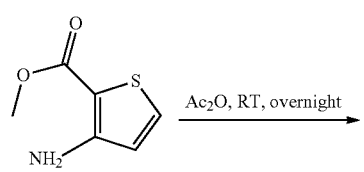

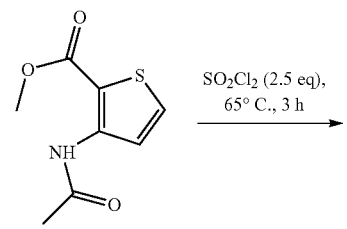

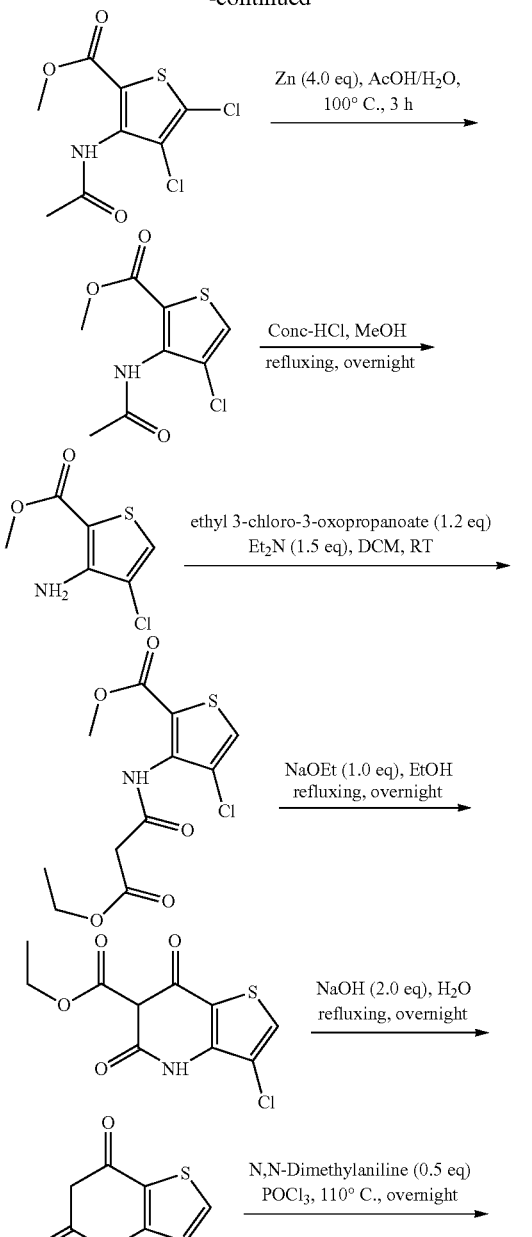

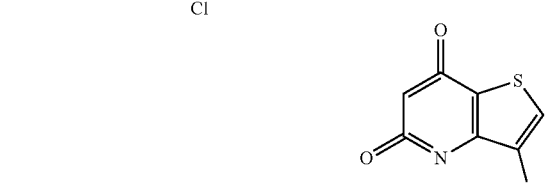

Step 1: Methyl 3-acetamidothiophene-2-carboxylate

To Ac$_2$O (300 mL) at room temperature was added methyl 3-aminothiophene-2-carboxylate (80 g, 508.9 mmol), and the mixture was stirred at room temperature overnight. The reaction was quenched with MeOH (800 mL), and the mixture was stirred at room temperature for 30 min. The solvent was removed in vacuo, and the residue was neutralized to pH=9-10 with aqueous saturated NaHCO₃ solution. The mixture was extracted with ethyl acetate (3×400 mL). The combined organic layers were dried over Na₂SO₄ and filtered. The filtrate was concentrated in vacuo to give methyl 3-acetamidothiophene-2-carboxylate (96 g, 94.7% yield) as an off-white solid. LC-MS: m/z: 200.1 [M+H]⁺; RT=1.63 min.

Step 2: Methyl 3-acetamido-4,5-dichlorothiophene-2-carboxylate

To a solution of methyl 3-acetamidothiophene-2-carboxylate (96 g, 482.6 mmol) in CHCl₃ (500 mL), SO₂Cl₂ (96 mL, 1206.1 mmol) was added dropwise. The mixture was stirred at 75° C. overnight, cooled to room temperature and concentrated in vacuo to give a solid, which was triturated with diethyl ether to give methyl 3-acetamido-4,5-dichlorothiophene-2-carboxylate (103.6 g, 80.2% yield) as an off-white solid. ¹H NMR 400 MHz (CDCl₃) δ ppm 8.24 (s, 1H), 3.87-3.90 (m, 3H), 2.23 (s, 3H).

Step 3: Methyl 3-acetamido-4-chlorothiophene-2-carboxylate

To a solution of methyl 3-acetamido-4,5-dichlorothiophene-2-carboxylate (103.5 g, 386.0 mmol) in H₂O and HOAc (3:1 (v/v), 800 mL) was added Zn powder (100.9 g, 1544.2 mmol). The mixture was stirred at 100° C. overnight. After cooling to room temperature, the mixture was filtered. The filtrate was extracted with ethyl acetate (3×1000 mL). The combined organic layers were washed with water and brine, dried over anhydrous Na₂SO₄ and evaporated in vacuo to give methyl 3-acetamido-4-chlorothiophene-2-carboxylate (72.2 g, 80.1% yield) as an off-white solid. ¹H NMR 400 MHz (CDCl₃) δ ppm 7.36 (s, 1H), 7.26 (s, 1H), 3.87-3.88 (m, 3H), 2.23 (s, 3H).

Step 4: Methyl 3-amino-4-chlorothiophene-2-carboxylate

A mixture of methyl 3-acetamido-4-chlorothiophene-2-carboxylate (70.0 g, 299.5 mmol) in MeOH and conc. HCl (1:1 (v/v), 300 mL) was stirred at 110° C. overnight, then cooled to room temperature and concentrated in vacuo. The resulting solid was dissolved in water (200 mL) and neutralized with aqueous NaHCO₃. The mixture was extracted with ethyl acetate (3×300 mL). The combined organic layers were dried over anhydrous Na₂SO₄ and concentrated. The residue was purified by silica gel column chromatography using petroleum ether/ethyl acetate (8:1) as eluent to give methyl 3-amino-4-chlorothiophene-2-carboxylate (47.1 g, 82.2% yield) as an off-white solid. LC-MS: m/z: 192.0 [M+H]⁺; RT=1.70 min.

Step 5: Methyl 4-chloro-3-(3-ethoxy-3-oxopropanamido)thiophene-2-carboxylate

To a solution of methyl 3-amino-4-chlorothiophene-2-carboxylate (45.0 g, 234.8 mmol) in DCM (300 mL) at 0° C. was added Et₃N (47.5 g, 469.7 mmol) followed by ethyl 3-chloro-3-oxopropanoate (53.1 g, 352.3 mmol) dropwise. The mixture was stirred at room temperature overnight and then washed with water (2×300 mL). The organic layer was dried over Na₂SO₄ and concentrated in vacuo. The residue was purified by silica gel column chromatography using petroleum ether/ethyl acetate (1:1) as eluent to give methyl 4-chloro-3-(3-ethoxy-3-oxopropanamido)thiophene-2-carboxylate (41.8 g, 58.3% yield) as an off-white solid. LC-MS: m/z: 306.0 [M+H]⁺; RT=1.55 min; ¹H NMR 400 MHz (CDCl₃) δ ppm 10.12 (s, 1H), 8.01 (s, 1H), 4.11-4.13 (m, 2H), 3.79 (s, 3H), 3.48 (s, 2H), 1.19-1.22 (m, 3H).

Step 6: Ethyl 3-chloro-5,7-dioxo-4,5,6,7-tetrahydrothieno[3,2-b]pyridine-6-carboxylate To a solution of methyl 4-chloro-3-(3-ethoxy-3-oxopropanamido)thiophene-2-carboxylate (40.0 g, 130.8 mmol) in EtOH (300 mL) was added NaOEt (9.0 g, 130.8 mmol). The mixture was stirred at 85° C. overnight, then cooled to room temperature. The product was obtained by filtration to give ethyl 3-chloro-5,7-dioxo-4,5,6,7-tetrahydrothieno[3,2-b]pyridine-6-carboxylate (34.3 g, 95.8% yield) as an off-white solid. LC-MS: m/z: 274.0 [M+H]⁺; RT=1.56 min; ¹H NMR 400 MHz (CDCl₃) δ ppm 7.55 (s, 1H), 4.07-4.09 (m, 2H), 3.44-3.46 (m, 1H), 1.18-1.21 (m, 3H), 1.06-1.08 (m, 1H).

Step 7: 3-Ethyl chlorothieno[3,2-b]pyridine-5,7(4H,6H)-dione

Ethyl 3-chloro-5,7-dioxo-4,5,6,7-tetrahydrothieno[3,2-b]pyridine-6-carboxylate (34.3 g, 125.2 mmol) was added to a solution of NaOH (10.0 g, 250.4 mmol) in H₂O (200 mL). The mixture was stirred at 105° C. overnight, then cooled to room temperature. The pH was adjusted to ~6-7 with conc. HCl. The filter cake was collected by filtration and dried in vacuo to give 3-chlorothieno[3,2-b]pyridine-5,7(4H,6H)-dione (22.3 g, 88.3% yield) as an off-white solid. LC-MS: m/z: 202.0 [M+H]⁺; RT=1.34 min.

Step 8: 3,5,7-Trichlorothieno[3,2-b]pyridine

3-Chlorothieno[3,2-b]pyridine-5,7(4H,6H)-dione (22.0 g, 109.1 mmol) and N,N-dimethylaniline (6.6 g, 0.5 eq, 54.5 mmol) were added to POCl₃ (150 mL). The mixture was stirred at 110° C. overnight, then cooled to room temperature. The excess POCl₃ was removed in vacuo, and the solid was poured into ice water (100 mL). A white solid was obtained by filtration, dried in vacuo and further purified by silica column chromatography using petroleum ether and ethyl acetate (5:1) to give 3,5,7-trichlorothieno[3,2-b]pyridine (18.7 g, 72.1% yield) as an off-white solid. LC-MS: m/z: 237.9, 239.9, 241.9 [M+H]⁺; RT=2.01 min; ¹H NMR (400 MHz, CDCl₃) δ ppm 8.49 (s, 1H), 7.99 (s, 1H).

Intermediate 6 tert-Butyl (5-chloro-2-iodo-3-methylthieno[3,2-b]pyridin-7-yl)(furan-2-ylmethyl)carbamate

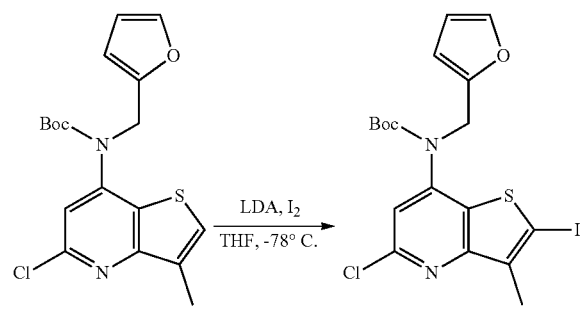 [SMILES: Cc1csc2c(N(Cc3ccco3)C(=O)OC(C)(C)C)cc(Cl)nc12 ; Cc1c(I)sc2c(N(Cc3ccco3)C(=O)OC(C)(C)C)cc(Cl)nc12]

To a solution of tert-butyl (5-chloro-3-methylthieno[3,2-b]pyridin-7-yl)(furan-2-ylmethyl)carbamate (410 mg, 1.08 mmol, 1.0 eq.), prepared according to the procedure in Example 2, in THF (3 mL) was added LDA (2.0M in THF, 0.60 mL, 1.1 eq.) at −78° C. After stirring for 15 min, a solution of iodine (288 mg, 1.14 mmol, 1.05 eq.) in THF (2 mL) was added dropwise and stirring was continued for 1 h. The reaction was quenched by addition of EtOAc and NH$_4$Cl (sat. aq.) and warmed to room temperature. The organic layers were washed with sodium thiosulfate solution, water and brine, dried over sodium sulfate and evaporated. The residue was purified by flash column chromatography on silica gel eluting with 0-15% EtOAc in hexane to provide tert-butyl (5-chloro-2-iodo-3-methylthieno[3,2-b]pyridin-7-yl)(furan-2-ylmethyl)carbamate (436 mg, 80% yield). MS m/z 505.5, 507.5 [M+H]$^+$.

Example 1 (Compound 2)

5-Chloro-N-[(furan-2-yl)methyl]-3-methylthieno[3,2-b]pyridin-7-amine

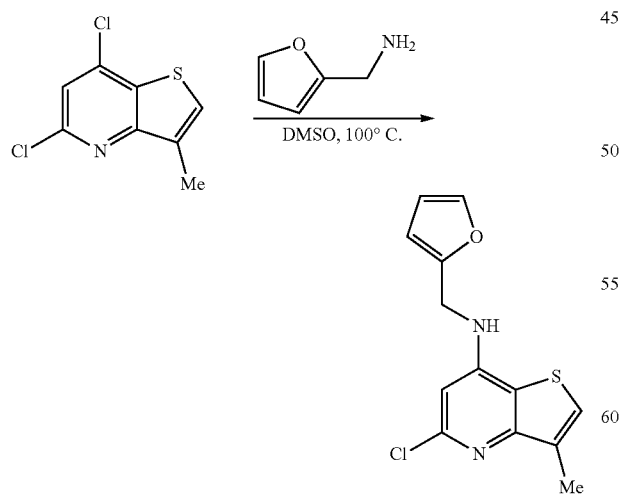

A mixture of 5,7-dichloro-3-methyl-thieno[3,2-b]pyridine (201 mg, 0.922 mmol, 1.00 eq.) and 2-furylmethanamine (895 mg, 0.81 mL, 9.22 mmol, 10.0 eq.) in DMSO (0.8 mL) was stirred at 100° C. for 24 h. The mixture was cooled, diluted with ethyl acetate, washed with water and brine, dried and evaporated. The residue was purified over silica gel with ethyl acetate and hexanes to give 5-chloro-N-(2-furylmethyl)-3-methyl-thieno[3,2-b]pyridin-7-amine (230 mg, 90% yield). MS m/z 279.1, 281.1 [M+H]$^+$, $^1$H NMR (400 MHz, CDCl$_3$) δ ppm 7.44 (d, J=1.2 Hz, 1H), 7.26 (d, J=1.1 Hz, 1H), 6.58 (s, 1H), 6.39 (dd, J=3.2, 1.8 Hz, 1H), 6.35 (d, J=3.2 Hz, 1H), 4.70 (br s, 1H), 4.54 (d, J=5.3 Hz, 2H), 2.49 (d, J=1.1 Hz, 3H).

The compounds below were prepared according to the procedure of Example 1 by substituting the appropriate starting materials, reagents and reaction conditions.

| Compound | Spectral Data |
|---|---|
| 1 | MS m/z 265.2, 267.2 [M + H]$^+$; $^1$H NMR (CDCl$_3$) δ: 7.63 (d, J = 5.3 Hz, 1H), 7.41-7.50 (m, 2H), 6.58 (s, 1H), 6.34-6.43 (m, 2H), 5.03 (br s, 1H), 4.56 (d, J = 4.9 Hz, 2H). |
| 6 | MS m/z 299.1, 301.1, 303.1[M + H]$^+$; $^1$H NMR (methanol-d$_4$) δ: 7.72 (s, 1H), 7.36 (d, J = 0.9 Hz, 1H), 6.60 (s, 1H), 6.21-6.32 (m, 2H), 4.46 (s, 2H), 1 NH not observed. |
| 7 | MS m/z 343.0, 345.1, 347.0 [M + H]$^+$; $^1$H NMR (methanol-d$_4$) δ: 7.75 (s, 1H), 7.34 (d, J = 1.1 Hz, 1H), 6.56 (s, 1H), 6.20-6.29 (m, 2H), 4.45 (s, 2H), 1 NH not observed. |
| 8 | MS m/z 315.9, 317.9, 319.9 [M + H]$^+$; $^1$H NMR (CDCl$_3$) δ: 7.82 (d, J = 3.2 Hz, 1H), 7.49 (s, 1H), 7.37 (d, J = 3.2 Hz, 1H), 6.57 (s, 1H), 5.83 (t, J = 5.2 Hz, 1H), 4.89 (d, J = 5.5 Hz, 2H). |
| 9 | MS m/z 360.0, 362.1, 364.0 [M + H]$^+$; $^1$H NMR (methanol-d$_4$) δ: 7.73 (d, J = 3.4 Hz, 1H), 7.62 (s, 1H), 7.31 (d, J = 3.2 Hz, 1H), 6.48 (s, 1H), 4.81 (s, 2H), 1 NH not observed. |
| 10 | MS m/z 296.0, 298.0 [M + H]$^+$; $^1$H NMR (methanol-d$_4$) δ: 8.29 (s, 1H), 7.97 (d, J = 3.4 Hz, 1H), 7.79 (d, J = 3.4 Hz, 1H), 7.02 (s, 1H), 5.25 (s, 2H), 2.74 (s, 3H). |

Example 2 (Compound 28)

2-[(2S)-2-Aminopropyl]-5-chloro-3-methyl-N-[(thiophen-2-yl)methyl]thieno[3,2-b]pyridin-7-amine dihydrochloride

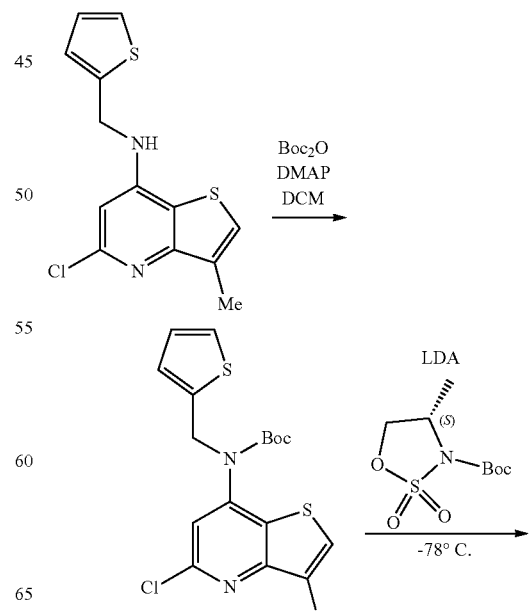

-continued

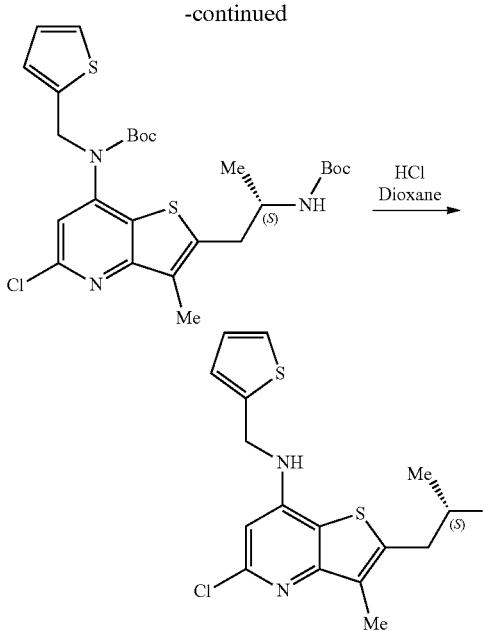

Step 1: tert-Butyl N-(5-chloro-3-methyl-thieno[3,2-b]pyridin-7-yl)-N-(2-thienylmethyl)carbamate To a solution of 5-chloro-3-methyl-N-(2-thienylmethyl)thieno[3,2-b]pyridin-7-amine (3.90 g, 13.0 mmol, 1.0 eq.), prepared according to the procedure in Example 1, in CH$_2$Cl$_2$ (53 mL) was added di-tert-butyl dicarbonate (5.8 g, 26.0 mmol, 2.0 eq.) followed by 4-(dimethylamino)pyridine (1.6 g, 13.0 mmol, 1.0 eq.). The mixture was stirred at room temperature for 2 h. The mixture was diluted with ethyl acetate and washed with water and brine. The organic layer was dried over Na$_2$SO$_4$, filtered and concentrated in vacuo. The residue was purified by silica gel column chromatography with ethyl acetate in hexanes (5 to 35% gradient) to give tert-butyl N-(5-chloro-3-methyl-thieno[3,2-b]pyridin-7-yl)-N-(2-thienylmethyl)carbamate (4.77 g, 91% yield). MS m/z 395.1 [M+H]$^+$; $^1$H NMR (400 MHz, CDCl$_3$) δ ppm 7.41 (s, 1H), 7.24 (dd, J=1.00 Hz, 1H), 7.06 (s, 1H), 6.89 (dd, J=1.00 Hz, 1H), 6.81 (d, J=1.00 Hz, 1H), 5.07 (s, 2H), 2.51 (d, J=1.07 Hz, 3H), 1.47 (s, 9H).

Step 2: tert-Butyl N-[2-[(2S)-2-(tert-butoxycarbonylamino)propyl]-5-chloro-3-methyl-thieno[3,2-b]pyridin-7-yl]-N-(2-thienylmethyl)carbamate To a solution of tert-butyl N-(5-chloro-3-methyl-thieno[3,2-b]pyridin-7-yl)-N-(2-thienylmethyl)carbamate (4.77 g, 12.1 mmol, 1.0 eq.) in THF (24 mL) at −78° C. was added lithium diisopropylamide (2.0 M) in THF/heptane/ethylbenzene (7.2 mL, 14.5 mmol, 1.2 eq.). After 15 min, a solution of tert-butyl (4S)-4-methyl-2,2-dioxo-oxathiazolidine-3-carboxylate (3.44 g, 14.5 mmol, 1.2 eq.) in THF (24 mL) was added to the reaction solution, and the mixture was stirred at −78° C. for 20 min. The reaction was quenched with 1.0 M citric acid, then was stirred for 30 min. The mixture was diluted with ethyl acetate and washed with water and brine. The combined organic layers were dried over Na$_2$SO$_4$, filtered and concentrated in vacuo. The residue was purified by silica gel column chromatography with ethyl acetate in CH$_2$Cl$_2$ (0 to 25% gradient) to give tert-butyl N-[2-[(2S)-2-(tert-butoxycarbonylamino)propyl]-5-chloro-3-methyl-thieno[3,2-b]pyridin-7-yl]-N-(2-thienylmethyl)carbamate (4.10 g, 61% yield). MS m/z 553.0, 555.0 [M+H]$^+$, $^1$H NMR (400 MHz, CDCl$_3$) δ ppm 7.22 (d, J=5.33 Hz, 1H), 6.99 (s, 1H), 6.86 (dd, J=5.04, 3.51 Hz, 1H), 6.78 (d, J=2.90 Hz, 1H), 5.02 (dd, J=1.00 Hz, 2H), 4.46 (br s, 1H), 4.01 (br s, 1H), 3.07-3.16 (m, 1H), 2.93-3.07 (m, 1H), 2.41 (s, 3H), 1.45 (s, 18H), 1.14 (d, J=6.71 Hz, 3H).

Step 3: 2-[(2S)-2-Aminopropyl]-5-chloro-3-methyl-N-(2-thienylmethyl)thieno[3,2-b]pyridin-7-amine General Boc-deprotection procedure: A mixture of tert-butyl N-[2-[(2S)-2-(tert-butoxycarbonylamino)propyl]-5-chloro-3-methyl-thieno[3,2-b]pyridin-7-yl]-N-(2-thienylmethyl)carbamate (4.10 g, 7.4 mmol, 1.0 eq.) and HCl (4 M) in dioxane (35 mL) was stirred at room temperature for 1 h. The mixture was diluted with diethyl ether (2×) and filtered. The filter cake was washed with ether, collected and dried to give 2-[(2S)-2-aminopropyl]-5-chloro-3-methyl-N-(2-thienylmethyl)thieno[3,2-b]pyridin-7-amine dihydrochloride (2.5 g, 96% yield). MS m/z 352.1, 354.1 [M+H]$^+$, $^1$H NMR (methanol-d$_4$) δ ppm 7.38 (dd, J=5.19, 1.07 Hz, 1H), 7.18 (d, J=2.75 Hz, 1H), 7.10 (s, 1H), 7.01 (dd, J=5.04, 3.51 Hz, 1H), 4.97 (s, 2H), 3.60-3.72 (m, 1H), 3.37-3.44 (m, 1H), 3.24-3.30 (m, 1H), 2.47 (s, 3H), 1.39 (d, J=6.56 Hz, 3H).

The compounds below were prepared according to the procedure of Example 2 by substituting the appropriate starting materials, reagents and reaction conditions.

| Compound | Spectral Data |
|---|---|
| 16 | MS m/z 322.2, 324.3 [M + H]$^+$; $^1$H NMR (methanol-d$_4$) δ: 7.52 (d, J = 1.2 Hz, 1H), 7.40 (s, 1H), 7.15 (s, 1H), 6.49 (s, 1H), 6.43 (s, 1H), 4.77 (s, 2H), 3.70-3.78 (m, 1H), 3.39-3.45 (m, 1H), 3.34-3.37 (m, 1H), 1.41 (d, J = 6.6 Hz, 3H), 3 NHs not observed. |
| 18 | MS m/z 336.1, 338.1 [M + H]$^+$; $^1$H NMR (methanol-d$_4$) δ: 7.45-7.54 (m, 1H), 7.10 (s, 1H), 6.46 (s, 1H), 6.42 (d, J = 1.8 Hz, 1H), 4.74 (s, 2H), 3.63-3.71 (m, 1H), 3.36-3.42 (m, 1H), 3.23-3.29 (m, 1H), 2.46 (s, 3H), 1.39 (d, J = 6.6 Hz, 3H), 3 NHs not observed. |
| 19 | MS m/z 350.3, 352.3 [M + H]$^+$; $^1$H NMR (methanol-d$_4$) δ: 7.51 (s, 1H), 7.15 (s, 1H), 6.46-6.52 (m, 1H), 6.39-6.45 (m, 1H), 4.76 (s, 2H), 3.47-3.57 (m, 1H), 3.30-3.40 (m, 2H), 2.47 (s, 3H), 1.68-1.89 (m, 2H), 1.11 (t, J = 7.5 Hz, 3H), 3 NHs not observed. |
| 29 | MS m/z 364.4, 366.4 [M + H]$^+$; $^1$H NMR (methanol-d$_4$) δ: 7.40-7.45 (m, 1H), 7.36-7.40 (m, 1H), 7.19-7.22 (m, 1H), 7.15-7.18 (m, 1H), 6.98 (s, 1H), 4.81 (s, 2H), 3.63-3.70 (m, 1H), 3.35-3.41 (m, 1H), 3.22-3.29 (m, 1H), 2.46 (s, 3H), 1.37 (d, J = 6.6 Hz, 3H), 3 NHs not observed. |
| 33 | MS m/z 366.3, 368.3 [M + H]$^+$; $^1$H NMR (methanol-d$_4$) δ: 7.37 (dd, J = 5.1, 1.1 Hz, 1H), 7.17 (d, J = 3.5 Hz, 1H), 7.04 (s, 1H), 7.01 (dd, J = 5.0, 3.5 Hz, 1H), 4.95 (s, 2H), 3.66 (s, 1H), 3.50-3.58 (m, 1H), 2.45 |

| Compound | Spectral Data |
|---|---|
|  | (s, 3H), 1.78-1.89 (m, 1H), 1.70-1.77 (m, 1H), 1.09 (t, J = 7.5 Hz, 3H), 1 H obscured by methanol peak, 3 NHs not observed. |
| 34 | MS m/z 302.3 [M + H]+; 1H NMR (methanol-d$_4$) δ: 8.20-8.34 (m, 1H), 7.49 (d, J = 1.1 Hz, 1H), 7.01-7.15 (m, 1H), 6.39-6.51 (m, 2H), 4.77 (br s, 2H), 3.68 (s, 1H), 3.41 (s, 1H), 3.30 (d, J = 8.2 Hz, 1H), 2.49 (s, 3H), 1.40 (d, J = 6.6 Hz, 3H), 3 NHs not observed. |
| 35 | MS m/z 365.4, 367.4 [M + H]+; 1H NMR (methanol-d$_4$) δ: 9.00 (br s, 1H), 8.69 (br d, J = 4.7 Hz, 1H), 7.99 (br t, J = 5.6 Hz, 1H), 7.02 (s, 1H), 5.14 (s, 2H), 3.65-3.74 (m, 1H), 3.39-3.45 (m, 1H), 2.49 (s, 3H), 1.39 (br d, J = 6.4 Hz, 3H), 1 H obscured by methanol peak, 3 NHs not observed. |
| 36 | MS m/z 356.2, 358.2, 360.2 [M + H]+; 1H NMR (methanol-d$_4$) δ: 7.39 (d, J = 1.1 Hz, 1H), 6.90 (s, 1H), 6.32 (d, J = 13.6 Hz, 2H), 4.58 (s, 2H), 3.59-3.70 (m, 1H), 3.29-3.36 (m, 1H), 3.23-3.27 (m, 1H), 1.30 (d, J = 6.6 Hz, 3H), 3 NHs not observed. |
| 37 | MS m/z 400.2, 402.2, 404.1 [M + H]+; 1H NMR (methanol-d$_4$) δ: 7.39 (d, J = 1.4 Hz, 1H), 6.98 (s, 1H), 6.36 (d, J = 3.2 Hz, 1H), 6.31 (dd, J = 3.1, 1.9 Hz, 1H), 4.62 (s, 2H), 3.62-3.74 (m, 1H), 3.34 (d, J = 6.4 Hz, 1H), 3.28 (d, J = 8.2 Hz, 1H), 1.31 (d, J = 6.6 Hz, 3H), 3 NHs not observed. |
| 38 | MS m/z 373.2, 375.2, 377.2 [M + H]+; 1H NMR (methanol-d$_4$) δ: 8.09 (d, J = 3.5 Hz, 1H), 7.91 (d, J = 3.5 Hz, 1H), 7.02 (s, 1H), 5.24 (s, 2H), 3.72-3.83 (m, 1H), 3.46 (d, J = 6.4 Hz, 1H), 3.40 (d, J = 8.1 Hz, 1H), 1.43 (d, J = 6.4 Hz, 3H), 3 NHs not observed. |
| 43 | MS m/z 417.1, 419.0, 421.1 [M + H]+; 1H NMR (methanol-d$_4$) δ: 8.10 (d, J = 3.7 Hz, 1H), 7.92 (d, J = 3.7 Hz, 1H), 6.97 (s, 1H), 5.23 (s, 2H), 3.73-3.85 (m, 1H), 3.42-3.51 (m, 1H), 3.33-3.41 (m, 1H), 1.41 (d, J = 6.6 Hz, 3H), 3 NHs not observed. |
| 46 | MS m/z 418.0, 420.1, 422.0 [M + H]+; 1H NMR (methanol-d$_4$) δ: 8.45 (br s, 1H), 7.47 (d, J = 1.2 Hz, 1H), 6.69 (s, 1H), 6.30-6.44 (m, 2H), 4.50-4.75 (m, 2H), 3.76-3.95 (m, 1H), 3.34-3.47 (m, 2H), 3 NHs not observed. |
| 52 | MS m/z 372.2, 374.1, 376.1 [M + H]+; 1H NMR (DMSO-d$_6$) δ: 8.00 (t, J = 6.0 Hz, 1H), 7.41 (dd, J = 5.0, 1.1 Hz, 1H), 7.11 (d, J = 3.1 Hz, 1H), 6.99 (dd, J = 5.0, 3.5 Hz, 1H), 6.60 (s, 1H), 4.73 (d, J = 6.1 Hz, 2H), 3.12-3.21 (m, 1H), 2.93 (t, J = 6.4 Hz, 2H), 1.65 (s, 2H), 1.05 (d, J = 6.4 Hz, 3H). |
| 53 | MS m/z 416.1, 418.1, 420.1 [M + H]+; 1H NMR (methanol-d$_4$) δ: 7.26 (d, J = 5.2 Hz, 1H), 7.04-7.09 (m, 1H), 6.89-6.92 (m, 1H), 6.85-6.87 (m, 1H), 4.81 (s, 2H), 3.63-3.72 (m, 1H), 3.32-3.39 (m, 1H), 3.23-3.30 (m, 1H), 1.31 (d, J = 6.7 Hz, 3H), 3 NHs not observed. |
| 57 | MS m/z 353.1, 355.1 [M + H]+; 1H NMR (methanol-d4) δ: 7.87 (d, J = 3.2 Hz, 1H), 7.70 (d, J = 3.4 Hz, 1H), 7.15 (s, 1H), 5.16 (s, 2H), 3.64-3.71 (m, 1H), 3.37-3.44 (m, 1H), 3.25-3.29 (m, 1H), 2.48 (s, 3H), 1.38 (d, J = 6.6 Hz, 3H), 3 NHs not observed. |
| 59 | MS m/z 354.1, 356.1 [M + H]+; 1H NMR (methanol-d$_4$) δ: 7.48 (s, 1H), 7.04 (s, 1H), 6.39-6.44 (m, 2H), 4.64-4.77 (m, 1H), 4.70 (s, 2H), 4.51-4.63 (m, 1H), 3.79-3.91 (m, 1H), 3.36-3.47 (m, 2H), 2.44 (s, 3H), 3 NHs not observed. |
| 61 | MS m/z 394.2, 396.2 [M + H]+; 1H NMR (methanol-d$_4$) δ: 7.37 (d, J = 5.1 Hz, 1 H), 7.16 (dd, J = 5.1, 3.3 Hz, 1 H), 7.02 (dd, J = 5.1, 3.3 Hz, 1 H), 6.94 (s, 1 H), 4.91 (s, 2 H), 3.60-3.62 (m, 1 H), 3.28-3.33 (m, 2 H), 2.42 (s, 3 H), 1.78-1.83 (m, 1 H), 1.58-1.62 (m, 2 H), 1.01 (d, J = 6.54 Hz, 3 H), 0.96 (d, J = 6.54 Hz, 3 H), 3 NHs not observed. |
| 62 | MS m/z 459.0, 461.1 [M + H]+; 1H NMR (methanol-d$_4$) δ: 7.83 (d, J = 3.3 Hz, 1 H), 7.60 (d, J = 3.3 Hz, 1 H), 6.67 (s, 1 H), 4.96 (s, 2 H), 3.72-3.75 (m, 1 H), 3.46-3.49 (m, 1 H), 3.37-3.39 (m, 1 H), 1.80-1.84 (m, 1 H), 1.61-1.64 (m, 2 H), 1.02 (d, J = 6.54 Hz, 3 H), 0.98 (d, J = 6.54 Hz, 3 H), 3 NHs not observed. |
| 63 | MS m/z 434.1, 436.1, 438.0 [M + H]+; 1H NMR (DMSO-d$_6$) δ: 8.62 (br s, 3H), 8.10-8.22 (m, 1H), 7.36-7.48 (m, 1H), 7.08-7.16 (m, 1H), 6.93-7.05 (m, 1H), 6.65 (s, 1H), 4.62-4.77 (m, J = 4.9 Hz, 3H), 4.48-4.62 (m, 1H), 3.65-3.84 (m, 1H), 3.34-3.45 (m, 2H). |
| 66 | MS m/z 435.2, 437.2, 439.2 [M + H]+; 1H NMR (methanol-d$_4$) δ: 8.04 (d, J = 3.5 Hz, 1H), 7.85 (d, J = 3.5 Hz, 1H), 6.88 (s, 1H), 5.16 (s, 2H), 4.55-4.81 (m, 2H), 3.93-4.06 (m, 1H), 3.51 (s, 2H), 3 NHs not observed. |
| 67 | MS m/z 391.1, 393.1, 395.1 [M + H]+; 1H NMR (methanol-d$_4$) δ: 7.93 (d, J = 3.5 Hz, 1H), 7.74 (d, J = 3.5 Hz, 1H), 6.83 (s, 1H), 5.07 (s, 2H), 4.54-4.72 (m, 2H), 3.81-3.93 (m, 1H), 3.36-3.44 (m, 2H), 3 NHs not observed. |
| 68 | MS m/z 395.2, 397.2 [M + H]+; 1H NMR (DMSO-d$_6$) δ: 7.93-7.95 (m, 1 H), 7.89 (br s, 3 H), 7.65 (d, J = 0.9 Hz, 1 H), 7.79 (d, J = 0.9 Hz, 1 H), 6.54 (s, 1 H), 4.86 (s, 2 H), 3.40-3.42 (m, 1 H), 3.18 (d, J = 6.70 Hz, 2 H), 2.27 (s, 3 H), 1.74-1.79 (m, 1 H), 1.49-1.54 (m, 1 H), 1.38-1.43 (m, 1 H), 0.89 (d, J = 6.54 Hz, 3 H), 0.84 (d, J = 6.54 Hz, 3 H). |
| 70 | MS m/z 435.0, 437.0, 439.0 [M + H]+; 1H NMR (methanol-d$_4$) δ: 8.07 (d, J = 3.4 Hz, 1H), 7.89 (d, J = 3.4 Hz, 1H), 6.91 (s, 1H), 5.20 (s, 2H), 4.58-4.83 (m, 2H), 3.94-4.07 (m, 1H), 3.53 (s, 2H), 3 NHs not observed. |

-continued

| Compound | Spectral Data |
|---|---|
| 73 | MS m/z 430.1, 432.2, 434.1 [M + H]$^+$; $^1$H NMR (DMSO-d$_6$) δ: 8.24 (br s, 3H), 8.11 (br s, 1H), 7.41 (d, J = 4.9 Hz, 1H), 7.11 (d, J = 3.1 Hz, 1H), 6.99 (t, J = 4.1 Hz, 1H), 6.65 (s, 1H), 5.75 (s, 1H), 4.74 (br d, J = 5.2 Hz, 2H), 3.38-3.45 (m, 1H), 3.25-3.33 (m, 2H), 1.64 (br t, J = 7.2 Hz, 2H), 0.97 (t, J = 7.5 Hz, 3H). |
| 76 | MS m/z 434.2, 436.2, 438.1 [M + H]$^+$; $^1$H NMR (DMSO-d$_6$) δ: 8.62 (br s, 3H), 8.13 (br s, 1H), 7.41 (d, J = 5.2 Hz, 1H), 7.11 (d, J = 2.7 Hz, 1H), 6.99 (t, J = 4.3 Hz, 1H), 6.66 (s, 1H), 4.62-4.80 (m, 3H), 4.45-4.61 (m, 1H), 3.67-3.85 (m, 1H), 3.29-3.43 (m, 2H). |
| 78 | MS m/z 431.1, 433.0 [M + H]$^+$; $^1$H NMR (methanol-d$_4$) δ: 8.03 (d, J = 3.3 Hz, 1 H), 7.85 (d, J = 3.3 Hz, 1 H), 6.91 (s, 1 H), 5.18 (s, 2H), 3.64-3.66 (m, 1 H), 3.45-3.50 (m, 1 H), 3.37-3.41 (m, 1 H), 1.74-1.84 (m, 2 H), 1.12 (t, J = 7.45 Hz, 3 H), 3 NHs not observed. |
| 79 | MS m/z 415.2, 417.2 [M + H]$^+$; $^1$H NMR (methanol-d$_4$) δ: 7.96 (d, J = 3.3 Hz, 1 H), 7.78 (d, J = 3.3 Hz, 1 H), 6.86 (dd, J = 3.2, 12.5 Hz, 1 H), 5.11 (s, 2 H), 3.71-3.74 (m, 1 H), 3.45-3.49 (m, 1 H), 3.37-3.39 (m, 1 H), 1.81-1.86 (m, 1 H), 1.61-1.64 (m, 2 H), 1.02 (d, J = 6.54 Hz, 3 H), 0.98 (d, J = 6.54 Hz, 3 H), 3 NHs not observed. |
| 81 | MS m/z 354.2, 356.2 [M + H]$^+$; $^1$H NMR (methanol-d$_4$) δ: 7.47 (s, 1H), 6.93 (s, 1H), 6.40 (br s, 2H), 4.73-4.76 (m, 1H), 4.66 (s, 2H), 4.51-4.62 (m, 1H), 3.78-3.90 (m, 1H), 3.35-3.45 (m, 2H), 2.42 (s, 3H), 3 NHs not observed. |
| 82 | MS m/z 387.1, 389.1 [M + H]$^+$; $^1$H NMR (methanol-d$_4$) δ: 7.90 (d, J = 0.9 Hz, 1 H), 7.68 (d, J = 0.9 Hz, 1 H), 6.78 (s, 1 H), 5.03 (s, 2H), 3.60-3.62 (m, 1 H), 3.42-3.47 (m, 1 H), 3.32-3.36 (m, 1 H), 1.74-1.84 (m, 2 H), 1.19 (t, J = 7.45 Hz, 3 H), 3 NHs not observed. |
| 83 | MS m/z 386.1, 388.1, 390.1 [M + H]$^+$; $^1$H NMR (methanol-d$_4$) δ: 7.36 (d, J = 5.0 Hz, 1H), 7.16 (d, J = 2.9 Hz, 1H), 7.00-7.03 (m, 1H), 6.99 (s, 1H), 4.91 (s, 2H), 3.60 (quin, J = 6.5 Hz, 1H), 3.42-3.48 (m, 1H), 3.34-3.40 (m, 1H), 1.79-1.90 (m, 1H), 1.71-1.79 (m, 1H), 1.10 (t, J = 7.5 Hz, 3H), 3 NHs not observed. |
| 84 | MS m/z 390.0, 392.0, 394.0 [M + H]$^+$; $^1$H NMR (methanol-d$_4$) δ: 7.29 (d, J = 5.0 Hz, 1H), 7.08 (d, J = 3.1 Hz, 1H), 6.97 (t, J = 4.2 Hz, 1H), 6.57 (s, 1H), 4.74 (s, 2H), 4.39-4.49 (m, 1H), 4.29-4.39 (m, 1H), 3.35-3.45 (m, 1H), 3.18-3.24 (m, 1H), 3.02-3.11 (m, 1H), 3 NHs not observed. |
| 85 | MS m/z 367.3, 369.3 [M + H]$^+$; $^1$H NMR (methanol-d$_4$) δ: 8.54 (s, 1 H), 7.80 (d, J = 3.3 Hz, 1 H), 7.55 (d, J = 3.3 Hz, 1 H), 6.51 (s, 1 H), 4.91 (s, 2 H), 3.47-3.44 (m, 1 H), 3.26-3.28 (m, 1 H), 3.19-3.22 (m, 1 H), 2.38 (s, 3 H), 1.79-1.83 (m, 1 H), 1.70-1.74 (m, 1 H), 1.39 (t, J = 7.45 Hz, 3 H), 3 NHs not observed, formic acid salt. |
| 90 | MS m/z 391.1, 393.1, 395.1 [M + H]$^+$; $^1$H NMR (methanol- d$_4$) δ: 7.96-8.02 (m, 1H), 7.80 (s, 1H), 6.88 (s, 1H), 5.12 (s, 2H), 4.57-4.83 (m, 2H), 3.90-4.04 (m, 1H), 3.45-3.56 (m, 2H), 3 NHs not observed |
| 91 | MS m/z 354.2, 354.2 [M + H]$^+$; $^1$H NMR (methanol-d$_4$) δ: 7.35 (d, J = 5.0 Hz, 1H), 7.12-7.15 (m, 1H), 7.00 (t, J = 4.0 Hz, 1H), 6.92 (s, 1H), 4.89 (s, 2H), 4.74 (br s, 1H), 4.51-4.63 (m, 1H), 3.80-3.93 (m, 1H), 3.36-3.46 (m, 2H), 2.43 (s, 3H), 3 NHs not observed. |
| 94 | MS m/z 374.2, 376.2 [M + H]$^+$; $^1$H NMR (methanol-d$_4$) δ: 7.46 (s, 1H), 6.77 (s, 1H), 6.35-6.39 (m, 2H), 4.75-4.78 (m, 1H), 4.66 (s, 1H), 4.58 (s, 2H), 3.86-3.97 (m, 1H), 3.43 (dd, J = 7.6, 3.7 Hz, 2H), 3 NHs not observed. |
| 125 | MS m/z 449.0, 451.0, 453.0 [M + H]$^+$; $^1$H NMR (methanol-d$_4$) δ: 8.05-8.13 (m, 1H), 7.92 (s, 1H), 6.94 (s, 1H), 5.22 (s, 2H), 4.99-5.16 (m, 1H), 3.93-4.07 (m, 1H), 3.58-3.63 (m, 1H), 3.34-3.40 (m, 1H), 1.49-1.62 (m, 3H), 3 NHs not observed. |
| 126 | MS m/z 384.1, 386.1 [M + H]$^+$; $^1$H NMR (methanol- d$_4$) δ: 7.34-7.39 (m, 1H), 7.14-7.20 (m, 1H), 6.97-7.06 (m, 2H), 4.98-5.13 (m, 1H), 4.94 (s, 2H), 3.82-3.93 (m, 1H), 3.51-3.56 (m, 1H), 3.40-3.47 (m, 1H), 2.46 (s, 3H), 1.47-1.57 (m, 3H), 3 NHs not observed. |
| 136 | MS m/z 352.1, 354.1 [M + H]$^+$; $^1$H NMR (methanol-d$_4$) δ: 7.49 (s, 1H), 7.10 (s, 1H), 6.46 (br s, 1H), 6.38-6.43 (m, 1H), 4.71-4.76 (m, 2H), 4.00 (s, 3H), 3.67-3.73 (m, 1H), 3.32-3.38 (m, 1H), 3.23-3.29 (m, 1H), 1.36-1.41 (m, 3H), 3 NHs not observed. |
| 139 | MS m/z 404.2, 406.2 [M + H]$^+$; $^1$H NMR (methanol-d$_4$) δ: 8.35-8.74 (br s, 1H), 7.36 (t, J = 77 Hz, 1H), 7.30-7.34 (m, 1H), 7.07-7.13 (m, 1H), 6.96-7.03 (m, 1H), 6.58-6.65 (m, 1H), 4.78 (s, 2H), 3.61-3.73 (m, 1H), 3.16-3.30 (m, 2H), 1.38 (br d, J = 6.7 Hz, 3H), 3 NHs not observed. |
| 152 | MS m/z 322.1, 323.1 [M + H]$^+$; $^1$H NMR (methanol-d$_4$) δ: 8.44 (s, 1 H), 7.34 (d, J = 0.95 Hz, 1 H), 6.48 (s, 1 H), 6.25-6.26 (m, 1 H), 6.20 (d, J = 3.05 Hz, 1 H), 4.42 (s, 2 H), 3.11-3.15 (m, 4 H), 2.24 (s, 3 H), 3 NHs not observed, formic acid salt. |

Example 3 (Compound 17)

(2R)-2-Amino-3-(5-chloro-7-{[(furan-2-yl)methyl]amino}thieno[3,2-b]pyridin-2-yl)propan-1-ol dihydrochloride

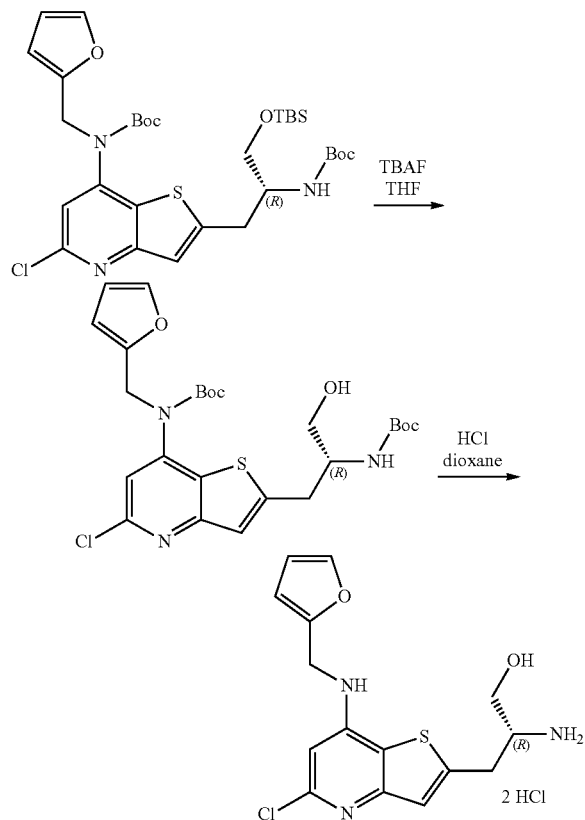

Step 1: tert-Butyl N-[2-[(2R)-2-(tert-butoxycarbonylamino)-3-hydroxy-propyl]-5-chloro-thieno[3,2-b]pyridin-7-yl]-N-(2-furylmethyl)carbamate To a solution of tert-butyl N-[2-[(2R)-2-(tert-butoxycarbonylamino)-3-[tert-butyl(dimethyl)silyl]oxy-propyl]-5-chloro-thieno[3,2-b]pyridin-7-yl]-N-(2-furylmethyl)carbamate (41 mg, 0.063 mmol, 1.0 eq.), prepared according to the procedure in Example 2, in THF (0.5 mL) at 0° C. was added TBAF (1.0 M in THF) (0.25 mL, 0.25 mmol, 4.0 eq.). After 1 h at room temperature, the mixture was diluted with ether, washed with water and brine, dried and evaporated. The residue was purified over silica gel with ethyl acetate and hexanes (5 to 65% gradient) to give tert-butyl N-[2-[(2R)-2-(tert-butoxycarbonylamino)-3-hydroxy-propyl]-5-chloro-thieno[3,2-b]pyridin-7-yl]-N-(2-furylmethyl)carbamate (33 mg, 98% yield). MS m/z 538.3, 540.1 [M+H]$^+$.

Step 2: (2R)-2-Amino-3-[5-chloro-7-(2-furylmethylamino)thieno[3,2-b]pyridin-2-yl]propan-1-ol A mixture of tert-butyl N-[2-[(2R)-2-(tert-butoxycarbonylamino)-3-hydroxy-propyl]-5-chloro-thieno[3,2-b]pyridin-7-yl]-N-(2-furylmethyl)carbamate (33 mg, 0.061 mmol, 1.0 eq.), anisole (0.1 mL) and HCl (4 M in dioxane) (1.0 mL) was stirred at room temperature for 30 min, then 3 drops of MeOH was added, and the mixture was stirred for another 30 min. The mixture was diluted with ether and filtered. The solid was collected and dried to give (2R)-2-amino-3-[5-chloro-7-(2-furylmethylamino)thieno[3,2-b]pyridin-2-yl]propan-1-ol dihydrochloride (21 mg, 83% yield). MS m/z 338.3, 340.2 [M+H]$^+$. $^1$H NMR (methanol-$d_4$) δ ppm 7.52 (d, J=1.2 Hz, 1H), 7.42 (s, 1H), 7.16 (s, 1H), 6.49 (s, 1H), 6.41-6.45 (m, 1H), 4.77 (s, 2H), 3.79-3.86 (m, 1H), 3.64-3.71 (m, 2H), 3.44-3.50 (m, 1H), 3.36-3.42 (m, 1H).

The compounds below were prepared according to the procedure of Example 3 by substituting the appropriate starting materials, reagents and reaction conditions.

| Compound | Spectral Data |
| --- | --- |
| 39 | MS m/z 372.2, 374.2, 376.2 [M + H]$^+$; $^1$H NMR (methanol-$d_4$) δ: 7.38 (dd, J = 1.7, 0.8 Hz, 1H), 6.90 (s, 1H), 6.25-6.37 (m, 2H), 4.58 (s, 2H), 3.71 (br d, J = 8.2 Hz, 1H), 3.56 (br d, J = 10.7 Hz, 2H), 3.26-3.37 (m, 2H), 3 NHs and 1 OH not observed. |
| 41 | MS m/z 414.2, 416.1, 418.1 [M + H]$^+$; $^1$H NMR (methanol-$d_4$) δ: 7.37 (dd, J = 1.7, 0.8 Hz, 1H), 6.80 (s, 1H), 6.22-6.36 (m, 2H), 4.54 (s, 2H), 3.70 (dd, J = 11.1, 2.9 Hz, 1H), 3.52-3.63 (m, 2H), 3.30 (dd, J = 13.9, 7.2 Hz, 2H), 3 NHs and 1 OH not observed. |
| 48 | MS m/z 403.2, 405.2, 407.2 [M + H]$^+$; $^1$H NMR (methanol-$d_4$) δ: 7.99 (d, J = 3.5 Hz, 1H), 7.80 (d, J = 3.5 Hz, 1H), 6.89 (s, 1H), 5.13 (s, 2H), 3.85 (d, J = 5.2 Hz, 3H), 3.46 (dd, J = 13.9, 7.2 Hz, 2H), 1.95 (t, J = 5.1 Hz, 2H), 3 NHs and 1 OH not observed. |
| 58 | MS m/z 352.1, 354.1 [M + H]$^+$; $^1$H NMR (methanol-$d_4$) δ: 7.48 (s, 1H), 6.86 (s, 1H), 6.40 (s, 2H), 4.64 (s, 2H), 3.79 (dd, J = 11.3, 3.1 Hz, 1H), 3.61-3.65 (m, 1H), 3.56-3.59 (m, 1H), 3.35-3.41 (m, 1H), 3.29 (br d, J = 6.3 Hz, 1H), 2.42 (s, 3H), 3 NHs and 1 OH not observed. |
| 71 | MS m/z 433.1, 435.1, 437.1 [M + H]$^+$; $^1$H NMR (methanol-$d_4$) δ: 8.06-8.13 (m, 1H), 7.89-7.95 (m, 1H), 6.94-7.01 (m, 1H), 5.19-5.27 (m, 2H), 3.81-3.87 (m, 1H), 3.66-3.79 (m, 2H), 3.41-3.54 (m, 2H), 3 NHs and 1 OH not observed. |
| 89 | MS m/z 447.2, 449.2, 451.2 [M + H]$^+$; δH NMR (methanol-$d_4$) δ: 8.03 (br s, 1H), 7.84 (d, J = 3.4 Hz, 1H), 6.90 (s, 1H), 5.16 (s, 2H), 3.83-3.93 (m, 2H), 3.74-3.81 (m, 1H), 3.41-3.55 (m, 2H), 1.89-2.01 (m, 2H), 3 NHs and 1 OH not observed. |

| Compound | Spectral Data |
|---|---|
| 100 | MS m/z 458.0, 460.1, 462.1 [M + H]$^+$; $^1$H NMR (methanol-d$_4$) δ: 7.38 (s, 2H), 7.12-7.20 (m, 2H), 6.56 (s, 1H), 4.66 (s, 2H), 3.81-3.89 (m, 2H), 3.73-3.80 (m, 1H), 3.42 (dd, J = 17.3, 7.2 Hz, 2H), 1.94 (s, 2H), 3 NHs and 1 OH not observed. |
| 162 | MS m/z 354.1, 356.1 [M + H]$^+$; $^1$H NMR (methanol-d$_4$) δ: 8.48 (br s, 1 H), 7.52 (d, J = 5.0 Hz, 1 H), 7.19 (s, 1 H), 7.09 (d, J = 3.35 Hz, 1 H), 6.99-7.01 (m, 1 H), 6.56 (s, 1 H), 4.77 (s, 2 H), 3.79-3.82 (m, 1 H), 3.64-3.68 (m, 1 H), 3.57-3.59 (m, 1 H), 3.23-3.27 (m, 2 H), 3 NHs and 1 OH not observed, formic acid salt. |
| 165 | MS m/z 430.4, 432.4, 434.4 [M + H]$^+$; $^1$H NMR (DMSO-d$_6$) δ: 7.99 (br s, 3H), 7.91 (br t, J = 5.7 Hz, 1H), 7.61 (s, 1H), 6.70 (s, 1H), 6.37-6.43 (m, 2H), 4.54 (br d, J = 5.6 Hz, 2H), 3.73-3.80 (m, 1H), 3.32-3.38 (m, 1H), 3.25-3.31 (m, 1H), 3.15-3.22 (m, 1H), 1.19 (d, J = 6.4 Hz, 3H), 1 OH not observed. |

Example 4 (Compound 42)

5-Chloro-N-[(furan-2-yl)methyl]-3-methyl-2-[(2S)-2-(methylamino)propyl]thieno[3,2-b]pyridin-7-amine hydrochloride

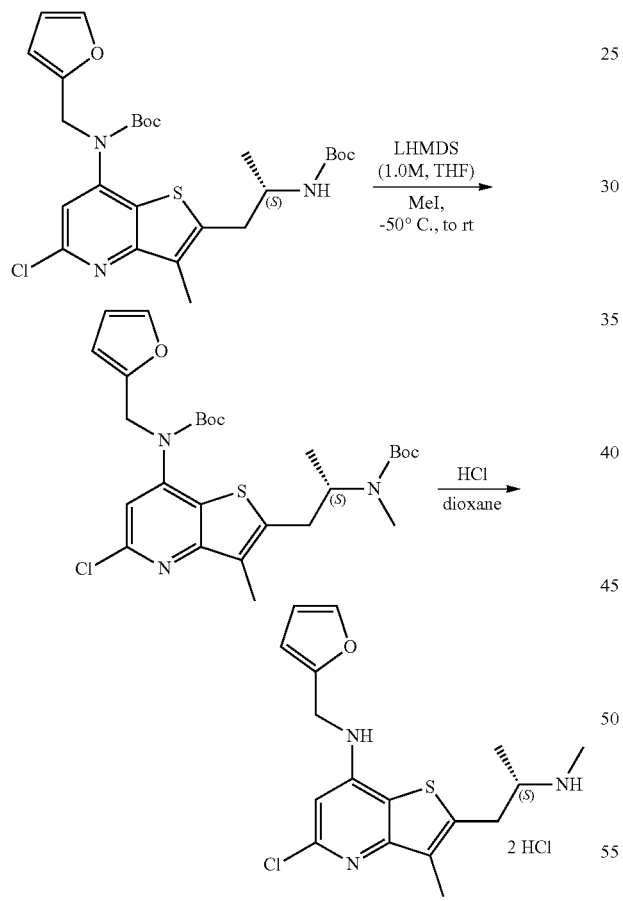

Step 1: tert-Butyl (S)-(2-(2-((tert-butoxycarbonyl)(methyl)amino)propyl)-5-chloro-3-methylthieno[3,2-b]pyridin-7-yl)(furan-2-ylmethyl)carbamate To a solution of tert-butyl (S)-(2-(2-((tert-butoxycarbonyl)amino)propyl)-5-chloro-3-methylthieno[3,2-b]pyridin-7-yl)(furan-2-ylmethyl)carbamate (120 mg, 0.22 mmol, 1.0 eq.) in THF (1 mL) was added LHMDS (1.0M in THF, 0.27 mL, 1.1 eq.) at −50° C. After 30 min, MeI (42 mg, 1.2 eq.) in THF (1 mL) was added. The mixture was gradually warmed up to room temperature over 1 h, stirred at room temperature for 1 h, cooled to −50° C., then quenched with a few drops of citric acid. After warming to room temperature, the reaction was diluted with water and EtOAc. The organic layer was washed with water, brine and dried over sodium sulfate and evaporated. The residue was purified by flash column chromatography on silica gel eluting with 0-10% EtOAc in DCM, followed by purification by preparative HPLC eluting with 20-100% ACN in water (with 0.1% formic acid) to provide tert-butyl (S)-(2-(2-((tert-butoxycarbonyl)(methyl)amino)propyl)-5-chloro-3-methyl-thieno[3,2-b]pyridin-7-yl)(furan-2-ylmethyl)carbamate (35 mg, 28% yield) as a white solid. MS m/z 550.2, 552.2 [M+H]$^+$.

Step 2: (S)-5-Chloro-N-(furan-2-ylmethyl)-3-methyl-2-(2-(methylamino)propyl)thieno[3,2-b]pyridin-7-amine tert-Butyl (S)-(2-(2-((tert-butoxycarbonyl)(methyl)amino)propyl)-5-chloro-3-methylthieno[3,2-b]pyridin-7-yl)(furan-2-ylmethyl)carbamate (35 mg, 0.064 mmol) was stirred in a solution of HCl (4 M in dioxane, 1 mL) at room temperature for 1 h. The mixture concentrated in vacuo. The solid was triturated with diethyl ether and filtered to afford (S)-5-chloro-N-(furan-2-ylmethyl)-3-methyl-2-(2-(methylamino)propyl)thieno[3,2-b]pyridin-7-amine dihydrochloride (12 mg, 49% yield). MS m/z 350.1, 352.1 [M+H]$^+$; $^1$H NMR (methanol-d$_4$) δ ppm 7.49 (t, J=1.2 Hz, 1H), 6.90 (s, 1H), 6.41 (d, J=1.3 Hz, 2H), 4.66 (s, 2H), 3.57-3.60 (m, 1H), 3.44-3.47 (m, 1H), 3.18-3.23 (m, 1H), 2.80 (s, 3H), 2.43 (s, 3H), 1.35 (d, J=6.6 Hz, 3H).

Example 5 (Compound 104)

2-[(2R)-2-Amino-3-(methylsulfanyl)propyl]-5-chloro-N-[(furan-2-yl)methyl]-3-methylthieno[3,2-b]pyridin-7-amine dihydrochloride

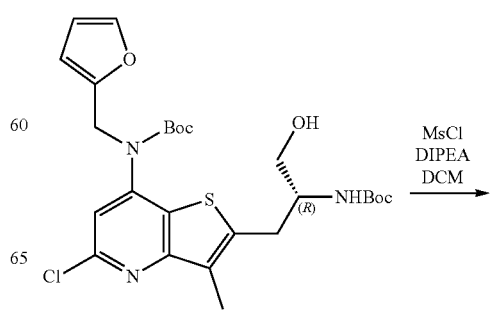

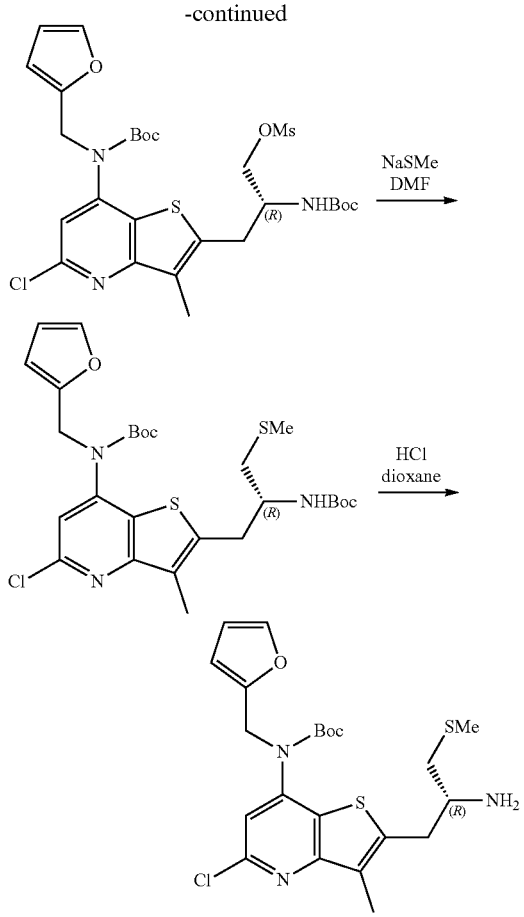

Step 1: [(2R)-2-(tert-Butoxycarbonylamino)-3-[7-[tert-butoxycarbonyl(2-furylmethyl)amino]-5-chloro-3-methyl-thieno[3,2-b]pyridin-2-yl]propyl] methanesulfonate To a solution of tert-butyl N-[2-[(2R)-2-(tert-butoxycarbonylamino)-3-hydroxy-propyl]-5-chloro-3-methyl-thieno[3,2-b]pyridin-7-yl]-N-(2-furylmethyl)carbamate (217.0 mg, 0.393 mmol, 1.0 eq.), prepared according to the procedure in Example 3, in DCM (2.5 mL) was added a solution of methanesulfonyl chloride (592 mg, 0.40 mL, 5.17 mmol, 13.1 eq.) in DCM (9.60 mL) followed by N,N-diisopropylethylamine (75.5 mg, 0.10 mL, 0.57 mmol, 1.46 eq.) at 0° C. The reaction was stirred at 0° C. for 1 h, then quenched by sodium bicarbonate (~5 mL) and extracted with DCM (5×10 mL) using a phase separator. The volatiles were removed under reduced pressure to afford [(2R)-2-(tert-butoxycarbonylamino)-3-[7-[tert-butoxycarbonyl(2-furylmethyl)amino]-5-chloro-3-methyl-thieno[3,2-b]pyridin-2-yl]propyl]methanesulfonate (262.2 mg, 0.42 mmol, 1.06 eq.) as a light yellow foam which was carried over to the next step without further purification. MS m/z 630.4, 632.3 [M+H]⁺.

Step 2: tert-Butyl N-[2-[(2R)-2-(tert-butoxycarbonylamino)-3-methylsulfanyl-propyl]-5-chloro-3-methyl-thieno[3,2-b]pyridin-7-yl]-N-(2-furylmethyl) carbamate To a solution of [(2R)-2-(tert-butoxycarbonylamino)-3-[7-[tert-butoxycarbonyl(2-furylmethyl)amino]-5-chloro-3-methyl-thieno[3,2-b]pyridin-2-yl]propyl]methanesulfonate (262.2 mg, 0.42 mmol, 1.0 eq.) in DMF (2.5 mL) was added sodium methanethiolate (45.0 mg, 0.58 mmol, 1.39 eq.) at room temperature. The mixture was stirred at room temperature overnight, then quenched with water (2 mL). The mixture was extracted with EtOAc (2×30 mL). The combined organic layers were washed with water followed by brine (30 mL) and dried over sodium sulfate. The volatiles were removed under reduced pressure, and the residue was purified by silica gel flash column chromatography (12 g, 0-20% EtOAc in hexanes with 10% DCM) to afford tert-butyl N-[2-[(2R)-2-(tert-butoxycarbonylamino)-3-methylsulfanyl-propyl]-5-chloro-3-methyl-thieno[3,2-b]pyridin-7-yl]-N-(2-furylmethyl)carbamate (202.3 mg, 84% yield) as a light yellow foam. MS m/z 582.3, 584.3 [M+H]⁺.

Step 3: (R)-2-(2-Amino-3-(methylthio)propyl)-5-chloro-N-(furan-2-ylmethyl)-3-methylthieno[3,2-b] pyridin-7-amine Removal of the Boc group following the general procedure described in Step 3 for Example 2 provided (R)-2-(2-amino-3-(methylthio)propyl)-5-chloro-N-(furan-2-ylmethyl)-3-methylthieno[3,2-b]pyridin-7-amine dihydrochloride MS m/z 382.3, 384.3 [M+H]⁺; ¹H NMR (500 MHz, DMSO-d₆) δ ppm 8.31-8.48 (m, 3H), 7.68 (br s, 1H), 7.59 (d, J=0.92 Hz, 1H), 6.60 (s, 1H), 6.40 (dd, J=3.05, 1.83 Hz, 1H), 6.35 (d, J=3.05 Hz, 1H), 4.51 (s, 2H), 3.46-3.54 (m, 1H), 3.36 (dd, J=14.84, 6.15 Hz, 1H), 3.29 (dd, J=14.92, 7.57 Hz, 1H), 2.83 (dd, J=14.21, 6.37 Hz, 1H), 2.76 (dd, J=14.14, 5.93 Hz, 1H), 2.28 (s, 3H), 2.11 (s, 3H).

The compounds below were prepared according to the procedure of Example 5 by substituting the appropriate starting materials, reagents and reaction conditions.

| Compound | Spectral Data |
|---|---|
| 114 | MS m/z 402.3, 404.3, 406.3 [M + H]⁺; ¹H NMR (DMSO-d₆) δ: 8.21 (br s, 3H), 7.94 (br t, J = 5.8 Hz, 1H), 7.60 (s, 1H), 6.71 (s, 1H), 6.37-6.43 (m, 2H), 4.54 (br d, J = 5.5 Hz, 2H), 3.58-3.67 (m, 1H), 3.31-3.36 (m, 2H), 2.74-2.83 (m, 2H), 2.12 (s, 3H). |
| 118 | MS m/z 446.2, 448.2, 450.2 [M + H]⁺; ¹H NMR (methanol-d₄) δ: 7.49 (s, 1H), 6.91 (s, 1H), 6.41 (s, 2H), 4.61-4.67 (m, 2H), 3.82-3.91 (m, 1H), 3.52-3.59 (m, 1H), 3.43-3.51 (m, 1H), 2.88-2.95 (m, 1H), 2.79-2.87 (m, 1H), 2.20 (s, 3H), 3 NHs not observed. |

Example 6 (Compound 111)

(3S)-3-Amino-4-(5-chloro-7-{[(furan-2-yl)methyl]amino}-3-methylthieno[3,2-b]pyridin-2-yl)butanenitrile dihydrochloride

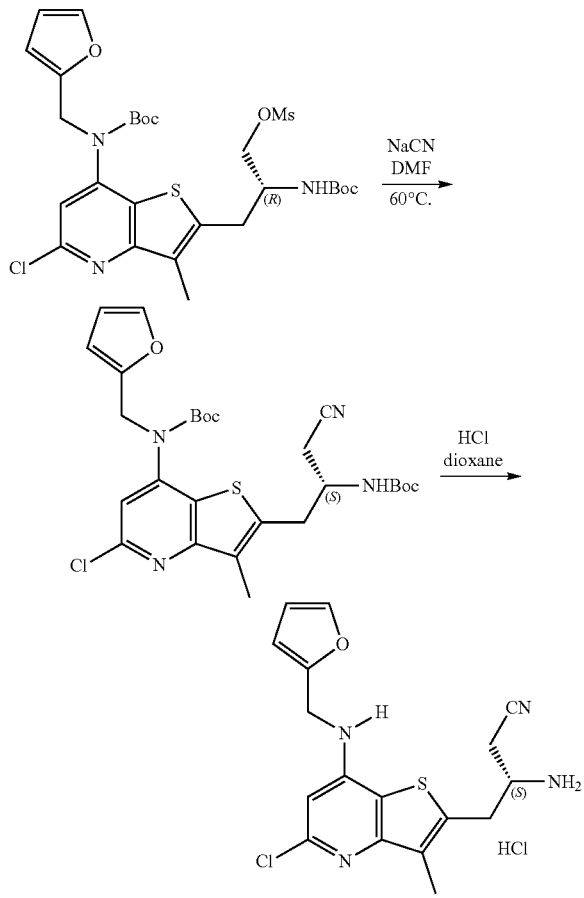

Step 1: tert-Butyl N-[2-[(2S)-2-(tert-butoxycarbonylamino)-3-cyano-propyl]-5-chloro-3-methyl-thieno[3,2-b]pyridin-7-yl]-N-(2-furylmethyl)carbamate To a solution of [(2R)-2-(tert-butoxycarbonylamino)-3-[7-[tert-butoxycarbonyl(2-furylmethyl)amino]-5-chloro-3-methyl-thieno[3,2-b]pyridin-2-yl]propyl]methanesulfonate (216 mg, 0.34 mmol, 1.0 eq.), prepared according to the procedure in Example 5, in DMF (2.5 mL) was added sodium cyanide (30 mg, 0.58 mmol, 1.7 eq.) at room temperature. The reaction was stirred at 60° C. for 3 h. The reaction was quenched with water (2.0 mL) and then extracted with EtOAc (2×40 mL). The combined organic phases were washed with water followed by brine (30 mL) then dried over sodium sulfate. The volatiles were removed under reduced pressure and the residue was purified by flash column chromatography (12 g, 0-20% EtOAc in hexanes with 10% DCM) to afford tert-butyl N-[2-[(2S)-2-(tert-butoxycarbonylamino)-3-cyano-propyl]-5-chloro-3-methyl-thieno[3,2-b]pyridin-7-yl]-N-(2-furylmethyl)carbamate (134.2 mg, 70% yield) as an off-white foam. MS m/z 561.3, 563.3 [M+H]$^+$.

Step 2: (S)-3-Amino-4-(5-chloro-7-((furan-2-ylmethyl)amino)-3-methylthieno[3,2-b]pyridin-2-yl)butanenitrile Removal of the Boc group following the general procedure described in Step 3 for Example 2 provided (S)-3-amino-4-(5-chloro-7-((furan-2-ylmethyl)amino)-3-methyl-thieno[3,2-b]pyridin-2-yl)butanenitrile hydrochloride. MS m/z 361.3, 363.3 [M+H]$^+$, 359.2, 361.2 [M−H]$^-$; $^1$H NMR 500 MHz (DMSO-d$_6$) δ ppm 8.61 (br s, 3H), 7.66 (br s, 1H), 7.59 (s, 1H), 6.60 (s, 1H), 6.40 (br s, 1H), 6.35 (br s, 1H), 4.51 (br s, 2H), 3.33-3.45 (m, 2H), 3.24 (br dd, J=14.95, 8.24 Hz, 1H), 2.91-3.06 (m, 2H), 2.28 (s, 3H).

The compounds below were prepared according to the procedure of Example 6 by substituting the appropriate starting materials, reagents and reaction conditions.

| Compound | Spectral Data |
|---|---|
| 103 | MS m/z 425.2, 427.2, 429.2 [M + H]$^+$; $^1$H NMR (methanol-d$_4$) δ: 8.01-8.57 (br s, 1H), 7.47 (d, J = 1.5 Hz, 1H), 6.67 (s, 1H), 6.32-6.41 (m, 2H), 4.55 (s, 2H), 3.77-3.92 (m, 1H), 3.37 (t, J = 7.1 Hz, 2H), 2.87 (dd, J = 13.6, 5.3 Hz, 2H), 3 NHs not observed. |
| 105 | MS m/z 377.2, 379.2 [M + H]$^+$; $^1$H NMR (methanol-d$_4$) δ: 7.37 (d, J = 5.0 Hz, 1H), 7.16 (br s, 1H), 7.03-7.05 (m, 1H), 7.01 (br t, J = 3.6 Hz, 1H), 4.94 (s, 2H), 3.94-4.04 (m, 1H), 3.50-3.57 (m, 1H), 3.44-3.50 (m, 1H), 2.97-3.08 (m, 2H), 2.49 (s, 3H), 3 NHs not observed. |
| 106 | MS m/z 397.1, 399.1, 401.1 [M + H]$^+$; $^1$H NMR (methanol-d$_4$) δ: 7.25 (br d, J = 4.1 Hz, 1H), 7.04 (br s, 1H), 6.91 (br d, J = 2.6 Hz, 1H), 6.77 (s, 1H), 3.91-4.00 (m, 1H), 3.44 (br d, J = 7.3 Hz, 2H), 3.30 (br d, J = 7.2 Hz, 1H), 2.93 (t, J = 5.1 Hz, 1H), 2 Hs obscured by water peak, 3 NHs not observed. |

Example 7 (Compound 64 and Compound 65)

2-[(2R)-2-Amino-3-(trifluoromethoxy)propyl]-3-bromo-5-chloro-N-[(1,3-thiazol-2-yl)methyl]thieno[3,2-b]pyridin-7-amine formate and (2R)-3-(3-Bromo-5-chloro-7-{[(1,3-thiazol-2-yl)methyl]amino}thieno[3,2-b]pyridin-2-yl)-2-[(trifluoromethyl)amino]propan-1-ol formate

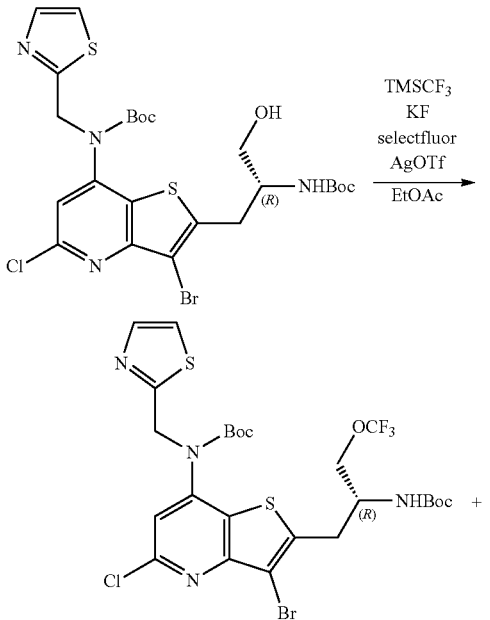

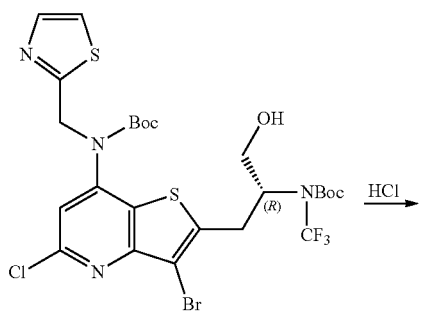

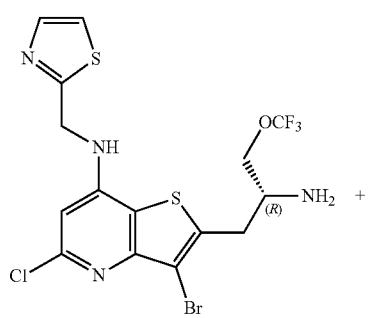

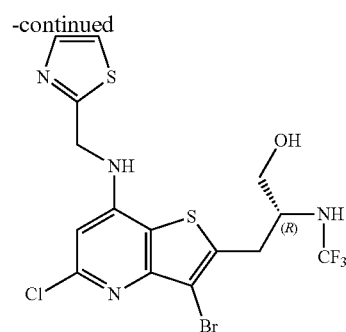

Step 1: tert-Butyl N-[3-bromo-2-[(2R)-2-(tert-butoxycarbonylamino)-3-(trifluoromethoxy)propyl]-5-chloro-thieno[3,2-b]pyridin-7-yl]-N-(thiazol-2-ylmethyl)carbamate and tert-butyl N-[(1R)-1-[[3-bromo-7-[tert-butoxycarbonyl(thiazol-2-ylmethyl)amino]-5-chloro-thieno[3,2-b]pyridin-2-yl]methyl]-2-hydroxy-ethyl]-N-(trifluoromethyl)carbamate To a mixture of tert-butyl N-[3-bromo-2-[(2R)-2-(tert-butoxycarbonylamino)-3-hydroxy-propyl]-5-chloro-thieno[3,2-b]pyridin-7-yl]-N-(thiazol-2-ylmethyl)carbamate (64 mg, 0.10 mmol, 1.0 eq.), prepared according to the procedure in Example 3, silver trifluoromethanesulfonate (78 mg, 0.30 mmol, 3.0 eq.), Selectfluor® (56 mg, 0.15 mmol, 1.5 eq.), potassium fluoride (23 mg, 0.40 mmol, 4.0 eq.) and 2,6-di-tert-butylphenol (11 mg, 0.050 mmol, 0.50 eq.) was added a solution of 2-fluoropyridine (30 mg, 0.027 mL, 0.30 mmol, 3.0 eq.) and (trifluoromethyl)trimethylsilane (43 mg, 0.046 mL, 0.30 mmol, 3.0 eq.) in EtOAc (0.5 mL). The mixture was stirred at room temperature overnight. The mixture was diluted with DCM and purified over silica gel with ethyl acetate in dichloromethane (0 to 25 to 75% gradient) to give, as the less polar fraction, tert-butyl N-[3-bromo-2-[(2R)-2-(tert-butoxycarbonylamino)-3-(trifluoromethoxy)propyl]-5-chloro-thieno[3,2-b]pyridin-7-yl]-N-(thiazol-2-ylmethyl)carbamate (3.5 mg, 4.9% yield), $^1$H NMR (CDCl$_3$) δ ppm 7.52-7.77 (m, 1H), 7.40-7.25 (m, 2H), 5.08 (br s, 2H), 4.68-4.82 (m, 1H), 4.11-4.23 (m, 1H), 3.98 (dd, J=17.3, 3.6 Hz, 2H), 3.23 (d, J=6.3 Hz, 2H), 1.29-1.42 (m, 18H), and tert-butyl N-[(1R)-1-[[3-bromo-7-[tert-butoxycarbonyl(thiazol-2-ylmethyl)amino]-5-chloro-thieno[3,2-b]pyridin-2-yl]methyl]-2-hydroxy-ethyl]-N-(trifluoromethyl)carbamate (35 mg, 49% yield), $^1$H NMR (chloroform-d) δ ppm 7.77 (br s, 1H), 7.44 (br s, 1H), 7.35 (s, 1H), 5.22 (d, J=6.6 Hz, 2H), 4.86 (br s, 1H), 4.26 (br s., 1H), 4.02-4.12 (m, 2H), 3.32 (d, J=6.0 Hz, 2H), 1.36-1.49 (m, 18H).

Step 2: 2-[(2R)-2-Amino-3-(trifluoromethoxy)propyl]-3-bromo-5-chloro-N-(thiazol-2-ylmethyl)thieno[3,2-b]pyridin-7-amine Removal of the Boc group following the general procedure described in Step 3 for Example 2, tert-butyl N-[3-bromo-2-[(2R)-2-(tert-butoxycarbonylamino)-3-(trifluoromethoxy)propyl]-5-chloro-thieno[3,2-b]pyridin-7-yl]-N-(thiazol-2-ylmethyl)carbamate (3.5 mg) was treated with HCl in dioxane, then purified by HPLC to give 2-[(2R)-2-amino-3-(trifluoromethoxy)propyl]-3-bromo-5-chloro-N-(thiazol-2-ylmethyl)thieno[3,2-b]pyridin-7-amine, formic acid salt, MS m/z 501.2, 503.1, 505.1 [M+H]$^+$; $^1$H NMR (methanol-d$_4$) δ ppm 8.39 (s, 1H), 7.74-7.82 (m, 1H), 7.51-7.58 (m, 1H), 6.57 (s, 1H), 4.90 (s, 2H), 4.04-4.22 (m, 2H), 3.62-3.79 (m, 1H), 3.33-3.41 (m, 1H), 3.19-3.27 (m, 1H).

(2R)-3-[3-Bromo-5-chloro-7-(thiazol-2-ylmethylamino)thieno[3,2-b]pyridin-2-yl]-2-(trifluoromethylamino)propan-1-ol formate Deprotection of tert-butyl N-[(1R)-1-[[3-bromo-7-[tert-butoxycarbonyl(thiazol-2-ylmethyl)amino]-5-chloro-thieno[3,2-b]pyridin-2-yl]methyl]-2-hydroxy-ethyl]-N-(trifluoromethyl)carbamate provided (2R)-3-[3-bromo-5-chloro-7-(thiazol-2-ylmethylamino)thieno[3,2-b]pyridin-2-yl]-2-(trifluoromethylamino)propan-1-ol, formic acid salt, MS m/z 501.2, 503.1, 505.1 [M+H]$^+$; $^1$H NMR (methanol-d$_4$) δ ppm 8.37 (s, 1H), 7.80 (d, J=3.1 Hz, 1H), 7.56 (d, J=3.2 Hz, 1H), 6.59 (s, 1H), 4.92 (s, 2H), 4.26 (br s, 1H), 4.14-4.22 (m, 1H), 3.80-3.94 (m, 1H), 3.35-3.47 (m, 2H).

Example 8 (Compound 113)

2-[(2R)-2-Amino-3-(methanesulfonyl)propyl]-3,5-dichloro-N-[(furan-2-yl)methyl]thieno[3,2-b]pyridin-7-amine dihydrochloride

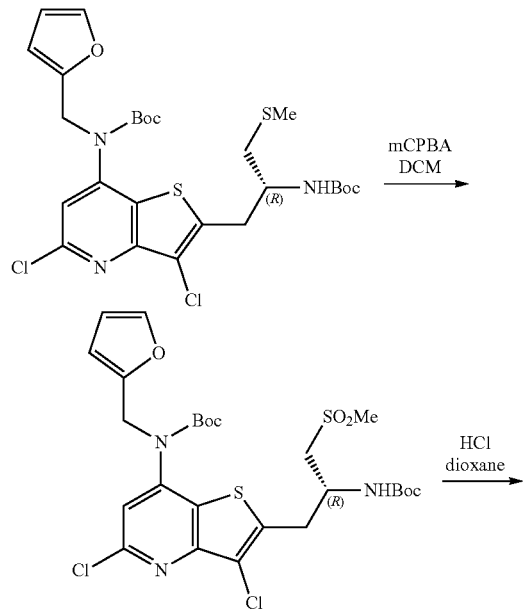

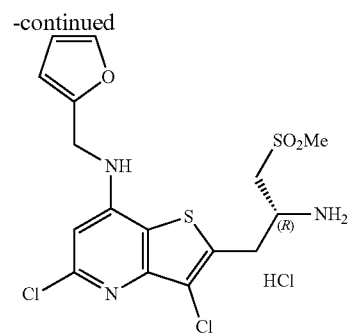

Step 1: tert-Butyl N-[2-[(2R)-2-(tert-butoxycarbonylamino)-3-methylsulfonyl-propyl]-3,5-dichloro-thieno[3,2-b]pyridin-7-yl]-N-(2-furylmethyl)carbamate To a solution of tert-butyl N-[2-[(2R)-2-(tert-butoxycarbonylamino)-3-methylsulfanyl-propyl]-3,5-dichloro-thieno[3,2-b]pyridin-7-yl]-N-(2-furylmethyl)carbamate (256.0 mg, 0.42 mmol, 1.0 eq.), prepared according to the procedure in Example 5, in DCM (3.0 mL) was added 3-chloroperoxybenzoic acid (189.4 mg, 0.82 mmol, 1.9 eq.) at 0° C. The reaction was stirred at 0° C. for 1 h then quenched with sodium bicarbonate (3.0 mL). The mixture was extracted by DCM (5×10 mL) using a phase separator. The combined organic phases were dried over sodium sulfate then concentrated. The residue was purified by flash column chromatography (24 g, 0-40% EtOAc in hexanes with 10% DCM) to afford tert-butyl N-[2-[(2R)-2-(tert-butoxycarbonylamino)-3-methylsulfonyl-propyl]-3,5-dichloro-thieno[3,2-b]pyridin-7-yl]-N-(2-furylmethyl)carbamate (232.8 mg, 86% yield) as an off-white foam. MS m/z 634.3 [M+H]$^+$, 656.4 [M+Na]$^+$.

Step 2: (R)-2-(2-Amino-3-(methylsulfonyl)propyl)-3,5-dichloro-N-(furan-2-ylmethyl)thieno[3,2-b]pyridin-7-amine Removal of the Boc group following the general procedure described in Step 3 for Example 2 provided (R)-2-(2-amino-3-(methylsulfonyl)propyl)-3,5-dichloro-N-(furan-2-ylmethyl)thieno[3,2-b]pyridin-7-amine dihydrochloride MS m/z 434.3, 436.3 [M+H]$^+$, 432.2 [M−H]$^-$; $^1$H NMR (500 MHz, DMSO-d$_6$) δ ppm 8.47 (br s, 3H), 7.98 (br t, J=5.49 Hz, 1H), 7.60 (s, 1H), 6.71 (s, 1H), 6.37-6.43 (m, 2H), 4.54 (br d, J=5.19 Hz, 2H), 3.95-4.06 (m, 1H), 3.45-3.66 (m, 4H), 3.17 (s, 3H).

The compounds below were prepared according to the procedure of Example 8 by substituting the appropriate starting materials, reagents and reaction conditions.

| Compound | Spectral Data |
| --- | --- |
| 108 | MS m/z 414.3, 416.3 [M + H]$^+$; $^1$H NMR (methanol-d$_4$) δ: 7.46 (s, 1H), 6.91 (s, 1H), 6.39 (br s, 2H), 4.64 (s, 2H), 4.15-4.22 (m, 1H), 3.58-3.63 (m, 1H), 3.47-3.56 (m, 3H), 3.11 (s, 3H), 2.42 (s, 3H), 3 NHs not observed. |
| 117 | MS m/z 478.2, 480.2, 482.2 [M + H]$^+$; $^1$H NMR (methanol-d$_4$) δ: 7.49 (s, 1H), 6.89-6.96 (m, 1H), 6.38-6.45 (m, 2H), 4.65 (s, 2H), 4.28-4.39 (m, 1H), 3.54-3.72 (m, 4H), 3.15 (s, 3H), 3 NHs not observed |

Example 9 (Compound 47)

2-[(2S)-2-Amino-4-fluorobutyl]-3,5-dichloro-N-[(1,3-thiazol-2-yl)methyl]thieno[3,2-b]pyridin-7-amine dihydrochloride

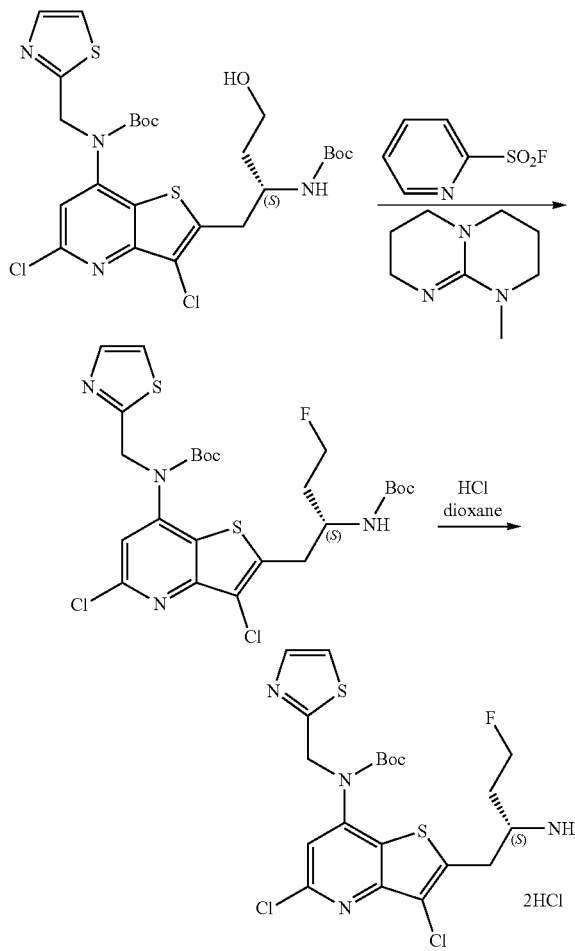

Step 1: tert-Butyl N-[2-[(2S)-2-(tert-butoxycarbonylamino)-4-fluoro-butyl]-3,5-dichloro-thieno[3,2-b]pyridin-7-yl]-N-(thiazol-2-ylmethyl)carbamate To a mixture of tert-butyl N-[2-[(2S)-2-(tert-butoxycarbonylamino)-4-hydroxy-butyl]-3,5-dichloro-thieno[3,2-b]pyridin-7-yl]-N-(thiazol-2-ylmethyl)carbamate (35 mg, 0.058 mmol, 1.0 eq.), prepared according to the procedure in Example 3, and pyridine-2-sulfonyl fluoride (11 mg, 0.064 mmol, 1.1 eq.) in toluene (0.2 mL) was added 7-methyl-1,5,7-triazabicyclo[4.4.0]dec-5-ene (18 mg, 0.017 mL, 0.12 mmol, 2.0 eq.). The mixture was stirred at room temperature over 3 d, then diluted with DCM and purified over silica gel with ethyl acetate in hexanes (5 to 50% gradient) to give tert-butyl N-[2-[(2S)-2-(tert-butoxycarbonylamino)-4-fluoro-butyl]-3,5-dichloro-thieno[3,2-b]pyridin-7-yl]-N-(thiazol-2-ylmethyl)carbamate (30 mg, 85% yield). MS m/z 627.2, 629.1 [M+Na]$^+$.

Step 2: (3S)-3-Amino-4-[3,5-dichloro-7-(thiazol-2-ylmethylamino)thieno[3,2-b]pyridin-2-yl]butan-1-ol The general Boc-deprotection procedure described in Step 3 for Example 2 using HCl in dioxane was followed to give (3S)-3-amino-4-[3,5-dichloro-7-(thiazol-2-ylmethylamino)thieno[3,2-b]pyridin-2-yl]butan-1-ol dihydrochloride (14 mg, 99% yield). MS m/z 405.1, 407.2, 409.1 [M+H]$^+$; $^1$H NMR (methanol-d$_4$) δ: 8.08 (d, J=3.5 Hz, 1H), 7.91 (d, J=3.5 Hz, 1H), 6.99 (s, 1H), 5.23 (s, 2H), 4.61-4.81 (m, 2H), 3.85-3.95 (m, 1H), 3.51 (qd, J=14.9, 7.2 Hz, 2H), 2.12-2.26 (m, 2H).

The compounds below were prepared according to the procedure of Example 9 by substituting the appropriate starting materials, reagents and reaction conditions.

| Compound | Spectral Data |
|---|---|
| 74 | MS m/z 448.2, 450.2, 452.2 [M + H]$^+$; $^1$H NMR (DMSO-d$_6$) δ: 8.45 (br s, 3H), 8.14 (br s, 1H), 7.40 (d, J = 5.2 Hz, 1H), 7.05-7.18 (m, 1H), 6.99 (s, 1H), 6.65 (s, 1H), 4.52-4.78 (m, 4H), 3.57-3.65 (m, 1H), 3.38 (br d, J = 7.0 Hz, 2H), 1.95-2.16 (m, 2H). |
| 88 | MS m/z 449.2, 451.2, 453.2 [M + H]$^+$; $^1$H NMR (methanol-d$_4$) δ: 8.01-8.20 (m, 1H), 7.82-7.95 (m, 1H), 6.86 (s, 1H), 5.02-5.18 (m, 2H), 4.61-4.81 (m, 2H), 3.86-3.97 (m, 1H), 3.41-3.57 (m, 2H), 2.08-2.27 (m, 2H), 3 NHs not observed. |
| 92 | MS m/z 384.3, 386.3 [M + H]$^+$; $^1$H NMR (methanol-d$_4$) δ: 7.34 (d, J = 4.9 Hz, 1H), 7.12 (br s, 1H), 6.99 (t, J = 4.0 Hz, 1H), 6.86 (s, 1H), 4.70-4.75 (m, 1H), 4.60-4.66 (m, 1H), 3.73-3.79 (m, 1H), 3.37 (br t, J = 6.7 Hz, 2H), 2.42 (s, 3H), 2.08-2.19 (m, 2H), 2 Hs obscured by water peak, 3 NHs not observed. |
| 93 | MS m/z 388.3, 390.3 [M + H]$^+$; $^1$H NMR (methanol-d$_4$) δ: 7.46 (s, 1H), 6.82 (s, 1H), 6.37 (s, 2H), 4.60 (s, 2H), 3.84 (quin, J = 6.7 Hz, 1H), 3.36-3.49 (m, 2H), 2.04-2.23 (m, 2H), 2 Hs obscured by water peak, 3 NHs not observed. |

-continued

| Compound | Spectral Data |
|---|---|
| 95 | MS m/z 368.3, 370.3 [M + H]$^+$; $^1$H NMR (DMSO-d$_6$) δ: 8.24 (br s, 3H), 7.61-7.67 (m, 1H), 7.59 (d, J = 0.8 Hz, 1H), 6.60 (s, 1H), 6.39-6.41 (m, 1H), 6.35 (d, J = 2.9 Hz, 1H), 4.62-4.73 (m, 1H), 4.54-4.62 (m, 1H), 4.51 (br d, J = 2.4 Hz, 2H), 3.44-3.52 (m, 1H), 3.27-3.32 (m, 1H), 3.20-3.25 (m, 1H), 2.26 (s, 3H), 1.95-2.09 (m, 2H). |
| 97 | MS m/z 432.1, 434.1, 436.1 [M + H]$^+$; $^1$H NMR (methanol-d$_4$) δ: 7.47 (s, 1H), 6.86 (s, 1H), 6.39 (s, 2H), 4.64-4.79 (m, 2H), 4.62 (s, 2H), 3.83-3.91 (m, 1H), 3.47 (d, J = 7.3 Hz, 1H), 3.38-3.43 (m, 1H), 2.15-2.23 (m, 1H), 2.09-2.14 (m, 1H), 3 NHs not observed. |
| 98 | MS m/z 404.2, 406.2, 408.2 [M + H]$^+$; $^1$H NMR (methanol-d$_4$) δ: 7.33 (dd, J = 5.0, 1.1 Hz, 1H), 7.12 (d, J = 2.6 Hz, 1H), 7.00 (dd, J = 5.0, 3.5 Hz, 1H), 6.80 (s, 1H), 4.83 (s, 2H), 4.71-4.80 (m, 1H), 4.60-4.68 (m, 1H), 3.81-3.90 (m, 1H), 3.44-3.51 (m, 1H), 3.38-3.43 (m, 1H), 2.15-2.23 (m, 1H), 2.08-2.15 (m, 1H), 3 NHs not observed. |
| 99 | MS m/z 385.2, 387.2 [M + H]$^+$; $^1$H NMR (methanol-d$_4$) δ: 8.34-8.73 (m, 1H), 8.00-8.24 (m, 1H), 6.96-7.10 (m, 1H), 4.49-4.71 (m, 4H), 3.66-3.77 (m, 1H), 3.31-3.40 (m, 2H), 2.39 (s, 3H), 1.99-2.14 (m, 2H), 3 NHs not observed |

Example 10 (Compound 107)

2-[(2S)-2-Amino-4,4-difluorobutyl]-3-bromo-5-chloro-N-[(thiophen-2-yl)methyl]thieno[3,2-b]pyridin-7-amine hydrochloride

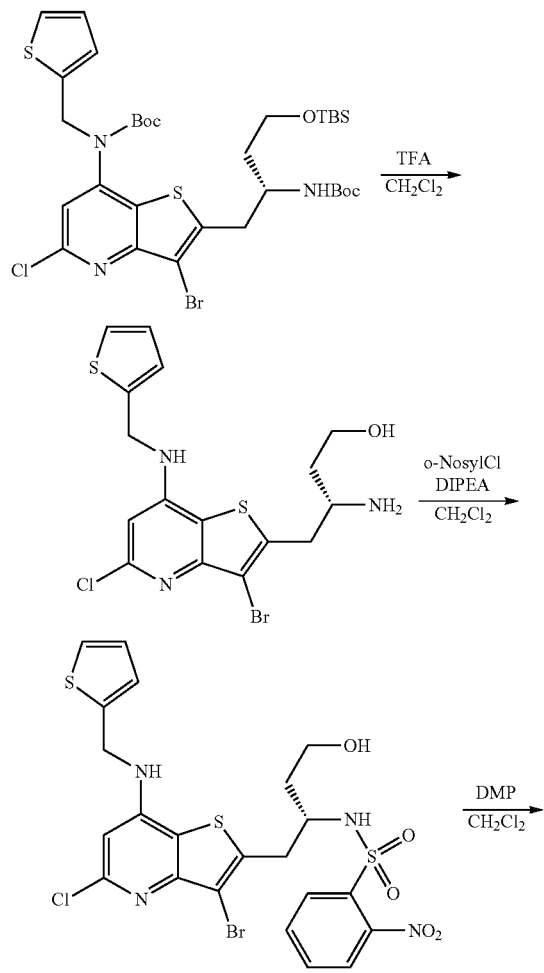

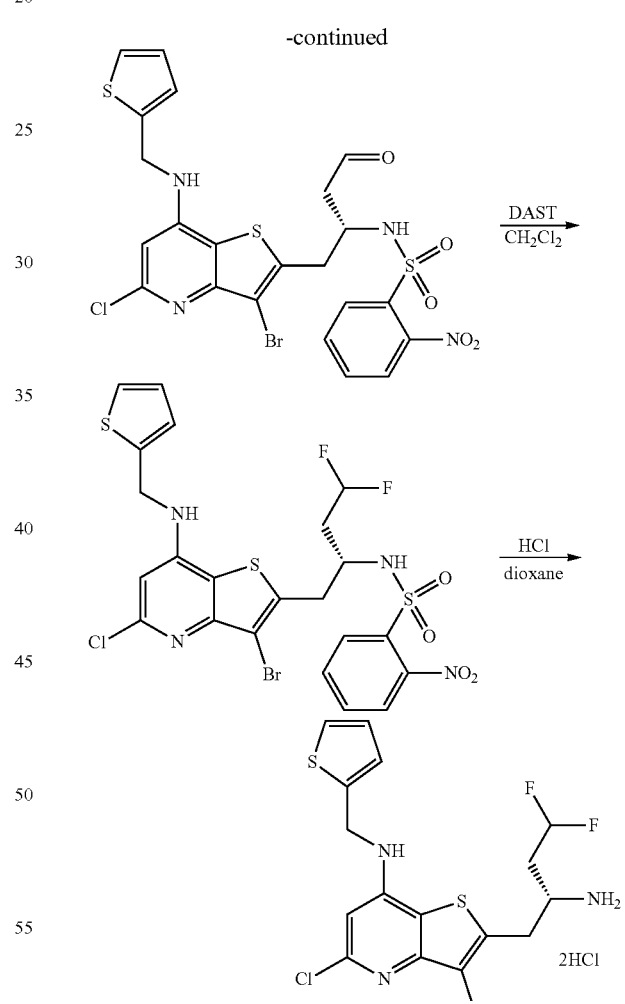

Step 1: (3S)-3-Amino-4-[3-bromo-5-chloro-7-(2-thienylmethylamino)thieno[3,2-b]pyridin-2-yl]butan-1-ol To a solution of tert-butyl N-[3-bromo-2-[(2S)-2-(tert-butoxycarbonylamino)-4-[tert-butyl(dimethyl)silyl]oxy-butyl]-5-chloro-thieno[3,2-b]pyridin-7-yl]-N-(2-thienylmethyl)carbamate (300 mg, 0.4 mmol), prepared according to the procedure in Example 2, in CH$_2$Cl$_2$ (3 mL) was added trifluoroacetic acid (0.5 mL, 7 mmol). After stirring at room temperature for 4 h, the reaction was concentrated under reduced pressure. The product was used in the subsequent step without further purification. MS m/z 446.8, 448.2, 450.2 [M+H]$^+$.

Step 2: N-[(1S)-1-[[3-Bromo-5-chloro-7-(2-thienylmethylamino)thieno[3,2-b]pyridin-2-yl]methyl]-3-hydroxy-propyl]-2-nitro-benzenesulfonamide To a solution (3S)-3-amino-4-[3-bromo-5-chloro-7-(2-thienylmethylamino)thieno[3,2-b]pyridin-2-yl]butan-1-ol (100 mg, 0.2 mmol) in CH$_2$Cl$_2$ (1 mL) at room temperature was added 2-nitrobenzenesulfonyl chloride (50 mg, 0.2 mmol, 1.0 eq) followed by N,N-diisopropylethylamine (0.12 mL, 0.69 mmol, 3.5 eq). After stirring at room temperature for 1 h, the mixture was diluted with water (5 mL) and extracted with CH$_2$Cl$_2$ (3×10 mL). The combined organic layers were washed with 1M HCl (10 mL) followed by saturated NaHCO$_3$ (10 mL), then dried over Na$_2$SO$_4$, filtered, and concentrated. The precipitate was triturated with diethyl ether and filtered to afford N-[(1S)-1-[[3-bromo-5-chloro-7-(2-thienylmethylamino)thieno[3,2-b]pyridin-2-yl]methyl]-3-hydroxy-propyl]-2-nitro-benzenesulfonamide (119 mg, 84% yield) as a light yellow solid. MS m/z 631.2, 633.2, 635.2 [M+H]$^+$; $^1$H NMR (DMSO-d$_6$) δ ppm 8.08 (br d, J=8.5 Hz, 1H), 7.84 (br t, J=5.8 Hz, 1H), 7.65 (t, J=7.9 Hz, 2H), 7.30-7.47 (m, 3H), 7.10-7.20 (m, 1H), 7.03 (t, J=4.1 Hz, 1H), 6.59 (s, 1H), 4.71 (br d, J=5.8 Hz, 2H), 4.41 (t, J=4.9 Hz, 1H), 3.78-3.97 (m, 1H), 3.44-3.54 (m, 1H), 3.15 (br dd, J=14.3, 5.2 Hz, 1H), 2.99 (dd, J=14.5, 8.7 Hz, 1H), 1.63-1.81 (m, 2H).

Step 3: N-[(1S)-1-[[3-Bromo-5-chloro-7-(2-thienylmethylamino)thieno[3,2-b]pyridin-2-yl]methyl]-3-oxo-propyl]-2-nitro-benzenesulfonamide To a suspension of N-[(1S)-1-[[3-bromo-5-chloro-7-(2-thienylmethylamino)thieno[3,2-b]pyridin-2-yl]methyl]-3-hydroxy-propyl]-2-nitro-benzenesulfonamide (50 mg, 0.08 mmol) in CH$_2$Cl$_2$ (2 mL) was added Dess-Martin periodinane, 1,1,1-tris(acetyloxy)-1,1-dihydro-1,2-benziodoxol-3-(1H)-one, (40 mg, 0.09 mmol, 1.1 eq.). After stirring at room temperature for 4 h, the mixture was concentrated to afford N-[(1S)-1-[[3-bromo-5-chloro-7-(2-thienylmethylamino)thieno[3,2-b]pyridin-2-yl]methyl]-3-oxo-propyl]-2-nitro-benzenesulfonamide which was used without further purification. MS m/z 629.2, 631.2, 633.2 [M+H]$^+$.

Step 4: (S)-N-(1-(3-Bromo-5-chloro-7-((thiophen-2-ylmethyl)amino)thieno[3,2-b]pyridin-2-yl)-4,4-difluorobutan-2-yl)-2-nitrobenzenesulfonamide To a solution of N-[(1S)-1-[[3-bromo-5-chloro-7-(2-thienylmethylamino)thieno[3,2-b]pyridin-2-yl]methyl]-3-oxo-propyl]-2-nitro-benzenesulfonamide from step 3 in CH$_2$Cl$_2$ (1 mL) was added diethylaminosulfur trifluoride (0.25 g, 1 M) at room temperature. After stirring for 30 min, the reaction was quenched with saturated NaHCO$_3$ (5 mL) and extracted with CH$_2$Cl$_2$ (10 mL). The organic layer was dried over Na$_2$SO$_4$, filtered, and concentrated to afford (S)-N-(1-(3-bromo-5-chloro-7-((thiophen-2-ylmethyl)amino)thieno[3,2-b]pyridin-2-yl)-4,4-difluorobutan-2-yl)-2-nitrobenzenesulfonamide which was used without further purification. MS m/z 651.1, 653.3 [M+H]$^+$.

Step 5: 2-[(2S)-2-Amino-4,4-difluoro-butyl]-3-bromo-5-chloro-N-(2-thienylmethyl)thieno[3,2-b]pyridin-7-amine To a solution of N-[(1S)-1-[[3-bromo-5-chloro-7-(2-thienylmethylamino)thieno[3,2-b]pyridin-2-yl]methyl]-3,3-difluoro-propyl]-2-nitro-benzenesulfonamide in DMF (1 mL, 12.9 mmol) was added thiophenol (0.02 mL, 0.2 mmol) and K$_2$CO$_3$ (40 mg, 0.29 mmol). After stirring at room temperature for 18 h, the mixture was diluted with MeOH (1 mL), filtered, and purified by preparative HPLC. The collected fractions were concentrated and then treated with 1M HCl/Et$_2$O (1 mL) to afford 2-[(2S)-2-amino-4,4-difluoro-butyl]-3-bromo-5-chloro-N-(2-thienylmethyl)thieno[3,2-b]pyridin-7-amine dihydrochloride (4.0 mg, 9.4% yield) as a white solid. MS m/z 466.1, 468.0, 470.1 [M+H]$^+$; $^1$H NMR (methanol-d$_4$) δ ppm 7.33 (d, J=5.2 Hz, 1H), 7.11 (d, J=3.1 Hz, 1H), 7.00 (t, J=4.3 Hz, 1H), 6.66 (s, 1H), 6.04-6.37 (m, 1H), 4.71-4.83 (m, 2H), 3.98 (quin, J=6.8 Hz, 1H), 3.36-3.51 (m, 2H), 2.25-2.45 (m, 2H).

Example 11 (Compound 45)

2-[(2R)-2-Amino-3-methoxypropyl]-5-chloro-N-[(furan-2-yl)methyl]-3-methylthieno[3,2-b]pyridin-7-amine dihydrochloride

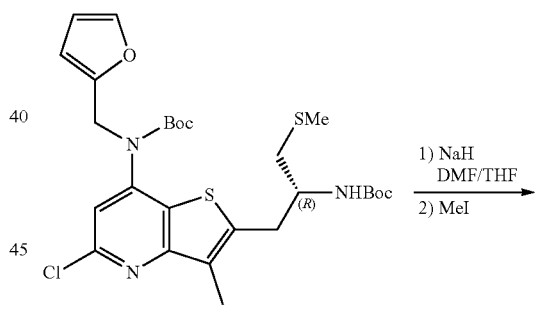

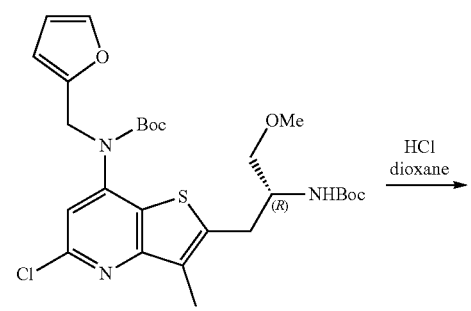

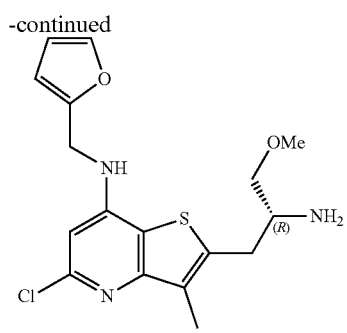

Step 1: tert-Butyl N-[2-[(2R)-2-(tert-butoxycarbonylamino)-3-methoxy-propyl]-5-chloro-3-methyl-thieno[3,2-b]pyridin-7-yl]-N-(2-furylmethyl)carbamate To a solution of tert-butyl N-[2-[(2R)-2-(tert-butoxycarbonylamino)-3-hydroxy-propyl]-5-chloro-3-methyl-thieno[3,2-b]pyridin-7-yl]-N-(2-furylmethyl)carbamate (126.6 mg, 0.23 mmol, 1.0 eq.), prepared according to the procedure in Example 3, in DMF (0.5 mL) and THF (2.0 mL) was added sodium hydride (60 mass %) in mineral oil (15 mg, 0.38 mmol, 1.6 eq.) at 0° C. The mixture was stirred for 5 min at 0° C., then iodomethane (2.0 M) in tert-butyl methyl ether (112 mg, 0.120 mL, 0.24 mmol, 1.0 eq.) was added. The reaction was warmed to room temperature, then stirred at room temperature overnight. The reaction was quenched with water (~5 mL), then extracted with EtOAc (2×40 mL). The combined organic phases were washed with water followed by brine (~30 mL). The volatiles were removed under reduced pressure, and the residue was purified by flash column chromatography (12 g, 0-30% EtOAc in hexanes with 10% DCM) to afford tert-butyl N-[2-[(2R)-2-(tert-butoxycarbonylamino)-3-methoxy-propyl]-5-chloro-3-methyl-thieno[3,2-b]pyridin-7-yl]-N-(2-furylmethyl)carbamate (88.0 mg, 0.155 mmol, 0.68 eq.) as an off-white solid. MS m/z 566.3 [M+H]$^+$, 588.2, 590.3 [M+Na]$^+$.

Step 2: (R)-2-(2-Amino-3-methoxypropyl)-5-chloro-N-(furan-2-ylmethyl)-3-methylthieno[3,2-b]pyridin-7-amine Removal of the Boc group following the general procedure described in Step 3 for Example 2 using HCl in dioxane gave (R)-2-(2-amino-3-methoxypropyl)-5-chloro-N-(furan-2-ylmethyl)-3-methylthieno[3,2-b]pyridin-7-amine hydrochloride. MS m/z 366.3, 368.2 [M+H]$^+$; $^1$H NMR 500 MHz (DMSO-d$_6$) δ ppm 8.33 (br s, 3H), 7.65 (br s, 1H), 7.56-7.62 (m, 1H), 6.60 (s, 1H), 6.39-6.42 (m, 1H), 6.36 (d, J=3.05 Hz, 1H), 4.51 (br s, 2H), 3.44-3.53 (m, 2H), 3.34-3.43 (m, 1H), 3.31 (s, 3H), 3.24 (dd, J=14.55, 5.29 Hz, 1H), 3.18 (dd, J=14.49, 9.25 Hz, 1H), 2.25 (s, 3H).

The compounds below were prepared according to the procedure of Example 11 by substituting the appropriate starting materials, reagents and reaction conditions.

Example 12 (Compound 115)

3-(5-Chloro-7-{[(furan-2-yl)methyl]amino}-3-methylthieno[3,2-b]pyridin-2-yl)-D-alanine dihydrochloride

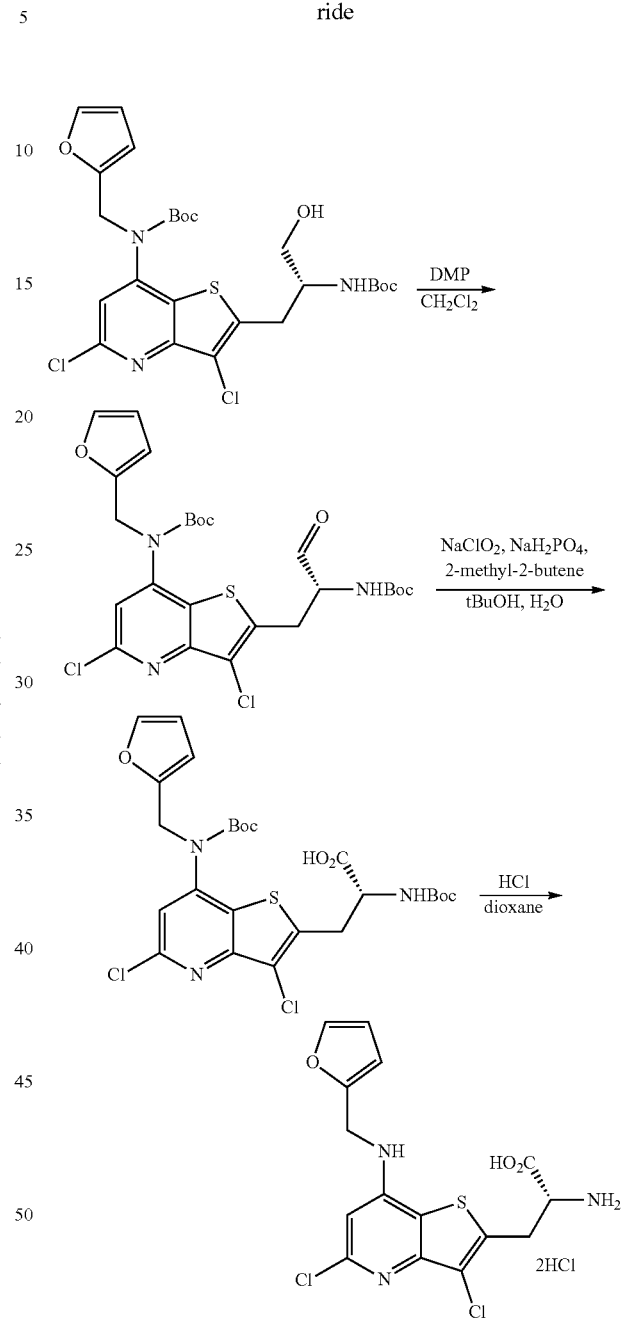

| Compound | Spectral Data |
|---|---|
| 40 | MS m/z 386.1, 388.1, 390.1 [M + H]$^+$; $^1$H NMR (methanol-d$_4$) δ: 7.37 (s, 1H), 6.68 (s, 1H), 6.19-6.36 (m, 2H), 4.49 (s, 2H), 3.62-3.71 (m, 1H), 3.47-3.53 (m, 1H), 3.37-3.42 (m, 1H), 3.34 (s, 3H), 3.25-3.33 (m, 2H), 3 NHs not observed. |
| 44 | MS m/z 430.0, 432.0, 434.0 [M + H]$^+$; $^1$H NMR (methanol-d$_4$) δ: 7.49 (d, J = 0.8 Hz, 1H), 6.91 (s, 1H), 6.38-6.45 (m, 2H), 4.65 (s, 2H), 3.77-3.85 (m, 1H), 3.58-3.65 (m, 1H), 3.47-3.52 (m, 1H), 3.46 (s, 3H), 3.40-3.44 (m, 2H), 3 NHs not observed. |

Step 1: tert-Butyl (R)-(2-(2-((tert-butoxycarbonyl)amino)-3-oxopropyl)-3,5-dichlorothieno[3,2-b]pyridin-7-yl)(furan-2-ylmethyl)carbamate To tert-butyl N-[2-[(2R)-2-(tert-butoxycarbonylamino)-3-hydroxy-propyl]-3,5-dichloro-thieno[3,2-b]pyridin-7-yl]-N-(2-furylmethyl)carbamate (614 mg, 1.0 mmol), prepared according to the procedure in Example 3, in $CH_2Cl_2$ (3 mL) was added Dess-Martin periodinane, 1,1,1-tris(acetyloxy)-1,1-dihydro-1,2-benziodoxol-3-(1H)-one, (546 mg, 1.3 mmol, 1.3 eq). After stirring at room temperature for 2 h, the mixture was concentrated under reduced pressure, diluted with diethyl ether (3 mL), and stirred with saturated $Na_2S_2O_3$ (1 mL) and saturated $NaHCO_3$ (1 mL) for 30 min. The organic layer was separated, dried over $MgSO_4$, filtered, and concentrated to afford tert-butyl (R)-(2-(2-((tert-butoxycarbonyl)amino)-3-oxopropyl)-3,5-dichlorothieno[3,2-b]pyridin-7-yl)(furan-2-ylmethyl)carbamate (510 mg, 83% yield) as a clear oil. MS m/z 569.9 [M+H]$^+$; $^1$H NMR (DMSO-$d_6$) δ ppm 9.51 (s, 1H), 7.55 (m, 2H), 6.33 (br s, 1H), 6.24 (br s, 1H), 4.90-4.98 (m, 2H), 4.10-4.23 (m, 1H), 3.35-3.41 (m, 1H), 3.13-3.26 (m, 1H), 1.39 (s, 9H), 1.36 (s, 9H).

Step 2: (2R)-2-(tert-Butoxycarbonylamino)-3-[7-[tert-butoxycarbonyl(2-furylmethyl)amino]-3,5-dichloro-thieno[3,2-b]pyridin-2-yl]propanoic acid To a solution of tert-butyl N-[2-[(2R)-2-(tert-butoxycarbonylamino)-3-oxo-propyl]-3,5-dichloro-thieno[3,2-b]pyridin-7-yl]-N-(2-furylmethyl)carbamate (510 mg, 0.9 mmol) in tert-butanol (4.0 mL) and water (1.0 mL) was added $NaH_2PO_4$ (322 mg, 2.7 mmol, 3 eq.) followed by 2-methyl-2-butene (0.8 mL, 9 mmol, 10 eq) and finally $NaClO_2$ (162 mg, 1.8 mmol, 2.0 eq.). After stirring at room temperature for 0.5 h, the mixture was diluted with $CH_2Cl_2$ (10 mL) and washed with water (10 mL). The organic layer was separated, dried over $Na_2SO_4$, filtered, and concentrated to afford (2R)-2-(tert-butoxycarbonylamino)-3-[7-[tert-butoxycarbonyl(2-furylmethyl)amino]-3,5-dichloro-thieno[3,2-b]pyridin-2-yl]propanoic acid (498 mg, 95% yield) as a white solid. MS m/z 586.1 [M+H]$^+$; $^1$H NMR (DMSO-$d_6$) δ ppm 12.79-13.13 (m, 1H), 7.55-7.59 (m, 1H), 7.51-7.54 (m, 1H), 7.25-7.33 (m, 1H), 6.29-6.36 (m, 1H), 6.20-6.26 (m, 1H), 4.90-5.01 (m, 2H), 4.19-4.25 (m, 1H), 3.50-3.59 (m, 1H), 3.21-3.29 (m, 1H), 1.37-1.40 (s, 9H), 1.33-1.37 (s, 9H).

Step 3: (2R)-2-Amino-3-[3,5-dichloro-7-(2-furylmethylamino)thieno[3,2-b]pyridin-2-yl]propanoic acid A mixture of (2R)-2-(tert-butoxycarbonylamino)-3-[7-[tert-butoxycarbonyl(2-furylmethyl)amino]-3,5-dichloro-thieno[3,2-b]pyridin-2-yl]propanoic acid (80 mg, 0.14 mmol) in a solution of HCl (4 M in dioxane) (1 mL, 4 mmol) was stirred at room temperature for 1 h. The mixture was concentrated under reduced pressure. The solid was triturated with diethyl ether and filtered to afford (2R)-2-amino-3-[3,5-dichloro-7-(2-furylmethylamino)thieno[3,2-b]pyridin-2-yl]propanoic acid dihydrochloride (55 mg, 88% yield). MS m/z 366.1, 368.2 [M+H]$^+$; $^1$H NMR (DMSO-$d_6$) δ ppm 8.64 (br s, 3H), 7.93-8.06 (m, 1H), 7.57-7.65 (m, 1H), 6.68-6.75 (m, 1H), 6.35-6.46 (m, 2H), 4.48-4.60 (m, 2H), 4.11-4.23 (m, 1H), 3.48-3.57 (m, 2H), COOH peak not observed.

The compound below was prepared according to the procedure of Example 12 by substituting the appropriate starting materials, reagents and reaction conditions.

| Compound | Spectral Data |
|---|---|
| 121 | MS m/z 386.0, 388.0 [M + H]$^+$; $^1$H NMR (DMSO-$d_6$) δ: 8.55-8.73 (m, 3H), 7.92-8.10 (m, 1H), 7.55-7.67 (m, 1H), 6.66-6.76 (m, 1H), 6.33-6.48 (m, 2H), 4.51-4.58 (m, 2H), 4.12-4.22 (m, 1H), 3.47-3.56 (m, 2H), COOH proton not observed. |

Example 13 (Compound 72)

2-[(2R)-2-Aminobut-3-en-1-yl]-3-bromo-5-chloro-N-[(1,3-thiazol-2-yl)methyl]thieno[3,2-b]pyridin-7-amine dihydrochloride

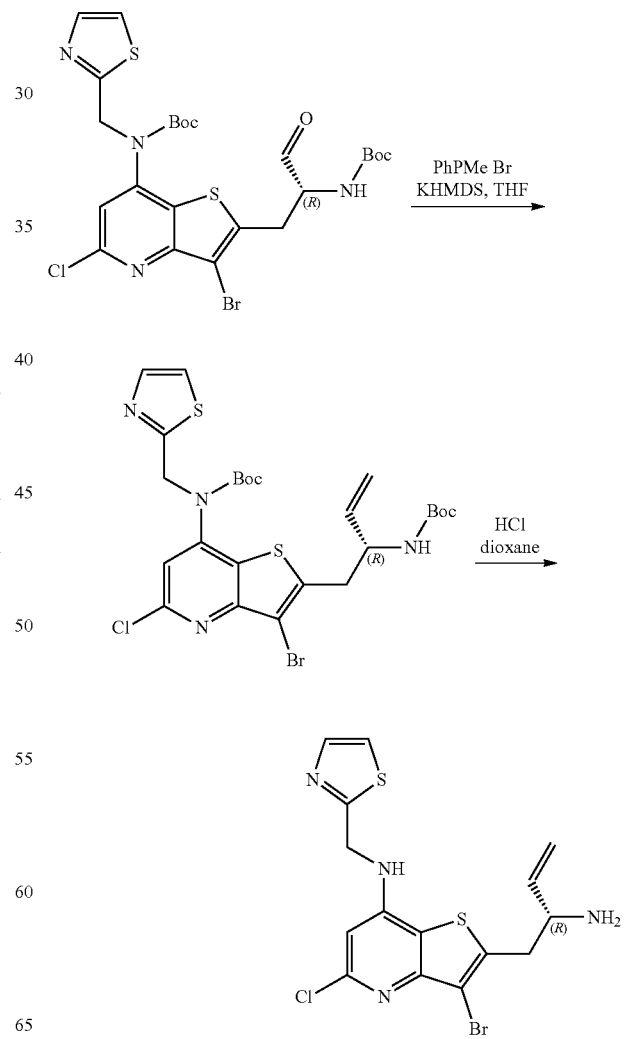

Step 1: tert-Butyl (R)-(3-bromo-2-(2-((tert-butoxy-carbonyl)amino)but-3-en-1-yl)-5-chlorothieno[3,2-b]pyridin-7-yl)(thiazol-2-ylmethyl)carbamate To a suspension of methyltriphenylphosphonium bromide (260 mg, 0.71 mmol, 2.1 eq.) in THF (3.5 mL) was added KHMDS (1 M) in THF (0.68 mL, 0.68 mmol, 2.0 eq.). The mixture was stirred at room temperature for 2 h, then cooled to −78° C. tert-Butyl (R)-(3-bromo-2-(2-((tert-butoxycarbonyl)amino)-3-oxopropyl)-5-chlorothieno[3,2-b]pyridin-7-yl)(thiazol-2-ylmethyl)carbamate (215 mg, 0.34 mmol, 1.0 eq.), prepared according to the procedure in Example 12, in THF (2.5 mL) was added, and the temperature was warmed to room temperature and stirred overnight. The reaction was quenched with saturated $NH_4Cl$, extracted with ethyl acetate, dried over sodium sulfate and evaporated. The residue was purified over silica gel with ethyl acetate and hexanes (5 to 35% gradient) to give tert-butyl (R)-(3-bromo-2-(2-((tert-butoxycarbonyl)amino)but-3-en-1-yl)-5-chlorothieno[3,2-b]pyridin-7-yl)(thiazol-2-ylmethyl)carbamate (86 mg, 40% yield). $^1$H NMR ($CDCl_3$) δ: 7.71 (d, J=3.1 Hz, 1H), 7.30-7.39 (m, 2H), 5.87 (s, 1H), 5.23 (d, J=17.1 Hz, 1H), 5.16-5.20 (m, 3H), 4.50-4.75 (m, 2H), 3.20-3.40 (m, 2H), 1.38-1.51 (m, 18H).

Step 2: 2-[(2R)-2-Aminobut-3-enyl]-3-bromo-5-chloro-N-(thiazol-2-ylmethyl)thieno[3,2-b]pyridin-7-amine Removal of the Boc group following the general procedure described in Step 3 for Example 2 using HCl in dioxane gave 2-[(2R)-2-aminobut-3-enyl]-3-bromo-5-chloro-N-(thiazol-2-ylmethyl)thieno[3,2-b]pyridin-7-amine dihydrochloride. MS m/z 429.0, 431.1, 433.0 [M+H]$^+$; $^1$H NMR (methanol-$d_4$) δ: 7.82-7.89 (m, 1H), 7.63-7.69 (m, 1H), 6.66-6.73 (m, 1H), 5.81-5.91 (m, 1H), 5.28-5.37 (m, 2H), 4.98 (s, 2H), 4.06-4.17 (m, 1H), 3.38-3.46 (m, 2H).

The compound below was prepared according to the procedure of Example 13 by substituting the appropriate starting materials, reagents and reaction conditions.

| Compound | Spectral Data |
|---|---|
| 119 | MS m/z 334.2, 336.2 [M + H]$^+$; $^1$H NMR (methanol-$d_4$) δ: 8.42-8.65 (br s, 1H), 7.47 (s, 1H), 7.16 (s, 1H), 6.60 (s, 1H), 6.39 (br s, 1H), 6.28-6.37 (m, 1H), 5.88-6.00 (m, 1H), 5.36-5.45 (m, 2H), 4.55 (s, 2H), 3.98-4.14 (m, 1H), 2 Hs obscured by water peak, 3 NHs not observed. |

Example 14 (Compound 123)

2-[(2R)-2-Aminobut-3-yn-1-yl]-3-methyl-5-chloro-N-[(furan-2-yl)methyl]thieno[3,2-b]pyridin-7-amine

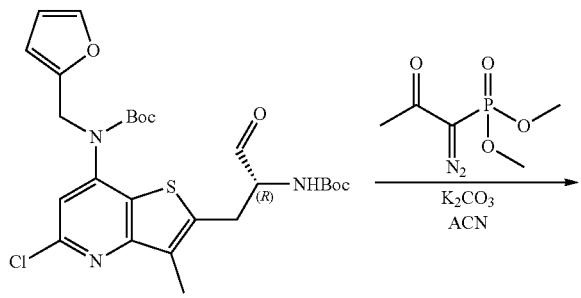

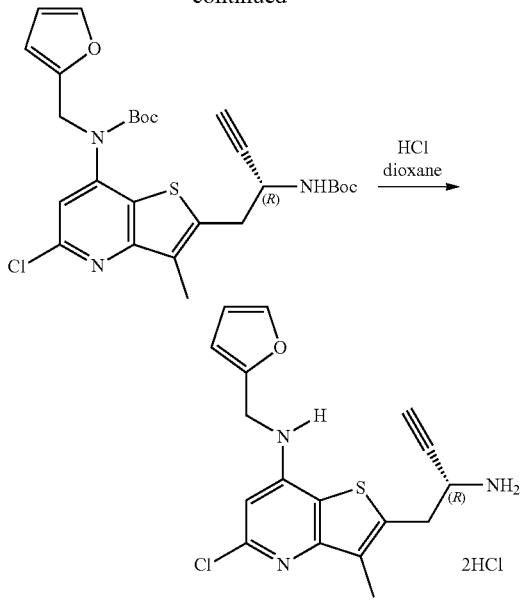

Step 1: tert-Butyl N-[2-[(2R)-2-(tert-butoxycarbonylamino)but-3-ynyl]-5-chloro-3-methyl-thieno[3,2-b]pyridin-7-yl]-N-(2-furylmethyl)carbamate To a stirred suspension of tert-butyl N-[2-[(2R)-2-(tert-butoxycarbonylamino)-3-oxo-propyl]-5-chloro-3-methyl-thieno[3,2-b]pyridin-7-yl]-N-(2-furylmethyl)carbamate (202 mg, 0.37 mmol, 1.0 eq.), prepared according to the procedure in Example 12, and potassium carbonate (100 mg, 0.043 mL, 0.72 mmol, 1.97 eq.) in MeOH (5.0 mL) was added dimethyl (1-diazo-2-oxopropyl)phosphonate (10 mass %) in acetonitrile (800 mg, 1.0 mL, 0.42 mmol, 1.1 eq.) at 0° C. The reaction was stirred at room temperature overnight. The volatiles were removed under reduced pressure and the residue was subjected to aqueous work-up and purification by flash column chromatography (24 g, 0-20% EtOAc/hexanes) to afford tert-butyl N-[2-[(2R)-2-(tert-butoxycarbonylamino)but-3-ynyl]-5-chloro-3-methyl-thieno[3,2-b]pyridin-7-yl]-N-(2-furylmethyl)carbamate (136.5 mg, 68% yield) as an off-white foam. MS m/z 546.2, 548.4 [M+H]$^+$.

Step 2: (R)-2-(2-Aminobut-3-yn-1-yl)-5-chloro-N-(furan-2-ylmethyl)-3-methylthieno[3,2-b]pyridin-7-amine The general deprotection procedure using HCl in dioxane was followed to give (R)-2-(2-aminobut-3-yn-1-yl)-5-chloro-N-(furan-2-ylmethyl)-3-methylthieno[3,2-b]pyridin-7-amine hydrochloride MS m/z 346.2, 348.3 [M+H]$^+$; $^1$H NMR (500 MHz, DMSO-$d_6$) δ ppm 8.84 (br d, J=4.27 Hz, 3H), 7.67 (br s, 1H), 7.55-7.63 (m, 1H), 6.60 (s, 1H), 6.40 (dd, J=3.05, 1.83 Hz, 1H), 6.36 (d, J=2.75 Hz, 1H), 4.51 (br s, 2H), 4.23-4.36 (m, 1H), 3.72 (d, J=2.25 Hz, 1H), 3.49 (dd, J=14.19, 4.73 Hz, 1H), 3.32 (dd, J=14.19, 10.25 Hz, 1H), 2.29 (s, 3H).

The compound below was prepared according to the procedure of Example 14 by substituting the appropriate starting materials, reagents and reaction conditions.

| Compound | Spectral Data |
|---|---|
| 166 | MS m/z 366.3, 368.3 [M + H]+; 1H NMR (methanol-d4) δ: 7.47 (s, 1H), 6.88 (s, 1H), 6.39 (s, 2H), 4.62 (s, 2H), 4.53-4.57 (m, 1H), 3.58 (d, J = 5.8 Hz, 1H), 3.54-3.57 (m, 1H), 3.37 (d, J = 2.3 Hz, 1H), 3 NHs not observed. |

Example 15 (Compound 124)

3-(3,5-Dichloro-7-{[(furan-2-yl)methyl]amino}thieno[3,2-b]pyridin-2-yl)-N-(2-fluorophenyl)-D-alaninamide dihydrochloride

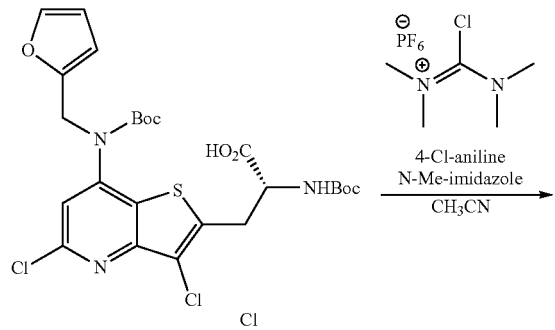

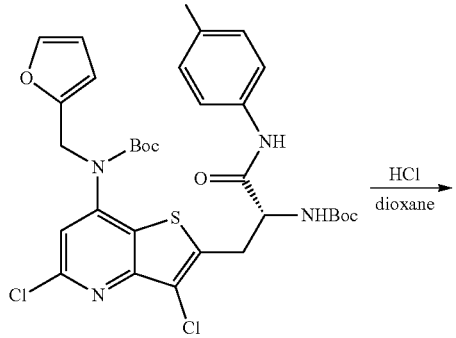

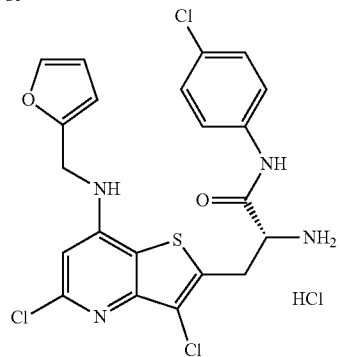

Step 1: tert-Butyl N-[2-[(2R)-2-(tert-butoxycarbonylamino)-3-(4-chloroanilino)-3-oxo-propyl]-3,5-dichloro-thieno[3,2-b]pyridin-7-yl]-N-(2-furylmethyl)carbamate To a solution of (2R)-2-(tert-butoxycarbonylamino)-3-[7-[tert-butoxycarbonyl(2-furylmethyl)amino]-3,5-dichloro-thieno[3,2-b]pyridin-2-yl]propanoic acid (100 mg, 0.17 mmol), prepared according to the procedure in Example 12, chloro-N,N,N',N'-tetramethylformamidinium hexafluorophosphate (55 mg, 0.2 mmol, 1.1 eq), and 4-chloroaniline (30 mg, 0.2 mmol, 1.1 eq.) in acetonitrile (1 mL) was added 1-methylimidazole (0.03 mL, 0.4 mmol, 2 eq.). After stirring at room temperature for 1 h, the mixture was diluted with water (5 mL) and extracted with ethyl acetate (3×10 mL). The combined organic phases were dried over MgSO4, filtered, and concentrated. The residue was purified on silica gel eluting with 0-30% ethyl acetate in hexanes to afford tert-butyl N-[2-[(2R)-2-(tert-butoxycarbonylamino)-3-(4-chloroanilino)-3-oxo-propyl]-3,5-dichloro-thieno[3,2-b]pyridin-7-yl]-N-(2-furylmethyl)carbamate (52 mg, 44% yield) as a clear foam. MS m/z 695.3, 697.3 [M+H]+; 1H NMR (CDCl3) δ ppm 8.51 (br s, 1H), 7.46 (d, J=8.5 Hz, 2H), 7.26-7.32 (m, 4H), 7.18 (s, 1H), 6.27 (br s, 1H), 6.19 (d, J=3.1 Hz, 1H), 4.79-4.86 (m, 2H), 4.65-4.72 (m, 1H), 3.52-3.64 (m, 2H), 1.44 (s, 9H), 1.41 (s, 9H).

Step 2: (2R)-2-Amino-N-(4-chlorophenyl)-3-[3,5-dichloro-7-(2-furylmethylamino)thieno[3,2-b]pyridin-2-yl]propanamide A mixture of tert-butyl N-[2-[(2R)-2-(tert-butoxycarbonylamino)-3-(4-chloroanilino)-3-oxo-propyl]-3,5-dichloro-thieno[3,2-b]pyridin-7-yl]-N-(2-furylmethyl)carbamate (52 mg, 0.07 mmol) in HCl (4 M in dioxane) (1 mL, 4 mmol) was stirred at room temperature for 4 h. The mixture was concentrated, and the solid was triturated with diethyl ether and filtered to afford (2R)-2-amino-N-(4-chlorophenyl)-3-[3,5-dichloro-7-(2-furylmethylamino)thieno[3,2-b]pyridin-2-yl]propanamide hydrochloride (33 mg, 78% yield) as a beige solid. MS m/z 495.0, 497.0 [M+H]+; 1H NMR (DMSO-d6) δ ppm 10.94-11.08 (s, 1H), 8.70-8.82 (br s, 3H), 7.90-8.02 (m, 1H), 7.54-7.66 (m, 3H), 7.40 (d, J=8.9 Hz, 2H), 6.68 (s, 1H), 6.32-6.44 (m, 2H), 4.47-4.59 (m, 2H), 4.22-4.32 (m, 1H), 3.51-3.67 (m, 2H).

The compounds below were prepared according to the procedure of Example 15 by substituting the appropriate starting materials, reagents and reaction conditions.

| Compound | Spectral Data |
|---|---|
| 116 | MS m/z 393.3, 395.1 [M + H]⁺; ¹H NMR (DMSO-d$_6$) δ: 8.47-8.57 (m, 3H), 7.64-7.73 (m, 1H), 7.58-7.63 (m, 1H), 6.58-6.62 (m, 1H), 6.39-6.43 (m, 1H), 6.34-6.37 (m, 1H), 4.50 (br s, 3H), 3.42-3.49 (m, 1H), 3.24-3.32 (m, 1H), 2.83 (s, 3H), 2.66 (s, 3H), 2.23 (s, 3H). |
| 120 | MS m/z 479.1, 481.1 [M + H]⁺; ¹H NMR (DMSO-d$_6$) δ: 10.47 (s, 1H), 8.76 (br d, J = 3.7 Hz, 3H), 7.92-8.00 (m, 1H), 7.80-7.88 (m, 1H), 7.60 (s, 1H), 7.21 (br s, 3H), 6.68 (s, 1H), 6.40 (br s, 1H), 6.35 (d, J = 3.1 Hz, 1H), 4.47-4.58 (m, 2H), 4.35-4.43 (m, 1H), 3.50-3.64 (m, 2H). |
| 122 | MS m/z 461.1, 463.1 [M + H]⁺; ¹H NMR (DMSO-d$_6$) δ: 10.69-10.75 (m, 1H), 8.61-8.80 (m, 3H), 7.89-8.00 (m, 1H), 7.59-7.62 (m, 1H), 7.52-7.57 (m, 2H), 7.28-7.41 (m, 2H), 7.07-7.17 (m, 1H), 6.66-6.73 (m, 1H), 6.38-6.43 (m, 1H), 6.32-6.39 (m, 1H), 4.49-4.56 (m, 2H), 4.20-4.29 (m, 1H), 3.53-3.62 (m, 2H). |
| 133 | MS m/z 466.3, 468.3 [M + H]⁺; ¹H NMR (DMSO-d$_6$) δ: 11.40 (br s, 1H), 8.71 (br s, 3H), 7.75-7.84 (m, 4H), 7.55-7.63 (m, 2H), 6.55-6.59 (m, 1H), 6.37-6.42 (m, 1H), 6.25-6.32 (m, 1H), 4.41-4.53 (m, 2H), 4.26-4.35 (m, 1H), 3.45-3.56 (m, 2H), 2.25 (s, 3H). |
| 134 | MS m/z 442.4, 444.3 [M + H]⁺; ¹H NMR (DMSO-d$_6$) δ: 11.16-11.24 (m, 1H), 8.61-8.77 (m, 3H), 8.28-8.36 (m, 1H), 8.06-8.12 (m, 1H), 7.82-7.91 (m, 1H), 7.48-7.64 (m, 2H), 7.15-7.23 (m, 1H), 6.54-6.61 (m, 1H), 6.36-6.43 (m, 1H), 6.26-6.32 (m, 1H), 4.45-4.56 (m, 2H), 4.24-4.38 (m, 1H), 3.38-3.55 (m, 2H), 2.24 (s, 3H). |
| 135 | MS m/z 443.4, 445.4 [M + H]⁺; ¹H NMR (DMSO-d$_6$) δ: 11.50 (s, 1H), 9.34 (s, 1H), 8.79 (br s, 3H), 8.39-8.48 (m, 2H), 7.54-7.67 (m, 2H), 6.54-6.62 (m, 1H), 6.37-6.43 (m, 1H), 6.25-6.31 (m, 1H), 4.42-4.56 (m, 2H), 4.28-4.41 (m, 1H), 3.53-3.62 (m, 1H), 3.41-3.51 (m, 1H), 2.26 (s, 3H). |
| 140 | MS m/z 442.2, 444.2 [M + H]⁺; ¹H NMR (DMSO-d$_6$) δ: 13.07 (s, 1H), 8.88 (br s, 3H), 8.75-8.82 (m, 2H), 8.16-8.28 (m, 2H), 7.54-7.67 (m, 2H), 6.57 (s, 1H), 6.37-6.44 (m, 1H), 6.26-6.37 (m, 1H), 4.39-4.62 (m, 3H), 3.58-3.73 (m, 2H), 2.27 (s, 3H). |
| 141 | MS m/z 455.2, 457.4 [M + H]⁺; ¹H NMR (DMSO-d$_6$) δ: 8.76 (br s, 3H), 7.57-7.66 (m, 2H), 7.27-7.34 (m, 1H), 7.08-7.21 (m, 2H), 6.62-6.66 (m, 1H), 6.41-6.47 (m, 1H), 6.35-6.40 (m, 1H), 4.46-4.61 (m, 2H), 3.92-4.06 (m, 1H), 3.18-3.30 (m, 2H), 3.15 (s, 3H), 1.88 (s, 3H). |
| 142 | MS m/z 455.4, 457.2 [M + H]⁺; ¹H NMR (DMSO-d$_6$) δ: 10.82-10.94 (m, 1H), 8.75-8.93 (m, 3H), 7.56-7.71 (m, 2H), 7.39-7.51 (m, 2H), 7.06-7.16 (m, 2H), 6.51-6.59 (m, 1H), 6.36-6.41 (m, 1H), 6.26-6.33 (m, 1H), 4.42-4.56 (m, 2H), 4.17-4.30 (m, 1H), 3.59-3.66 (m, 1H), 3.38-3.50 (m, 1H), 2.25 (s, 6H). |
| 143 | MS m/z 475.1, 477.1 [M + H]⁺; ¹H NMR (DMSO-d$_6$) δ: 11.10 (br s, 1H), 8.69 (br s, 3H), 7.74-7.78 (m, 1H), 7.60-7.65 (m, 1H), 7.57-7.60 (m, 1H), 7.43-7.47 (m, 1H), 7.34-7.40 (m, 1H), 7.16-7.21 (m, 1H), 6.54-6.64 (m, 1H), 6.35-6.43 (m, 1H), 6.27-6.35 (m, 1H), 4.43-4.56 (m, 2H), 4.20-4.30 (m, 1H), 3.50-3.57 (m, 1H), 3.43-3.50 (m, 1H), 2.26 (s, 3H). |
| 144 | MS m/z 471.1, 473.2 [M + H]⁺; ¹H NMR (DMSO-d$_6$) δ: 10.73 (s, 1H), 8.70 (br s, 3H), 7.53-7.69 (m, 2H), 7.18-7.30 (m, 2H), 7.05-7.15 (m, 1H), 6.67-6.76 (m, 1H), 6.54-6.63 (m, 1H), 6.36-6.44 (m, 1H), 6.26-6.36 (m, 1H), 4.43-4.56 (m, 2H), 4.12-4.27 (m, 1H), 3.72 (s, 3H), 3.39-3.54 (m, 2H), 2.25 (s, 3H). |
| 145 | MS m/z 445.2, 447.2 [M + H]⁺; ¹H NMR (DMSO-d$_6$) δ: 10.78 (br s, 1H), 8.72 (br s, 3H), 7.62-7.70 (m, 1H), 7.57-7.62 (m, 1H), 7.32-7.38 (m, 1H), 6.58-6.63 (m, 1H), 6.39-6.43 (m, 1H), 6.31-6.36 (m, 1H), 6.10-6.21 (m, 1H), 4.46-4.57 (m, 2H), 4.23-4.36 (m, 1H), 3.52-3.56 (m, 1H), 3.50 (s, 3H), 3.36-3.44 (m, 1H), 2.28 (s, 3H). |

Example 16 (Compound 51)

2-[(2S)-2-Aminopropyl]-5-chloro-3-cyclopropyl-N-[(furan-2-yl)methyl]thieno[3,2-b]pyridin-7-amine hydrochloride

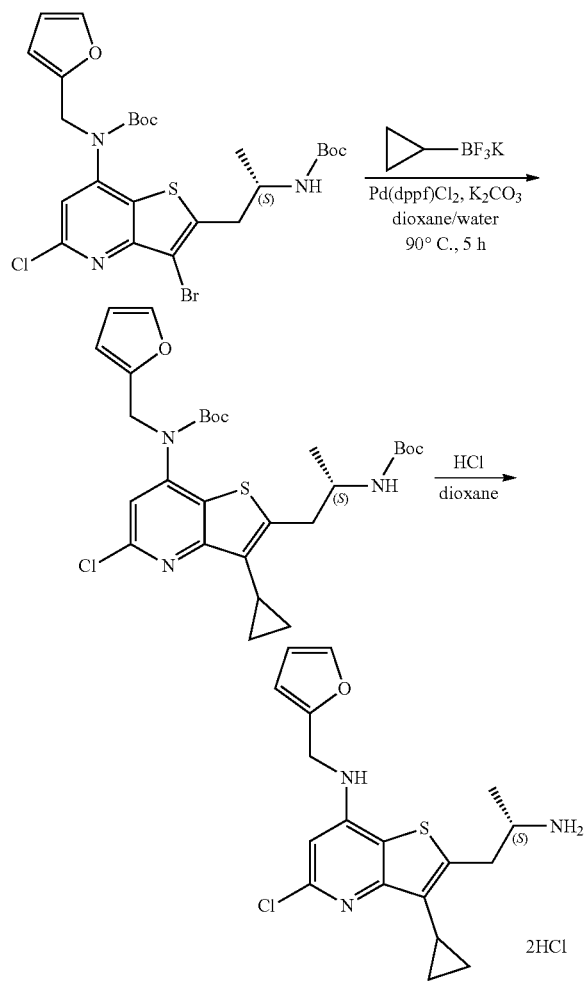

Step 1: tert-Butyl (S)-(2-(2-((tert-butoxycarbonyl)amino)propyl)-5-chloro-3-cyclopropylthieno[3,2-b]pyridin-7-yl)(furan-2-ylmethyl)carbamate To a solution of tert-butyl (S)-(3-bromo-2-(2-((tert-butoxycarbonyl)amino)propyl)-5-chlorothieno[3,2-b]pyridin-7-yl)(furan-2-ylmethyl)carbamate (88 mg, 0.15 mmol, 1.0 eq.), prepared according to the procedure in Example 2, and potassium cyclopropyltrifluoroborate (29 mg, 0.19 mmol, 1.3 eq.) in dioxane (0.8 mL) was added Pd(dppf)Cl$_2$ (12 mg, 0.1000 eq.) and K$_2$CO$_3$ (2M in H$_2$O, 0.22 mL, 3.0 eq.). The sealed tube was heated to 90° C. for 5 h. After cooling, the mixture was diluted with EtOAc and NH$_4$Cl (aq.) and extracted with EtOAc. The combined organic phases were dried and concentrated. The residue was purified by flash column chromatography on silica gel eluting with 0-10% EtOAc in DCM to provide a mixture of the desired product and unreacted starting material, which was then further purified on preparative HPLC with 25-100% CH$_3$CN in water with 0.1% TFA to provide tert-butyl (S)-(2-(2-((tert-butoxycarbonyl)amino)propyl)-5-chloro-3-cyclopropylthieno[3,2-b]pyridin-7-yl)(furan-2-ylmethyl)carbamate (53 mg, 64% yield) as a white solid. MS m/z 562.2, 564.2 [M+H]$^+$.

Step 2: (S)-2-(2-Aminopropyl)-5-chloro-3-cyclopropyl-N-(furan-2-ylmethyl)thieno[3,2-b]pyridin-7-amine tert-Butyl (S)-(2-(2-((tert-butoxycarbonyl)amino)propyl)-5-chloro-3-cyclopropylthieno[3,2-b]pyridin-7-yl)(furan-2-ylmethyl)carbamate (53 mg, 0.094 mmol) was stirred in a solution of HCl (4 M in dioxane, 1 mL) at room temperature for 1 h. The organic volatiles were removed. The residue was triturated with diethyl ether and filtered to afford (S)-2-(2-aminopropyl)-5-chloro-3-cyclopropyl-N-(furan-2-ylmethyl)thieno[3,2-b]pyridin-7-amine (33 mg, 89% yield) as the hydrochloride salt. MS m/z 362.1, 364.2 [M+H]$^+$; $^1$H NMR (methanol-d$_4$) δ ppm 7.49 (t, J=0.9 Hz, 1H), 7.04 (s, 1H), 6.42 (dd, J=3.2, 12.5 Hz, 2H), 4.71 (s, 2H), 3.75-3.78 (m, 1H), 3.42-3.44 (m, 1H), 3.38-3.40 (m, 1H), 1.84-1.87 (m, 1H), 1.39 (d, J=6.6 Hz, 3H), 1.19-1.21 (m, 2H), 0.85-0.86 (m, 2H).

The compounds below were prepared according to the procedure of Example 16 by substituting the appropriate starting materials, reagents and reaction conditions.

| Compound | Spectral Data |
| --- | --- |
| 69 | MS m/z 455.2, 457.2 [M + H]$^+$; $^1$H NMR (methanol-d$_4$) δ: 7.83 (d, J = 0.9 Hz, 1 H), 7.65 (d, J = 0.9 Hz, 1 H), 7.33-7.37 (m, 4 H), 7.27-7.29 (m, 1 H), 7.06 (s, 1 H), 5.11 (s, 2 H), 4.0-4.03 (m, 1 H), 3.47-3.51 (m, 1 H), 3.38-3.42 (m, 1 H), 3.13-3.18 (m, 1 H), 2.99-3.04 (m, 1 H), 1.76-1.79 (m, 1 H), 1.14-1.16 (m, 1 H), 0.98-1.0 (m, 1 H), 0.75-0.77 (m, 1 H), 0.72-0.74 (m, 1 H), 3 NHs not observed. |
| 75 | MS m/z 371.1, 373.1 [M + H]$^+$; $^1$H NMR (methanol-d$_4$) δ: 8.00 (d, J = 3.2 Hz, 1H), 7.84 (d, J = 3.2 Hz, 1H), 7.23 (s, 1H), 5.26 (s, 2H), 4.54-4.82 (m, 2H), 3.85-3.98 (m, 1H), 3.44-3.55 (m, 2H), 2.51 (s, 3H), 3 NHs not observed. |
| 77 | MS m/z 392.3, 394.3 [M + H]$^+$; $^1$H NMR (DMSO-d$_6$) δ: 8.15 (br s, 3H), 7.71 (br s, 1H), 7.38 (d, J = 4.9 Hz, 1H), 7.08 (d, J = 3.1 Hz, 1H), 6.98 (t, J = 4.3 Hz, 1H), 6.50 (s, 1H), 4.69 (br d, J = 4.3 Hz, 2H), 3.21-3.37 (m, 3H), 1.84-2.02 (m, 1H), 1.51-1.71 (m, 1H), 1.16-1.32 (m, 2H), 1.09 (t, J = 6.9 Hz, 3H), 0.96 (t, J = 7.5 Hz, 2H), 0.81-0.92 (m, 2H). |

-continued

| Compound | Spectral Data |
|---|---|
| 80 | MS m/z 393.1, 395.1 [M + H]+; 1H NMR (methanol-d4) δ: 7.93 (d, J = 0.9 Hz, 1 H), 7.76 (d, J = 0.9 Hz, 1 H), 7.20 (s, 1 H), 5.22 (s, 2 H), 3.53-3.60 (m, 1 H), 3.44-3.49 (m, 1 H), 3.32-3.33 (m, 1 H), 1.78-1.90 (m, 3 H), 1.24-1.27 (m, 2 H), 1.13 (t, J = 7.54 Hz, 3 H), 0.76-0.78 (m, 2 H), 3 NHs not observed. |
| 86 | MS m/z 397.2, 399.2 [M + H]+; 1H NMR (methanol-d4) δ: 7.85-7.93 (m, 1H), 7.65-7.77 (m, 1H), 7.16 (s, 1H), 5.17 (s, 2H), 4.56-4.83 (m, 2H), 3.96-4.09 (m, 1H), 3.51-3.70 (m, 2H), 1.84-1.94 (m, 1H), 1.20-1.28 (m, 2H), 0.73-0.85 (m, 2H), 3 NHs not observed. |
| 87 | MS m/z 396.3, 398.3 [M + H]+; 1H NMR (DMSO-d6) δ: 8.60 (br s, 3H), 7.69-7.81 (m, 1H), 7.39 (d, J = 4.9 Hz, 1H), 7.06-7.12 (m, 1H), 6.95-7.02 (m, 1H), 6.48-6.54 (m, 1H), 4.49-4.78 (m, 4H), 3.65-3.80 (m, 1H), 3.29-3.36 (m, 2H), 1.90-2.01 (m, 1H), 1.23-1.36 (m, 2H), 0.83-0.94 (m, 2H). |
| 96 | MS m/z 379.2, 381.2 [M + H]+; 1H NMR (methanol-d4) δ: 7.87 (d, J = 3.3 Hz, 1 H), 7.69 (d, J = 3.3 Hz, 1 H), 7.15 (s, 1 H), 5.16 (s, 2 H), 3.79-3.83 (m, 1 H), 3.44-3.53 (m, 2 H), 1.86-1.90 (m, 1 H), 1.41 (d, J = 6.55 Hz, 3 H), 1.24-1.27 (m, 2 H), 0.76-0.78 (m, 2 H), 3 NHs not observed. |
| 128 | MS m/z 385.2, 387.2 3 [M + H]+; 1H NMR (methanol-d4) δ: 7.81-7.87 (m, 1H), 7.63-7.70 (m, 1H), 7.05-7.13 (m, 1H), 5.13 (s, 2H), 4.97-5.10 (m, 1H), 3.83-3.94 (m, 1H), 3.42-3.58 (m, 2H), 2.47 (s, 3H), 1.46-1.56 (m, 3H), 3 NHs not observed. |

Example 17 (Compound 109)

2-[(2S)-2-Aminopropyl]-5-chloro-7-{[(furan-2-yl)methyl]amino}thieno[3,2-b]pyridine-3-carbonitrile formate

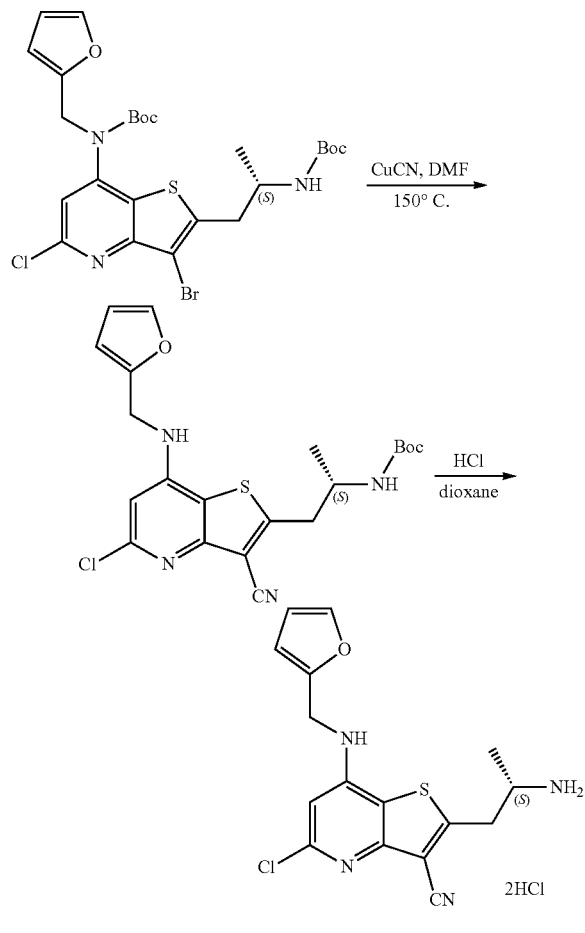

Step 1: tert-Butyl (S)-(1-(5-chloro-3-cyano-7-((furan-2-ylmethyl)amino)thieno[3,2-b]pyridin-2-yl)propan-2-yl)carbamate A mixture of tert-butyl (S)-(3-bromo-2-(2-((tert-butoxycarbonyl)amino)propyl)-5-chlorothieno[3,2-b]pyridin-7-yl)(furan-2-ylmethyl)carbamate (67 mg, 0.11 mmol, 1.0 eq.), prepared according to the procedure in Example 2, and CuCN (22 mg, 2.2 eq.) in DMF (0.6 mL) were degassed with argon. The sealed tube was heated at 150° C. for 8 h. After cooling, 0.1 mL of NH4Cl (sat. aq.) and 0.1 mL of NaHCO3 (sat. aq.) were added. The mixture was stirred for 15 min, filtered and washed with MeOH (0.5 mL×3). The combined filtrate was purified by preparative HPLC eluting with 10-100% ACN in water with 0.1% formic acid to provide tert-butyl (S)-(1-(5-chloro-3-cyano-7-((furan-2-ylmethyl)amino)thieno[3,2-b]pyridin-2-yl)propan-2-yl)carbamate (15 mg, 30% yield). MS m/z 447.2, 449.2 [M+H]+.

Step 2: (S)-2-(2-Aminopropyl)-5-chloro-7-((furan-2-ylmethyl)amino)thieno[3,2-b]pyridine-3-carbonitrile tert-Butyl (S)-(1-(5-chloro-3-cyano-7-((furan-2-ylmethyl)amino)thieno[3,2-b]pyridin-2-yl)propan-2-yl)carbamate (15 mg, 0.034 mmol) was stirred in a solution of HCl (4 M in dioxane, 1 mL) at room temperature for 1 h. The organic volatiles were removed. The solid was purified by preparative HPLC eluting with 5-50% ACN in water with 0.1% formic acid to afford (S)-2-(2-aminopropyl)-5-chloro-7-((furan-2-ylmethyl)amino)thieno[3,2-b]pyridine-3-carbonitrile (5 mg, 36% yield) as a formic acid salt. MS m/z 347.1, 349.1 [M+H]+; 1H NMR (methanol-d4) δ ppm 8.44 (s, 1H), 7.36 (s, 1H), 6.61 (s, 1H), 6.27 (d, J=1.3 Hz, 2H), 4.45 (s, 2H), 3.48-3.51 (m, 1H), 3.27-3.31 (m, 2H), 1.21 (d, J=6.6 Hz, 3H).

Example 18 (Compound 50 and Compound 49)

2-[(2S)-2-Aminopropyl]-7-{[(furan-2-yl)methyl]amino}thieno[3,2-b]pyridine-3,5-dicarbonitrile hydrochloride and 2-[(2S)-2-Aminopropyl]-3-bromo-7-{[(furan-2-yl)methyl]amino}thieno[3,2-b]pyridine-5-carbonitrile hydrochloride

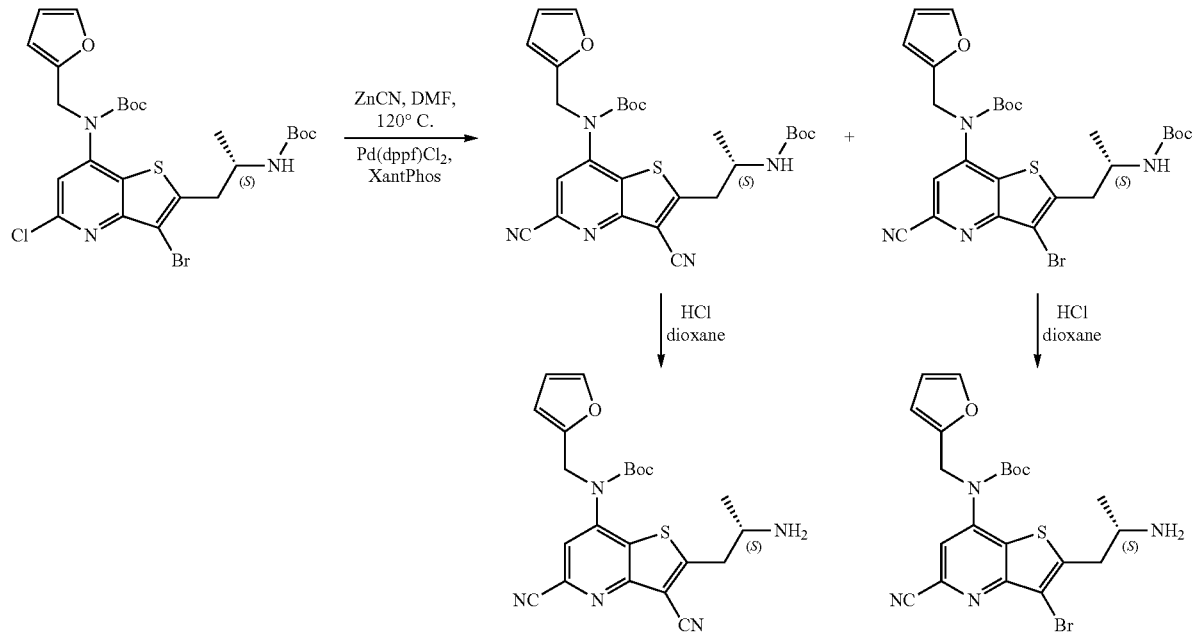

Step 1: tert-Butyl (S)-(2-(2-((tert-butoxycarbonyl)amino)propyl)-3,5-dicyanothieno[3,2-b]pyridin-7-yl)(furan-2-ylmethyl)carbamate and tert-Butyl (S)-(3-bromo-2-(2-((tert-butoxycarbonyl)amino)propyl)-5-cyanothieno[3,2-b]pyridin-7-yl)(furan-2-ylmethyl)carbamate To a solution of tert-butyl (S)-(3-bromo-2-(2-((tert-butoxycarbonyl)amino)propyl)-5-chlorothieno[3,2-b]pyridin-7-yl)(furan-2-ylmethyl)carbamate (90 mg, 0.15 mmol, 1.0 eq), prepared according to the procedure in Example 2, in DMF (1 mL) was added zinc cyanide (11 mg, 0.60 eq.), Pd$_2$(dba)$_3$ (7.1 mg, 0.05 eq.) and XantPhos (8.9 mg, 0.10 eq.). The sealed tube was stirred at 120° C. for 1 h. After cooling, the mixture was diluted with EtOAc and NH$_4$Cl (aq.) and extracted with EtOAc. The combined organic phases were dried and concentrated. The residue was purified by flash column chromatography on silica gel eluting with 0-10% EtOAc in DCM to provide a mixture, which was further purified by preparative HPLC with 25-100% ACN in water with 0.1% TFA to provide tert-butyl (S)-(2-(2-((tert-butoxycarbonyl)amino)propyl)-3,5-dicyanothieno[3,2-b]pyridin-7-yl)(furan-2-ylmethyl)carbamate (23 mg, 29% yield) MS m/z 536.3 [M–H]$^-$, and tert-butyl (S)-(3-bromo-2-(2-((tert-butoxycarbonyl)amino)propyl)-5-cyanothieno[3,2-b]pyridin-7-yl)(furan-2-ylmethyl)carbamate (35 mg, 40% yield). MS m/z 591.2, 593.2 [M+H]$^+$.

Step 2: (S)-2-(2-Aminopropyl)-7-((furan-2-ylmethyl)amino)thieno[3,2-b]pyridine-3,5-dicarbonitrile Deprotection of tert-butyl (S)-(2-(2-((tert-butoxycarbonyl)amino)propyl)-3,5-dicyanothieno[3,2-b]pyridin-7-yl)(furan-2-ylmethyl)carbamate using the general Boc-deprotection described in Step 3 of Example 2 gave (S)-2-(2-aminopropyl)-7-((furan-2-ylmethyl)amino)thieno[3,2-b]pyridine-3,5-dicarbonitrile (17 mg, 95% yield) as the hydrochloride salt. MS m/z 338.0 [M+H]$^+$; $^1$H NMR (methanol-d$_4$) δ ppm 7.48 (d, J=0.9 Hz, 1H), 7.20 (s, 1H), 6.40-6.42 (m, 2H), 4.64 (s, 2H), 3.79-3.81 (m, 1H), 3.55-3.59 (m, 1H), 3.45-3.49 (m, 1H), 1.42 (d, J=6.6 Hz, 3H).

(S)-2-(2-Aminopropyl)-3-bromo-7-((furan-2-ylmethyl)amino)thieno[3,2-b]pyridine-5-carbonitrile Deprotection of tert-butyl (S)-(3-bromo-2-(2-((tert-butoxycarbonyl)amino)propyl)-5-cyanothieno[3,2-b]pyridin-7-yl)(furan-2-ylmethyl)carbamate using the general Boc-deprotection procedure described in Step 3 of Example 2 gave (S)-2-(2-aminopropyl)-3-bromo-7-((furan-2-ylmethyl)amino)thieno[3,2-b]pyridine-5-carbonitrile (19 mg, 83% yield) as the hydrochloride salt. MS m/z 391.0, 393.0 [M+H]$^+$; $^1$H NMR (methanol-d$_4$) δ ppm 7.49 (d, J=0.9 Hz, 1H), 7.22 (s, 1H), 6.40-6.42 (m, 2H), 4.66 (s, 2H), 3.76-3.80 (m, 1H), 3.41-3.45 (m, 1H), 3.37-3.39 (m, 1H), 1.42 (d, J=6.6 Hz, 3H).

The compounds below were prepared according to the procedure of Example 18 by substituting the appropriate starting materials, reagents and reaction conditions.

| Compound | Starting Material and Spectral Data |
|---|---|
| 11 | Corresponding 3-bromo-5-chlorothieno[3,2-b]pyridine<br>MS m/z 350.0, 352.0 [M + H]$^+$; $^1$H NMR (DMSO-d$_6$) δ: 8.34 (br s, 2 H), 7.41 (t, J = 1.2 Hz, 1 H), 7.24 (s, 1 H), 7.15 (d, J = 3.2 Hz, 1 H), 7.0 (d, J = 3.2 Hz, 1 H), 4.81 (d, J = 5.3 Hz, 2 H). |
| 12 | Corresponding 3-bromo-5-chlorothieno[3,2-b]pyridine<br>MS m/z 297.1 [M + H]$^+$; $^1$H NMR (DMSO-d$_6$) δ: 9.15 (s, 1H), 8.57 (t, J = 5.9 Hz, 1 H), 7.44 (dd, J = 1.2, 3.2 Hz, 1 H), 7.31 (s, 1 H), 7.17 (d, J = 3.2 Hz, 1 H), 6.99-7.01 (m, 1 H), 4.82 (d, J = 5.3 Hz, 2 H). |
| 13 | Corresponding 3-bromo-5-chlorothieno[3,2-b]pyridine<br>MS m/z 306.0, 308.0 [M + H]$^+$; $^1$H NMR (DMSO-d$_6$) δ: 9.02 (s, 1 H), 8.34 (t, J = 5.6 Hz, 1 H), 7.42 (d, J = 5.1 Hz, 1 H), 7.13 (s, 1 H), 7.0 (d, J = 3.9 Hz, 1 H), 6.72 (s, 1 H), 4.76 (d, J = 5.3 Hz, 2 H). |
| 14 | Corresponding 3-bromo-5-chlorothieno[3,2-b]pyridine<br>MS m/z 290.1, 292.1 [M + H]$^+$; $^1$H NMR (DMSO-d$_6$) δ: 9.01 (s, 1 H), 8.19 (t, J = 5.6 Hz, 1 H), 7.62 (s, 1 H), 6.76 (s, 1 H), 6.42 (s, 2 H), 4.55 (d, J = 5.6 Hz, 2 H). |
| 15 | Corresponding 3-bromo-5-chlorothieno[3,2-b]pyridine<br>MS m/z 281.1 [M + H]$^+$; $^1$H NMR (DMSO-d$_6$) δ: 9.14 (s, 1H), 8.44 (t, J = 5.3 Hz, 1 H), 7.63 (s, 1 H), 7.34 (s, 1 H), 6.46 (s, 1 H), 6.42 (d, J = 1.4 Hz, 1 H), 4.62 (d, J = 5.3 Hz, 2 H). |
| 20 | MS m/z 327.3 [M + H]$^+$; $^1$H NMR (methanol-d$_4$) δ: 7.34 (dd, J = 1.8, 0.8 Hz, 1H), 6.95 (s, 1H), 6.21-6.29 (m, 2H), 4.48 (s, 2H), 3.45-3.59 (m, 1H), 3.17 (d, J = 6.4 Hz, 1H), 3.09 (d, J = 8.2 Hz, 1H), 2.28 (s, 3H), 1.24 (d, J = 6.6 Hz, 3H), 3 NHs not observed. |
| 54 | MS m/z 343.2 [M + H]$^+$; $^1$H NMR (methanol-d$_4$) δ: 8.53 (s, 1H), 7.32 (dd, J = 5.2, 0.9 Hz, 1H), 7.12 (d, J = 3.4 Hz, 1H), 6.98-7.02 (m, 1H), 6.96 (s, 1H), 4.82 (s, 2H), 3.60-3.69 (m, 1H), 3.32 (br s, 1H), 3.17-3.24 (m, 1H), 2.41 (s, 3H), 1.38 (d, J = 6.4 Hz, 3H), 3 NHs not observed |
| 101 | MS m/z 407.1, 409.1 [M + H]$^+$; $^1$H NMR (methanol-d$_4$) δ: 8.42 (s, 1 H), 7.22 (dd, J = 5.05, 0.9 Hz, 1 H), 7.01 (d, J = 3.45 Hz, 1 H), 6.93 (s, 1 H), 6.89 (dd, J = 5.05, 3.55 Hz, 1 H), 4.72 (s, 2 H), 3.54-3.58 (m, 1 H), 3.15-3.19 (m, 2 H), 1.24 (d, J = 6.6 Hz, 3 H), 3 NHs not observed, formic acid salt. |
| 102 | MS m/z 354.1 [M + H]$^+$; $^1$H NMR (methanol-d$_4$) δ: 8.42 (s, 1 H), 7.22 (dd, J = 5.05, 0.9 Hz, 1 H), 7.02 (d, J = 2.75 Hz, 1 H), 6.97 (s, 1 H), 6.89 (dd, J = 5.05, 3.55 Hz, 1 H), 4.72 (s, 2 H), 3.53-3.56 (m, 1 H), 3.33-3.38 (m, 1 H), 3.26-3.30 (m, 1 H), 1.24 (d, J = 6.6 Hz, 3 H), 3 NHs not observed, formic acid salt. |
| 110 | MS m/z 363.1, 365.1 [M + H]$^+$; $^1$H NMR (methanol-d$_4$) δ: 8.44 (s, 1 H), 7.21 (d, J = 5.05 Hz, 1 H), 6.98 (d, J = 2.75 Hz, 1 H), 6.89 (dd, J = 5.05, 3.55 Hz, 1 H), 6.53 (s, 1 H), 4.66 (s, 2 H), 3.42-3.45 (m, 1 H), 3.23-3.27 (m, 2 H), 1.18 (d, J = 6.6 Hz, 3 H), 3 NHs not observed, formic acid salt. |
| 112 | MS m/z 363.1, 365.1 [M + H]$^+$; $^1$H NMR (methanol-d$_4$) δ: 7.22 (d, J = 5.0 Hz, 1H), 7.02 (d, J = 2.7 Hz, 1H), 6.95 (s, 1H), 6.89 (t, J = 4.2 Hz, 1H), 4.73 (s, 2H), 3.56-3.66 (m, 1H), 3.25-3.27 (m, 1H), 3.15-3.19 (m, 1H), 1.28 (d, J = 6.4 Hz, 3H), 3 NHs not observed. |

Example 19 (Compound 60)

2-[(2S)-2-Aminopropyl]-3-chloro-5-methyl-N-[(1,3-thiazol-2-yl)methyl]thieno[3,2-b]pyridin-7-amine dihydrochloride

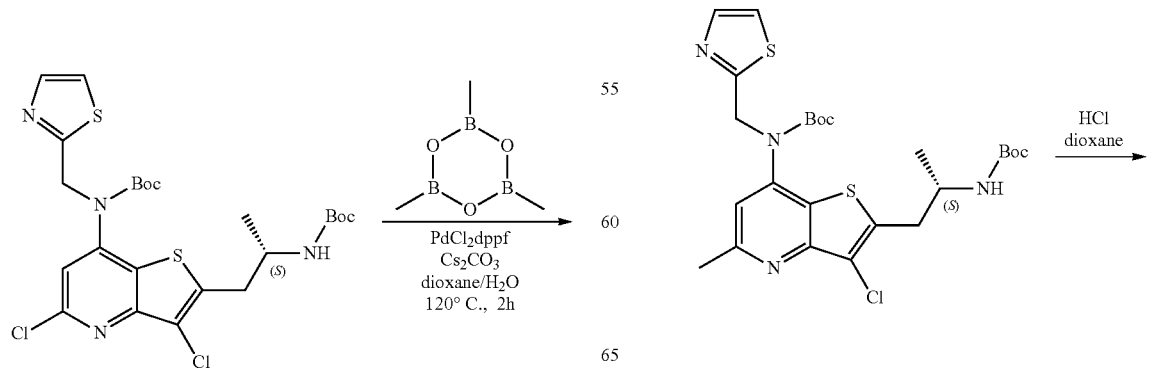

-continued

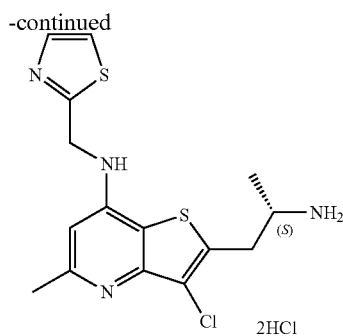

2HCl

Step 1: tert-Butyl N-(3-chloro-5-methyl-thieno[3,2-b]pyridin-7-yl)-N-(thiazol-2-ylmethyl)carbamate A mixture of tert-butyl N-(3,5-dichlorothieno[3,2-b]pyridin-7-yl)-N-(thiazol-2-ylmethyl)carbamate (100 mg, 0.240 mmol, 1.0 eq.), prepared according to the procedure in Example 2, 2,4,6-trimethyl-1,3,5,2,4,6-trioxatriborinane (44 mg, 0.049 mL, 0.35 mmol, 1.5 eq.), Cs$_2$CO$_3$ (171 mg, 0.524 mmol, 2.2 eq.), and PdCl$_2$dppf DCM (14.4 mg, 0.0175 mmol, 0.0727 eq.) in dioxane (1.0 mL) and water (0.1 mL) was stirred at 120° C. for 2 h, then cooled, diluted with ethyl acetate and washed with brine, dried and evaporated. The residue was purified over silica gel with ethyl acetate and dichloromethane (0 to 50% gradient) to give tert-butyl N-(3-chloro-5-methyl-thieno[3,2-b]pyridin-7-yl)-N-(thiazol-2-ylmethyl)carbamate (71 mg, 75% yield). $^1$H NMR (CDCl$_3$) δ: 7.69 (d, J=2.6 Hz, 1H), 7.34 (d, J=2.9 Hz, 1H), 7.07-7.20 (m, 1H), 5.19 (br s, 2H), 4.40-4.63 (m, 1H), 4.00-4.11 (m, 1H), 3.22 (br s, 2H), 2.74 (br s, 3H), 1.46 (s, 18H), 1.19 (d, J=5.8 Hz, 3H).

Step 2: 2-[(2S)-2-Aminopropyl]-3-chloro-5-methyl-N-(thiazol-2-ylmethyl)thieno[3,2-b]pyridin-7-amine Deprotection of tert-butyl N-(3-chloro-5-methyl-thieno[3,2-b]pyridin-7-yl)-N-(thiazol-2-ylmethyl)carbamate using the general Boc-deprotection procedure with HCl in dioxane gave 2-[(2S)-2-aminopropyl]-3-chloro-5-methyl-N-(thiazol-2-ylmethyl)thieno[3,2-b]pyridin-7-amine dihydrochloride (52 mg, 96% yield). MS m/z 353.1, 355.1 [M+H]$^+$. $^1$H NMR (methanol-d$_4$) δ: 7.88-7.95 (m, 1H), 7.71-7.78 (m, 1H), 6.97-7.05 (m, 1H), 5.21 (s, 2H), 3.73-3.85 (m, 1H), 3.46-3.54 (m, 1H), 3.37-3.44 (m, 1H), 2.73 (s, 3H), 1.43 (d, J=6.6 Hz, 3H).

Example 20 (Compound 21)

2-[(1S)-1-Aminoethyl]-5-chloro-N-[(furan-2-yl)methyl]-3-methylthieno[3,2-b]pyridin-7-amine hydrochloride

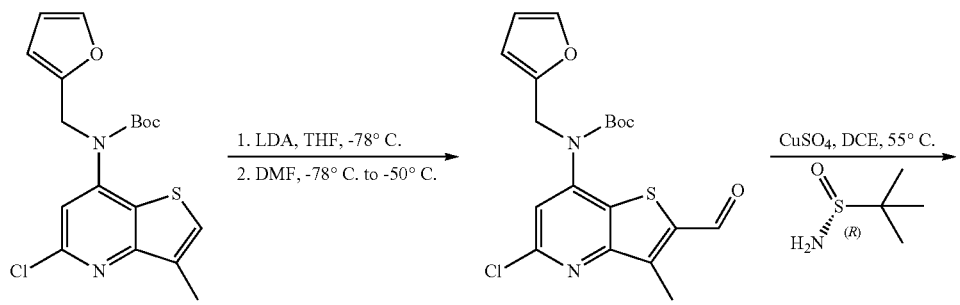

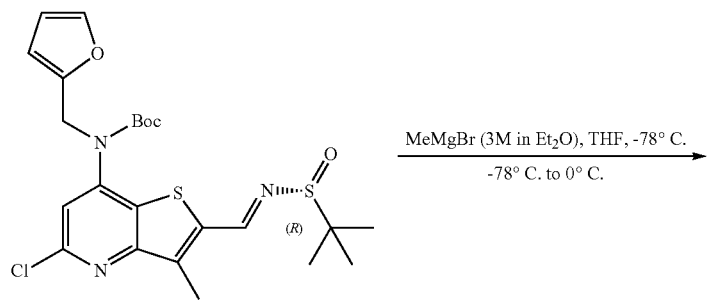

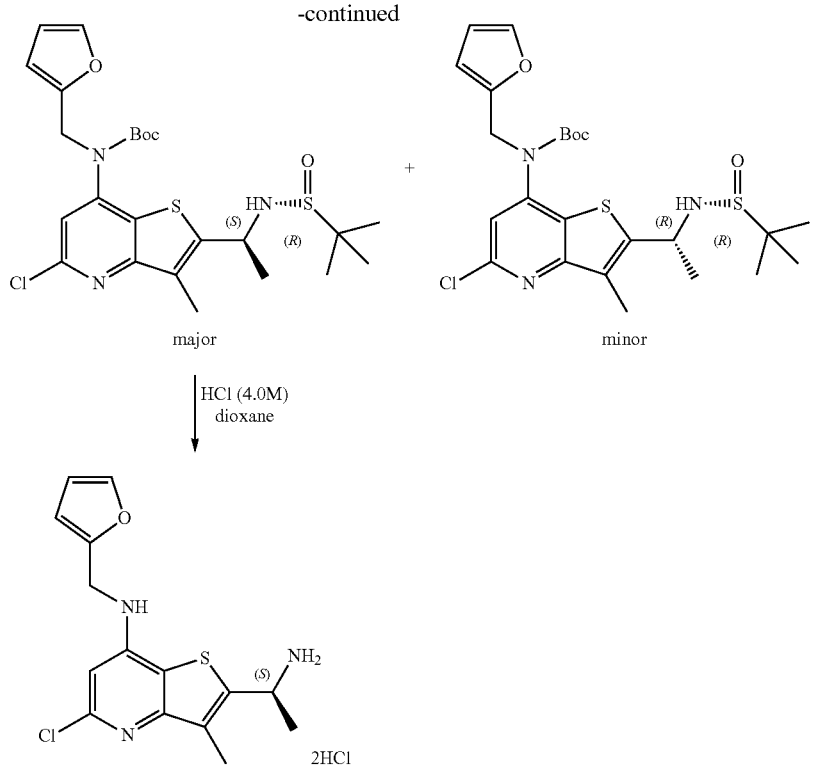

Step 1: tert-Butyl (5-chloro-2-formyl-3-methylthieno[3,2-b]pyridin-7-yl)(furan-2-ylmethyl)carbamate To a solution of tert-butyl N-(5-chloro-3-methyl-thieno[3,2-b]pyridin-7-yl)-N-(2-furylmethyl)carbamate (90 mg, 0.24 mmol, 1.0 eq.), prepared according to the procedure in Example 2, in THF (1 mL) at −78° C. was added LDA (2.0 M in THF, 0.14 mL, 1.2 eq.). After 30 min, DMF (0.11 mL, 1.4 mmol, 5.8 eq.) was added dropwise. The temperature was warmed to −50° C., and the reaction was quenched with saturated aqueous NH$_4$Cl, then diluted with EtOAc. The mixture was washed with water followed by brine, and the organic layer was dried over sodium sulfate and evaporated. The residue was purified by flash column chromatography on silica gel eluting with 0-25% EtOAc in hexane to provide tert-butyl (5-chloro-2-formyl-3-methylthieno[3,2-b]pyridin-7-yl)(furan-2-ylmethyl)carbamate (83 mg, 86% yield) as a white solid. $^1$H NMR (acetone-d$_6$) δ ppm 10.5 (s, 1H), 7.55 (s, 1H), 7.45 (s, 1H), 6.29-6.33 (m, 2H), 5.03 (s, 2H), 2.84 (s, 3H), 1.43 (s, 9H).

Step 2: tert-Butyl (R,E)-(2-(((tert-butylsulfinyl)imino)methyl)-5-chloro-3-methylthieno[3,2-b]pyridin-7-yl)(furan-2-ylmethyl)carbamate A mixture of tert-butyl (5-chloro-2-formyl-3-methylthieno[3,2-b]pyridin-7-yl)(furan-2-ylmethyl)carbamate (151 mg, 0.37 mmol, 1.0 eq.), R-(+)-2-methylpropane-2-sulfinamide (54 mg, 0.45 mmol, 1.2 eq.) and CuSO$_4$ (91 mg, 0.56 mmol, 1.5 eq.) in DCE (0.4 mL) was stirred at 55° C. for 18 h. After cooling, the mixture was purified by flash column chromatography on silica gel eluting with 0-50% EtOAc in hexane to provide tert-butyl (R,E)-(2-(((tert-butylsulfinyl)imino)methyl)-5-chloro-3-methylthieno[3,2-b]pyridin-7-yl)(furan-2-ylmethyl)carbamate (140 mg, 74% yield). MS m/z 510.4, 512.4 [M+H]$^+$.

Step 3: tert-Butyl (2-((S)-1-(((R)-tert-butylsulfinyl)amino)ethyl)-5-chloro-3-methylthieno[3,2-b]pyridin-7-yl)(furan-2-ylmethyl)carbamate and tert-Butyl (2-((R)-1-(((R)-tert-butylsulfinyl)amino)ethyl)-5-chloro-3-methylthieno[3,2-b]pyridin-7-yl)(furan-2-ylmethyl)carbamate To a solution of tert-butyl (R,E)-(2-(((tert-butylsulfinyl)imino)methyl)-5-chloro-3-methylthieno[3,2-b]pyridin-7-yl)(furan-2-ylmethyl)carbamate (140 mg, 0.27 mmol, 0.74 eq.) in THF (2.3 mL) was added MeMgBr (3.0 M in Et$_2$O, 0.31 mL, 2.5 eq.) at −78° C. The mixture was warmed to 0° C. over 1 h, then quenched with a saturated solution of NH$_4$Cl and EtOAc. The mixture was washed with water followed by brine, and the organic layer was dried over sodium sulfate and evaporated. The residue was purified by flash column chromatography on silica gel eluting with 0-100% EtOAc in hexanes to provide tert-butyl (2-((S)-1-(((R)-tert-butylsulfinyl)amino)ethyl)-5-chloro-3-methylthieno[3,2-b]pyridin-7-yl)(furan-2-ylmethyl)carbamate (88 mg, 45% yield, the major diastereomer), MS m/z 526.5, 528.5 [M+H]$^+$; $^1$H NMR (acetone-d$_6$) δ ppm 7.44 (d, J=0.9 Hz, 1H), 7.25 (s, 1H), 6.30-6.32 (m, 1H), 6.25-6.27 (m, 1H), 5.07-5.10 (m, 1H), 4.95-4.97 (m, 3H), 2.41 (t, 3H), 1.60 (d, J=6.6 Hz, 3H), 1.41 (s, 9H), 1.20 (s, 9H), and tert-butyl (2-((R)-1-(((R)-tert-butylsulfinyl)amino)ethyl)-5-chloro-3-methylthieno[3,2-b]pyridin-7-yl)(furan-2-ylmethyl)carbamate (26 mg, 13% yield, the minor diastereomer), MS m/z 526.5, 528.5 [M+H]$^+$; $^1$H NMR (acetone-d$_6$) δ ppm 7.43 (s, 1H), 7.26 (s, 1H), 6.29-6.31 (m, 1H), 6.23-6.25 (m, 1H), 5.10-5.11 (m, 1H), 4.97 (d, J=4.9 Hz, 2H), 4.69 (br s, 1H), 2.43 (t, 3H), 1.60 (d, J=6.6 Hz, 3H), 1.41 (s, 9H), 1.20 (s, 9H).

Step 4: (S)-2-(1-Aminoethyl)-5-chloro-N-(furan-2-ylmethyl)-3-methylthieno[3,2-b]pyridin-7-amine A solution of (2-((S)-1-(((R)-tert-butylsulfinyl)amino)ethyl)-5-chloro-3-methylthieno[3,2-b]pyridin-7-yl)(furan-2-ylmethyl)carbamate (20 mg, 0.038 mmol) in HCl (4 M in dioxane, 1 mL) was stirred at room temperature for 1 h. The organic volatiles were removed, and the residue was triturated with diethyl ether and filtered to afford (S)-2-(1-aminoethyl)-5-chloro-N-(furan-2-ylmethyl)-3-methylthieno[3,2-b]pyridin-7-amine (12 mg, 74% yield) as the dihydrochloride salt. MS m/z 322.1, 324.1 [M+H]$^+$; $^1$H NMR (DMSO-d$_6$) δ ppm 8.67 (br s, 3H), 7.80 (br s, 1H), 7.60 (d, J=0.9 Hz, 1H), 6.63 (s, 1H), 6.40-6.41 (m, 1H), 6.35-6.37 (m, 1H), 4.96-4.99 (m, 1H), 4.53 (br s, 2H), 2.36 (s, 3H), 1.64 (d, J=6.8 Hz, 3H).

Example 21 (Compound 26)

5-Chloro-N-[(furan-2-yl)methyl]-3-methyl-2-[(1S)-1-(methylamino)ethyl]thieno[3,2-b]pyridin-7-amine hydrochloride

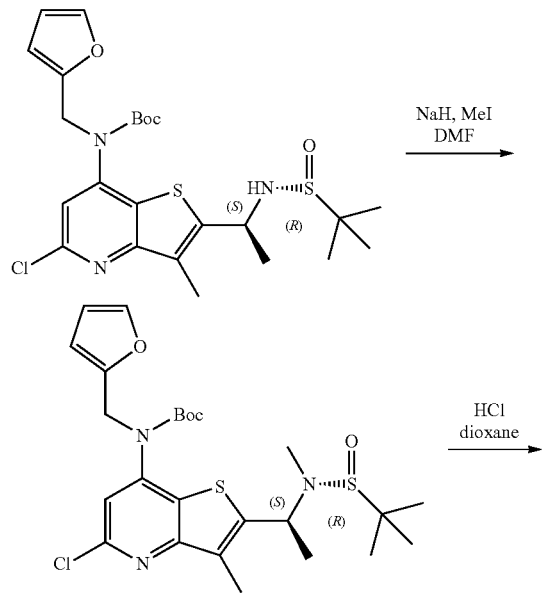

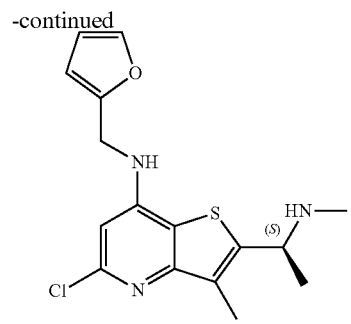

Step 1: tert-Butyl (2-((S)-1-(((R)-tert-butylsulfinyl)(methyl)amino)ethyl)-5-chloro-3-methylthieno[3,2-b]pyridin-7-yl)(furan-2-ylmethyl)carbamate To a solution of tert-butyl (2-((S)-1-(((R)-tert-butylsulfinyl)amino)ethyl)-5-chloro-3-methylthieno[3,2-b]pyridin-7-yl)(furan-2-ylmethyl)carbamate (88 mg, 0.17 mmol, 1.0 eq.) in DMF (0.3 mL) was added NaH (60% in oil, 8.7 mg, 1.3 eq.) at 0° C. After 10 min, a solution of iodomethane (31.0 mg, 1.3 eq.) in DMF (0.3 mL) was added. After 30 min, the reaction was quenched with citric acid (1.0 M) and diluted with EtOAc. The organic phases were washed with water and brine, dried over sodium sulfate and evaporated. The residue was purified by flash column chromatography on silica gel eluting with 0-70% EtOAc in hexane to provide tert-butyl (2-((S)-1-(((R)-tert-butylsulfinyl)(methyl)amino)ethyl)-5-chloro-3-methylthieno[3,2-b]pyridin-7-yl)(furan-2-ylmethyl)carbamate (79 mg, 87% yield). MS m/z 540.6, 542.6, [M+H]$^+$.

Step 2: (S)-2-(1-Aminoethyl)-5-chloro-N-(furan-2-ylmethyl)-3-methylthieno[3,2-b]pyridin-7-amine A solution of tert-butyl (2-((S)-1-(((R)-tert-butylsulfinyl)(methyl)amino)ethyl)-5-chloro-3-methylthieno[3,2-b]pyridin-7-yl)(furan-2-ylmethyl)carbamate (79 mg, 0.15 mmol) in HCl (4 M in dioxane, 1 mL) was stirred at room temperature for 1 h. The organic volatiles were removed. The residue was triturated with diethyl ether and filtered to afford (S)-2-(1-aminoethyl)-5-chloro-N-(furan-2-ylmethyl)-3-methylthieno[3,2-b]pyridin-7-amine (41 mg, 72% yield) as the hydrochloride salt. MS m/z 336.3, 338.1 [M+H]$^+$; $^1$H NMR (DMSO-d$_6$) δ ppm 9.38 (br s, 1H), 9.07 (br s, 1H), 7.79 (t, J=6.0 Hz, 1H), 7.60 (s, 1H), 6.66 (s, 1H), 6.37-6.42 (m, 2H), 4.93-4.98 (m, 1H), 4.53 (d, J=5.8 Hz, 2H), 2.60 (br s, 3H), 2.38 (s, 3H), 1.64 (d, J=6.8 Hz, 3H).

The compound below was prepared according to the procedure of Example 21 by substituting the appropriate starting materials, reagents and reaction conditions.

| Compound | Spectral Data |
|---|---|
| 32 | MS m/z 364.4, 366.4 [M + H]$^+$; $^1$H NMR (DMSO-d$_6$) δ: 9.35 (br s, 1 H), 9.19 (br s, 1 H), 7.80 (t, J = 5.3 Hz, 1 H), 7.60 (d, J = 0.95 Hz, 1 H), 6.67 (s, 1 H), 6.39-6.42 (m, 2 H), 4.63-4.68 (m, 1 H), 4.53 (d, J = 5.5 Hz, 2 H), 2.30-2.39 (m, 7 H), 1.12 (d, J = 6.54 Hz, 3 H), 0.88 (d, J = 6.54 Hz, 3 H). |

Example 22 (Compound 22 and Compound 3)

2-[(1R)-1-Aminoethyl]-5-chloro-N-[(furan-2-yl)methyl]-3-methylthieno[3,2-b]pyridin-7-amine hydrochloride and 1-(5-Chloro-7-{[(furan-2-yl)methyl]amino}-3-methylthieno[3,2-b]pyridin-2-yl)ethan-1-ol

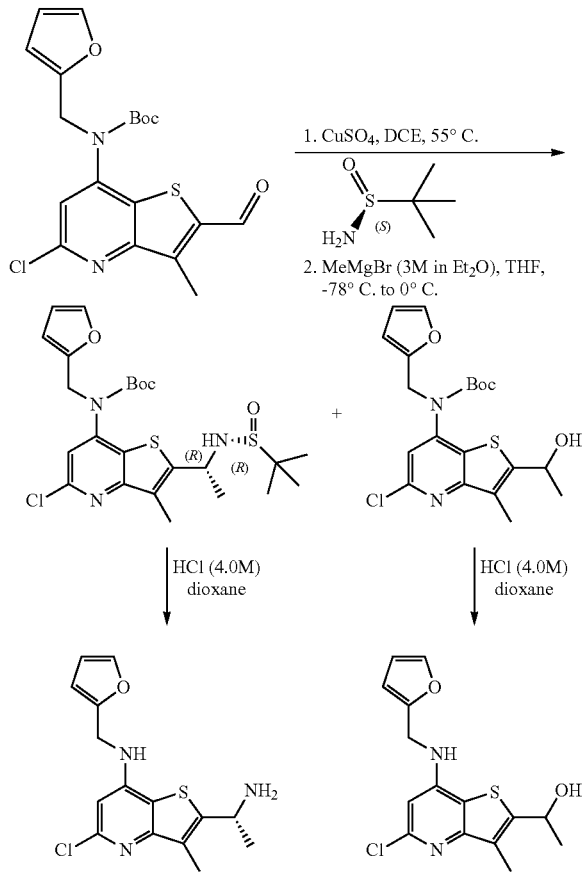

Step 1: tert-Butyl (5-chloro-2-(1-hydroxyethyl)-3-methylthieno[3,2-b]pyridin-7-yl)(furan-2-ylmethyl)carbamate and tert-Butyl (2-((R)-1-(((R)-tert-Butylsulfinyl)amino)ethyl)-5-chloro-3-methylthieno[3,2-b]pyridin-7-yl)(furan-2-ylmethyl)carbamate A mixture of tert-butyl N-(5-chloro-2-formyl-3-methylthieno[3,2-b]pyridin-7-yl)-N-(2-furylmethyl)carbamate (160 mg, 0.39 mmol, 1.0 eq.), prepared according to the procedure in Example 20, S-(+)-2-methylpropane-2-sulfinamide (54 mg, 0.45 mmol, 1.2 eq.) and $CuSO_4$ (96 mg, 0.59 mmol, 1.5 eq.) in DCE (0.4 mL) was stirred at 55° C. for 18 h. The mixture was filtered through a pad of Celite, washing the solids with DCE. The filtrate was concentrated. To a solution of the residue in THF (2 mL) was added MeMgBr (3.0 M in $Et_2O$, 0.52 mL, 4.0 eq.) at −78° C. The mixture was gradually warmed to 0° C. over a 1 h, then quenched with a saturated solution of $NH_4Cl$ and EtOAc. The mixture was washed with water followed by brine, and the organic layer was dried over sodium sulfate and evaporated. The residue was purified by flash column chromatography on silica gel eluting with 0-60% EtOAc in hexane to provide tert-butyl (5-chloro-2-(1-hydroxyethyl)-3-methylthieno[3,2-b]pyridin-7-yl)(furan-2-ylmethyl)carbamate (44 mg, 27%), MS m/z 423.2, 425.2 $[M+H]^+$, then with 100% EtOAc to provide tert-butyl (2-((R)-1-(((R)-tert-butylsulfinyl)amino)ethyl)-5-chloro-3-methylthieno[3,2-b]pyridin-7-yl)(furan-2-ylmethyl)carbamate (40 mg, 27%, the major diastereomer), MS m/z 526.5, 528.5 $[M+H]^+$.

Step 2: 1-(5-Chloro-7-((furan-2-ylmethyl)amino)-3-methylthieno[3,2-b]pyridin-2-yl)ethan-1-ol (2-((R)-1-(((R)-tert-Butylsulfinyl)amino)ethyl)-5-chloro-3-methylthieno[3,2-b]pyridin-7-yl)(furan-2-ylmethyl)carbamate (20 mg, 0.038 mmol) was stirred in a solution of HCl (4 M in dioxane, 1 mL) at room temperature for 1 h and then the organic volatiles were removed. The residue was triturated with diethyl ether and filtered to afford (R)-2-(1-aminoethyl)-5-chloro-N-(furan-2-ylmethyl)-3-methylthieno[3,2-b]pyridin-7-amine (12 mg, 74% yield) as the hydrochloride salt. MS m/z 322.1, 324.1 $[M+H]^+$; $^1$H NMR (DMSO-$d_6$) δ ppm 8.67 (br s, 3H), 7.80 (br s, 1H), 7.60 (d, J=0.9 Hz, 1H), 6.63 (s, 1H), 6.40-6.41 (m, 1H), 6.35-6.37 (m, 1H), 4.96-4.99 (m, 1H), 4.53 (br s, 2H), 2.36 (s, 3H), 1.64 (d, J=6.8 Hz, 3H). t-Butyl (5-chloro-2-(1-hydroxyethyl)-3-methylthieno[3,2-b]pyridin-7-yl)(furan-2-ylmethyl)carbamate (35 mg, 0.083 mmol) was stirred in a solution of HCl (4 M in dioxane, 1 mL) at room temperature for 1 h and then the organic volatiles were removed. The residue was triturated with diethyl ether and filtered to afford 1-(5-chloro-7-((furan-2-ylmethyl)amino)-3-methylthieno[3,2-b]pyridin-2-yl)ethan-1-ol (13 mg, 49% yield) as a white solid. MS m/z 323.1, 325.1 $[M+H]^+$; $^1$H NMR (acetone-$d_6$) δ ppm 7.45 (s, 1H), 6.58 (s, 1H), 6.32-6.33 (m, 2H), 5.31 (q, J=6.4 Hz, 1H), 4.59 (d, J=5.3 Hz, 2H), 3.50 (br s, 1H), 2.25 (s, 3H), 1.45 (d, J=6.4 Hz, 3H).

The compounds below were prepared according to the procedure of Example 22 by substituting the appropriate starting materials, reagents and reaction conditions.

| Compound | Spectral Data |
|---|---|
| 4 | MS m/z 309.1, 311.1 $[M + H]^+$; $^1$H NMR (DMSO-$d_6$) δ: 7.63 (t, J = 5.8 Hz, 1 H), 7.60 (s, 1 H), 7.12 (s, 1 H), 6.53 (s, 1 H), 6.40 (d, J = 1.00 Hz, 1 H), 6.36 (d, J = 3.1 Hz, 1 H), 5.21 (q, J = 6.4 Hz, 1 H), 4.50 (d, J = 5.7 Hz, 2 H), 1.46 (t, J = 6.4 Hz, 3 H), OH not observed. |
| 23 | MS m/z 308.1, 310.1 $[M + H]^+$; $^1$H NMR (methanol-$d_4$) δ: 7.35 (s, 1 H), 7.29 (s, 1 H), 6.57 (s, 1 H), 6.28 (dd, J = 3.2, 1.9 Hz, 1 H), 6.23 (d, J = 3.15 Hz, 1 H), 4.78-4.80 (m, 1 H), 4.46 (s, 2 H), 1.66 (d, J = 6.85 Hz, 3 H), 3 NHs not observed |
| 24 | MS m/z 308.1, 310.1 $[M + H]^+$; 1H NMR (methanol-$d_4$) δ: 7.36 (s, 1 H), 7.30 (s, 1 H), 6.60 (s, 1 H), 6.27 (dd, J = 3.2, 1.9 Hz, 1 H), 6.25 (d, J = 3.15 Hz, 1 H), 4.78-4.80 (m, 1 H), 4.47 (s, 2 H), 1.66 (d, J = 6.85 Hz, 3 H), 3 NHs not observed |

-continued

| Compound | Spectral Data |
|---|---|
| 30 | MS m/z 350.3, 352.3 [M + H]+; 1H NMR (DMSO-d6) δ: 8.63 (br s, 3 H), 7.77 (t, J = 5.3 Hz, 1 H), 7.60 (d, J = 0.95 Hz, 1 H), 6.65 (s, 1 H), 6.41 (dd, J = 3.15, 1.8 Hz, 1 H), 6.37 (d, J = 1.95 Hz, 1 H), 4.52-4.54 (m, 3 H), 2.34 (s, 3 H), 2.19-2.23 (m, 1 H), 1.14 (d, J = 6.54 Hz, 3 H), 0.83 (d, J = 6.54 Hz, 3 H). |
| 31 | MS m/z 350.3, 352.3 [M + H]+; 1H NMR (DMSO-d6) δ: 8.65 (br s, 3 H), 7.78 (t, J = 5.3 Hz, 1 H), 7.60 (d, J = 0.95 Hz, 1 H), 6.65 (s, 1 H), 6.41 (dd, J = 3.15, 1.8 Hz, 1 H), 6.37 (d, J = 1.95 Hz, 1 H), 4.53-4.54 (m, 3 H), 2.34 (s, 3 H), 2.19-2.24 (m, 1 H), 1.14 (d, J = 6.54 Hz, 3 H), 0.83 (d, J = 6.54 Hz, 3 H). |
| 55 | MS m/z 338.2, 340.2 [M + H]+; 1H NMR (methanol-d4) δ: 7.37 (d, J = 5.1 Hz, 1 H), 7.15 (d, J = 3.3 Hz, 1 H), 7.02 (dd, J = 5.1, 3.3 Hz, 1 H), 6.91 (s, 1 H), 5.16 (q, J = 6.8 Hz, 1 H), 4.90 (s, 2 H), 2.51 (s, 3 H), 1.80 (d, J = 6.8 Hz, 3 H), 3 NHs not observed. |
| 56 | MS m/z 338.2, 340.2 [M + H]+; 1H NMR (methanol-d4) δ: 7.37 (d, J = 5.1 Hz, 1 H), 7.17 (d, J = 3.3 Hz, 1 H), 7.02 (dd, J = 5.1, 3.3 Hz, 1 H), 6.98 (s, 1 H), 5.17 (q, J = 6.8 Hz, 1 H), 4.93 (s, 2 H), 2.52 (s, 3 H), 1.80 (d, J = 6.8 Hz, 3 H), 3 NHs not observed. |

Example 23 (Compound 5 and Compound 25)

(5-Chloro-7-((furan-2-ylmethyl)amino)thieno[3,2-b]pyridin-2-yl)methanol and 5-Chloro-N-(furan-2-ylmethyl)-2-((methylamino)methyl)thieno[3,2-b]pyridin-7-amine hydrochloride

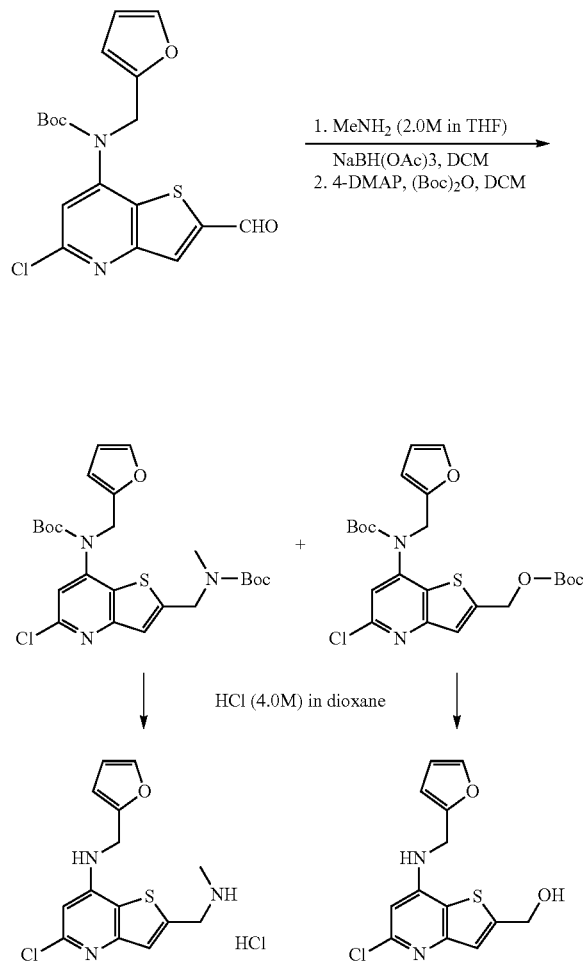

Step 1: tert-Butyl ((7-((tert-butoxycarbonyl)(furan-2-ylmethyl)amino)-5-chlorothieno[3,2-b]pyridin-2-yl)methyl)(methyl)carbamate and tert-Butyl (2-(((tert-butoxycarbonyl)oxy)methyl)-5-chlorothieno[3,2-b]pyridin-7-yl)(furan-2-ylmethyl)carbamate To a solution tert-butyl N-(5-chloro-2-formyl-3-methyl-thieno[3,2-b]pyridin-7-yl)-N-(2-furylmethyl)carbamate (40 mg, 0.10 mmol, 1.0 eq.), prepared according to the procedure in Example 20, in DCM was added a solution of methylamine (2.0 M in THF, 0.2 mL, 4 eq.) and sodium triacetoxyborohydride (64 mg, 0.30 mmol). The reaction mixture was stirred at room temperature overnight, and then quenched by addition of NaHCO3 (sat. aq.). The crude product was extracted with DCM and the combined organic phases were dried and concentrated. This crude material was mixed with 4-DMAP (5 mg) and di-tert-butyl dicarbonate (50 mg) in DCM (1 mL). After stirring at room temperature for 1-2 h, the reaction was concentrated and purified directly by flash column chromatography on silica gel eluting with 0-100% EtOAc in hexane to provide tert-butyl ((7-((tert-butoxycarbonyl)(furan-2-ylmethyl)amino)-5-chlorothieno[3,2-b]pyridin-2-yl)methyl)(methyl)carbamate. MS m/z 508.1, 510.1, [M+H]+ and tert-butyl (2-(((tert-butoxycarbonyl)oxy)methyl)-5-chlorothieno[3,2-b]pyridin-7-yl)(furan-2-ylmethyl)carbamate.

Step 2: 5-Chloro-N-(furan-2-ylmethyl)-2-((methylamino)methyl)thieno[3,2-b]pyridin-7-amine and (5-chloro-7-((furan-2-ylmethyl)amino)thieno[3,2-b]pyridin-2-yl)methanol The intermediate, tert-butyl ((7-((tert-butoxycarbonyl)(furan-2-ylmethyl)amino)-5-chlorothieno[3,2-b]pyridin-2-yl)methyl)(methyl)carbamate, was stirred in a solution of HCl (4 M in dioxane, 0.5 mL) at room temperature for 1 h and then the organic volatiles were removed. The crude solid was triturated with diethyl ether and filtered to afford 5-chloro-N-(furan-2-ylmethyl)-2-((methylamino)methyl)thieno[3,2-b]pyridin-7-amine (1.8 mg, 5.8% yield over 3 steps) as a hydrochloride salt. MS m/z 308.1, 310.1 [M+H]+; 1H NMR (methanol-d4) δ: 7.61 (s, 1H), 7.51 (s, 1H), 7.06 (s, 1H), 6.42-6.46 (m, 2H), 4.73 (s, 2H), 4.63 (s, 2H), 2.83 (s, 3H).

(5-Chloro-7-((furan-2-ylmethyl)amino)thieno[3,2-b]pyridin-2-yl)methanol

The intermediate, tert-butyl (2-(((tert-butoxycarbonyl)oxy)methyl)-5-chlorothieno[3,2-b]pyridin-7-yl)(furan-2-ylmethyl)carbamate, was stirred in a solution of HCl (4 M in dioxane, 0.5 mL) at room temperature for 1 h and then the organic volatiles were removed. The crude solid was triturated with diethyl ether and filtered to afford (5-chloro-7-((furan-2-ylmethyl)amino)thieno[3,2-b]pyridin-2-yl)methanol (9 mg, 31% yield over 3 steps). MS m/z 295.0, 297.0 [M+H]$^+$; $^1$H NMR (methanol-d$_4$) δ: 7.35 (s, 1H), 7.29 (s, 1H), 6.66 (s, 1H), 6.26-6.27 (m, 2H), 4.49 (s, 2H), 4.29 (br s, 2H).

The following compound was prepared according to the reductive amination procedure of Example 23 by substituting the appropriate starting materials, reagents and reaction conditions.

| Compound | Spectral Data |
|---|---|
| 27 | MS m/z 322.1, 324.1 [M + H]$^+$; $^1$H NMR (DMSO-d$_6$) δ: 8.80 (br s, 2 H), 7.70 (t, J = 5.35 Hz, 1 H), 7.54 (dd, J = 1.75, 0.7 Hz, 1 H), 6.59 (s, 1 H), 6.33-6.35 (m, 1 H), 6.30 (d, J = 3.15 Hz, 1 H), 4.47 (d, J = 5.85 Hz, 2 H), 4.41 (d, J = 5.35 Hz, 2 H), 2.57 (t, J = 5.2 Hz, 3 H), 2.30 (s, 3 H). |

Example 24 (Compound 163)

N$^2$-[(2S)-2-aminopropyl]-5-chloro-3-methyl-N$^7$-[(thiophen-2-yl)methyl]thieno[3,2-b]pyridine-2,7-diamine

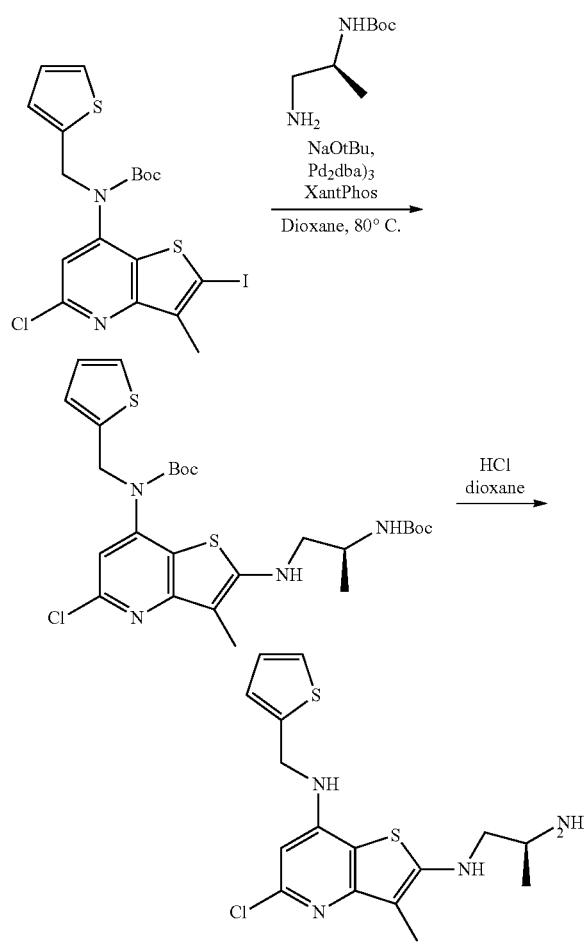

Step 1: tert-Butyl (S)-(2-((2-((tert-butoxycarbonyl)amino)propyl)amino)-5-chloro-3-methylthieno[3,2-b]pyridin-7-yl)(thiophen-2-ylmethyl)carbamate A mixture of tert-butyl (5-chloro-2-iodo-3-methylthieno[3,2-b]pyridin-7-yl)(thiophen-2-ylmethyl)carbamate (100 mg, 0.19 mmol, 1.0 eq), prepared according to Intermediate 6, tert-butyl (S)-(1-aminopropan-2-yl)carbamate (50 mg, 0.29 mmol, 1.5 eq), Cs$_2$CO$_3$ (200 mg, 0.61 mmol, 3.0 eq), Pd$_2$(dba)$_3$ (9 mg, 0.01 mmol, 0.1 eq), XantPhos (12 mg, 0.02 mmol, 0.2 eq), and toluene (1 mL) was heated at 100° C. under an Argon atmosphere for 3 h. The crude reaction mixture was allowed to cool to rt and diluted with EtOAc (20 mL). The organic phase was washed with H$_2$O (20 mL) followed by brine (20 mL). The organic phase was dried over MgSO$_4$, filtered, and concentrated in vacuo. The crude residue was purified by silica gel column chromatography eluting with 0-30% EtOAc in hexanes to afford tert-butyl (S)-(2-((2-((tert-butoxycarbonyl)amino)propyl)amino)-5-chloro-3-methylthieno[3,2-b]pyridin-7-yl)(thiophen-2-ylmethyl)carbamate (80 mg, 74%) as a yellow foam. MS m/z 567.2, 569.2 [M+H]$^+$; $^1$H NMR (DMSO-d$_6$) δ: 7.39-7.43 (m, 1H), 6.71-6.95 (m, 5H), 5.00 (s, 2H), 3.67-3.80 (m, 1H), 3.14-3.23 (m, 1H), 3.03-3.13 (m, 1H), 2.05 (s, 3H), 1.39 (s, 18H), 1.03-1.10 (d, J=6.4 Hz, 3H).

Step 2: N$^2$-[(2S)-2-aminopropyl]-5-chloro-3-methyl-N$^7$-[(thiophen-2-yl)methyl]thieno[3,2-b]pyridine-2,7-diamine A mixture of tert-butyl (S)-(2-((2-((tert-butoxycarbonyl)amino)propyl)amino)-5-chloro-3-methylthieno[3,2-b]pyridin-7-yl)(thiophen-2-ylmethyl)carbamate (80 mg, 0.14 mmol) in a solution of HCl (4 M in dioxane, 1 mL) at room temperature for 1 h. The organic volatiles were removed. The residue was triturated with diethyl ether and filtered to afford (S)-N$^2$-(2-aminopropyl)-5-chloro-3-methyl-N$^7$-(thiophen-2-ylmethyl)thieno[3,2-b]pyridine-2,7-diamine (52 mg, 62% yield) as the hydrochloride salt. MS m/z 367.2, 369.2 [M+H]$^+$; $^1$H NMR (DMSO-d$_6$) δ: 8.34 (br s, 4H), 8.11 (br s, 1H), 7.39-7.46 (m, 1H), 7.08-7.14 (m, 1H), 6.97-7.02 (m, 1H), 6.58 (s, 1H), 4.71-4.80 (m, 2H), 3.47-3.55 (m, 1H), 3.41-3.45 (m, 1H), 3.31-3.36 (m, 1H), 2.15 (s, 3H), 1.29 (d, J=6.4 Hz, 3H).

The compounds below were prepared according to the procedure of Example 24 by substituting the appropriate starting materials, reagents and reaction conditions.

| Compound | Spectral Data |
|---|---|
| 164 | MS m/z 367.2, 369.2 [M + H]$^+$; $^1$H NMR (DMSO-d$_6$) δ: 8.30 (br s, 4H), 8.09 (br s, 1H), 7.37-7.42 (m, 1H), 7.08-7.14 (m, 1H), 6.97-7.02 (m, 1H), 6.58 (s, 1H), 4.71-4.77 (m, 2H), 3.47-3.54 (m, 1H), 3.40-3.45 (m, 1H), 3.31-3.36 (m, 1H), 2.15 (s, 3H), 1.29 (d, J = 6.4 Hz, 3H). |

Example 25 (Compound 131)

Methyl 3-(5-chloro-7-{[(furan-2-yl)methyl]amino}-3-methylthieno[3,2-b]pyridin-2-yl)-D-alaninate

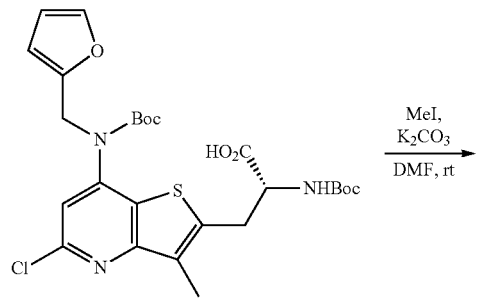

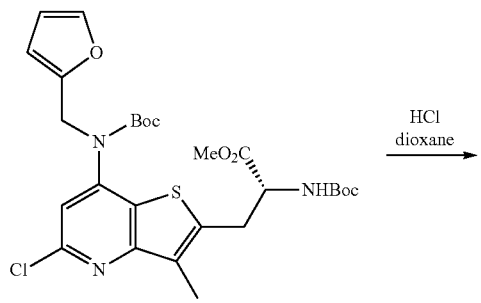

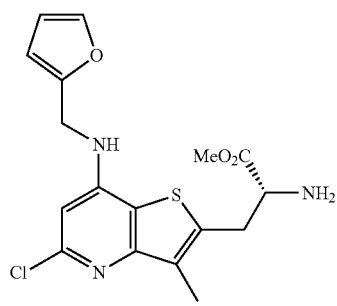

Step 1: Methyl (R)-3-(7-((tert-butoxycarbonyl)(furan-2-ylmethyl)amino)-5-chloro-3-methylthieno[3,2-b]pyridin-2-yl)-2-((tert-butoxycarbonyl)amino)propanoate To a solution of (R)-3-(7-((tert-butoxycarbonyl)(furan-2-ylmethyl)amino)-5-chloro-3-methylthieno[3,2-b]pyridin-2-yl)-2-((tert-butoxycarbonyl)amino)propanoic acid (45 mg, 0.08 mmol, 1.0 eq.), prepared according to Example 12 step 2, and K$_2$CO$_3$ (35 mg, 0.25 mmol, 3.0 eq.) in DMF (1 mL) was added MeI (25 μL, 0.4 mmol, 5 eq.) and then stirred at 50° C. for 12 h. The reaction mixture was cooled to room temperature and diluted with H$_2$O (10 mL). The aqueous phase was extracted with EtOAc (2×30 mL). The combined organic phases were washed with brine, dried over MgSO$_4$, filtered, and concentrated in vacuo. The crude residue was purified by silica gel column chromatography eluting with 0-30% EtOAc in hexanes to afford methyl (R)-3-(7-((tert-butoxycarbonyl)(furan-2-ylmethyl)amino)-5-chloro-3-methylthieno[3,2-b]pyridin-2-yl)-2-((tert-butoxycarbonyl)amino)propanoate (28 mg, 60%) as a clear oil. MS m/z 580.2 [M+H]$^+$; $^1$H NMR (methanol-d$_4$) δ: 7.36-7.48 (m, 1H), 7.12-7.20 (m, 1H), 6.27-6.35 (m, 1H), 6.16-6.26 (m, 1H), 4.88-4.95 (m, 2H), 4.46-4.55 (m, 1H), 4.06-4.18 (m, 1H), 3.75 (s, 3H), 3.45-3.57 (m, 1H), 2.38 (s, 3H), 1.44 (s, 9H), 1.42 (s, 9H), 1 NH not observed.

Step 2: Methyl 3-(5-chloro-7-{[(furan-2-yl)methyl]amino}-3-methylthieno[3,2-b]pyridin-2-yl)-D-alaninate A mixture of (R)-3-(7-((tert-butoxycarbonyl)(furan-2-ylmethyl)amino)-5-chloro-3-methylthieno[3,2-b]pyridin-2-yl)-2-((tert-butoxycarbonyl)amino)propanoate (28 mg, 0.05 mmol) in a solution of HCl (4 M in dioxane) (1 mL, 4 mmol) was stirred at room temperature for 1 h. The mixture was concentrated under reduced pressure. The solid was triturated with diethyl ether and filtered to afford methyl (R)-2-amino-3-(5-chloro-7-((furan-2-ylmethyl)amino)-3-methylthieno[3,2-b]pyridin-2-yl)propanoate dihydrochloride (12 mg, 65% yield). MS m/z 380.1, 382.1 [M+H]$^+$; $^1$H NMR (methanol-d$_4$) δ: 7.49-7.56 (m, 1H), 7.12-7.18 (m, 1H), 6.45-6.51 (m, 1H), 6.40-6.44 (m, 1H), 4.75 (s, 2H), 4.46-4.53 (m, 1H), 3.90 (s, 3H), 3.67-3.74 (m, 1H), 3.58-3.66 (m, 1H), 2.46 (s, 3H), 3 NHs not observed.

Example 26 (Compound 127 and Compound 130 and Compound 132)

(2S)-2-Amino-1-[3,5-dichloro-7-(2-thienylmethyl-amino)thieno[3,2-b]pyridin-2-yl]propan-1-ol dihydrochloride and 2-[(2S)-2-amino-1-fluoro-propyl]-3,5-dichloro-N-(2-thienylmethyl)thieno[3,2-b]pyridin-7-amine formate and 2-[(2S)-2-amino-1,1-difluoro-propyl]-3,5-dichloro-N-(2-thienylmethyl)thieno[3,2-b]pyridin-7-amine

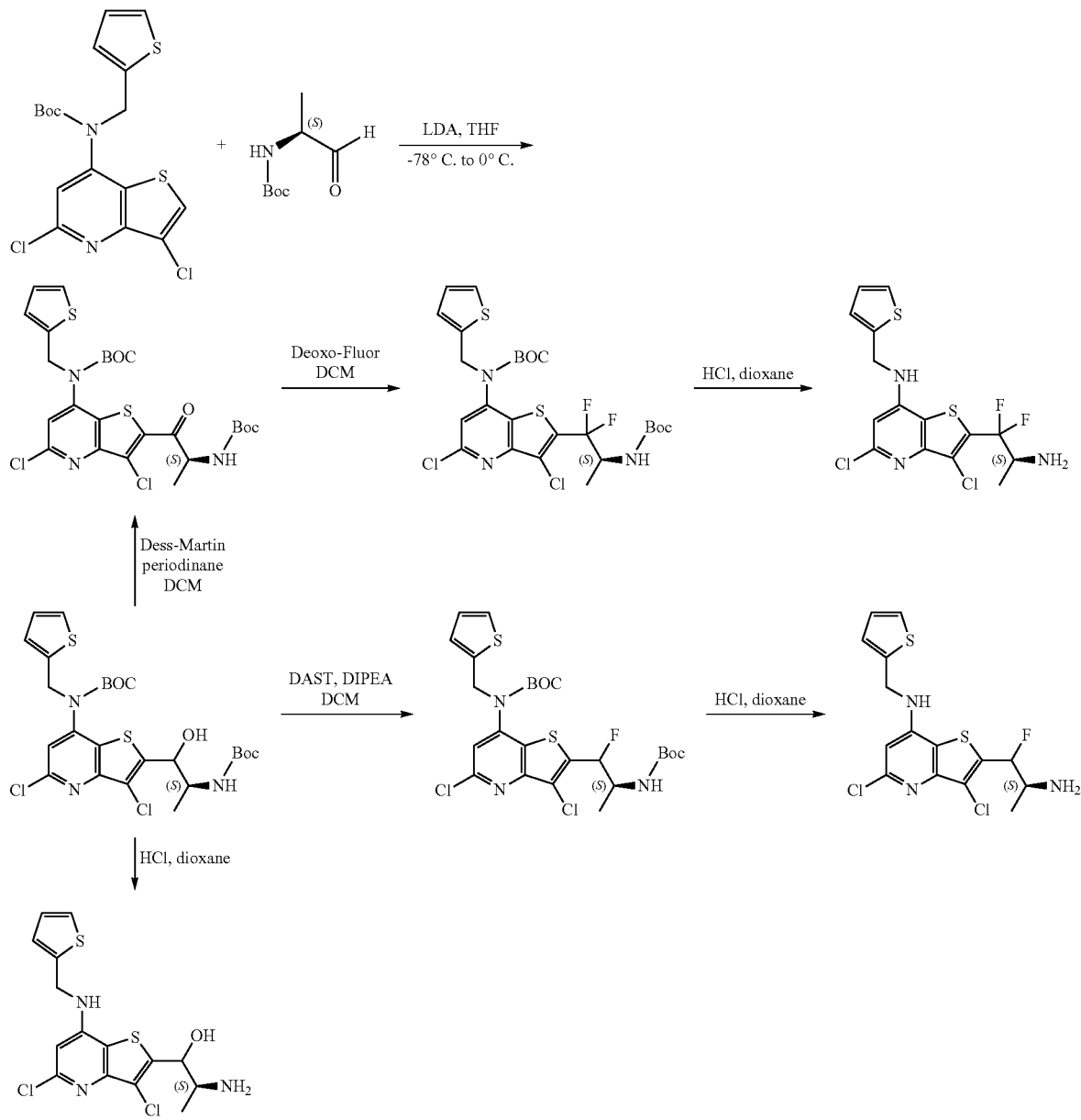

Step 1: N-[2-[(2S)-2-(tert-Butoxycarbonylamino)-1-hydroxy-propyl]-3,5-dichloro-thieno[3,2-b]pyridin-7-yl]-N-(2-thienylmethyl)carbamate To a solution of tert-butyl N-(3,5-dichlorothieno[3,2-b]pyridin-7-yl)-N-(2-thienylmethyl)-carbamate (110 mg, 0.27 mmol, 2.0 eq.) in THF (1.0 mL) cooled at −78° C. was added LDA (2.0 M, 0.15 mL, 0.30 mmol, 2.2 eq.). After 15 min, a solution of Boc-L-alaninal (25 mg, 0.14 mmol, 1.0 eq.) in THF (0.5 mL) was added dropwise and the temperature warmed to 0° C. over 30 min. The reaction was quenched with saturated NH₄Cl, then diluted with ethyl acetate and washed with brine, dried and then concentrated. The residue was purified over silica gel with ethyl acetate in hexanes (10 to 50% gradient) to provide tert-butyl N-[2-[(2S)-2-(tert-butoxycarbonylamino)-1-hydroxy-propyl]-3,5-dichloro-thieno[3,2-b]pyridin-7-yl]-N-(2-thienylmethyl)carbamate (28 mg, 35% yield). MS m/z 588.2, 590.2, 592.5 [M+H]$^+$.

Step 2: (2S)-2-Amino-1-[3,5-dichloro-7-(2-thienyl-methylamino)thieno[3,2-b]pyridin-2-yl]propan-1-ol dihydrochloride The general deprotection procedure using HCl in dioxane was followed to give (2S)-2-amino-1-[3,5-dichloro-7-(2-thienylmethylamino)thieno[3,2-b]pyridin-2-yl]propan-1-ol dihydrochloride (20 mg). MS m/z 388.2, 390.2, 392.2 [M+H]$^+$; $^1$H NMR (methanol-d$_4$) δ: 7.34 (d, J=5.2 Hz, 1H), 7.07-7.20 (m, 1H), 7.00 (t, J=4.0 Hz, 1H), 6.89 (s, 1H), 5.25 (d, J=7.6 Hz, 1H), 4.87 (s, 2H), 3.59-3.70 (m, 1H), 1.33 (d, J=6.7 Hz, 3H), 3 NHs and 1 OH not observed.

Step 3: tert-Butyl N-[2-[(2S)-2-(tert-butoxycarbonylamino)-1-fluoro-propyl]-3,5-dichloro-thieno[3,2-b]pyridin-7-yl]-N-(2-thienylmethyl)carbamate To a solution of tert-butyl N-[2-[(2S)-2-(tert-butoxycarbonylamino)-1-hydroxy-propyl]-3,5-dichloro-thieno[3,2-b]pyridin-7-yl]-N-(2-thienylmethyl)carbamate (30.0 mg, 0.0510 mmol, 1.00 eq.) and DIPEA (26.9 mg, 0.036 mL, 0.20 mmol, 4.00 eq.) in DCM (0.5 mL) at −78° C. was added DAST (1.0 M in DCM, 0.20 mL, 0.20 mmol, 4.00 eq.). The temperature then slowly rose to room temperature and was stirred at room temperature overnight. The reaction intermediate was observed on LC/MS. The reaction was quenched with saturated sodium bicarbonate, then diluted with ethyl acetate and washed with brine, dried and then evaporated. The residue was purified over silica with ethyl acetate and hexanes (10 to 50% gradient) to give tert-butyl N-[2-[(2S)-2-(tert-butoxycarbonylamino)-1-fluoro-propyl]-3,5-dichloro-thieno[3,2-b]pyridin-7-yl]-N-(2-thienylmethyl)carbamate (17 mg, 56% yield). MS m/z 590.3, 592.2, 594.2 [M+H]$^+$.

Step 4: 2-[(2S)-2-Amino-1-fluoro-propyl]-3,5-dichloro-N-(2-thienylmethyl)thieno[3,2-b]pyridin-7-amine formate The general deprotection procedure using HCl in dioxane followed by reverse phase HPLC purification with formic acid used as the mobile phase modifier provided 2-[(2S)-2-amino-1-fluoro-propyl]-3,5-dichloro-N-(2-thienylmethyl)thieno[3,2-b]pyridin-7-amine formic acid salt (8.0 mg, 64% yield). MS m/z 390.2, 392.2, 394.2 [M+H]$^+$; $^1$H NMR (methanol-d$_4$) δ: 8.23-8.56 (br s, 1H), 7.33 (d, J=4.3 Hz, 1H), 7.06-7.17 (m, 1H), 7.00 (t, J=4.3 Hz, 1H), 6.68 (s, 1H), 6.34 (d, J=45.3 Hz, 1H), 4.79 (s, 2H), 3.89-4.07 (m, 1H), 1.39 (d, J=6.4 Hz, 3H), 3 NHs not observed.

Step 5: tert-Butyl N-[2-[(2S)-2-(tert-butoxycarbonylamino)propanoyl]-3,5-dichloro-thieno[3,2-b]pyridin-7-yl]-N-(2-thienylmethyl)carbamate A mixture of tert-butyl N-[2-[(2S)-2-(tert-butoxycarbonylamino)-1-hydroxy-propyl]-3,5-dichloro-thieno[3,2-b]pyridin-7-yl]-N-(2-thienylmethyl)carbamate (28 mg, 0.048 mmol, 1.0 eq.) and Dess-Martin periodinane (31 mg, 0.071 mmol, 1.5 eq.) in DCM (0.5 mL) was stirred at room temperature for 1 h. DCM was removed and the residue was diluted with ether, to which was added 1.0 M Na$_2$S$_2$O$_3$ and saturated sodium bicarbonate. The mixture was separated. The organic layer was washed with 2.0 M K$_2$CO$_3$ and brine, dried over sodium sulfate and evaporated to give tert-butyl N-[2-[(2S)-2-(tert-butoxycarbonylamino)propanoyl]-3,5-dichloro-thieno[3,2-b]pyridin-7-yl]-N-(2-thienylmethyl)carbamate (32 mg), which was used in the next step without further purification. MS m/z 586.2, 588.3, 590.3 [M+H]$^+$.

Step 6: tert-Butyl N-[2-[(2S)-2-(tert-butoxycarbonylamino)-1,1-difluoro-propyl]-3,5-dichloro-thieno[3,2-b]pyridin-7-yl]-N-(2-thienylmethyl)carbamate A mixture of tert-butyl N-[2-[(2S)-2-(tert-butoxycarbonylamino)propanoyl]-3,5-dichloro-thieno[3,2-b]pyridin-7-yl]-N-(2-thienylmethyl)carbamate (32 mg, 0.055 mmol, 1.1 eq.) and DAST (1.0 M in DCM) (1.0 mL, 1.0 mmol, 21 eq.) was stirred at room temperature overnight. LC/MS showed ~13% of desired product. The mixture was transferred to an Eppendorf vial, to which was added Deoxo-Fluor (55 mg, 0.046 mL, 0.24 mmol, 5.0 eq.) and the mixture was stirred at room temperature for 6 h, then quenched with saturated sodium bicarbonate. The mixture was extracted with ethyl acetate, washed with water and brine, dried over sodium sulfate and evaporated. The residue was purified over silica gel with ethyl acetate in hexanes (5 to 50% gradient) to give tert-butyl N-[2-[(2S)-2-(tert-butoxycarbonylamino)-1,1-difluoro-propyl]-3,5-dichloro-thieno[3,2-b]pyridin-7-yl]-N-(2-thienylmethyl)carbamate (3.5 mg, 12% yield). MS m/z 608.2, 610.2, 612.2 [M+H]$^+$.

Step 7: 2-[(2S)-2-Amino-1,1-difluoro-propyl]-3,5-dichloro-N-(2-thienylmethyl)thieno[3,2-b]pyridin-7-amine The general deprotection procedure using HCl in dioxane followed by reverse phase HPLC purification with formic acid used as the mobile phase modifier provided 2-[(2S)-2-amino-1,1-difluoro-propyl]-3,5-dichloro-N-(2-thienylmethyl)thieno[3,2-b]pyridin-7-amine (2.3 mg, 98% yield) as the free base. MS m/z 408.3, 410.3, 412.2 [M+H]$^+$; $^1$H NMR (methanol-d$_4$) δ: 7.28-7.38 (m, 1H), 7.07-7.17 (m, 1H), 6.95-7.05 (m, 1H), 6.73 (s, 1H), 4.79 (s, 2H), 4.47-4.58 (br s, 1H), 1.40 (br d, J=7.0 Hz, 3H), 3 NHs not observed.

The compounds below were prepared according to the procedure of Example 26 by substituting the appropriate starting materials, reagents and reaction conditions.

| Compound | Spectral Data |
| --- | --- |
| 147 | MS m/z 353.1, 355.1 [M + H]$^+$; $^1$H NMR (methanol-d$_4$) δ: 7.43 (s, 1 H), 6.50 (s, 1 H), 6.34 (d, J = 1.3 Hz, 1 H), 6.28 (d, J = 1.3 Hz, 1 H), 4.51 (s, 2 H), 3.71-3.79 (m, 2 H), 2.43 (s, 3 H), 1.66 (s, 3 H), 3 NHs not observed. |
| 153 | MS m/z 416.1, 418.1, 420.0 [M + H]$^+$; $^1$H NMR (methanol-d$_4$) δ: 7.33-7.42 (m, 1H), 6.72 (s, 1H), 6.28 (s, 2H), 5.11-5.19 (m, 1H), 4.51 (s, 2H), 3.49-3.59 (m, 1H), 1.20-1.25 (m, 3H), 3 NHs and 1 OH not observed. |

-continued

| Compound | Spectral Data |
|---|---|
| 154 | MS m/z 418.1, 420.1, 422.0 [M + H]+; 1H NMR (methanol-$d_4$) δ: 7.45-7.55 (m, 1H), 7.04 (s, 1H), 6.33-6.52 (m, 3H), 4.70 (s, 2H), 4.00-4.16 (m, 1H), 1.35-1.43 (m, 3H), 3 NHs not observed. |
| 155 | MS m/z 432.1, 434.1, 436.1 [M + H]+; 1H NMR (methanol-$d_4$) δ: 7.19-7.26 (m, 1H), 6.99-7.05 (m, 1H), 6.86-6.93 (m, 1H), 6.61-6.68 (m, 1H), 5.10-5.19 (m, 1H), 4.70-4.74 (m, 2H), 3.49-3.60 (m, 1H), 1.20-1.26 (m, 3H), 3 NHs and 1OH not observed. |
| 156 | MS m/z 430.1, 432.1, 434.1 [M + H]+; 1H NMR (methanol-$d_4$) δ: 7.18-7.26 (m, 1H), 6.97-7.05 (m, 1H), 6.85-6.93 (m, 1H), 6.62 (s, 1H), 5.22-5.31 (m, 1H), 4.66-4.71 (m, 2H), 1.57-1.66 (m, 3H), 3 NHs not observed. |
| 157 | MS m/z 414.0, 416.1, 418.0 [M + H]+; 1H NMR (methanol-$d_4$) δ: 7.37 (s, 1H), 6.69 (s, 1H), 6.23-6.33 (m, 2H), 5.22-5.32 (m, 1H), 4.48 (s, 2H), 1.60 (d, J = 7.3 Hz, 3H), 3 NHs not observed. |
| 158 | MS m/z 434.1, 436.1, 438.1 [M + H]+; 1H NMR (methanol-$d_4$) δ: 7.19-7.27 (m, 1H), 6.97-7.05 (m, 1H), 6.85-6.92 (m, 1H), 6.62 (s, 1H), 6.17-6.33 (m, 1H), 4.66-4.71 (m, 2H), 3.87-4.01 (m, 1H), 1.25-1.32 (m, 3H), 3 NHs not observed. |
| 159 | MS m/z 433.1, 435.1, 437.1 [M + H]+; 1H NMR (methanol-$d_4$) δ: 7.79-7.88 (m, 1H), 7.56-7.67 (m, 1H), 6.67 (s, 1H), 5.12-5.21 (m, 1H), 4.96 (s, 2H), 3.52-3.58 (s, 1H), 1.24 (d, J = 6.7 Hz, 3H), 3 NHs and 1 OH not observed. |
| 160 | MS m/z 431.1, 433.1, 435.1 [M + H]+; 1H NMR (methanol-$d_4$) δ: 7.83 (d, J = 3.7 Hz, 1H), 7.62 (d, J = 3.7 Hz, 1H), 6.67 (s, 1H), 5.24-5.34 (m, 1H), 4.94 (s, 2H), 1.57-1.66 (m, 3H) and 3 NHs not observed. |
| 161 | MS m/z 435.1, 437.1, 439.1 [M + H]+; 1H NMR (methanol-$d_4$) δ: 7.78-7.86 (m, 1H), 7.56-7.65 (m, 1H), 6.60-6.67 (m, 1H), 6.20-6.35 (m, 1H), 4.93 (s, 2H), 3.88-4.03 (m, 1H), 1.29 (d, J = 7.0 Hz, 3H), 3 NHs not observed. |

Example 27 (Compound 149)

5-Chloro-3-(difluoromethoxy)-N-(2-thienylmethyl)thieno[3,2-b]pyridin-7-amine

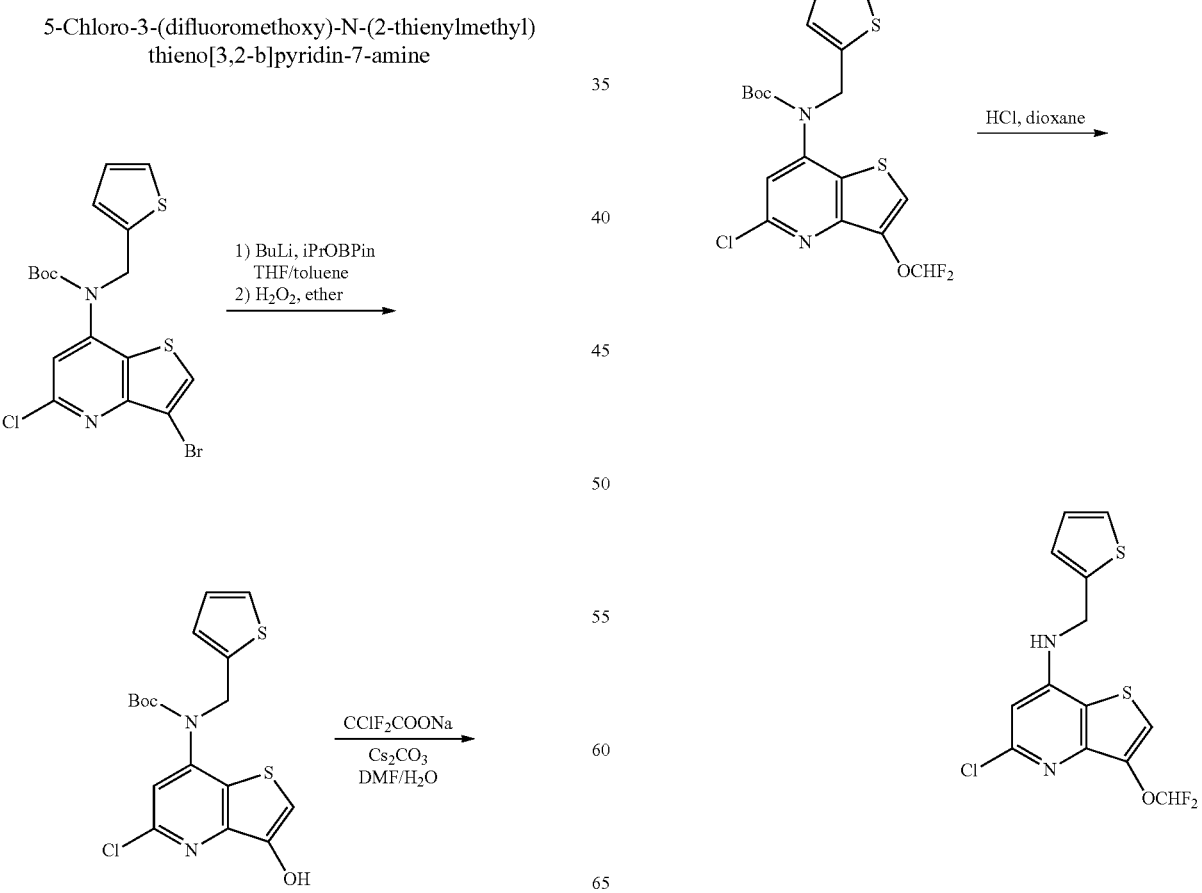

Step 1: tert-Butyl N-(5-chloro-3-hydroxy-thieno[3,2-b]pyridin-7-yl)-N-(2-thienylmethyl)carbamate To a mixture of tert-butyl N-(3-bromo-5-chloro-thieno[3,2-b]pyridin-7-yl)-N-(2-thienylmethyl)carbamate (460 mg, 1.0 mmol, 1.0 eq.) and 2-isopropoxy-4,4,5,5-tetramethyl-1,3,2-dioxaborolane (220 mg, 0.24 mL, 1.2 mmol, 1.2 eq.) in THF (1.0 mL) and toluene (4.0 mL) cooled at −78° C. was added n-BuLi (2.5 M in hexane, 0.48 mL, 1.2 mmol, 1.2 eq.) dropwise. The mixture was stirred at −78° C. for 1 h then quenched with saturated ammonium chloride, diluted with ethyl acetate, washed with brine, and then dried and concentrated. To the residue was added $Et_2O$ (10 mL), followed by hydrogen peroxide (30 mass % in water, 0.41 mL, 4.0 mmol, 4.0 eq.). The mixture was stirred at room temperature for 16 h, then diluted with ether, treated with saturated sodium thiosulfate and separated. The organic layer was washed with water and brine, dried over sodium sulfate and concentrated. The residue was purified over silica with ethyl acetate in hexanes (5 to 40% gradient) to give tert-butyl N-(5-chloro-3-hydroxy-thieno[3,2-b]pyridin-7-yl)-N-(2-thienylmethyl)carbamate (294 mg, 74% yield). MS m/z 397.3, 399.3 [M+H]⁺.

Step 2: tert-Butyl N-[5-chloro-3-(difluoromethoxy)thieno[3,2-b]pyridin-7-yl]-N-(2-thienylmethyl)carbamate A mixture of tert-butyl N-(5-chloro-3-hydroxy-thieno[3,2-b]pyridin-7-yl)-N-(2-thienylmethyl)carbamate (100 mg, 0.252 mmol, 1.00 eq.), sodium chlorodifluoroacetate (91.1 mg, 0.579 mmol, 2.30 eq.) and $Cs_2CO_3$ (115 mg, 0.353 mmol, 1.40 eq.) in DMF (240 mg) and water (0.025 mL) was stirred at 100° C. for 16 h, then cooled, diluted with ethyl acetate and then washed with brine, dried and evaporated. The residue was purified over silica gel with ethyl acetate in hexanes (5 to 25% gradient) to give tert-butyl N-[5-chloro-3-(difluoromethoxy)thieno[3,2-b]pyridin-7-yl]-N-(2-thienylmethyl)carbamate (29 mg, 26% yield). MS m/z 447.1, 449.1 [M+H]⁺.

Step 3: 5-Chloro-3-(difluoromethoxy)-N-(2-thienylmethyl)thieno[3,2-b]pyridin-7-amine The general deprotection procedure using HCl in dioxane was followed to give 5-chloro-3-(difluoromethoxy)-N-(2-thienylmethyl)thieno[3,2-b]pyridin-7-amine after purification using C18 EZ-Prep with formic acid as the modifier. MS m/z 347.0, 349.0 [M+H]⁺; ¹H NMR (CDCl₃) δ: 7.31-7.36 (m, 1H), 7.22-7.26 (m, 1H), 7.10-7.15 (m, 1H), 7.03-7.07 (m, 1H), 6.95-6.98 (t, J=77 Hz, 1H), 6.62 (s, 1H), 4.87-5.01 (m, 1H), 4.75 (br s, 2H).

The compounds below were prepared according to the procedure of Example 27 by substituting the appropriate starting materials, reagents and reaction conditions.

| Compound | Spectral Data |
|---|---|
| 137 | MS m/z 295.0, 296.9 [M + H]⁺; ¹H NMR (methanol-d₄) δ: 7.48 (d, J = 0.9 Hz, 1H), 7.12 (s, 1H), 6.92 (s, 1H), 6.34-6.46 (m, 2H), 4.67 (s, 2H), 4.03 (s, 3H), 1 NH not observed. |
| 138 | MS m/z 296.9, 298.9 [M + H]⁺; ¹H NMR (methanol-d₄) δ: 7.40 (dd, J = 5.2, 1.2 Hz, 1H), 7.18 (d, J = 3.4 Hz, 1H), 6.99-7.07 (m, 3H), 4.97 (s, 2H), 1 NH and 1 OH not observed. |

Example 28 (Compound 167)

2-[(2R)-2-Amino-3-methylsulfinyl-propyl]-3,5-dichloro-N-(2-furylmethyl)thieno[3,2-b]pyridin-7-amine

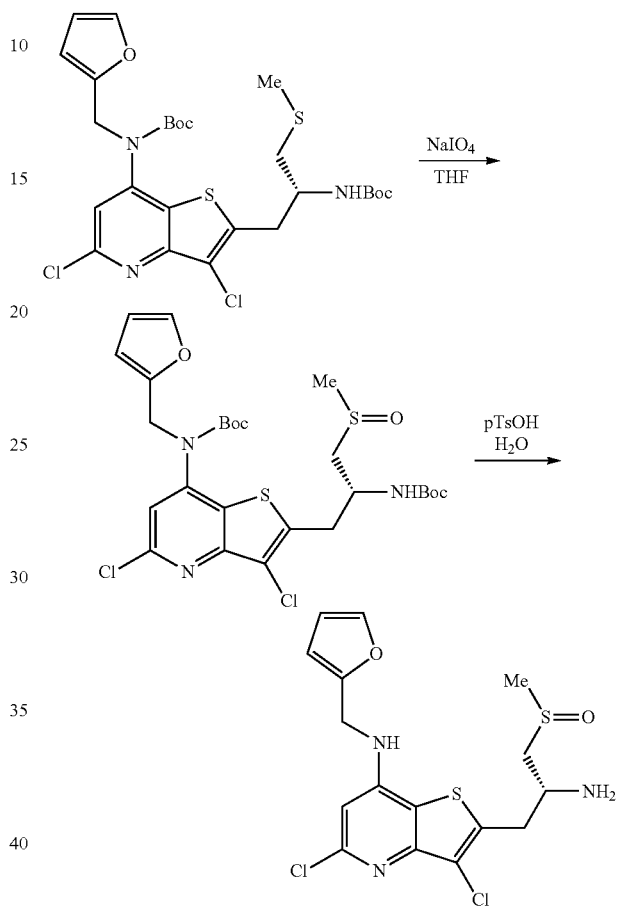

Step 1: tert-Butyl N-[2-[(2R)-2-(tert-butoxycarbonylamino)-3-methylsulfinyl-propyl]-3,5-dichloro-thieno[3,2-b]pyridin-7-yl]-N-(2-furylmethyl)carbamate To a stirred solution of tert-butyl N-[2-[(2R)-2-(tert-butoxycarbonylamino)-3-methylsulfanyl-propyl]-3,5-dichloro-thieno[3,2-b]pyridin-7-yl]-N-(2-furylmethyl)carbamate (119.6 mg, 0.19 mmol, 1.0 eq.) in a mixed solvent of THF (2.0 mL) and water (1.0 mL) was added sodium periodate (60 mg, 0.28 mmol, 1.4 eq.) at 0° C. The reaction was stirred at 0° C. for 1 h and then warmed to room temperature and stirred for 48 h. The reaction was quenched with water then extracted with EtOAc (2×30 mL). The combined organic phases were washed with brine, dried over sodium sulfate and then concentrated to give the crude product which was purified by flash column chromatography (0-80% EtOAc in DCM) to afford tert-butyl N-[2-[(2R)-2-(tert-butoxycarbonylamino)-3-methylsulfinyl-propyl]-3,5-dichloro-thieno[3,2-b]pyridin-7-yl]-N-(2-furylmethyl)carbamate (103.3 mg, 84% yield) as a light yellow foam. MS m/z 640.1, 642.1, [M+Na]+; 1H NMR (acetone-d6) δ ppm: 7.46 (br d, J=4.4 Hz, 1H), 7.39 (s, 1H), 6.44 (br d, J=8.1 Hz, 1H), 6.30-6.32 (m, 1H), 6.27 (t, J=2.7 Hz, 1H), 4.98 (s, 2H), 4.33-4.46 (m, 1H), 3.49-3.56 (m, 1H), 3.42 (br dd, J=14.0, 7.9 Hz, 1H), 2.91-3.18 (m, 2H), 2.63 (s, 2H), 2.58 (s, 1H), 1.43 (s, 9H), 1.37 (s, 9H).

Step 2: tert-2-[(2R)-2-Amino-3-methylsulfinyl-propyl]-3,5-dichloro-N-(2-furylmethyl)thieno[3,2-b]pyridin-7-amine To a solution of tert-butyl N-[2-[(2R)-2-(tert-butoxycarbonylamino)-3-methylsulfinyl-propyl]-3,5-dichloro-thieno[3,2-b]pyridin-7-yl]-N-(2-furylmethyl)carbamate (103.3 mg, 0.167 mmol, 1.0 eq.) in acetonitrile (3.0 mL) and THF (1.0 mL) was added p-toluenesulfonic acid monohydrate (135 mg, 0.672 mmol, 4.0 eq.) and was heated to 60° C. and then stirred for 1 h at 60° C. LC-MS analysis indicated the complete consumption of starting material. The reaction mixture was quenched with sodium carbonate (aq. 0.3 M, 5 mL) then extracted with EtOAc (2×30 mL). The combined organic phases were dried over sodium sulfate and then concentrated to give crude product which was dried under high vacuum overnight to afford 2-[(2R)-2-amino-3-methylsulfinyl-propyl]-3,5-dichloro-N-(2-furylmethyl)thieno[3,2-b]pyridin-7-amine (55.8 mg, 80% yield) as an off-white solid. MS m/z 418.4, 420.4, [M+H]+; 1H NMR (DMSO-d6) δ ppm: 7.83-7.91 (m, 1H), 7.60 (s, 1H), 6.65 (d, J=4.0 Hz, 1H), 6.37-6.43 (m, 2H), 4.50-4.55 (m, 2H), 3.39-3.57 (m, 1H), 3.31 (s, 3H), 3.19 (td, J=14.6, 5.5 Hz, 1H), 3.05 (ddd, J=14.5, 12.4, 7.3 Hz, 1H), 2.72-2.84 (m, 2H), 2 NHs not observed.

Example 29 (Compound 129)

2-[(2S)-2-Aminopropyl]-5-chloro-N-[(5-fluorothiazol-2-yl)methyl]-3-methyl-thieno[3,2-b]pyridin-7-amine

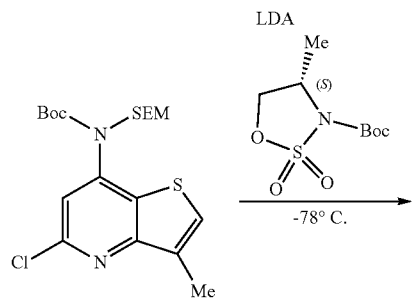

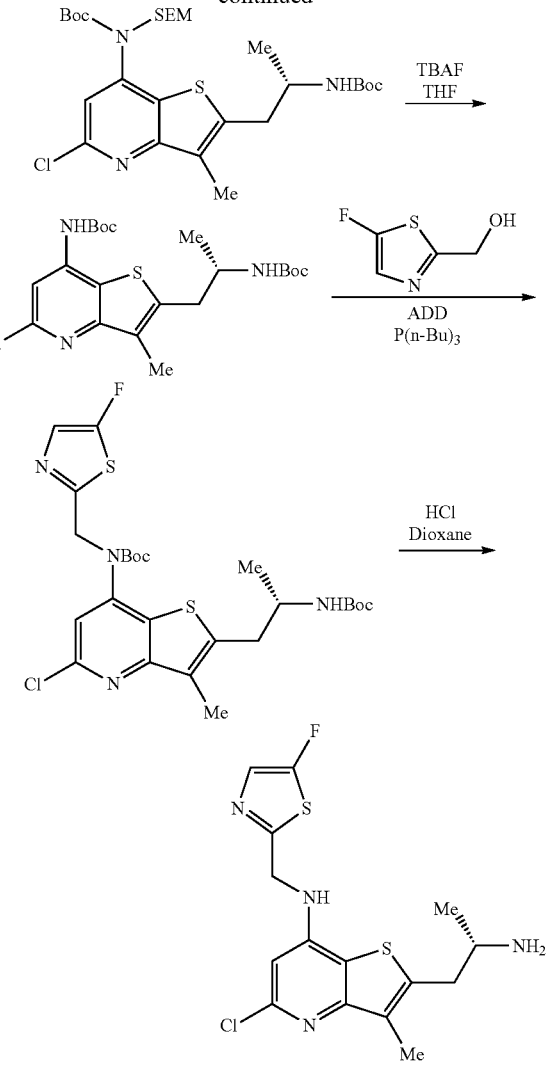

Step 1: tert-Butyl N-[2-[(2S)-2-(tert-butoxycarbonylamino)propyl]-5-chloro-3-methyl-thieno[3,2-b]pyridin-7-yl]-N-(2-trimethylsilylethoxymethyl)carbamate To a two neck round bottom flask was added tert-butyl N-(5-chloro-3-methyl-thieno[3,2-b]pyridin-7-yl)-N-(2-trimethylsilylethoxymethyl)carbamate (1.95 g, 4.55 mmol, 1.0 eq.) dissolved in THF (0.25 M) followed by tert-butyl (4S)-4-methyl-2,2-dioxo-oxathiazolidine-3-carboxylate (1.40 g, 5.91 mmol, 1.3 eq.). The mixture was cooled to −78° C. To the cooled reaction mixture was added lithium diisopropylamide in THF/heptane/ethylbenzene (2.0 M, 2.7 mL, 5.45 mmol, 1.2 eq.) dropwise and the reaction was stirred to completion as monitored by UPLC. Once the reaction was complete (~1.5 h) the reaction was removed from the bath and was quenched with 1.0M citric acid and extracted with ethyl acetate. The combined extracts were washed with water and brine and dried with Na2SO4 and concentrated. The crude mixture was subjected to column chromatography (EtOAc/DCM, 0-15%) to furnish tert-butyl N-[2-[(2S)-2-(tert-butoxycarbonylamino)propyl]-5-chloro-3-methylthieno[3,2-b]pyridin-7-yl]-N-(2-trimethylsilylethoxymethyl)carbamate (1.91 g, 72% yield). MS m/z 586.4, 588.4, [M+H]+;

$^1$H NMR (CDCl$_3$) δ ppm: 7.25 (s, 1H), 5.07 (s, 2H), 4.47 (br d, J=1.7 Hz, 1H), 4.02 (br s, 1H), 3.13-3.19 (m, 1H), 3.05 (br s, 1H), 2.43 (s, 3H), 1.65 (br s, 1H), 1.44 (s, 18H), 1.17 (d, J=6.7 Hz, 3H), 0.98 (s, 1H), 0.95 (s, 1H), 0.03 (s, 9H), 1 NH not observed.

Step 2: tert-Butyl N-[(1S)-2-[7-(tert-butoxycarbonylamino)-5-chloro-3-methyl-thieno[3,2-b]pyridin-2-yl]-1-methyl-ethyl]carbamate To a reaction tube with tert-butyl N-[2-[(2S)-2-(tert-butoxycarbonylamino)propyl]-5-chloro-3-methyl-thieno[3,2-b]pyridin-7-yl]-N-(2-trimethylsilylethoxymethyl)carbamate (0.41 g, 0.70 mmol, 1.0 eq.) was added THF (7.0 mL) and tetrabutylammonium fluoride (1 mol/L) in THF (7 mL, 7.0 mmol, 10 eq.) under an atmosphere of nitrogen. The reaction was stirred for 12 h at 40° C. Upon completion, the reaction was cooled to room temperature and diluted with ethyl acetate, washed with water, dried and concentrated. The crude material was subjected to column chromatography (EtOAc/DCM, 0-15%) to furnish tert-butyl N-[(1S)-2-[7-(tert-butoxycarbonylamino)-5-chloro-3-methyl-thieno[3,2-b]pyridin-2-yl]-1-methyl-ethyl]carbamate (19 mg, 6.0% yield). MS m/z 456.4, 458.4, [M+H]+, $^1$H NMR (CDCl$_3$) δ ppm: 6.61 (s, 1H), 4.47 (br s, 1H), 4.02 (br s, 1H), 3.32-3.32 (m, 1H), 3.09-3.16 (m, 1H), 3.01-3.06 (m, 1H), 2.41 (s, 3H), 1.57 (s, 9H), 1.43 (s, 9H), 1.18 (d, J=6.7 Hz, 3H).

Step 3: tert-Butyl N-[2-[(2S)-2-(tert-butoxycarbonylamino)propyl]-5-chloro-3-methyl-thieno[3,2-b]pyridin-7-yl]-N-[(5-fluorothiazol-2-yl)methyl]carbamate A solution of tert-butyl N-[(1S)-2-[7-(tert-butoxycarbonylamino)-5-chloro-3-methyl-thieno[3,2-b]pyridin-2-yl]-1-methyl-ethyl]carbamate (19 mg, 0.041 mmol, 1.0 eq.) and (5-fluorothiazol-2-yl)methanol (17 mg, 0.125 mmol, 3.0 eq.) in toluene (0.1 M) was sparged with N$_2$ for 30 min. To this mixture was added 1,1'-(azodicarbonyl)dipiperidine (33 mg, 0.129 mmol, 3.1 eq.) and the mixture was again sparged with N$_2$ and stirred an additional 10 min. Tri-n-butylphosphine (28 mg, 0.138 mmol, 3.3 eq.) was added and the reaction mixture was stirred at 30° C. for about 17 h. The mixture was cooled to room temperature and concentrated in vacuo. The crude material was purified by silica gel flash chromatography to provide tert-butyl N-[2-[(2S)-2-(tert-butoxycarbonylamino)propyl]-5-chloro-3-methyl-thieno[3,2-b]pyridin-7-yl]-N-[(5-fluorothiazol-2-yl)methyl]carbamate (13 mg, 55% yield). MS m/z 571.3, 573.3 [M+H]+, $^1$H NMR (CDCl$_3$) δ ppm: 7.20 (d, J=2.4 Hz, 1H), 7.14 (s, 1H), 4.99 (s, 2H), 4.47 (br d, J=1.1 Hz, 1H), 4.01 (br s, 1H), 3.12-3.17 (m, 1H), 3.05 (br s, 1H), 2.41 (s, 3H), 1.44 (s, 18H), 1.16 (d, J=6.7 Hz, 3H).

Step 4: 2-[(2S)-2-Aminopropyl]-5-chloro-N-[(5-fluorothiazol-2-yl)methyl]-3-methyl-thieno[3,2-b]pyridin-7-amine To a reaction tube with tert-butyl N-[2-[(2S)-2-(tert-butoxycarbonylamino)propyl]-5-chloro-3-methyl-thieno[3,2-b]pyridin-7-yl]-N-[(5-fluorothiazol-2-yl)methyl]carbamate (13 mg, 0.022 mmol, 1.0 eq.) was added hydrochloric acid in dioxane (4.0 M, 1.0 mL, 4.0 mmol) and was allowed to stir for 1 h at room temperature. Upon completion, the reaction was diluted with diethyl ether and was filtered to provide 2-[(2S)-2-aminopropyl]-5-chloro-N-[(5-fluorothiazol-2-yl)methyl]-3-methyl-thieno[3,2-b]pyridin-7-amine (5.6 mg, 66% yield). MS m/z 371.2, 373.2, [M+H]+, $^1$H NMR (methanol-d$_4$) δ ppm: 7.41 (d, J=2.0 Hz, 1H), 7.04 (s, 1H), 4.92 (s, 2H), 3.63-3.71 (m, 1H), 3.35-3.42 (m, 1H), 3.23-3.29 (m, 1H), 2.45 (s, 3H), 1.38 (d, J=6.4 Hz, 3H), 3 NHs not observed.

Example 30 (Compound 148)

2-(1-Aminopropan-2-yl)-5-chloro-N-(furan-2-ylmethyl)-3-methylthieno[3,2-b]pyridin-7-amine

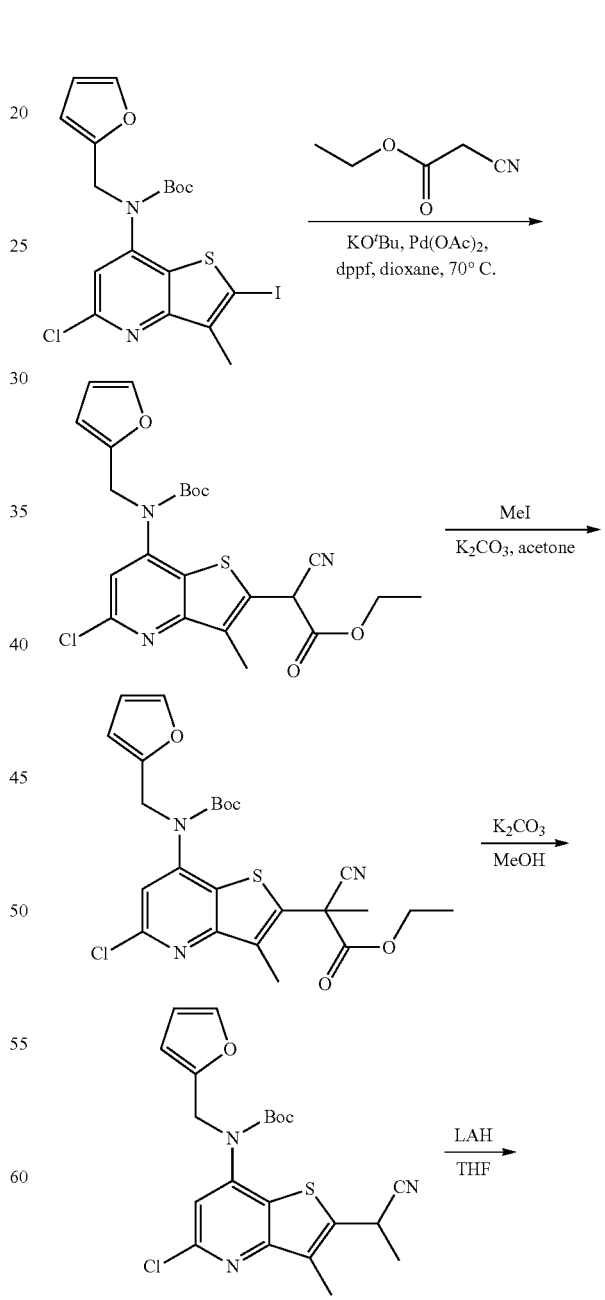

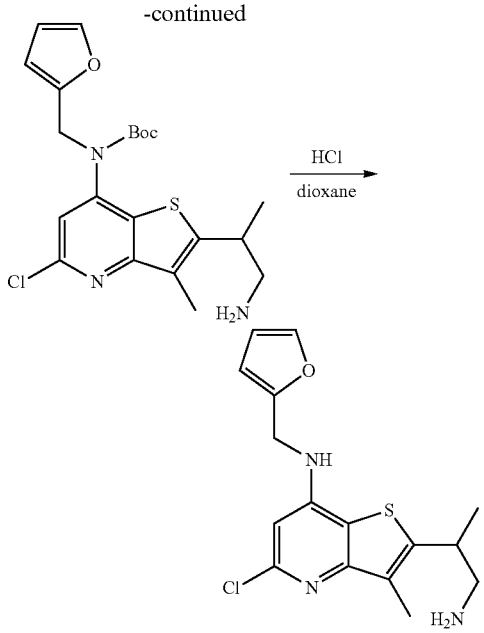

Step 1: Ethyl 2-(7-((tert-butoxycarbonyl)(furan-2-ylmethyl)amino)-5-chloro-3-methylthieno[3,2-b]pyridin-2-yl)-2-cyanoacetate A solution of tert-butyl (5-chloro-2-iodo-3-methylthieno[3,2-b]pyridin-7-yl)(furan-2-ylmethyl)carbamate (202 mg, 0.40 mmol, 1.0 eq.), prepared according to the procedure in Intermediate 6, and ethyl 2-cyanoacetate (50 mg, 1.1 eq.) in dioxane (1.6 mL) was added into a suspension of KOtBu (116 mg, 2.5 eq.) in dioxane (0.5 mL) under argon, followed by addition of Pd(OAc)$_2$ (4.5 mg, 0.05 eq.) and dppf (23 mg, 0.100 eq.). After bubbling argon for 2 min, the reaction was sealed and was heated to 70° C. for 2 h. After cooling, the reaction was quenched with citric acid (1.0 M) and EtOAc, then extracted with EtOAc. The crude material was purified by flash column chromatography on silica gel eluting with 0-60% EtOAc in hexanes to provide ethyl 2-(7-((tert-butoxycarbonyl)(furan-2-ylmethyl)amino)-5-chloro-3-methylthieno[3,2-b]pyridin-2-yl)-2-cyanoacetate (145 mg, 74. % yield) as orange oil. MS m/z 490.1, 492.1 [M+H]$^+$.

Step 2: Ethyl 2-(7-((tert-butoxycarbonyl)(furan-2-ylmethyl)amino)-5-chloro-3-methylthieno[3,2-b]pyridin-2-yl)-2-cyanopropanoate To a cold mixture of ethyl 2-(7-((tert-butoxycarbonyl)(furan-2-ylmethyl)amino)-5-chloro-3-methylthieno[3,2-b]pyridin-2-yl)-2-cyanoacetate (145 mg, 0.30 mmol, 1.0 eq.) and K$_2$CO$_3$ (62 mg, 1.5 eq.) in acetone (0.6 mL) was added MeI (127 mg, 3.0 eq.) under argon. The mixture was stirred at room temperature for 3 h with UPLC analysis indicating completion of the reaction. After cooling to 0° C., the reaction was quenched with citric acid (1.0M) and EtOAc. The crude product was applied directly to the next step without further purification. MS m/z 504.1, 506.1 [M+H]$^+$.

Step 3: tert-Butyl (5-chloro-2-(1-cyanoethyl)-3-methylthieno[3,2-b]pyridin-7-yl)(furan-2-ylmethyl)carbamate A mixture of ethyl 2-(7-((tert-butoxycarbonyl)(furan-2-ylmethyl)amino)-5-chloro-3-methylthieno[3,2-b]pyridin-2-yl)-2-cyanopropanoate (149 mg, 0.30 mmol, 1.0 eq.) and K$_2$CO$_3$ (62 mg, 1.5 eq.) was stirred in MeOH (0.60 mL) at room temperature for 3 h, then quenched with EtOAc and citric acid (1.0 M, aq.). The crude material was purified by flash column chromatography on silica gel eluting with 0-50% EtOAc in hexane to provide tert-butyl (5-chloro-2-(1-cyanoethyl)-3-methylthieno[3,2-b]pyridin-7-yl)(furan-2-ylmethyl)carbamate (81 mg, 63% yield). MS m/z 432.1, 434.2 [M+H]$^+$.

Step 4: tert-Butyl (2-(1-aminopropan-2-yl)-5-chloro-3-methylthieno[3,2-b]pyridin-7-yl)(furan-2-ylmethyl)carbamate To a cold solution of tert-butyl (5-chloro-2-(1-cyanoethyl)-3-methylthieno[3,2-b]pyridin-7-yl)(furan-2-ylmethyl)carbamate (81 mg, 0.19 mmol, 1.0 eq.) in THF (2.0 mL) was added LAH (1.0 M in THF, 0.28 mL, 1.5 eq.) dropwise at 0° C. After stirring 15 min, the mixture was brought to room temperature and continued to stir at room temperature for 3 h. The reaction was quenched with the addition of Na$_2$SO$_4$·xH$_2$O (solid) at 0° C. The mixture was stirred at room temperature for 1 h, filtered, and the solids were washed with MeOH. The combined filtrate was concentrated and purified by prep HPLC eluting with 5-100% ACN in water with 0.1% formic acid to provide tert-butyl (2-(1-aminopropan-2-yl)-5-chloro-3-methylthieno[3,2-b]pyridin-7-yl)(furan-2-ylmethyl)carbamate (10 mg, 12% yield). MS m/z 436.2, 438.2 [M+H]$^+$.

Step 5: 2-(1-Aminopropan-2-yl)-5-chloro-N-(furan-2-ylmethyl)-3-methylthieno[3,2-b]pyridin-7-amine General Boc-deprotection procedure: A mixture of tert-butyl (2-(1-aminopropan-2-yl)-5-chloro-3-methylthieno[3,2-b]pyridin-7-yl)(furan-2-ylmethyl)carbamate (10 mg, 0.022 mmol) was stirred in a solution of HCl (4 M in dioxane, 1 mL) at room temperature for 1 h and then the organic volatiles were removed. The crude solid was purified on prep HPLC eluting with 5-40% ACN in water with 0.1% formic acid to afford 2-(1-aminopropan-2-yl)-5-chloro-N-(furan-2-ylmethyl)-3-methylthieno[3,2-b]pyridin-7-amine as the formic acid salt (5.0 mg, 65% yield). MS m/z 335.8, 338.0 [M+H]$^+$; $^1$H NMR (methanol-d$_4$) δ: 8.44 (s, 1H), 7.46 (t, J=1.2 Hz, 1H), 6.62 (s, 1H), 6.38 (d, J=1.3 Hz, 1H), 4.55 (s, 2H), 3.69-3.74 (m, 1H), 3.23-3.25 (m, 1H), 3.18-3.20 (m, 1H), 2.39 (s, 3H), 1.48 (d, J=6.6 Hz, 3H), 3 NHs not observed, formic acid salt.

Example 31 (Compound 146)

2-(5-Chloro-7-((furan-2-ylmethyl)amino)-3-methylthieno[3,2-b]pyridin-2-yl)propan-1-ol

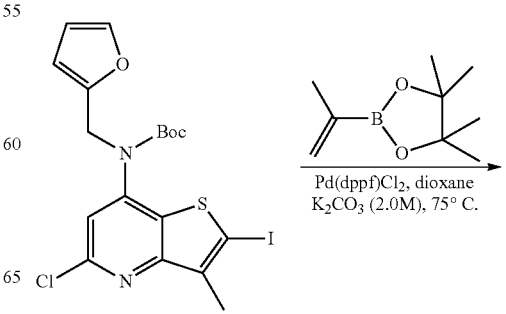

-continued

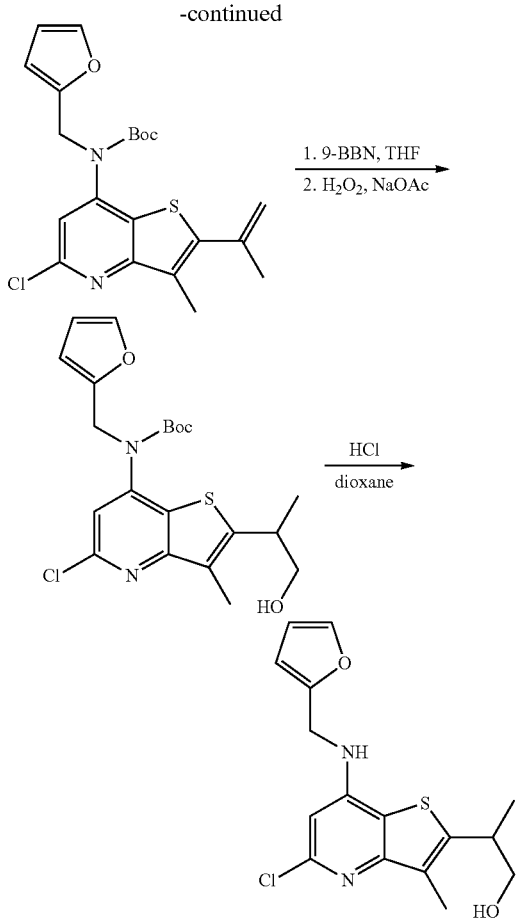

Step 1: tert-Butyl (5-chloro-3-methyl-2-(prop-1-en-2-yl)thieno[3,2-b]pyridin-7-yl)(furan-2-ylmethyl)carbamate A mixture of tert-butyl (5-chloro-2-iodo-3-methylthieno[3,2-b]pyridin-7-yl)(furan-2-ylmethyl)carbamate (101 mg, 0.20 mmol, 1.0 eq.), prepared according to the procedure in Intermediate 6, and 4,4,5,5-tetramethyl-2-(prop-1-en-2-yl)-1,3,2-dioxaborolane (46.0 mg, 1.3 eq.) and Pd(dppf)Cl$_2$ (8.3 mg, 0.05 eq.) in dioxane (1 mL) and K$_2$CO$_3$ (2M in H$_2$O, 0.30 mL, 3.0 eq.) was stirred at 75° C. for 3 h. The reaction was quenched with EtOAc and water. The crude material was purified by flash column chromatography on silica gel eluting with 0-5% EtOAc in hexanes to provide tert-butyl (5-chloro-3-methyl-2-(prop-1-en-2-yl)thieno[3,2-b]pyridin-7-yl)(furan-2-ylmethyl)carbamate (75 mg, 90% yield) as colorless oil, which was used directly in the next step. MS m/z 419.2, 421.2 [M+H]$^+$.

Step 2: tert-Butyl (5-chloro-2-(1-hydroxypropan-2-yl)-3-methylthieno[3,2-b]pyridin-7-yl)(furan-2-ylmethyl)carbamate To a cold solution of tert-butyl (5-chloro-3-methyl-2-(prop-1-en-2-yl)thieno[3,2-b]pyridin-7-yl)(furan-2-ylmethyl)carbamate (75 mg, 1.0 eq.) in THF (1 mL) was added 9-BBN (0.5 M in THF, 1 mL, 4.0 eq.) dropwise at 0° C. After stirring at 0° C. for 1 h, the mixture was brought to room temperature, and continued stirring overnight. The mixture was then cooled to 0° C. EtOH (0.2 mL) was added followed by addition of NaOAc (sat., 0.5 mL) and hydrogen peroxide (30 wt % in water, 0.2 mL). The mixture was continued to stir at 0° C. for 1 h and at room temperature for 5 h, then quenched with EtOAc and water. The organic phases were washed with water and brine. The crude material was purified by flash column chromatography on silica gel eluting with 0-60% EtOAc in hexanes to provide tert-butyl (5-chloro-2-(1-hydroxypropan-2-yl)-3-methylthieno[3,2-b]pyridin-7-yl)(furan-2-ylmethyl)carbamate (62 mg, 79% yield) as a light yellow oil. MS m/z 437.2, 439.2 [M+H]$^+$.

Step 3: 2-(5-Chloro-7-((furan-2-ylmethyl)amino)-3-methylthieno[3,2-b]pyridin-2-yl)propan-1-ol A mixture of tert-butyl (5-chloro-2-(1-hydroxypropan-2-yl)-3-methylthieno[3,2-b]pyridin-7-yl)(furan-2-ylmethyl)carbamate (16 mg, 0.037 mmol) and HCl (4 M) in dioxane (1.0 mL) was stirred at room temperature for 1 h. The mixture was diluted with diethyl ether (2×) and filtered. The filter cake was washed with ether, collected and dried to give 2-(5-chloro-7-((furan-2-ylmethyl)amino)-3-methylthieno[3,2-b]pyridin-2-yl)propan-1-ol (6 mg, 48% yield). MS m/z 337.1, 339.1 [M+H]$^+$; $^1$H NMR (DMSO-d$_6$) δ: 7.59 (s, 1H), 7.50 (br s, 1H), 6.52 (s, 1H), 6.39 (d, J=1.3 Hz, 1H), 6.34 (d, J=1.3 Hz, 1H), 4.90 (br s, 1H), 4.49 (s, 2H), 3.51-3.55 (m, 2H), 3.43-3.48 (m, 1H), 2.24 (s, 3H), 1.27 (d, J=6.1 Hz, 3H).

Example 32 (Compound 150 and Compound 151)

2-[(2R,3S)-3-aminobutan-2-yl]-5-chloro-N-[(furan-2-yl)methyl]-3-methylthieno[3,2-b]pyridin-7-amine and 2-[(2S,3S)-3-aminobutan-2-yl]-5-chloro-N-[(furan-2-yl)methyl]-3-methylthieno[3,2-b]pyridin-7-amine

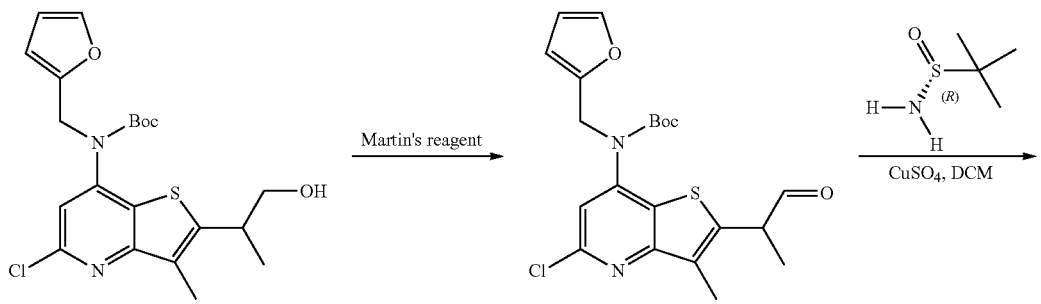

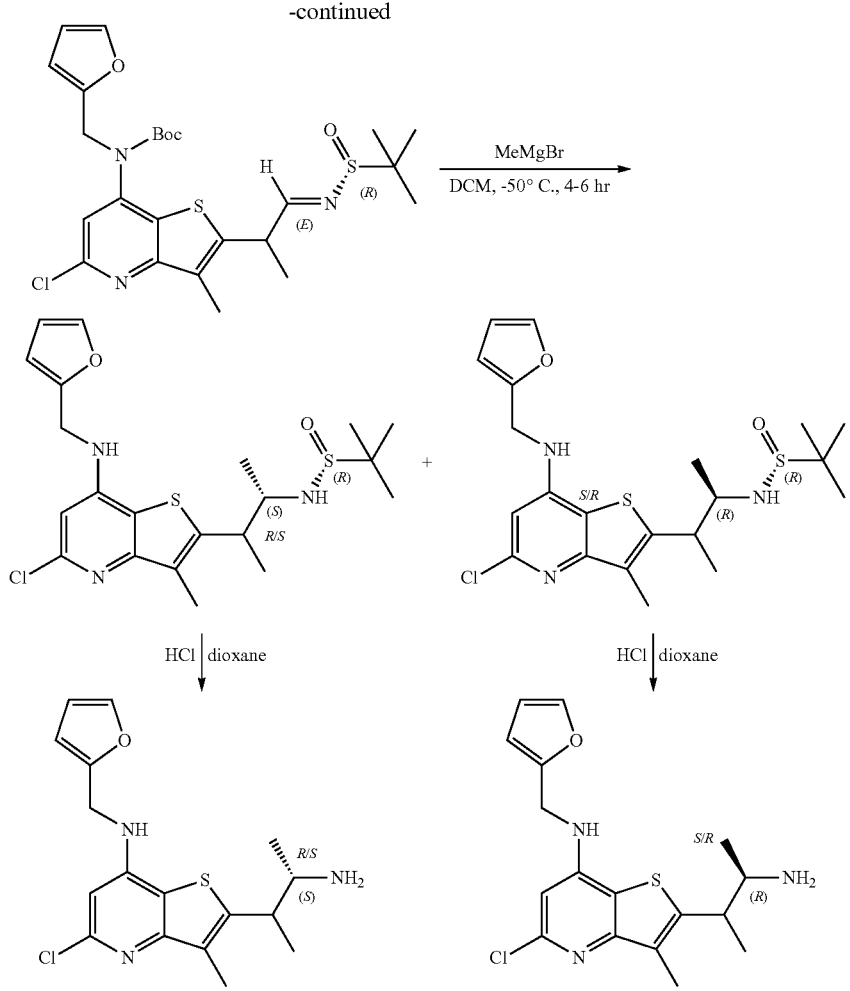

Step 1: tert-Butyl (5-chloro-3-methyl-2-(1-oxopropan-2-yl)thieno[3,2-b]pyridin-7-yl)(furan-2-ylmethyl)carbamate To a solution of tert-butyl (5-chloro-2-(1-hydroxypropan-2-yl)-3-methylthieno[3,2-b]pyridin-7-yl)(furan-2-ylmethyl)carbamate (141 mg, 0.32 mmol, 1.0 eq.), prepared according to the procedure in Example 31, in DCM (1.0 mL) was added Martin's reagent (171 mg, 1.2 eq.) at 0° C. The light pink solution was stirred at room temperature for 1 h, and UPLC analysis indicated that the reaction was complete. The mixture was filtered and the solid was washed with DCM. The filtrate was combined, washed with NaHCO$_3$ (sat. aq.) and concentrated. The resulting crude product was applied to the next step without purification. MS m/z 433.3, 435.3 [M−H]$^+$.

Step 2: tert-Butyl (2-((E)-1-(((R)-tert-butylsulfinyl)imino)propan-2-yl)-5-chloro-3-methylthieno[3,2-b]pyridin-7-yl)(furan-2-ylmethyl)carbamate A mixture of tert-butyl (5-chloro-3-methyl-2-(1-oxopropan-2-yl)thieno[3,2-b]pyridin-7-yl)(furan-2-ylmethyl)carbamate (115 mg, 0.26 mmol, 1.0 eq.), R-(+)-2-methylpropane-2-sulfinamide (48 mg, 1.5 eq.) and CuSO$_4$ (215 mg, 5.0 eq.) in DCE (0.5 mL) was stirred at room temperature for 18 h. After cooling, the mixture was purified by flash column chromatography on silica gel eluting with 0-30% EtOAc in hexanes to provide tert-butyl (2-((E)-1-(((R)-tert-butylsulfinyl)imino)propan-2-yl)-5-chloro-3-methylthieno[3,2-b]pyridin-7-yl)(furan-2-ylmethyl)carbamate (79 mg, 49% yield). MS m/z 560.2, 562.2 [M+Na]$^+$.

Step 3: (R)-N-((2S,3R/S)-3-(5-Chloro-7-((furan-2-ylmethyl)amino)-3-methylthieno[3,2-b]pyridin-2-yl)butan-2-yl)-2-methylpropane-2-sulfinamide and (R)-N-((2S,3S/R)-3-(5-chloro-7-((furan-2-ylmethyl)amino)-3-methylthieno[3,2-b]pyridin-2-yl)butan-2-yl)-2-methylpropane-2-sulfinamide To a solution of tert-butyl (2-((E)-1-(((R)-tert-butylsulfinyl)imino)propan-2-yl)-5-chloro-3-methylthieno[3,2-b]pyridin-7-yl)(furan-2-ylmethyl)carbamate (70 mg, 0.13 mmol, 1.0 eq.) in DCM (0.9 mL) was added MeMgBr (3.0 M in Et$_2$O, 0.11 mL, 2.5 eq.) at −78° C. The mixture was warmed to −50° C. and maintained at −50° C. for 4 h, then warmed to room temperature and continued to stir overnight. The reaction was quenched with a saturated solution of NH$_4$Cl. The mixture was diluted with EtOAc, then washed with water followed by brine, and the organic layer was dried over sodium sulfate and evaporated. The residue was purified by flash column chromatography on silica gel eluting with 0-100% EtOAc in hexanes to provide a mixture of two diastereomers, which were further purified on prep- HPLC eluting with 10-80% CH₃CN in water with 0.1% formic acid to provide (R)-N-((2S,3R/S)-3-(5-Chloro-7-((furan-2-ylmethyl)amino)-3-methylthieno[3,2-b]pyridin-2-yl)butan-2-yl)-2-methylpropane-2-sulfinamide (18 mg, 45% yield), MS m/z 454.3, 456.3 [M+H]⁺; and (R)-N-((2S,3S/R)-3-(5-chloro-7-((furan-2-ylmethyl)amino)-3-methylthieno[3,2-b]pyridin-2-yl)butan-2-yl)-2-methylpropane-2-sulfinamide (20 mg, 42% yield), MS m/z 454.3, 456.3 [M+H]⁺.

Step 4: 2-[(2R,3S)-3-aminobutan-2-yl]-5-chloro-N-[(furan-2-yl)methyl]-3-methylthieno[3,2-b]pyridin-7-amine A mixture of (R)-N-((2S,3R/S)-3-(5-chloro-7-((furan-2-ylmethyl)amino)-3-methylthieno[3,2-b]pyridin-2-yl)butan-2-yl)-2-methylpropane-2-sulfinamide (18 mg, 0.04 mmol) and HCl (4 M) in dioxane (1.0 mL) was stirred at room temperature for 1 h. The mixture was diluted with diethyl ether (2×) and filtered. The filter cake was washed with ether, collected and dried to give 2-((2R/S,3S)-3-aminobutan-2-yl)-5-chloro-N-(furan-2-ylmethyl)-3-methylthieno[3,2-b]pyridin-7-amine (5.4 mg, 41% yield) as an HCl salt. MS m/z 350.2, 352.2 [M+H]⁺;

$^1$H NMR (methanol-d₄) δ: 7.50 (d, J=1.1 Hz, 1H), 7.16 (s, 1H), 6.48 (d, J=3.0 Hz, 1H), 6.42 (dd, J=3.0, 1.1 Hz, 1H), 4.77 (s, 2H), 3.69-3.71 (m, 1H), 3.58-3.61 (m, 1H), 2.50 (s, 3H), 1.50 (d, J=7.0 Hz, 3H), 1.44 (d, J=6.56 Hz, 3H), 3 NHs not observed.

2-[(2S,3S)-3-aminobutan-2-yl]-5-chloro-N-[(furan-2-yl)methyl]-3-methylthieno[3,2-b]pyridin-7-amine A mixture of (R)-N-((2S,3S/R)-3-(5-chloro-7-((furan-2-ylmethyl)amino)-3-methylthieno[3,2-b]pyridin-2-yl)butan-2-yl)-2-methylpropane-2-sulfinamide (20 mg, 0.04 mmol) and HCl (4 M) in dioxane (1.0 mL) was stirred at room temperature for 1 h. The mixture was diluted with diethyl ether (2×) and filtered. The filter cake was washed with ether, collected and dried to give 2-((2R/S, 3S)-3-aminobutan-2-yl)-5-chloro-N-(furan-2-ylmethyl)-3-methylthieno[3,2-b]pyridin-7-amine (7.4 mg, 53% yield) as an HCl salt. MS m/z 350.2, 352.2 [M+H]⁺;

$^1$H NMR (methanol-d₄) δ: 7.50 (d, J=1.1 Hz, 1H), 7.10 (s, 1H), 6.46 (d, J=3.2 Hz, 1H), 6.42 (dd, J=3.0, 1.1 Hz, 1H), 4.74 (s, 2H), 3.64-3.67 (m, 1H), 3.55-3.58 (m, 1H), 2.47 (s, 3H), 1.54 (d, J=7.0 Hz, 3H), 1.27 (d, J=6.56 Hz, 3H), 3 NHs not observed.

BIOLOGICAL EXAMPLES

The following in vitro biological examples demonstrate the usefulness of the compounds of the present description for treating familial dysautonomia.

To describe in more detail and assist in understanding the present description, the following non-limiting biological examples are offered to more fully illustrate the scope of the description and are not to be construed as specifically limiting the scope thereof. Such variations of the present description that may be now known or later developed, which would be within the purview of one skilled in the art to ascertain, are considered to fall within the scope of the present description and as hereinafter claimed.

Example 1

IKBKAP-HTRF Assay

The assay is used for the quantitative determination of Elongator complex protein 1 (ELP1, also referred to as IKBKAP) concentration in cell lysates using the HTRF® (Homogeneous Time-Resolved Fluorescence) technology. IKBKAP is detected in a sandwich HTRF assay by use of an anti-IKAP antibody labeled with a donor and an anti-IKAP antibody labeled with an acceptor.

| Materials | Source |
| --- | --- |
| FD Patient-derived fibroblasts | GM04589 (Coriell Institute) |
| DMEM | Invitrogen Catalogue No. 11960-044 |
| LB4 (4X) Lysis Buffer | Cisbio |
| Protease Inhibitor Cocktail | Roche Catalogue No. 11836145001 |
| Anti IKAP-K(9 + 8) 50X | Cisbio |
| Anti IKAP-d2 50X | Cisbio |
| IKAP Detection Buffer | Cisbio |
| EnVision Plate Reader | Perkin Elmer Model No. 2103 |

Protocol

Cells were thawed and incubated in DMEM-10% FBS for 72 hours. Cells were trypsinized, counted, and re-suspended to a concentration of 50,000 cells/mL in DMEM-10% FBS. A 199 μL aliquot of the cell suspensions were plated at 10,000 cells per well in a 96 well microtiter plate and incubated for 3 to 5 hours. To provide a control signal, three wells did not receive cells and served as Blank control wells. Test compounds were serially diluted 3.16-fold in 100% DMSO to generate a 7-point concentration curve. A 1 μL aliquot of 200× compound solution was transferred to cell-containing wells, and cells were incubated for 48 hours in a cell culture incubator (37° C., 5% CO₂, 100% relative humidity). Triplicate samples were set up for each compound concentration. After 48 hours, the supernatant was removed from the cells and 50 μL of the 1×LB4 lysis buffer, containing protease inhibitors, was added to the cells and incubated with shaking at room temperature for 1 hour. A 36 μL aliquot of this lysate was subsequently transferred to the 384-well plate containing 4 μL of the antibody solution (1:50 dilution of anti IKAP d2 and anti-IKAP K(9+8) in detection buffer). The 384-well plate was then centrifuged for 1 minute to bring the solutions to the bottom of the plate and incubated overnight at 4° C. Fluorescence for each well of the plate at 665 nm and 620 nm was measured was on the EnVision plate reader (Perkin Elmer). The ΔF for each sample is calculated by:

$$\Delta F = \frac{(\text{Signal} - \text{Blank}) \times 100}{\text{Blank}}$$

wherein Signal is the normalized fluorescence for each sample well and Blank is the average normalized average fluorescence for the Blank control wells.

The maximum fold increase (MFI) in IKBKAP protein abundance for compounds of Formula (I) or a form thereof relative to the vehicle control are provided in Table 1. MFI was calculated by dividing the ΔF value for each sample well by the sample ΔF for the vehicle control wells.

An MFI≤1.9 is indicated by one star (*), between >1.9 and ≤2.9 is indicated by two stars (), between >2.9 and ≤3.9 is indicated by three stars (*), between >3.9 and ≤4.9 is indicated by four stars (**), and >4.9 is indicated by five stars (***).

The $EC_{2x}$ for IKBKAP protein expression obtained from the 7-point concentration curve generated for each test compound according to the protocol in Biological Example 1 are also provided in Table 1. The term "$EC_{2x}$ for IKBKAP protein expression" is defined as the concentration of test compound that is effective in producing two times the amount of IKBKAP protein in a FD patient cell compared to the amount produced from the DMSO vehicle control.

An $EC_{2x} > 1$ μM is indicated by one star (*), between >0.5 μM and ≤1 μM is indicated by two stars (), between >0.02 μM and ≤0.5 μM is indicated by three stars (*), between >0.005 μM and ≤0.02 μM is indicated by four stars (**), and ≤0.005 μM is indicated by five stars (***).

TABLE 1

| Cpd | MFI | $EC_{2x}$ |
| --- | --- | --- |
| 1 | *** | * |
| 2 | ***** | *** |
| 3 | *** | *** |
| 4 | ** | * |
| 5 | * | * |
| 6 | ***** | *** |
| 7 | ***** | *** |
| 8 | ***** | *** |
| 9 | ***** | *** |
| 10 | * | * |
| 11 | ** | *** |
| 12 | ** | *** |
| 13 | ***** | |
| 14 | ***** | *** |
| 15 | * | * |
| 16 | **** | ***** |
| 17 | **** | ***** |
| 18 | ***** | ***** |
| 19 | ***** | ***** |
| 20 | ***** | ***** |
| 21 | **** | **** |
| 22 | ** | * |
| 23 | ** | * |
| 24 | ** | * |
| 25 | *** | *** |
| 26 | **** | *** |
| 27 | **** | *** |
| 28 | ***** | ***** |
| 29 | ***** | ***** |
| 30 | * | * |
| 31 | * | * |
| 32 | * | * |
| 33 | ***** | ***** |
| 34 | ***** | **** |
| 35 | ***** | ***** |
| 36 | ***** | ***** |
| 37 | ***** | ***** |
| 38 | ***** | ***** |
| 39 | ***** | ***** |
| 40 | ***** | ***** |
| 41 | ***** | ***** |
| 42 | ***** | **** |
| 43 | ***** | ***** |
| 44 | ***** | ***** |
| 45 | ***** | ***** |
| 46 | ***** | ***** |
| 47 | ***** | ***** |
| 48 | ***** | ***** |
| 49 | ***** | ***** |
| 50 | **** | **** |
| 51 | ***** | ***** |
| 52 | ***** | ***** |
| 53 | ***** | ***** |
| 54 | ***** | ***** |
| 55 | **** | **** |
| 56 | * | * |
| 57 | ***** | ***** |
| 58 | ***** | ***** |
| 59 | ** | *** |
| 60 | ***** | **** |
| 61 | ***** | ***** |
| 62 | ***** | ***** |
| 63 | ** | *** |
| 64 | ***** | **** |
| 65 | ***** | *** |
| 66 | * | *** |
| 67 | * | * |
| 68 | ***** | **** |
| 69 | ***** | ***** |
| 70 | ***** | ***** |
| 71 | ***** | ***** |
| 72 | ***** | ***** |
| 73 | ***** | ***** |
| 74 | ***** | ***** |
| 75 | ***** | *** |
| 76 | ***** | ***** |
| 77 | **** | *** |
| 78 | ***** | ***** |
| 79 | ***** | ***** |
| 80 | *** | *** |
| 81 | ***** | ***** |
| 82 | ***** | ***** |
| 83 | ***** | ***** |
| 84 | ***** | ***** |
| 85 | ***** | ***** |
| 86 | **** | *** |
| 87 | *** | *** |
| 88 | ***** | ***** |
| 89 | ***** | ***** |
| 90 | ***** | ***** |
| 91 | ***** | ***** |
| 92 | ***** | ***** |
| 93 | ***** | ***** |
| 94 | **** | ***** |
| 95 | ***** | ***** |
| 96 | ***** | **** |
| 97 | ***** | ***** |
| 98 | ***** | ***** |
| 99 | ***** | ***** |
| 100 | ***** | ***** |
| 101 | ***** | ***** |
| 102 | ***** | ***** |
| 103 | **** | **** |
| 104 | ***** | ***** |
| 105 | ***** | ***** |
| 106 | ***** | ***** |
| 107 | ***** | ***** |
| 108 | ***** | **** |
| 109 | ***** | ***** |
| 110 | **** | ***** |
| 111 | ***** | **** |
| 112 | ***** | ***** |
| 113 | ***** | **** |
| 114 | ***** | ***** |
| 115 | ***** | ***** |
| 116 | ***** | **** |
| 117 | ***** | **** |
| 118 | ***** | ***** |
| 119 | **** | **** |
| 120 | **** | **** |
| 121 | **** | **** |
| 122 | ***** | **** |
| 123 | ***** | ***** |
| 124 | ***** | **** |
| 125 | ***** | ***** |
| 126 | ***** | ***** |
| 127 | ***** | **** |
| 128 | ***** | ***** |
| 129 | ***** | **** |
| 130 | ***** | ***** |
| 131 | **** | **** |
| 132 | ***** | **** |
| 133 | ***** | ***** |
| 134 | ***** | **** |
| 135 | **** | ***** |
| 136 | ***** | ***** |
| 137 | ***** | *** |
| 138 | ** | *** |

TABLE 1-continued

| Cpd | MFI | EC$_{2x}$ |
|---|---|---|
| 139 | **** | ***** |
| 140 | ***** | ***** |
| 141 | **** | *** |
| 142 | ***** | **** |
| 143 | ***** | *** |
| 144 | ***** | **** |
| 145 | ***** | *** |
| 146 | * | * |
| 147 | ** | *** |
| 148 | **** | ***** |
| 149 | **** | *** |
| 150 | ***** | ***** |
| 151 | ** | *** |
| 152 | ** | *** |
| 153 | ** | *** |
| 154 | **** | ***** |
| 155 | * | * |
| 156 | *** | *** |
| 157 | **** | *** |
| 158 | ***** | ***** |
| 159 | ** | *** |
| 160 | **** | *** |
| 161 | *** | ***** |
| 162 | **** | ***** |
| 163 | **** | *** |
| 164 | *** | *** |
| 165 | ***** | ***** |
| 166 | **** | ***** |
| 167 | ***** | ***** |

Without regard to whether a document cited herein was specifically and individually indicated as being incorporated by reference, all documents referred to herein are incorporated by reference into the present application for any and all purposes to the same extent as if each individual reference was fully set forth herein.

Having now fully described the subject matter of the claims, it will be understood by those having ordinary skill in the art that the same can be performed within a wide range of equivalents without affecting the scope of the subject matter or particular aspects described herein. It is intended that the appended claims be interpreted to include all such equivalents.

What is claimed is:

1. A compound of Formula (I):

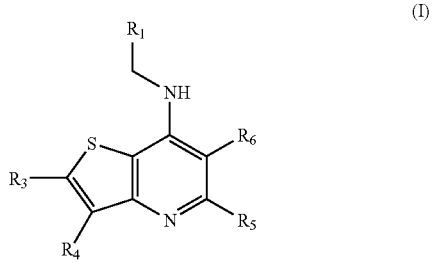

(I)

or a form thereof, wherein

R$_1$ is selected from the group consisting of phenyl and heteroaryl, optionally substituted with one, two, three, or four independently selected R$_{1a}$ substituents,
wherein heteroaryl is a 5-8 membered monocyclic or bicyclic aromatic carbon atom ring structure radical containing 1-3 heteroatoms selected from N, O, and S;
R$_{1a}$ is selected from the group consisting of cyano, halo, hydroxy, C$_{1-6}$alkyl, halo-C$_{1-6}$alkyl, and C$_{1-6}$alkoxy;
R$_3$ is selected from the group consisting of hydrogen, C$_{1-6}$alkyl, C$_{2-6}$alkenyl, C$_{2-6}$alkynyl, and C$_{1-6}$alkyl-amino,
wherein each instance of C$_{1-6}$alkyl, C$_{2-6}$alkenyl, and C$_{2-6}$alkynyl is optionally substituted with one, two, three, or four independently selected R$_{3a}$ substituents, and
wherein each instance of C$_{1-6}$alkyl, C$_{2-6}$alkenyl, and C$_{2-6}$alkynyl may optionally contain a chiral carbon having an (R) or(S) configuration;
R$_{3a}$ is selected from the group consisting of cyano, halo, hydroxy, oxo, C$_{1-6}$alkyl, halo-C$_{1-6}$alkyl, C$_{1-6}$alkoxy, halo-C$_{1-6}$alkoxy, carboxyl, amino, C$_{1-6}$alkoxy-carbonyl, C$_{1-6}$alkyl-amino, halo-C$_{1-6}$alkyl-amino, (C$_{1-6}$alkyl) 2-amino, phenyl-amino, heterocyclyl-amino, heteroaryl-amino, phenyl-(C$_{1-6}$alkyl)-amino, heterocyclyl-(C$_{1-6}$alkyl)-amino, heteroaryl-(C$_{1-6}$alkyl)-amino, C$_{1-6}$alkyl-thio, C$_{1-6}$alkyl-sulfoxyl, and C$_{1-6}$alkyl-sulfonyl,
wherein heterocyclyl is a 3-7 membered monocyclic carbon atom ring structure radical containing 1-3 heteroatoms selected from N, O, and S,
wherein heteroaryl is a 5-8 membered monocyclic or bicyclic aromatic carbon atom ring structure radical containing 1-3 heteroatoms selected from N, O, and S, and
wherein each instance of phenyl, heterocyclyl, and heteroaryl is optionally substituted with one, two, three or four independently selected R$_{3a'}$ substituents;
R$_{3a'}$ is selected from the group consisting of cyano, halo, hydroxy, C$_{1-6}$alkyl, halo-C$_{1-6}$alkyl, C$_{1-6}$alkoxy, and amino;
R$_4$ is selected from the group consisting of hydrogen, cyano, halo, hydroxy, C$_{1-6}$alkyl, halo-C$_{1-6}$alkyl, C$_{1-6}$alkoxy, halo-C$_{1-6}$alkoxy, amino, C$_{1-6}$alkyl-amino, (C$_{1-6}$alkyl) 2-amino, C$_{3-10}$cycloalkyl, phenyl, heterocyclyl, and heteroaryl,
wherein heterocyclyl is a 3-7 membered monocyclic carbon atom ring structure radical containing 1-3 heteroatoms selected from N, O, and S,
wherein heteroaryl is a 5-8 membered monocyclic or bicyclic aromatic carbon atom ring structure radical containing 1-3 heteroatoms selected from N, O, and S, and
wherein each instance of C$_{1-6}$alkyl, C$_{3-10}$cycloalkyl, phenyl, heterocyclyl, or heteroaryl is optionally substituted with one, two, three, or four independently selected R$_{4a}$ substituents;
R$_{4a}$ is selected from the group consisting of cyano, halo, hydroxy, C$_{1-6}$alkyl, halo-C$_{1-6}$alkyl, and C$_{1-6}$alkoxy;
R$_5$ is selected from the group consisting of hydrogen, cyano, halo, hydroxy, C$_{1-6}$alkyl, halo-C$_{1-6}$alkyl, C$_{1-6}$alkoxy, carbamoyl, C$_{3-10}$cycloalkyl, and heterocyclyl,
wherein heterocyclyl is a 3-7 membered monocyclic carbon atom ring structure radical containing 1-3 heteroatoms selected from N, O, and S;
R$_6$ is selected from the group consisting of hydrogen, halo, and C$_{1-6}$alkyl; and
wherein the form of the compound is selected from the group consisting of a salt, hydrate, solvate, and tautomer form thereof.

2. The compound of claim 1 wherein R$_1$ is selected from the group consisting of phenyl, furanyl, thiophenyl, 1H-pyrazolyl, 1H-imidazolyl, isoxazolyl, 1,3-thiazolyl, 1,3- oxazolyl, 1,2,3-triazolyl, 1,2,4-oxadiazolyl, 1,3,4-oxadiazolyl, 1,2,3-thiadiazolyl, pyridinyl, pyrimidinyl, pyrazinyl, and pyridazinyl.

3. The compound of claim 2 wherein $R_1$ is selected from the group consisting of furanyl, thiophenyl, 1,3-thiazolyl, and pyridinyl.

4. The compound of claim 1 wherein $R_3$ is $C_{1-6}$alkyl containing a chiral carbon having the(S) configuration.

5. The compound of claim 1 wherein $R_3$ is $C_{1-6}$alkyl containing a chiral carbon having the (R) configuration.

6. A compound, or a form thereof, wherein the compound is selected from the group consisting of:

5-chloro-N-[(furan-2-yl)methyl]thieno[3,2-b]pyridin-7-amine;
5-chloro-N-[(furan-2-yl)methyl]-3-methylthieno[3,2-b]pyridin-7-amine;
1-(5-chloro-7-{[(furan-2-yl)methyl]amino}-3-methylthieno[3,2-b]pyridin-2-yl)ethan-1-ol;
1-(5-chloro-7-{[(furan-2-yl)methyl]amino}thieno[3,2-b]pyridin-2-yl)ethan-1-ol;
(5-chloro-7-{[(furan-2-yl)methyl]amino}thieno[3,2-b]pyridin-2-yl)methanol;
3,5-dichloro-N-[(furan-2-yl)methyl]thieno[3,2-b]pyridin-7-amine;
3-bromo-5-chloro-N-[(furan-2-yl)methyl]thieno[3,2-b]pyridin-7-amine;
3,5-dichloro-N-[(1,3-thiazol-2-yl)methyl]thieno[3,2-b]pyridin-7-amine;
3-bromo-5-chloro-N-[(1,3-thiazol-2-yl)methyl]thieno[3,2-b]pyridin-7-amine;
3-chloro-5-methyl-N-[(1,3-thiazol-2-yl)methyl]thieno[3,2-b]pyridin-7-amine;
3-bromo-7-{[(thiophen-2-yl)methyl]amino}thieno[3,2-b]pyridine-5-carbonitrile;
7-{[(thiophen-2-yl)methyl]amino}thieno[3,2-b]pyridine-3,5-dicarbonitrile;
5-chloro-7-{[(thiophen-2-yl)methyl]amino}thieno[3,2-b]pyridine-3-carbonitrile;
5-chloro-7-{[(furan-2-yl)methyl]amino}thieno[3,2-b]pyridine-3-carbonitrile;
7-{[(furan-2-yl)methyl]amino}thieno[3,2-b]pyridine-3,5-dicarbonitrile;
2-[(2S)-2-aminopropyl]-5-chloro-N-[(furan-2-yl)methyl]thieno[3,2-b]pyridin-7-amine;
(2R)-2-amino-3-(5-chloro-7-{[(furan-2-yl)methyl]amino}thieno[3,2-b]pyridin-2-yl)propan-1-ol;
2-[(2S)-2-aminopropyl]-5-chloro-N-[(furan-2-yl)methyl]-3-methylthieno[3,2-b]pyridin-7-amine;
2-[(2S)-2-aminobutyl]-5-chloro-N-[(furan-2-yl)methyl]-3-methylthieno[3,2-b]pyridin-7-amine;
2-[(2S)-2-aminopropyl]-7-{[(furan-2-yl)methyl]amino}-3-methylthieno[3,2-b]pyridine-5-carbonitrile;
2-[(1S)-1-aminoethyl]-5-chloro-N-[(furan-2-yl)methyl]-3-methylthieno[3,2-b]pyridin-7-amine;
2-[(1R)-1-aminoethyl]-5-chloro-N-[(furan-2-yl)methyl]-3-methylthieno[3,2-b]pyridin-7-amine;
2-[(1R)-1-aminoethyl]-5-chloro-N-[(furan-2-yl)methyl]thieno[3,2-b]pyridin-7-amine;
2-[(1S)-1-aminoethyl]-5-chloro-N-[(furan-2-yl)methyl]thieno[3,2-b]pyridin-7-amine;
5-chloro-N-[(furan-2-yl)methyl]-2-[(methylamino)methyl]thieno[3,2-b]pyridin-7-amine;
5-chloro-N-[(furan-2-yl)methyl]-3-methyl-2-[(1S)-1-(methylamino)ethyl]thieno[3,2-b]pyridin-7-amine;
5-chloro-N-[(furan-2-yl)methyl]-3-methyl-2-[(methylamino)methyl]thieno[3,2-b]pyridin-7-amine;
2-[(2S)-2-aminopropyl]-5-chloro-3-methyl-N-[(thiophen-2-yl)methyl]thieno[3,2-b]pyridin-7-amine;
2-[(2S)-2-aminopropyl]-5-chloro-N-[(2-fluorophenyl)methyl]-3-methylthieno[3,2-b]pyridin-7-amine;
2-[(1S)-1-amino-2-methylpropyl]-5-chloro-N-[(furan-2-yl)methyl]-3-methylthieno[3,2-b]pyridin-7-amine;
2-[(1R)-1-amino-2-methylpropyl]-5-chloro-N-[(furan-2-yl)methyl]-3-methylthieno[3,2-b]pyridin-7-amine;
5-chloro-N-[(furan-2-yl)methyl]-3-methyl-2-[(1S)-2-methyl-1-(methylamino)propyl]thieno[3,2-b]pyridin-7-amine;
2-[(2S)-2-aminobutyl]-5-chloro-3-methyl-N-[(thiophen-2-yl)methyl]thieno[3,2-b]pyridin-7-amine;
2-[(2S)-2-aminopropyl]-N-[(furan-2-yl)methyl]-3-methylthieno[3,2-b]pyridin-7-amine;
2-[(2S)-2-aminopropyl]-5-chloro-N-[(3-fluoropyridin-4-yl)methyl]-3-methylthieno[3,2-b]pyridin-7-amine;
2-[(2S)-2-aminopropyl]-3,5-dichloro-N-[(furan-2-yl)methyl]thieno[3,2-b]pyridin-7-amine;
2-[(2S)-2-aminopropyl]-3-bromo-5-chloro-N-[(furan-2-yl)methyl]thieno[3,2-b]pyridin-7-amine;
2-[(2S)-2-aminopropyl]-3,5-dichloro-N-[(1,3-thiazol-2-yl)methyl]thieno[3,2-b]pyridin-7-amine;
(2R)-2-amino-3-(3,5-dichloro-7-{[(furan-2-yl)methyl]amino}thieno[3,2-b]pyridin-2-yl)propan-1-ol;
2-[(2R)-2-amino-3-methoxypropyl]-3,5-dichloro-N-[(furan-2-yl)methyl]thieno[3,2-b]pyridin-7-amine;
(2R)-2-amino-3-(3-bromo-5-chloro-7-{[(furan-2-yl)methyl]amino}thieno[3,2-b]pyridin-2-yl)propan-1-ol;
5-chloro-N-[(furan-2-yl)methyl]-3-methyl-2-[(2S)-2-(methylamino)propyl]thieno[3,2-b]pyridin-7-amine;
2-[(2S)-2-aminopropyl]-3-bromo-5-chloro-N-[(1,3-thiazol-2-yl)methyl]thieno[3,2-b]pyridin-7-amine;
2-[(2R)-2-amino-3-methoxypropyl]-3-bromo-5-chloro-N-[(furan-2-yl)methyl]thieno[3,2-b]pyridin-7-amine;
2-[(2R)-2-amino-3-methoxypropyl]-5-chloro-N-[(furan-2-yl)methyl]-3-methylthieno[3,2-b]pyridin-7-amine;
2-[(2R)-2-amino-3-fluoropropyl]-3-bromo-5-chloro-N-[(furan-2-yl)methyl]thieno[3,2-b]pyridin-7-amine;
2-[(2S)-2-amino-4-fluorobutyl]-3,5-dichloro-N-[(1,3-thiazol-2-yl)methyl]thieno[3,2-b]pyridin-7-amine;
(3S)-3-amino-4-(3,5-dichloro-7-{[(1,3-thiazol-2-yl)methyl]amino}thieno[3,2-b]pyridin-2-yl)butan-1-ol;
2-[(2S)-2-aminopropyl]-3-bromo-7-{[(furan-2-yl)methyl]amino}thieno[3,2-b]pyridine-5-carbonitrile;
2-[(2S)-2-aminopropyl]-7-{[(furan-2-yl)methyl]amino}thieno[3,2-b]pyridine-3,5-dicarbonitrile;
2-[(2S)-2-aminopropyl]-5-chloro-3-cyclopropyl-N-[(furan-2-yl)methyl]thieno[3,2-b]pyridin-7-amine;
2-[(2S)-2-aminopropyl]-3,5-dichloro-N-[(thiophen-2-yl)methyl]thieno[3,2-b]pyridin-7-amine;
2-[(2S)-2-aminopropyl]-3-bromo-5-chloro-N-[(thiophen-2-yl)methyl]thieno[3,2-b]pyridin-7-amine;
2-[(2S)-2-aminopropyl]-3-methyl-7-{[(thiophen-2-yl)methyl]amino}thieno[3,2-b]pyridine-5-carbonitrile;
2-[(1S)-1-aminoethyl]-5-chloro-3-methyl-N-[(thiophen-2-yl)methyl]thieno[3,2-b]pyridin-7-amine;
2-[(1R)-1-aminoethyl]-5-chloro-3-methyl-N-[(thiophen-2-yl)methyl]thieno[3,2-b]pyridin-7-amine;
2-[(2S)-2-aminopropyl]-5-chloro-3-methyl-N-[(1,3-thiazol-2-yl)methyl]thieno[3,2-b]pyridin-7-amine;
(2R)-2-amino-3-(5-chloro-7-{[(furan-2-yl)methyl]amino}-3-methylthieno[3,2-b]pyridin-2-yl)propan-1-ol;
2-[(2S)-2-amino-3-fluoropropyl]-5-chloro-N-[(furan-2-yl)methyl]-3-methylthieno[3,2-b]pyridin-7-amine;

2-[(2S)-2-aminopropyl]-3-chloro-5-methyl-N-[(1,3-thiazol-2-yl)methyl]thieno[3,2-b]pyridin-7-amine;
2-[(2S)-2-amino-4-methylpentyl]-5-chloro-3-methyl-N-[(thiophen-2-yl)methyl]thieno[3,2-b]pyridin-7-amine;
2-[(2S)-2-amino-4-methylpentyl]-3-bromo-5-chloro-N-[(1,3-thiazol-2-yl)methyl]thieno[3,2-b]pyridin-7-amine;
2-[(2S)-2-amino-3-fluoropropyl]-3-bromo-5-chloro-N-[(thiophen-2-yl)methyl]thieno[3,2-b]pyridin-7-amine;
2-[(2R)-2-amino-3-(trifluoromethoxy)propyl]-3-bromo-5-chloro-N-[(1,3-thiazol-2-yl)methyl]thieno[3,2-b]pyridin-7-amine;
(2R)-3-(3-bromo-5-chloro-7-{[(1,3-thiazol-2-yl)methyl]amino}thieno[3,2-b]pyridin-2-yl)-2-[(trifluoromethyl)amino]propan-1-ol;
2-[(2S)-2-amino-3-fluoropropyl]-3-bromo-5-chloro-N-[(1,3-thiazol-2-yl)methyl]thieno[3,2-b]pyridin-7-amine;
2-[(2S)-2-amino-3-fluoropropyl]-3,5-dichloro-N-[(1,3-thiazol-2-yl)methyl]thieno[3,2-b]pyridin-7-amine;
2-[(2S)-2-amino-4-methylpentyl]-5-chloro-3-methyl-N-[(1,3-thiazol-2-yl)methyl]thieno[3,2-b]pyridin-7-amine;
2-[(2R)-2-amino-3-fluoropropyl]-5-chloro-3-methyl-N-[(1,3-thiazol-2-yl)methyl]thieno[3,2-b]pyridin-7-amine;
2-[(2R)-2-amino-3-fluoropropyl]-3-bromo-5-chloro-N-[(1,3-thiazol-2-yl)methyl]thieno[3,2-b]pyridin-7-amine;
(2R)-2-amino-3-(3-bromo-5-chloro-7-{[(1,3-thiazol-2-yl)methyl]amino}thieno[3,2-b]pyridin-2-yl)propan-1-ol;
2-[(2R)-2-aminobut-3-en-1-yl]-3-bromo-5-chloro-N-[(1,3-thiazol-2-yl)methyl]thieno[3,2-b]pyridin-7-amine;
2-[(2S)-2-aminobutyl]-3-bromo-5-chloro-N-[(thiophen-2-yl)methyl]thieno[3,2-b]pyridin-7-amine;
2-[(2S)-2-amino-4-fluorobutyl]-3-bromo-5-chloro-N-[(thiophen-2-yl)methyl]thieno[3,2-b]pyridin-7-amine;
2-[(2S)-2-aminobutyl]-5-chloro-3-cyclopropyl-N-[(thiophen-2-yl)methyl]thieno[3,2-b]pyridin-7-amine;
2-[(2R)-2-amino-3-fluoropropyl]-3-bromo-5-chloro-N-[(thiophen-2-yl)methyl]thieno[3,2-b]pyridin-7-amine;
2-[(2R)-2-amino-3-fluoropropyl]-5-chloro-3-cyclopropyl-N-[(thiophen-2-yl)methyl]thieno[3,2-b]pyridin-7-amine;
2-[(2S)-2-aminobutyl]-3-bromo-5-chloro-N-[(1,3-thiazol-2-yl)methyl]thieno[3,2-b]pyridin-7-amine;
2-[(2S)-2-amino-4-methylpentyl]-3,5-dichloro-N-[(1,3-thiazol-2-yl)methyl]thieno[3,2-b]pyridin-7-amine;
2-[(2S)-2-amino-4-methylpentyl]-5-chloro-3-cyclopropyl-N-[(1,3-thiazol-2-yl)methyl]thieno[3,2-b]pyridin-7-amine;
2-[(2R)-2-amino-3-fluoropropyl]-5-chloro-N-[(furan-2-yl)methyl]-3-methylthieno[3,2-b]pyridin-7-amine;
2-[(2S)-2-aminobutyl]-3,5-dichloro-N-[(1,3-thiazol-2-yl)methyl]thieno[3,2-b]pyridin-7-amine;
2-[(2S)-2-aminobutyl]-3,5-dichloro-N-[(thiophen-2-yl)methyl]thieno[3,2-b]pyridin-7-amine;
2-[(2R)-2-amino-3-fluoropropyl]-3,5-dichloro-N-[(thiophen-2-yl)methyl]thieno[3,2-b]pyridin-7-amine;
2-[(2S)-2-aminobutyl]-5-chloro-3-methyl-N-[(1,3-thiazol-2-yl)methyl]thieno[3,2-b]pyridin-7-amine;
2-[(2S)-2-aminobutyl]-5-chloro-3-cyclopropyl-N-[(1,3-thiazol-2-yl)methyl]thieno[3,2-b]pyridin-7-amine;
2-[(2R)-2-amino-3-fluoropropyl]-5-chloro-3-cyclopropyl-N-[(1,3-thiazol-2-yl)methyl]thieno[3,2-b]pyridin-7-amine;
2-[(2S)-2-amino-4-fluorobutyl]-3-bromo-5-chloro-N-[(1,3-thiazol-2-yl)methyl]thieno[3,2-b]pyridin-7-amine;
(3S)-3-amino-4-(3-bromo-5-chloro-7-{[(1,3-thiazol-2-yl)methyl]amino}thieno[3,2-b]pyridin-2-yl)butan-1-ol;
2-[(2R)-2-amino-3-fluoropropyl]-3,5-dichloro-N-[(1,3-thiazol-2-yl)methyl]thieno[3,2-b]pyridin-7-amine;
2-[(2R)-2-amino-3-fluoropropyl]-5-chloro-3-methyl-N-[(thiophen-2-yl)methyl]thieno[3,2-b]pyridin-7-amine;
2-[(2S)-2-amino-4-fluorobutyl]-5-chloro-3-methyl-N-[(thiophen-2-yl)methyl]thieno[3,2-b]pyridin-7-amine;
2-[(2S)-2-amino-4-fluorobutyl]-3,5-dichloro-N-[(furan-2-yl)methyl]thieno[3,2-b]pyridin-7-amine;
2-[(2R)-2-amino-3-fluoropropyl]-3,5-dichloro-N-[(furan-2-yl)methyl]thieno[3,2-b]pyridin-7-amine;
2-[(2S)-2-amino-4-fluorobutyl]-5-chloro-N-[(furan-2-yl)methyl]-3-methylthieno[3,2-b]pyridin-7-amine;
2-[(2S)-2-aminopropyl]-5-chloro-3-cyclopropyl-N-[(1,3-thiazol-2-yl)methyl]thieno[3,2-b]pyridin-7-amine;
2-[(2S)-2-amino-4-fluorobutyl]-3-bromo-5-chloro-N-[(furan-2-yl)methyl]thieno[3,2-b]pyridin-7-amine;
2-[(2S)-2-amino-4-fluorobutyl]-3,5-dichloro-N-[(thiophen-2-yl)methyl]thieno[3,2-b]pyridin-7-amine;
2-[(2S)-2-amino-4-fluorobutyl]-5-chloro-3-methyl-N-[(1,3-thiazol-2-yl)methyl]thieno[3,2-b]pyridin-7-amine;
(3S)-3-amino-4-(3-bromo-5-chloro-7-{[(2-fluorophenyl)methyl]amino}thieno[3,2-b]pyridin-2-yl)butan-1-ol;
2-[(2S)-2-aminopropyl]-3-bromo-7-{[(thiophen-2-yl)methyl]amino}thieno[3,2-b]pyridine-5-carbonitrile;
2-[(2S)-2-aminopropyl]-7-{[(thiophen-2-yl)methyl]amino}thieno[3,2-b]pyridine-3,5-dicarbonitrile;
(3S)-3-amino-4-(3-bromo-5-chloro-7-{[(furan-2-yl)methyl]amino}thieno[3,2-b]pyridin-2-yl)butanenitrile;
2-[(2R)-2-amino-3-(methylsulfanyl)propyl]-5-chloro-N-[(furan-2-yl)methyl]-3-methylthieno[3,2-b]pyridin-7-amine;
(3S)-3-amino-4-(5-chloro-3-methyl-7-{[(thiophen-2-yl)methyl]amino}thieno[3,2-b]pyridin-2-yl)butanenitrile;
(3S)-3-amino-4-(3,5-dichloro-7-{[(thiophen-2-yl)methyl]amino}thieno[3,2-b]pyridin-2-yl)butanenitrile;
2-[(2S)-2-amino-4,4-difluorobutyl]-3-bromo-5-chloro-N-[(thiophen-2-yl)methyl]thieno[3,2-b]pyridin-7-amine;
2-[(2R)-2-amino-3-(methanesulfonyl)propyl]-5-chloro-N-[(furan-2-yl)methyl]-3-methylthieno[3,2-b]pyridin-7-amine;
2-[(2S)-2-aminopropyl]-5-chloro-7-{[(furan-2-yl)methyl]amino}thieno[3,2-b]pyridine-3-carbonitrile;
2-[(2S)-2-aminopropyl]-5-chloro-7-{[(thiophen-2-yl)methyl]amino}thieno[3,2-b]pyridine-3-carbonitrile;
(3S)-3-amino-4-(5-chloro-7-{[(furan-2-yl)methyl]amino}-3-methylthieno[3,2-b]pyridin-2-yl)butanenitrile;
2-[(2S)-2-aminopropyl]-3-chloro-7-{[(thiophen-2-yl)methyl]amino}thieno[3,2-b]pyridine-5-carbonitrile;
2-[(2R)-2-amino-3-(methanesulfonyl)propyl]-3,5-dichloro-N-[(furan-2-yl)methyl]thieno[3,2-b]pyridin-7-amine;
2-[(2R)-2-amino-3-(methylsulfanyl)propyl]-3,5-dichloro-N-[(furan-2-yl)methyl]thieno[3,2-b]pyridin-7-amine;
3-(5-chloro-7-{[(furan-2-yl)methyl]amino}-3-methylthieno[3,2-b]pyridin-2-yl)-D-alanine;
3-(5-chloro-7-{[(furan-2-yl)methyl]amino}-3-methylthieno[3,2-b]pyridin-2-yl)-N,N-dimethyl-D-alaninamide;

2-[(2R)-2-amino-3-(methanesulfonyl)propyl]-3-bromo-5-chloro-N-[(furan-2-yl)methyl]thieno[3,2-b]pyridin-7-amine;

2-[(2R)-2-amino-3-(methylsulfanyl)propyl]-3-bromo-5-chloro-N-[(furan-2-yl)methyl]thieno[3,2-b]pyridin-7-amine;

2-[(2R)-2-aminobut-3-en-1-yl]-5-chloro-N-[(furan-2-yl)methyl]thieno[3,2-b]pyridin-7-amine;

3-(3,5-dichloro-7-{[(furan-2-yl)methyl]amino}thieno[3,2-b]pyridin-2-yl)-D-alanine;

3-(3,5-dichloro-7-{[(furan-2-yl)methyl]amino}thieno[3,2-b]pyridin-2-yl)-N-phenyl-D-alaninamide;

2-[(2R)-2-aminobut-3-yn-1-yl]-3-methyl-5-chloro-N-[(furan-2-yl)methyl]thieno[3,2-b]pyridin-7-amine;

3-(3,5-dichloro-7-{[(furan-2-yl)methyl]amino}thieno[3,2-b]pyridin-2-yl)-N-(2-fluorophenyl)-D-alaninamide;

2-[(2R,3S)-2-amino-3-fluorobutyl]-3-bromo-5-chloro-N-[(1,3-thiazol-2-yl)methyl]thieno[3,2-b]pyridin-7-amine;

2-[(2R,3S)-2-amino-3-fluorobutyl]-5-chloro-3-methyl-N-[(thiophen-2-yl)methyl]thieno[3,2-b]pyridin-7-amine;

(2S)-2-amino-1-(3,5-dichloro-7-{[(thiophen-2-yl)methyl]amino}thieno[3,2-b]pyridin-2-yl)propan-1-ol;

2-[(2R,3S)-2-amino-3-fluorobutyl]-5-chloro-3-methyl-N-[(1,3-thiazol-2-yl)methyl]thieno[3,2-b]pyridin-7-amine;

2-[(2S)-2-aminopropyl]-5-chloro-N-[(5-fluoro-1,3-thiazol-2-yl)methyl]-3-methylthieno[3,2-b]pyridin-7-amine;

2-[(2S)-2-amino-1-fluoropropyl]-3,5-dichloro-N-[(thiophen-2-yl)methyl]thieno[3,2-b]pyridin-7-amine;

methyl 3-(5-chloro-7-{[(furan-2-yl)methyl]amino}-3-methylthieno[3,2-b]pyridin-2-yl)-D-alaninate;

2-[(2S)-2-amino-1,1-difluoropropyl]-3,5-dichloro-N-[(thiophen-2-yl)methyl]thieno[3,2-b]pyridin-7-amine;

3-(5-chloro-7-{[(furan-2-yl)methyl]amino}-3-methylthieno[3,2-b]pyridin-2-yl)-N-(4-cyanophenyl)-D-alaninamide;

3-(5-chloro-7-{[(furan-2-yl)methyl]amino}-3-methylthieno[3,2-b]pyridin-2-yl)-N-pyridin-2-yl-D-alaninamide;

3-(5-chloro-7-{[(furan-2-yl)methyl]amino}-3-methylthieno[3,2-b]pyridin-2-yl)-N-pyrazin-2-yl-D-alaninamide;

2-[(2S)-2-aminopropyl]-5-chloro-N-[(furan-2-yl)methyl]-3-methoxythieno[3,2-b]pyridin-7-amine;

5-chloro-N-[(furan-2-yl)methyl]-3-methoxythieno[3,2-b]pyridin-7-amine;

5-chloro-7-{[(thiophen-2-yl)methyl]amino}thieno[3,2-b]pyridin-3-ol;

2-[(2S)-2-aminopropyl]-5-chloro-3-(difluoromethoxy)-N-[(thiophen-2-yl)methyl]thieno[3,2-b]pyridin-7-amine;

3-(5-chloro-7-{[(furan-2-yl)methyl]amino}-3-methylthieno[3,2-b]pyridin-2-yl)-N-pyridin-4-yl-D-alaninamide;

3-(5-chloro-7-{[(furan-2-yl)methyl]amino}-3-methylthieno[3,2-b]pyridin-2-yl)-N-methyl-N-phenyl-D-alaninamide;

3-(5-chloro-7-{[(furan-2-yl)methyl]amino}-3-methylthieno[3,2-b]pyridin-2-yl)-N-(4-methylphenyl)-D-alaninamide;

3-(5-chloro-7-{[(furan-2-yl)methyl]amino}-3-methylthieno[3,2-b]pyridin-2-yl)-N-(3-chlorophenyl)-D-alaninamide;

3-(5-chloro-7-{[(furan-2-yl)methyl]amino}-3-methylthieno[3,2-b]pyridin-2-yl)-N-(3-methoxyphenyl)-D-alaninamide;

3-(5-chloro-7-{[(furan-2-yl)methyl]amino}-3-methylthieno[3,2-b]pyridin-2-yl)-N-(1-methyl-1H-pyrazol-5-yl)-D-alaninamide;

2-(5-chloro-7-{[(furan-2-yl)methyl]amino}-3-methylthieno[3,2-b]pyridin-2-yl)propan-1-ol;

2-(5-chloro-7-{[(furan-2-yl)methyl]amino}-3-methylthieno[3,2-b]pyridin-2-yl)propane-1,2-diol;

2-(1-aminopropan-2-yl)-5-chloro-N-[(furan-2-yl)methyl]-3-methylthieno[3,2-b]pyridin-7-amine;

5-chloro-3-(difluoromethoxy)-N-[(thiophen-2-yl)methyl]thieno[3,2-b]pyridin-7-amine;

2-[(2R,3S)-3-aminobutan-2-yl]-5-chloro-N-[(furan-2-yl)methyl]-3-methylthieno[3,2-b]pyridin-7-amine;

2-[(2S,3S)-3-aminobutan-2-yl]-5-chloro-N-[(furan-2-yl)methyl]-3-methylthieno[3,2-b]pyridin-7-amine;

2-(2-aminoethyl)-5-chloro-N-[(furan-2-yl)methyl]-3-methylthieno[3,2-b]pyridin-7-amine;

(2S)-2-amino-1-(3-bromo-5-chloro-7-{[(furan-2-yl)methyl]amino}thieno[3,2-b]pyridin-2-yl)propan-1-ol;

2-[(2S)-2-amino-1-fluoropropyl]-3-bromo-5-chloro-N-[(furan-2-yl)methyl]thieno[3,2-b]pyridin-7-amine;

(2S)-2-amino-1-(3-bromo-5-chloro-7-{[(thiophen-2-yl)methyl]amino}thieno[3,2-b]pyridin-2-yl)propan-1-ol;

(2S)-2-amino-1-(3-bromo-5-chloro-7-{[(thiophen-2-yl)methyl]amino}thieno[3,2-b]pyridin-2-yl)propan-1-one;

(2S)-2-amino-1-(3-bromo-5-chloro-7-{[(furan-2-yl)methyl]amino}thieno[3,2-b]pyridin-2-yl)propan-1-one;

2-[(2S)-2-amino-1-fluoropropyl]-3-bromo-5-chloro-N-[(thiophen-2-yl)methyl]thieno[3,2-b]pyridin-7-amine;

(2S)-2-amino-1-(3-bromo-5-chloro-7-{[(1,3-thiazol-2-yl)methyl]amino}thieno[3,2-b]pyridin-2-yl)propan-1-ol;

(2S)-2-amino-1-(3-bromo-5-chloro-7-{[(1,3-thiazol-2-yl)methyl]amino}thieno[3,2-b]pyridin-2-yl)propan-1-one;

2-[(2S)-2-amino-1-fluoropropyl]-3-bromo-5-chloro-N-[(1,3-thiazol-2-yl)methyl]thieno[3,2-b]pyridin-7-amine;

(2R)-2-amino-3-(5-chloro-7-{[(thiophen-2-yl)methyl]amino}thieno[3,2-b]pyridin-2-yl)propan-1-ol;

$N^2$-[(2S)-2-aminopropyl]-5-chloro-3-methyl-$N^7$-[(thiophen-2-yl)methyl]thieno[3,2-b]pyridine-2,7-diamine;

$N^2$-[(2R)-2-aminopropyl]-5-chloro-3-methyl-$N^7$-[(thiophen-2-yl)methyl]thieno[3,2-b]pyridine-2,7-diamine;

(2R,3R)-3-amino-4-(3-bromo-5-chloro-7-{[(furan-2-yl)methyl]amino}thieno[3,2-b]pyridin-2-yl)butan-2-ol;

2-[(2R)-2-aminobut-3-yn-1-yl]-3,5-dichloro-N-[(furan-2-yl)methyl]thieno[3,2-b]pyridin-7-amine; and

[(2R)-2-amino-3-(3,5-dichloro-7-{[(furan-2-yl)methyl]amino}thieno[3,2-b]pyridin-2-yl)propyl](methyl)sulfaniumolate;

and wherein the form of the compound is selected from the group consisting of a salt, hydrate, solvate, and tautomer form thereof.

7. A compound salt, or a form thereof, wherein the compound salt is selected from the group consisting of:

3,5-dichloro-N-[(furan-2-yl)methyl]thieno[3,2-b]pyridin-7-amine hydrochloride;

3-bromo-5-chloro-N-[(furan-2-yl)methyl]thieno[3,2-b]pyridin-7-amine hydrochloride;

3-chloro-5-methyl-N-[(1,3-thiazol-2-yl)methyl]thieno[3,2-b]pyridin-7-amine hydrochloride;

2-[(2S)-2-aminopropyl]-5-chloro-N-[(furan-2-yl)methyl]thieno[3,2-b]pyridin-7-amine dihydrochloride;

(2R)-2-amino-3-(5-chloro-7-{[(furan-2-yl)methyl]amino}thieno[3,2-b]pyridin-2-yl)propan-1-ol dihydrochloride;

2-[(2S)-2-aminopropyl]-5-chloro-N-[(furan-2-yl)methyl]-3-methylthieno[3,2-b]pyridin-7-amine dihydrochloride;

2-[(2S)-2-aminobutyl]-5-chloro-N-[(furan-2-yl)methyl]-3-methylthieno[3,2-b]pyridin-7-amine dihydrochloride;

2-[(2S)-2-aminopropyl]-7-{[(furan-2-yl)methyl]amino}-3-methylthieno[3,2-b]pyridine-5-carbonitrile trifluoroacetate;

2-[(1S)-1-aminoethyl]-5-chloro-N-[(furan-2-yl)methyl]-3-methylthieno[3,2-b]pyridin-7-amine hydrochloride;

2-[(1R)-1-aminoethyl]-5-chloro-N-[(furan-2-yl)methyl]-3-methylthieno[3,2-b]pyridin-7-amine hydrochloride;

2-[(1R)-1-aminoethyl]-5-chloro-N-[(furan-2-yl)methyl]thieno[3,2-b]pyridin-7-amine hydrochloride;

2-[(1S)-1-aminoethyl]-5-chloro-N-[(furan-2-yl)methyl]thieno[3,2-b]pyridin-7-amine hydrochloride;

5-chloro-N-[(furan-2-yl)methyl]-2-[(methylamino)methyl]thieno[3,2-b]pyridin-7-amine hydrochloride;

5-chloro-N-[(furan-2-yl)methyl]-3-methyl-2-[(1S)-1-(methylamino)ethyl]thieno[3,2-b]pyridin-7-amine hydrochloride;

5-chloro-N-[(furan-2-yl)methyl]-3-methyl-2-[(methylamino)methyl]thieno[3,2-b]pyridin-7-amine hydrochloride;

2-[(2S)-2-aminopropyl]-5-chloro-3-methyl-N-[(thiophen-2-yl)methyl]thieno[3,2-b]pyridin-7-amine dihydrochloride;

2-[(2S)-2-aminopropyl]-5-chloro-N-[(2-fluorophenyl)methyl]-3-methylthieno[3,2-b]pyridin-7-amine dihydrochloride;

2-[(1S)-1-amino-2-methylpropyl]-5-chloro-N-[(furan-2-yl)methyl]-3-methylthieno[3,2-b]pyridin-7-amine hydrochloride;

2-[(1R)-1-amino-2-methylpropyl]-5-chloro-N-[(furan-2-yl)methyl]-3-methylthieno[3,2-b]pyridin-7-amine hydrochloride;

5-chloro-N-[(furan-2-yl)methyl]-3-methyl-2-[(1S)-2-methyl-1-(methylamino)propyl]thieno[3,2-b]pyridin-7-amine hydrochloride;

2-[(2S)-2-aminobutyl]-5-chloro-3-methyl-N-[(thiophen-2-yl)methyl]thieno[3,2-b]pyridin-7-amine dihydrochloride;

2-[(2S)-2-aminopropyl]-N-[(furan-2-yl)methyl]-3-methylthieno[3,2-b]pyridin-7-amine dihydrochloride;

2-[(2S)-2-aminopropyl]-5-chloro-N-[(3-fluoropyridin-4-yl)methyl]-3-methylthieno[3,2-b]pyridin-7-amine dihydrochloride;

2-[(2S)-2-aminopropyl]-3,5-dichloro-N-[(furan-2-yl)methyl]thieno[3,2-b]pyridin-7-amine dihydrochloride;

2-[(2S)-2-aminopropyl]-3-bromo-5-chloro-N-[(furan-2-yl)methyl]thieno[3,2-b]pyridin-7-amine dihydrochloride;

2-[(2S)-2-aminopropyl]-3,5-dichloro-N-[(1,3-thiazol-2-yl)methyl]thieno[3,2-b]pyridin-7-amine dihydrochloride;

(2R)-2-amino-3-(3,5-dichloro-7-{[(furan-2-yl)methyl]amino}thieno[3,2-b]pyridin-2-yl)propan-1-ol dihydrochloride;

2-[(2R)-2-amino-3-methoxypropyl]-3,5-dichloro-N-[(furan-2-yl)methyl]thieno[3,2-b]pyridin-7-amine dihydrochloride;

(2R)-2-amino-3-(3-bromo-5-chloro-7-{[(furan-2-yl)methyl]amino}thieno[3,2-b]pyridin-2-yl)propan-1-ol dihydrochloride;

5-chloro-N-[(furan-2-yl)methyl]-3-methyl-2-[(2S)-2-(methylamino)propyl]thieno[3,2-b]pyridin-7-amine hydrochloride;

2-[(2S)-2-aminopropyl]-3-bromo-5-chloro-N-[(1,3-thiazol-2-yl)methyl]thieno[3,2-b]pyridin-7-amine dihydrochloride;

2-[(2R)-2-amino-3-methoxypropyl]-3-bromo-5-chloro-N-[(furan-2-yl)methyl]thieno[3,2-b]pyridin-7-amine dihydrochloride;

2-[(2R)-2-amino-3-methoxypropyl]-5-chloro-N-[(furan-2-yl)methyl]-3-methylthieno[3,2-b]pyridin-7-amine dihydrochloride;

2-[(2R)-2-amino-3-fluoropropyl]-3-bromo-5-chloro-N-[(furan-2-yl)methyl]thieno[3,2-b]pyridin-7-amine formate;

2-[(2S)-2-amino-4-fluorobutyl]-3,5-dichloro-N-[(1,3-thiazol-2-yl)methyl]thieno[3,2-b]pyridin-7-amine dihydrochloride;

(3S)-3-amino-4-(3,5-dichloro-7-{[(1,3-thiazol-2-yl)methyl]amino}thieno[3,2-b]pyridin-2-yl)butan-1-ol dihydrochloride;

2-[(2S)-2-aminopropyl]-3-bromo-7-{[(furan-2-yl)methyl]amino}thieno[3,2-b]pyridine-5-carbonitrile hydrochloride;

2-[(2S)-2-aminopropyl]-7-{[(furan-2-yl)methyl]amino}thieno[3,2-b]pyridine-3,5-dicarbonitrile hydrochloride;

2-[(2S)-2-aminopropyl]-5-chloro-3-cyclopropyl-N-[(furan-2-yl)methyl]thieno[3,2-b]pyridin-7-amine hydrochloride;

2-[(2S)-2-aminopropyl]-3,5-dichloro-N-[(thiophen-2-yl)methyl]thieno[3,2-b]pyridin-7-amine dihydrochloride;

2-[(2S)-2-aminopropyl]-3-bromo-5-chloro-N-[(thiophen-2-yl)methyl]thieno[3,2-b]pyridin-7-amine dihydrochloride;

2-[(2S)-2-aminopropyl]-3-methyl-7-{[(thiophen-2-yl)methyl]amino}thieno[3,2-b]pyridine-5-carbonitrile formate;

2-[(1S)-1-aminoethyl]-5-chloro-3-methyl-N-[(thiophen-2-yl)methyl]thieno[3,2-b]pyridin-7-amine hydrochloride;

2-[(1R)-1-aminoethyl]-5-chloro-3-methyl-N-[(thiophen-2-yl)methyl]thieno[3,2-b]pyridin-7-amine hydrochloride;

2-[(2S)-2-aminopropyl]-5-chloro-3-methyl-N-[(1,3-thiazol-2-yl)methyl]thieno[3,2-b]pyridin-7-amine dihydrochloride;

(2R)-2-amino-3-(5-chloro-7-{[(furan-2-yl)methyl]amino}-3-methylthieno[3,2-b]pyridin-2-yl)propan-1-ol dihydrochloride;

2-[(2S)-2-amino-3-fluoropropyl]-5-chloro-N-[(furan-2-yl)methyl]-3-methylthieno[3,2-b]pyridin-7-amine dihydrochloride;

2-[(2S)-2-aminopropyl]-3-chloro-5-methyl-N-[(1,3-thiazol-2-yl)methyl]thieno[3,2-b]pyridin-7-amine dihydrochloride;

2-[(2S)-2-amino-4-methylpentyl]-5-chloro-3-methyl-N-[(thiophen-2-yl)methyl]thieno[3,2-b]pyridin-7-amine hydrochloride;

2-[(2S)-2-amino-4-methylpentyl]-3-bromo-5-chloro-N-[(1,3-thiazol-2-yl)methyl]thieno[3,2-b]pyridin-7-amine hydrochloride;

2-[(2S)-2-amino-3-fluoropropyl]-3-bromo-5-chloro-N-[(thiophen-2-yl)methyl]thieno[3,2-b]pyridin-7-amine hydrochloride;

2-[(2R)-2-amino-3-(trifluoromethoxy)propyl]-3-bromo-5-chloro-N-[(1,3-thiazol-2-yl)methyl]thieno[3,2-b]pyridin-7-amine formate;

(2R)-3-(3-bromo-5-chloro-7-{[(1,3-thiazol-2-yl)methyl]amino}thieno[3,2-b]pyridin-2-yl)-2-[(trifluoromethyl)amino]propan-1-ol formate;

2-[(2S)-2-amino-3-fluoropropyl]-3-bromo-5-chloro-N-[(1,3-thiazol-2-yl)methyl]thieno[3,2-b]pyridin-7-amine dihydrochloride;

2-[(2S)-2-amino-3-fluoropropyl]-3,5-dichloro-N-[(1,3-thiazol-2-yl)methyl]thieno[3,2-b]pyridin-7-amine dihydrochloride;

2-[(2S)-2-amino-4-methylpentyl]-5-chloro-3-methyl-N-[(1,3-thiazol-2-yl)methyl]thieno[3,2-b]pyridin-7-amine hydrochloride;

2-[(2R)-2-amino-3-fluoropropyl]-5-chloro-3-methyl-N-[(1,3-thiazol-2-yl)methyl]thieno[3,2-b]pyridin-7-amine dihydrochloride;

2-[(2R)-2-amino-3-fluoropropyl]-3-bromo-5-chloro-N-[(1,3-thiazol-2-yl)methyl]thieno[3,2-b]pyridin-7-amine dihydrochloride;

(2R)-2-amino-3-(3-bromo-5-chloro-7-{[(1,3-thiazol-2-yl)methyl]amino}thieno[3,2-b]pyridin-2-yl)propan-1-ol dihydrochloride;

2-[(2R)-2-aminobut-3-en-1-yl]-3-bromo-5-chloro-N-[(1,3-thiazol-2-yl)methyl]thieno[3,2-b]pyridin-7-amine dihydrochloride;

2-[(2S)-2-aminobutyl]-3-bromo-5-chloro-N-[(thiophen-2-yl)methyl]thieno[3,2-b]pyridin-7-amine dihydrochloride;

2-[(2S)-2-amino-4-fluorobutyl]-3-bromo-5-chloro-N-[(thiophen-2-yl)methyl]thieno[3,2-b]pyridin-7-amine hydrochloride;

2-[(2S)-2-aminobutyl]-5-chloro-3-cyclopropyl-N-[(thiophen-2-yl)methyl]thieno[3,2-b]pyridin-7-amine dihydrochloride;

2-[(2R)-2-amino-3-fluoropropyl]-3-bromo-5-chloro-N-[(thiophen-2-yl)methyl]thieno[3,2-b]pyridin-7-amine hydrochloride;

2-[(2R)-2-amino-3-fluoropropyl]-5-chloro-3-cyclopropyl-N-[(thiophen-2-yl)methyl]thieno[3,2-b]pyridin-7-amine hydrochloride;

2-[(2S)-2-aminobutyl]-3-bromo-5-chloro-N-[(1,3-thiazol-2-yl)methyl]thieno[3,2-b]pyridin-7-amine hydrochloride;

2-[(2S)-2-amino-4-methylpentyl]-3,5-dichloro-N-[(1,3-thiazol-2-yl)methyl]thieno[3,2-b]pyridin-7-amine hydrochloride;

2-[(2S)-2-amino-4-methylpentyl]-5-chloro-3-cyclopropyl-N-[(1,3-thiazol-2-yl)methyl]thieno[3,2-b]pyridin-7-amine hydrochloride;

2-[(2R)-2-amino-3-fluoropropyl]-5-chloro-N-[(furan-2-yl)methyl]-3-methylthieno[3,2-b]pyridin-7-amine dihydrochloride;

2-[(2S)-2-aminobutyl]-3,5-dichloro-N-[(1,3-thiazol-2-yl)methyl]thieno[3,2-b]pyridin-7-amine hydrochloride;

2-[(2S)-2-aminobutyl]-3,5-dichloro-N-[(thiophen-2-yl)methyl]thieno[3,2-b]pyridin-7-amine dihydrochloride;

2-[(2S)-2-aminobutyl]-5-chloro-3-methyl-N-[(1,3-thiazol-2-yl)methyl]thieno[3,2-b]pyridin-7-amine formate;

2-[(2S)-2-aminobutyl]-5-chloro-3-cyclopropyl-N-[(1,3-thiazol-2-yl)methyl]thieno[3,2-b]pyridin-7-amine hydrochloride;

2-[(2R)-2-amino-3-fluoropropyl]-5-chloro-3-cyclopropyl-N-[(1,3-thiazol-2-yl)methyl]thieno[3,2-b]pyridin-7-amine dihydrochloride;

2-[(2S)-2-amino-4-fluorobutyl]-3-bromo-5-chloro-N-[(1,3-thiazol-2-yl)methyl]thieno[3,2-b]pyridin-7-amine dihydrochloride;

(3S)-3-amino-4-(3-bromo-5-chloro-7-{[(1,3-thiazol-2-yl)methyl]amino}thieno[3,2-b]pyridin-2-yl)butan-1-ol dihydrochloride;

2-[(2R)-2-amino-3-fluoropropyl]-3,5-dichloro-N-[(1,3-thiazol-2-yl)methyl]thieno[3,2-b]pyridin-7-amine dihydrochloride;

2-[(2R)-2-amino-3-fluoropropyl]-5-chloro-3-methyl-N-[(thiophen-2-yl)methyl]thieno[3,2-b]pyridin-7-amine dihydrochloride;

2-[(2S)-2-amino-4-fluorobutyl]-5-chloro-3-methyl-N-[(thiophen-2-yl)methyl]thieno[3,2-b]pyridin-7-amine dihydrochloride;

2-[(2S)-2-amino-4-fluorobutyl]-3,5-dichloro-N-[(furan-2-yl)methyl]thieno[3,2-b]pyridin-7-amine dihydrochloride;

2-[(2R)-2-amino-3-fluoropropyl]-3,5-dichloro-N-[(furan-2-yl)methyl]thieno[3,2-b]pyridin-7-amine dihydrochloride;

2-[(2S)-2-amino-4-fluorobutyl]-5-chloro-N-[(furan-2-yl)methyl]-3-methylthieno[3,2-b]pyridin-7-amine hydrochloride;

2-[(2S)-2-aminopropyl]-5-chloro-3-cyclopropyl-N-[(1,3-thiazol-2-yl)methyl]thieno[3,2-b]pyridin-7-amine hydrochloride;

2-[(2S)-2-amino-4-fluorobutyl]-3-bromo-5-chloro-N-[(furan-2-yl)methyl]thieno[3,2-b]pyridin-7-amine dihydrochloride;

2-[(2S)-2-amino-4-fluorobutyl]-3,5-dichloro-N-[(thiophen-2-yl)methyl]thieno[3,2-b]pyridin-7-amine dihydrochloride;

2-[(2S)-2-amino-4-fluorobutyl]-5-chloro-3-methyl-N-[(1,3-thiazol-2-yl)methyl]thieno[3,2-b]pyridin-7-amine formate;

(3S)-3-amino-4-(3-bromo-5-chloro-7-{[(2-fluorophenyl)methyl]amino}thieno[3,2-b]pyridin-2-yl)butan-1-ol dihydrochloride;

2-[(2S)-2-aminopropyl]-3-bromo-7-{[(thiophen-2-yl)methyl]amino}thieno[3,2-b]pyridine-5-carbonitrile formate;

2-[(2S)-2-aminopropyl]-7-{[(thiophen-2-yl)methyl]amino}thieno[3,2-b]pyridine-3,5-dicarbonitrile formate;

(3S)-3-amino-4-(3-bromo-5-chloro-7-{[(furan-2-yl)methyl]amino}thieno[3,2-b]pyridin-2-yl)butanenitrile formate;

2-[(2R)-2-amino-3-(methylsulfanyl)propyl]-5-chloro-N-[(furan-2-yl)methyl]-3-methylthieno[3,2-b]pyridin-7-amine dihydrochloride;

(3S)-3-amino-4-(5-chloro-3-methyl-7-{[(thiophen-2-yl)methyl]amino}thieno[3,2-b]pyridin-2-yl)butanenitrile dihydrochloride;

(3S)-3-amino-4-(3,5-dichloro-7-{[(thiophen-2-yl)methyl]amino}thieno[3,2-b]pyridin-2-yl)butanenitrile dihydrochloride;

2-[(2S)-2-amino-4,4-difluorobutyl]-3-bromo-5-chloro-N-[(thiophen-2-yl)methyl]thieno[3,2-b]pyridin-7-amine dihydrochloride;

2-[(2R)-2-amino-3-(methanesulfonyl)propyl]-5-chloro-N-[(furan-2-yl)methyl]-3-methylthieno[3,2-b]pyridin-7-amine dihydrochloride;

2-[(2S)-2-aminopropyl]-5-chloro-7-{[(furan-2-yl)methyl]amino}thieno[3,2-b]pyridine-3-carbonitrile formate;

2-[(2S)-2-aminopropyl]-5-chloro-7-{[(thiophen-2-yl)methyl]amino}thieno[3,2-b]pyridine-3-carbonitrile formate;

(3S)-3-amino-4-(5-chloro-7-{[(furan-2-yl)methyl]amino}-3-methylthieno[3,2-b]pyridin-2-yl)butanenitrile dihydrochloride;

2-[(2S)-2-aminopropyl]-3-chloro-7-{[(thiophen-2-yl)methyl]amino}thieno[3,2-b]pyridine-5-carbonitrile formate;

2-[(2R)-2-amino-3-(methanesulfonyl)propyl]-3,5-dichloro-N-[(furan-2-yl)methyl]thieno[3,2-b]pyridin-7-amine dihydrochloride;

2-[(2R)-2-amino-3-(methylsulfanyl)propyl]-3,5-dichloro-N-[(furan-2-yl)methyl]thieno[3,2-b]pyridin-7-amine hydrochloride;

3-(5-chloro-7-{[(furan-2-yl)methyl]amino}-3-methylthieno[3,2-b]pyridin-2-yl)-D-alanine dihydrochloride;

3-(5-chloro-7-{[(furan-2-yl)methyl]amino}-3-methylthieno[3,2-b]pyridin-2-yl)-N,N-dimethyl-D-alaninamide dihydrochloride;

2-[(2R)-2-amino-3-(methanesulfonyl)propyl]-3-bromo-5-chloro-N-[(furan-2-yl)methyl]thieno[3,2-b]pyridin-7-amine dihydrochloride;

2-[(2R)-2-amino-3-(methylsulfanyl)propyl]-3-bromo-5-chloro-N-[(furan-2-yl)methyl]thieno[3,2-b]pyridin-7-amine dihydrochloride;

2-[(2R)-2-aminobut-3-en-1-yl]-5-chloro-N-[(furan-2-yl)methyl]thieno[3,2-b]pyridin-7-amine formate;

3-(3,5-dichloro-7-{[(furan-2-yl)methyl]amino}thieno[3,2-b]pyridin-2-yl)-D-alanine dihydrochloride;

3-(3,5-dichloro-7-{[(furan-2-yl)methyl]amino}thieno[3,2-b]pyridin-2-yl)-N-phenyl-D-alaninamide hydrochloride;

2-[(2R)-2-aminobut-3-yn-1-yl]-3-methyl-5-chloro-N-[(furan-2-yl)methyl]thieno[3,2-b]pyridin-7-amine dihydrochloride;

3-(3,5-dichloro-7-{[(furan-2-yl)methyl]amino}thieno[3,2-b]pyridin-2-yl)-N-(2-fluorophenyl)-D-alaninamide dihydrochloride;

2-[(2R,3S)-2-amino-3-fluorobutyl]-3-bromo-5-chloro-N-[(1,3-thiazol-2-yl)methyl]thieno[3,2-b]pyridin-7-amine dihydrochloride;

2-[(2R,3S)-2-amino-3-fluorobutyl]-5-chloro-3-methyl-N-[(thiophen-2-yl)methyl]thieno[3,2-b]pyridin-7-amine dihydrochloride;

(2S)-2-amino-1-(3,5-dichloro-7-{[(thiophen-2-yl)methyl]amino}thieno[3,2-b]pyridin-2-yl)propan-1-ol dihydrochloride;

2-[(2R,3S)-2-amino-3-fluorobutyl]-5-chloro-3-methyl-N-[(1,3-thiazol-2-yl)methyl]thieno[3,2-b]pyridin-7-amine dihydrochloride;

2-[(2S)-2-aminopropyl]-5-chloro-N-[(5-fluoro-1,3-thiazol-2-yl)methyl]-3-methylthieno[3,2-b]pyridin-7-amine dihydrochloride;

2-[(2S)-2-amino-1-fluoropropyl]-3,5-dichloro-N-[(thiophen-2-yl)methyl]thieno[3,2-b]pyridin-7-amine formate;

methyl 3-(5-chloro-7-{[(furan-2-yl)methyl]amino}-3-methylthieno[3,2-b]pyridin-2-yl)-D-alaninate dihydrochloride;

3-(5-chloro-7-{[(furan-2-yl)methyl]amino}-3-methylthieno[3,2-b]pyridin-2-yl)-N-(4-cyanophenyl)-D-alaninamide hydrochloride;

3-(5-chloro-7-{[(furan-2-yl)methyl]amino}-3-methylthieno[3,2-b]pyridin-2-yl)-N-pyridin-2-yl-D-alaninamide hydrochloride;

3-(5-chloro-7-{[(furan-2-yl)methyl]amino}-3-methylthieno[3,2-b]pyridin-2-yl)-N-pyrazin-2-yl-D-alaninamide hydrochloride;

2-[(2S)-2-aminopropyl]-5-chloro-N-[(furan-2-yl)methyl]-3-methoxythieno[3,2-b]pyridin-7-amine dihydrochloride;

5-chloro-N-[(furan-2-yl)methyl]-3-methoxythieno[3,2-b]pyridin-7-amine hydrochloride;

5-chloro-7-{[(thiophen-2-yl)methyl]amino}thieno[3,2-b]pyridin-3-ol hydrochloride;

2-[(2S)-2-aminopropyl]-5-chloro-3-(difluoromethoxy)-N-[(thiophen-2-yl)methyl]thieno[3,2-b]pyridin-7-amine formate;

3-(5-chloro-7-{[(furan-2-yl)methyl]amino}-3-methylthieno[3,2-b]pyridin-2-yl)-N-pyridin-4-yl-D-alaninamide hydrochloride;

3-(5-chloro-7-{[(furan-2-yl)methyl]amino}-3-methylthieno[3,2-b]pyridin-2-yl)-N-methyl-N-phenyl-D-alaninamide hydrochloride;

3-(5-chloro-7-{[(furan-2-yl)methyl]amino}-3-methylthieno[3,2-b]pyridin-2-yl)-N-(4-methylphenyl)-D-alaninamide hydrochloride;

3-(5-chloro-7-{[(furan-2-yl)methyl]amino}-3-methylthieno[3,2-b]pyridin-2-yl)-N-(3-chlorophenyl)-D-alaninamide hydrochloride;

3-(5-chloro-7-{[(furan-2-yl)methyl]amino}-3-methylthieno[3,2-b]pyridin-2-yl)-N-(3-methoxyphenyl)-D-alaninamide hydrochloride;

3-(5-chloro-7-{[(furan-2-yl)methyl]amino}-3-methylthieno[3,2-b]pyridin-2-yl)-N-(1-methyl-1H-pyrazol-5-yl)-D-alaninamide hydrochloride;

2-(1-aminopropan-2-yl)-5-chloro-N-[(furan-2-yl)methyl]-3-methylthieno[3,2-b]pyridin-7-amine formate;

2-[(2R,3S)-3-aminobutan-2-yl]-5-chloro-N-[(furan-2-yl)methyl]-3-methylthieno[3,2-b]pyridin-7-amine dihydrochloride;

2-[(2S,3S)-3-aminobutan-2-yl]-5-chloro-N-[(furan-2-yl)methyl]-3-methylthieno[3,2-b]pyridin-7-amine dihydrochloride;

2-(2-aminoethyl)-5-chloro-N-[(furan-2-yl)methyl]-3-methylthieno[3,2-b]pyridin-7-amine formate;

(2S)-2-amino-1-(3-bromo-5-chloro-7-{[(furan-2-yl)methyl]amino}thieno[3,2-b]pyridin-2-yl)propan-1-ol dihydrochloride;

2-[(2S)-2-amino-1-fluoropropyl]-3-bromo-5-chloro-N-[(furan-2-yl)methyl]thieno[3,2-b]pyridin-7-amine dihydrochloride;

(2S)-2-amino-1-(3-bromo-5-chloro-7-{[(thiophen-2-yl)methyl]amino}thieno[3,2-b]pyridin-2-yl)propan-1-ol dihydrochloride;

(2S)-2-amino-1-(3-bromo-5-chloro-7-{[(thiophen-2-yl)methyl]amino}thieno[3,2-b]pyridin-2-yl)propan-1-one dihydrochloride;

(2S)-2-amino-1-(3-bromo-5-chloro-7-{[(furan-2-yl)methyl]amino}thieno[3,2-b]pyridin-2-yl)propan-1-one dihydrochloride;

2-[(2S)-2-amino-1-fluoropropyl]-3-bromo-5-chloro-N-[(thiophen-2-yl)methyl]thieno[3,2-b]pyridin-7-amine dihydrochloride;

(2S)-2-amino-1-(3-bromo-5-chloro-7-{[(1,3-thiazol-2-yl)methyl]amino}thieno[3,2-b]pyridin-2-yl)propan-1-ol dihydrochloride;

(2S)-2-amino-1-(3-bromo-5-chloro-7-{[(1,3-thiazol-2-yl)methyl]amino}thieno[3,2-b]pyridin-2-yl)propan-1-one dihydrochloride;

2-[(2S)-2-amino-1-fluoropropyl]-3-bromo-5-chloro-N-[(1,3-thiazol-2-yl)methyl]thieno[3,2-b]pyridin-7-amine dihydrochloride;

(2R)-2-amino-3-(5-chloro-7-{[(thiophen-2-yl)methyl]amino}thieno[3,2-b]pyridin-2-yl)propan-1-ol formate;

$N^2$-[(2S)-2-aminopropyl]-5-chloro-3-methyl-$N^7$-[(thiophen-2-yl)methyl]thieno[3,2-b]pyridine-2,7-diamine hydrochloride;

$N^2$-[(2R)-2-aminopropyl]-5-chloro-3-methyl-$N^7$-[(thiophen-2-yl)methyl]thieno[3,2-b]pyridine-2,7-diamine hydrochloride;

(2R,3R)-3-amino-4-(3-bromo-5-chloro-7-{[(furan-2-yl)methyl]amino}thieno[3,2-b]pyridin-2-yl)butan-2-ol hydrochloride; and 2-[(2R)-2-aminobut-3-yn-1-yl]-3,5-dichloro-N-[(furan-2-yl)methyl]thieno[3,2-b]pyridin-7-amine dihydrochloride;

and wherein the form of the compound salt is selected from the group consisting of a hydrate, solvate, and tautomer form thereof.

8. A method of treating familial dysautonomia comprising administering to a subject in need thereof an effective amount of a compound of Formula (I):

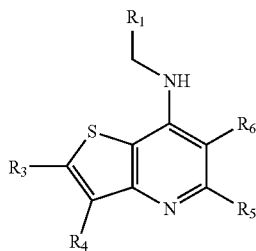

or a form thereof, wherein $R_1$ is selected from the group consisting of phenyl, furanyl, thiophenyl, 1,3-thiazolyl, and pyridinyl, optionally substituted with one, two, three, or four $R_{1a}$ substituents;

$R_{1a}$ is halo;

$R_3$ is selected from the group consisting of hydrogen, $C_{1-6}$alkyl, $C_{2-6}$alkenyl, $C_{2-6}$alkynyl, and $C_{1-6}$alkyl-amino, wherein each instance of $C_{1-6}$alkyl, $C_{2-6}$alkenyl, and $C_{2-6}$alkynyl is optionally substituted with one, two, three, or four independently selected $R_{3a}$ substituents, and wherein each instance of $C_{1-6}$alkyl, $C_{2-6}$alkenyl, and $C_{2-6}$alkynyl may optionally contain a chiral carbon having an (R) or(S) configuration;

$R_{3a}$ is selected from the group consisting of cyano, halo, hydroxy, oxo, $C_{1-6}$alkyl, halo-$C_{1-6}$alkyl, $C_{1-6}$alkoxy, halo-$C_{1-6}$alkoxy, carboxyl, amino, $C_{1-6}$alkoxy-carbonyl, $C_{1-6}$alkyl-amino, halo-$C_{1-6}$alkyl-amino, ($C_{1-6}$alkyl)$_2$-amino, phenyl-amino, heteroaryl-amino, phenyl-($C_{1-6}$alkyl)-amino, $C_{1-6}$alkyl-thio, $C_{1-6}$alkyl-sulfoxyl, and $C_{1-6}$alkyl-sulfonyl, wherein heteroaryl is a 5-8 membered monocyclic or bicyclic aromatic carbon atom ring structure radical containing 1-3 heteroatoms selected from N, O, and S, and wherein each instance of phenyl, and heteroaryl is optionally substituted with one, two, three or four independently selected $R_{3a'}$ substituents;

$R_{3a'}$ is selected from the group consisting of cyano, halo, $C_{1-6}$alkyl, and $C_{1-6}$alkoxy;

$R_4$ is selected from the group consisting of cyano, halo, hydroxy, $C_{1-6}$alkyl, $C_{1-6}$alkoxy, halo-$C_{1-6}$alkoxy, and $C_{3-10}$cycloalkyl;

$R_5$ is selected from the group consisting of hydrogen, cyano, halo, and $C_{1-6}$alkyl;

$R_6$ is hydrogen; and wherein the form of the compound is selected from the group consisting of a salt, hydrate, solvate, and tautomer form thereof.

9. A method of treating familial dysautonomia comprising administering to a subject in need thereof an effective amount of the compound of claim 6.

10. A method of treating familial dysautonomia comprising administering to a subject in need thereof an effective amount of the compound salt of claim 7.

11. A pharmaceutical composition comprising an effective amount of the compound of claim 1 in admixture with a pharmaceutically acceptable excipient.

12. A pharmaceutical composition comprising an effective amount of the compound of claim 6 in admixture with a pharmaceutically acceptable excipient.

13. A pharmaceutical composition comprising an effective amount of the compound salt of claim 7 in admixture with a pharmaceutically acceptable excipient.

14. A compound of claim 1, wherein the compound is 2-[(2S)-2-aminopropyl]-5-chloro-3-methyl-N-[(thiophen-2-yl)methyl]thieno[3,2-b]pyridin-7-amine.

15. A compound of claim 1, wherein the compound is 2-[(2S)-2-aminopropyl]-3,5-dichloro-N-[(thiophen-2-yl)methyl]thieno[3,2-b]pyridin-7-amine.

16. A compound of claim 1, wherein the compound is a compound salt, and wherein the compound salt is 2-[(2S)-2-aminopropyl]-5-chloro-3-methyl-N-[(thiophen-2-yl)methyl]thieno[3,2-b]pyridin-7-amine dihydrochloride.

17. A compound of claim 1, wherein the compound is a compound salt, and wherein the compound salt is 2-[(2S)-2-aminopropyl]-3,5-dichloro-N-[(thiophen-2-yl)methyl]thieno[3,2-b]pyridin-7-amine dihydrochloride.

* * * * *